US009290536B2

(12) United States Patent
Anderson et al.

(10) Patent No.: US 9,290,536 B2
(45) Date of Patent: Mar. 22, 2016

(54) C4 MONOMETHYL TRITERPENOID DERIVATIVES AND METHODS OF USE THEREOF

(75) Inventors: Eric Anderson, Southlake, TX (US); Christopher F. Bender, Garland, TX (US); Xiaofeng Liu, Coppell, TX (US); Xin Jiang, Coppell, TX (US); Melean Visnick, Irving, TX (US)

(73) Assignee: Reata Pharmaceuticals, Inc., Irving, TX (US)

( * ) Notice: Subject to any disclaimer, the term of this patent is extended or adjusted under 35 U.S.C. 154(b) by 280 days.

(21) Appl. No.: 13/417,519

(22) Filed: Mar. 12, 2012

(65) Prior Publication Data

US 2012/0252776 A1 Oct. 4, 2012

Related U.S. Application Data

(60) Provisional application No. 61/452,017, filed on Mar. 11, 2011.

(51) Int. Cl.

| | |
|---|---|
| ***C07D 265/30*** | (2006.01) |
| ***A61K 31/215*** | (2006.01) |
| ***C07J 63/00*** | (2006.01) |
| ***C07J 71/00*** | (2006.01) |

(52) U.S. Cl.

CPC ............ *C07J 63/008* (2013.01); *C07J 71/0005* (2013.01)

(58) Field of Classification Search

CPC ............................ A61K 31/215; C07D 265/30

USPC .......................................... 544/106; 514/508

See application file for complete search history.

(56) References Cited

U.S. PATENT DOCUMENTS

| | | | |
|---|---|---|---|
| 4,395,423 | A | 7/1983 | Neumann |
| 5,064,823 | A | 11/1991 | Lee et al. |
| 6,326,507 | B1 | 12/2001 | Gribble et al. |
| 6,369,101 | B1 | 4/2002 | Carlson et al. |
| 6,552,075 | B2 | 4/2003 | Gribble et al. |
| 6,642,217 | B2 | 11/2003 | Krasutsky et al. |
| 6,649,654 | B1 | 11/2003 | Karin et al. |
| 6,951,847 | B2 | 10/2005 | Gibson et al. |
| 6,974,801 | B2 | 12/2005 | Honda et al. |
| 7,053,119 | B2 | 5/2006 | Karin et al. |
| 7,144,875 | B2 | 12/2006 | Gibson et al. |
| 7,176,237 | B2 | 2/2007 | Honda et al. |
| 7,288,568 | B2 | 10/2007 | Gribble et al. |
| 7,399,606 | B2 | 7/2008 | Karin et al. |
| 7,410,958 | B2 | 8/2008 | Krasutsky et al. |
| 7,435,755 | B2 | 10/2008 | Konopleva et al. |
| 7,678,830 | B2 | 3/2010 | Honda et al. |
| 7,714,012 | B2 | 5/2010 | Honda et al. |
| 7,795,305 | B2 | 9/2010 | Konopleva et al. |
| 7,863,327 | B2 | 1/2011 | Gribble et al. |
| 7,915,402 | B2 | 3/2011 | Anderson et al. |
| 7,943,778 | B2 | 5/2011 | Jiang et al. |
| 8,034,955 | B2 | 10/2011 | Gribble et al. |
| 8,067,394 | B2 | 11/2011 | Honda et al. |
| 8,067,465 | B2 | 11/2011 | Honda et al. |
| 8,071,632 | B2 | 12/2011 | Jiang et al. |
| 8,088,824 | B2 | 1/2012 | Walling et al. |
| 8,124,656 | B2 | 2/2012 | Anderson et al. |
| 8,124,799 | B2 | 2/2012 | Anderson et al. |
| 8,129,429 | B2 | 3/2012 | Sporn et al. |
| 8,258,329 | B2 | 9/2012 | Anderson et al. |
| 8,299,046 | B2 | 10/2012 | Sporn et al. |
| 8,309,601 | B2 | 11/2012 | Walling et al. |
| 8,314,137 | B2 | 11/2012 | Honda et al. |
| 8,338,618 | B2 | 12/2012 | Jiang et al. |

(Continued)

FOREIGN PATENT DOCUMENTS

| | | |
|---|---|---|
| CN | 101 117 348 | 2/2008 |
| CN | 102 070 697 A | 12/2010 |

(Continued)

OTHER PUBLICATIONS

STN online search results Anderson (2009).*

(Continued)

*Primary Examiner* — Scarlett Goon

*Assistant Examiner* — Sonya Wright

(74) *Attorney, Agent, or Firm* — Parker Highlander PLLC

(57) ABSTRACT

Disclosed herein are novel C4-monomethyl triterpenoid compounds and derivatives thereof, including those of the formula:

(I)

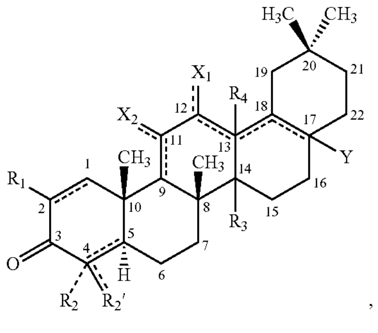

, wherein the variables are defined herein. Also provided are pharmaceutical compositions, kits and articles of manufacture comprising such compounds. Methods and intermediates useful for making the compounds, and methods of using the compounds, for example as antioxidant inflammation modulators, and compositions thereof are also provided.

27 Claims, No Drawings

(56) References Cited

U.S. PATENT DOCUMENTS

| | | | |
|---|---|---|---|
| 8,394,967 | B2 | 3/2013 | Jiang et al. |
| 8,440,820 | B2 | 5/2013 | Anderson et al. |
| 8,440,854 | B2 | 5/2013 | Anderson et al. |
| 8,455,544 | B2 | 6/2013 | Sporn et al. |
| 2002/0042535 | A1 | 4/2002 | Gribble et al. |
| 2003/0119732 | A1 | 6/2003 | Konopleva et al. |
| 2003/0232786 | A1 | 12/2003 | Honda et al. |
| 2003/0236303 | A1 | 12/2003 | Gribble et al. |
| 2004/0002463 | A1 | 1/2004 | Honda et al. |
| 2004/0097436 | A1 | 5/2004 | Krasutsky et al. |
| 2005/0208151 | A1 | 9/2005 | Hurez et al. |
| 2005/0288363 | A1 | 12/2005 | Gribble et al. |
| 2006/0258752 | A1 | 11/2006 | Vander Jagt et al. |
| 2007/0155742 | A1 | 7/2007 | Honda et al. |
| 2007/0232577 | A1 | 10/2007 | Xu et al. |
| 2007/0244081 | A1 | 10/2007 | Krasutsky et al. |
| 2007/0249561 | A1 | 10/2007 | Taylor |
| 2007/0259839 | A1 | 11/2007 | Krasutsky et al. |
| 2007/0259842 | A1 | 11/2007 | Krasutsky et al. |
| 2008/0220057 | A1 | 9/2008 | Gribble et al. |
| 2008/0233195 | A1 | 9/2008 | Sporn et al. |
| 2008/0261985 | A1 | 10/2008 | Honda et al. |
| 2009/0048204 | A1 | 2/2009 | Walling et al. |
| 2009/0048205 | A1 | 2/2009 | Meyer et al. |
| 2009/0060873 | A1 | 3/2009 | Sporn et al. |
| 2009/0093447 | A1 | 4/2009 | Konopleva et al. |
| 2009/0326063 | A1 | 12/2009 | Sporn et al. |
| 2010/0041904 | A1 | 2/2010 | Jiang et al. |
| 2010/0048887 | A1 | 2/2010 | Anderson et al. |
| 2010/0048892 | A1 | 2/2010 | Anderson et al. |
| 2010/0048911 | A1 | 2/2010 | Jiang et al. |
| 2010/0056777 | A1 | 3/2010 | Anderson et al. |
| 2010/0261930 | A1 | 10/2010 | Honda et al. |
| 2011/0009363 | A1 | 1/2011 | Honda et al. |
| 2011/0196007 | A1 | 8/2011 | Honda et al. |
| 2011/0245206 | A1 | 10/2011 | Jiang et al. |
| 2011/0245233 | A1 | 10/2011 | Anderson et al. |
| 2011/0281955 | A1 | 11/2011 | Meyer et al. |
| 2012/0071684 | A1 | 3/2012 | Walling et al. |
| 2012/0101149 | A1 | 4/2012 | Honda et al. |
| 2012/0214814 | A1 | 8/2012 | Anderson et al. |
| 2012/0220652 | A1 | 8/2012 | Sporn et al. |
| 2012/0238767 | A1 | 9/2012 | Jiang et al. |
| 2012/0245374 | A1 | 9/2012 | Anderson et al. |
| 2012/0283450 | A1 | 11/2012 | Anderson et al. |

FOREIGN PATENT DOCUMENTS

| | | |
|---|---|---|
| JP | 55-055153 | 4/1980 |
| JP | 2001 240573 | 9/2001 |
| JP | 2005-314381 | 11/2005 |
| JP | 2008-110962 | 5/2008 |
| JP | 2008-247898 | 10/2008 |
| WO | WO 99/65478 | 12/1999 |
| WO | WO 00/73253 | 12/2000 |
| WO | WO 02/03996 | 1/2002 |
| WO | WO 02/26761 | 4/2002 |
| WO | WO 02/26762 | 4/2002 |
| WO | WO 02/32410 | 4/2002 |
| WO | WO 02/47611 | 6/2002 |
| WO | WO 02/92768 | 11/2002 |
| WO | WO 03/059339 | 7/2003 |
| WO | WO 03/062260 | 7/2003 |
| WO | WO 2004/064723 | 8/2004 |
| WO | WO 2004/089357 | 10/2004 |
| WO | WO 2005/042002 | 5/2005 |
| WO | WO 2005/046732 | 5/2005 |
| WO | WO 2006/029221 | 3/2006 |
| WO | WO 2007/005879 | 1/2007 |
| WO | WO 2007/112043 | 10/2007 |
| WO | WO 2007/127791 | 11/2007 |
| WO | WO 2008/000068 | 1/2008 |
| WO | WO 2008/000070 | 1/2008 |
| WO | WO 2008/016095 | 2/2008 |
| WO | WO 2008/064132 | 5/2008 |
| WO | WO 2008/064133 | 5/2008 |
| WO | WO 2008/097596 | 8/2008 |
| WO | WO 2008/111497 | 9/2008 |
| WO | WO 2008/136838 | 11/2008 |
| WO | WO 2009/023232 | 2/2009 |
| WO | WO 2009/023845 | 2/2009 |
| WO | WO 2009/058849 | 5/2009 |
| WO | WO 2009/089545 | 7/2009 |
| WO | WO 2009/129545 | 10/2009 |
| WO | WO 2009/129546 | 10/2009 |
| WO | WO 2009/129548 | 10/2009 |
| WO | WO 2009/146216 | 12/2009 |
| WO | WO 2009/146218 | 12/2009 |
| WO | WO 2010/011782 | 1/2010 |
| WO | WO 2010/053817 | 5/2010 |
| WO | WO 2010/093944 | 8/2010 |
| WO | WO 2011/130302 | 10/2011 |
| WO | WO 2011/140078 | 11/2011 |
| WO | WO 2012/106190 | 8/2012 |
| WO | WO 2012/125488 | 9/2012 |

OTHER PUBLICATIONS

Alabran, et al., "Human neuroblastoma cells rapidly enter cell cycle arrest and apoptosis following exposure to C-28 derivatives of the synthetic triterpenoid CDDO," *Cancer Biology & Therapy*, 7(5):709-717, 2008.

Chadalapaka, et al., "Structure-dependent inhibition of bladder and pancreatic cancer cell growth by 2-substituted glycyrrhetinic and ursolic acid derivatives," *Bioorganic & Medicinal Chemistry Letters*, 18:2633-2639, 2008.

Deeb, et al., "CDDO-Me inhibits proliferation, induces apoptosis, down-regulates Akt, mTOR, NF-κB and NF-κB-regulated antiapoptotic and proangiogenic proteins in TRAMP prostate cancer cells," *J. of Experimental Therapeutics and Oncology*, 7:31-39, 2008.

Heather E. Ferguson, "PPARγ ligands have potent anti-fibrotic activity: mechanism of action and implications for therapy of pulmonary fibrosis," Dissertation, University of Rochester, 2008.

Hughes, et al., "The synthetic triterpenoid CDDO-Im inhibits fatty acid synthase expression and has antiproliferative and proapoptotic effects in human liposarcoma cells," Cancer Investigation, 26:118-127, 2008.

Hyer, et al., "Apoptotic activity and mechanism of 2-cyano-3,12-dioxoolean-1,9-dien-28-oic acid and related synthetic triterpenoids in prostate cancer," *Cancer Res.*, 68:2927-2933, 2008.

Liu, et al., "Coordinate regulation of enzyme markers for inflammation and for protection against oxidants and electrophiles," *Proc. Natl. Acad. Sci.*, 105(41):15926-15931, 2008.

Andrew E. Place, "Pre-clincial evaluation of the novel synthetic triterpenoid CDDO-Imidazolide," Thesis, Dartmouth College, May 5, 2004.

Riccioni, et al., "Resistance of acute myeloid leukemic cells to the triterpenoid CDDO-Imidazolide is associated with low caspase-8 and FADD levels," *Leukemia Research*, 32:1244-1258, 2008.

Samudio, et al., "Inhibition of mitochondrial metabolism by methyl-2-cyano-3,12-dioxoolean-1,9-diene-28-oate induces apoptotic or autophagic cell death in chronic myelogenous leukemia cells," *Mol. Cancer Ther.*, 7(5):1130-1139, 2008.

Subba Rao, et al., "Chemical modifications of natural triterpenes—glycyrrhetinic and boswellic acids: evaluation of their biological activity," *Tetrahedron*, 64(51):11541-11548, 2008.

Sun, et al., "Therapeutic potential of synthetic tritcrpenoids in neuroblastoma," *Cancer Biology & Therapy*, 7(5):720-722, 2008.

To, et al., "The synthetic triterpenoid 2-cyano-3,12-dioxooleana-1,9-dien-28-oic acid-imidazolide alters transforming growth factor β-dependent signaling and cell migration by affecting the cytoskeleton and the polarity complex," *J. Biol. Chem.*, 283:11700-11713, 2008.

Venè, et al., "Glycogen synthase kinase 3β regulates cell death induced by synthetic triterpenoids," *Cancer Res.*, 68:6987-6996, 2008.

Wang, "Differentiating and anti-inflammatory activities of the triterpenoid, CDDO," Thesis, Dartmouth College, May 4, 2001.

(56) References Cited

OTHER PUBLICATIONS

Wen, et al., "Naturally occurring pentacyclic triterpenes as inhibitors of glycogen phosphorylase: synthesis, structure-activity relationships, and X-ray crystallographic studies," *J. Med. Chem.*, 51:3540-3554, 2008.
Xu, et al., "Inhibition of the signal transducer and activator of transcription-3 (STAT3) signaling pathway by 4-oxo-1-phenyl-1,4-dihydroquinoline-3-carboxylic acid esters," *J. Med. Chem.*, 51:4115-4121, 2008.
Zou, et al., "c-Flip downregulation contributes to apoptosis induction by the novel synthetic triterpenoid methyl-2-cyano-3,12-dioxooleana-1,9-dien-28-oate (CDDO-Me) in human lung cancer cells," *Cancer Biology & Therapy*, 6(10):1614-1620, 2007.
Zou, et al., "Coupling of endoplasmic reticulum stress to CDDO-Me-induced up-regulation of death receptor 5 via a CHOP-dependent mechanism involving JNK activation," *Cancer Res.*, 68:7484-7492, 2008.
"CDDO in treating patients with metastatic or unresectable solid tumors or lymphoma," http://www.clinicaltrials.gov/ct2/show/NCT00352040?term=CDDO&rank=1, Dec. 14, 2008.
"Phase IIa trail to determine the effects of bardoxolone methyl on renal function in patients with diabetic nephropathy," http://www.clinicaltrials.gov/ct2/show/NCT00664027?term=rta&rank=10, Dec. 14, 2000.
"RTA 402 in advanced solid tumors or lymphoid malignancies," http://www.clinicaltrials.gov/ct2/show/NCT00508807?term=rta&rank=2&show_desc=Y, Dec. 14, 2008.
"RTA 402, Therapeutic Properties I", slides/handouts presented by Reata Pharmaceuticals, Inc. at private partnering meetings at BioSquare 2006 conference, Mar. 8-10, 2006, Geneva, Switzerland.
"RTA 402, Therapeutic Properties II", slides/handouts presented by Reata Pharmaceuticals, Inc. at private partnering meetings at BIO 2006 conference, Apr. 9-12, 2006, Chicago, Illinois.
"RTA 402, Therapeutic Properties III", slides presented by Reata Pharmaceuticals, Inc. as a podium presentation at BIO 2006 conference, Apr. 9-12, 2006, Chicago, Illinois.
"RTA 402, Therapeutic Properties IV", slides/handouts presented by Reata Pharmaceuticals, Inc. at private partnering meetings at BioPartnering Europe 2006 conference, Oct. 8-10, 2006, London, England.
"RTA 402, Therapeutic Properties IX", slides/handouts presented by Reata Pharmaceuticals, Inc. at a private partnering meeting at BIO Europe 2007 conference, Nov. 12-14, 2007, Hamburg, Germany.
"RTA 402, Therapeutic Properties V", slides/handouts presented by Reata Pharmaceuticals, Inc. at private partnering meetings at BIO 2007 conference, May 6-9, 2007, Boston Massachusetts.
"RTA 402, Therapeutic Properties VI", slides/handouts presented by Reata Pharmaceuticals, Inc. at private partnering meetings at BIO 2007 conference, May 6-9, 2007, Boston, Massachusetts.
"RTA 402, Therapeutic Properties VII", slides presented by Reata Pharmaceuticals, Inc. as a podium presentation at BIO 2007 conference, May 6-9, 2007, Boston, Massachusetts.
"RTA 402, Therapeutic Properties VIII", slides/handouts presented by Reata Pharmaceuticals, Inc. at private partnering meetings at BIO Europe 2007 conference, Nov. 12-14, 2007, Hamburg, Germany.
"Study to assess the safety, tolerability, and pharmacodynamics of RTA 402 in patients with hepatic dysfunction," http://www.clinicaltrials.gov/ct2/show/NCT00550849?term=rta&rank=4, Dec. 14, 2008.
Ahmad et al., "Triterpenoid CDDO-Me blocks the NF-kappaB pathway by direct inhibition of IKKbeta on Cys-179," *J. Biol. Chem.*, 281:35764-35769, 2006.
Ahmad et al., "Triterpenoid CDDO-methyl ester inhibits the Janus-activated kinase-1 (JAK1)àsignal transducer and activator of transcription-3 (STAT3) pathway by direct inhibition of JAK1 and STAT3," *Cancer Res.*, 68 (8): 2920-2926, 2008.
Akiyama et al., "Cell mediators of inflammation in the Alzheimer disease brain," *Alzheimer Dis. Assoc. Disord.*, 14 (1): S47-S53, 2000.
Albini and Sporn, "Opinion: the tumour microenvironment as a target for chemoprevention," *Nature Reviews Cancer*, 7: 139-147, 2007.
Andreef et al., "PPARgamma nuclear resceptor as a novel molecular target in leukemias," 2002 Keystone Symposia, Abstract 501:149, 2002.
Ballesta-Acosta et al., "A new 24-nor-oleanane triterpenoid from Salvia carduacea," *J. Nat. Prod.*, 65(10): 1513-1515, 2002.
Bore et al., "The anti-inflammatory triterpenoid methyl 2-cyano-3, 12-dioxoolean 1,9(11)-dien-28-oate methanol solvate hydrate," *Acta Crystallorg C.*, 58(Pt 3):o199-o200, 2002.
Bowden et al, "Constituents of the fruit of pseudopanax arboretum (Araliaceae)," *Australian Journal of Chemistry*, 28(1): 91-107, 1975.
Brookes et al., "The triterpenoid 2-cyano-3,12-dioxooleana-1,9-dien-28-oic acid and its derivatives elicit human lymphoid cell apoptosis through a novel pathway involving the unregulated mitochondrial permeability transition pore," *Cancer Res.*, 67:1793-1802, 2007.
Buchanan et al., "The conversion of turraeanthin and turraeanthin A into simple melaiacins by a route involving an oxidative rearrangement of probable biogenetic importance," *J Chem. Soc C*, 17:2280-2284, 1970.
Chauhan et al., "The bortezomib/proteasome inhibitor PS-341 and triterpenoid CDDO-Im induce synergistic anti-multiple myeloma (MM) activity and overcome bortezomib resistance," *Blood*, 103:3158-3166, 2004.
Chintharlapalli et al., "2-Cyano-3,12-dioxoolean-1,9-dien-28-oic acid and related compounds inhibit growth of colon cancer cells through peroxisome proliferator-activated receptor gamma-dependent and -independent pathways," *Mol. Pharmacol.*, 68:119-128, 2005.
Chintharlapalli et al., "2-Cyano-1up-1-en-3-oxo-20-oic acid, a cyano derivative of betulinic acid, activates peroxisome proliferator-activated receptor [gamma] in colon and pancreatic cancer cells.," *Carcinogenesis*, 28 (11): 2337-2346, 2007.
Chintharlapalli et al., "Structure-dependent activity of glycyrrhetinic acid derivatives as peroxisome proliferator-activated receptor {gamma} agonists in colon cancer cells," Molecular *Cancer Therapeutics*, 6 (5): 1588-1598, 2007.
ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Jul. 6, 2009.
ClinicalTrials.gov study record NCT 00508807, "RTA 402 in advanced solid tumors or lymphoid malignancies conditions: lymphoid malignancies; solid tumors," update of Oct. 5, 2010.
ClinicalTrials.gov study record NCT 00529113, "Study with gemcitabine and RTA 402 for patients with unresectable pancreatic cancer," update of Dec. 1, 2010.
ClinicalTrials.gov study record NCT 00529438, "RTA 402 in patients with advanced solid tumors or lymphoid malignancies conditions: advanced solid tumors; lymphoid malignancies," update of Dec. 21, 2008.
ClinicalTrials.gov study record NCT 00535314, "Study of two dose levels of RTA 402 in patients with advanced malignant melanoma condition: malignant melanoma," update of Dec. 10, 2007.
ClinicalTrials.gov study record NCT 00550849, "Study to assess the safety, tolerability, and pharmacodynamics of RTA 402 in patients with hepatic dysfunction condition: liver disease," update of Nov. 6, 2007.
ClinicalTrials.gov study record NCT 00664027, "Phase IIa trial to determine the effects of bardoxolone methyl on renal function in patients with diabetic nephropathy condition: diabetic nephropathy," update of Feb. 18, 2009.
ClinicalTrials.gov study record NCT 00811889, "Trial to determine the effects of bardoxolone methyl on eGFR in patients with type 2 diabetes and chronic kidney disease conditions: chronic kidney disease; type 2 diabetes; diabetic nephropathy," update of Jan. 6, 2011.
ClinicalTrials.gov study record NCT 01053936, "Phase II Pharmacodynamic Trial to Determine the Effects of Bardoxolone Methyl on eGFR in Patients With Type 2 Diabetes and Chronic Kidney Disease," update of Aug. 27, 2010.
Cohen et al., "A general method for removal of a 4-methyl group from triterpenoids. Synthesis of 4beta-demethylglycyrrhetinic acid," *J Chem. Soc, Perkin Trans 1*, (19): 2076-2082, 1973.

(56) References Cited

OTHER PUBLICATIONS

Connolly et al., "Grandiofolione: a novel tetranortriterpenoid," *Chemical Communications*, 23:867-568, 1966.
Couch et al., "2-cyano-3,12-dioxooleana-1,9(11)-diene-28-oic acid disrupts microtubule polymerization: a possible mechanism contributing to apoptosis," *Molecular Pharmacology*, 69 (4): 1158-1165, 2006.
Couch et al., "Studies on the reactivity of CDDO, a promising new chemopreventive and chemotherapeutic agent: implications for a molecular mechanism of action," *Bioorganic and Medicinal Chemistry Letters*, 15 (9): 2215-2219, 2005.
Damsté et al., "A sedimentary tetrahydrophenanthrene derivative of tetrahymanol," *Tetrahedron Letters*, 40(20: 3949-3952, 1999.
De Mico et al., "A Versatile and Highly Selective Hypervalent Iodine (III)/2,2,6,6-Tetramethyl-1-piperidinyloxyl-Mediated Oxidation of Alcohols to Carbonyl Compounds," *J. Org. Chem.*, 62: 6974, 1997.
Dean et al., "Halogenolysis of methyl glycyrrhetate with lithium iodidedimethylformamide," *J. Chem. Soc.*, 6655-6659, 1965.
Deng and Snyder, "Preparation of a 24-Nor-1,4-dien-3-one triterpene derivative from betulin: a new route to 24-nortriterpene analogues," *J. of Organic Chemistry*, 67 (9): 2864-2873, 2002.
Dezube et al., "Interim results of a phase I trial with a novel orally administered synthetic triterpenoid RTA 402 (CDDO-Me) in patients with solid tumors and lymphoid malignancies," *J. Clin. Oncol.*, 2007 ASCO Annual Meeting Proceedings, 25(18S):14101, 2007.
Dinkova-Kostova et al., "Direct evidence that sulfhydryl groups of Keapl are the sensors regulating induction of phase 2 enzymes that protect against carcinogens and oxidants," *Proc. Natl. Acad. Sci.*, 99(18): 11908-11913, 2002.
Dinkova-Kostova et al., "Extremely potent triterpenoid inducers of the phase 2 response: correlations of protection against oxidant and inflammatory stress," *Proc. Natl. Acad. Sci.*, 102(12): 4584-4589, 2005.
Dirsch et al., "The triterpenoid quinonemethide pristimerin inhibits induction of inducible nitric oxide synthase in murine macrophages," *Eur J Pharmacol.*, 336(2-3): 211-217, 1997.
Dracinsky et al., "Preparation and Conformational Study of 19β,28-Epoxy-18α-olean-5-ene Derivatives," *Collection of Czechoslovak Chemical Communications*, 71(3): 387-410, 2006.
Dragnev et al., "Specific chemopreventive agents trigger proteasomal degradation of G1 cyclins: implications for combination therapy," *Clin. Cancer Research*, 10 (7): 2570-2577, 2004.
Duan et al., "Di- and triterpenoids from Triptergium hypoglaucum," *Phytochemistry*, 46(3): 535-543, 1997.
Duan et al., "Immunosuppressive terpenoids from extracts of tripterygium wilfordii," *Tetrahedron*, 57 (40): 8413-8424, 2001.
Elliot et al., "The triterpenoid CDDO inhibits expression of matrix metalloproteinase-1, matrix metalloproteinase-13 and Bcl-3 in primary human chondrocytes," *Arthritis Res. Ther.*, 5:R285-R291, 2003.
Elsawa et al., "Preferential Inhibition of Malignant Cell Growth by CDDO in Waldenstrom Macroglobulinemia," *Blood*, 108(11):2528, 2006.
Favaloro et al., "Design and synthesis of tricyclic compounds with enone functionalities in rings A and C: a novel class of highly active inhibitors of nitric oxide production in mouse macrophages," *J. Med. Chem.*, 45:4801-4805, 2002.
Finlay et al., "Novel A-ring cleaved analogs of oleanolic and ursolic acids which affect growth regulation in NRP.152 prostate cells," *Biorg. Med. Chem. Lett.*, 7(13): 1769-1772, 1997.
Finlay et al., "The Effect of A and C Ring Modification of Oleanolic and Ursolic Acid on the Inhibition of Nitric Oxide Formation in Mouse Macrophages," 213th American Chemical Society National Meeting, Abstract: 084, 1997.
Gao et al., "Synthetic triterpenoids inhibit growth and induce apoptosis in human glioblastoma and neuroblastoma cells through inhibition of prosurvival Akt, NF-κB and Notch1 signaling," J. *of Neuro-oncology*, 84 (2): 147-157, 2007.
Grant et al., "Boron trifluoride catalyzed rearrangements of novel expoxide derivatives of manool and manoyl oxide," *Australian Journal of Chemistry*, 46 (8): 1125-1145, 1993.
Grieco and Speake, "Synthetic Studies on Quassinoids: Total Synthesis and Biological Evaluation of (+)-Des-D-chaparrinone," *J. Org. Chem.*, 63:5929-5936, 1998.
Hail et al., "Evidence supporting a role for calcium in apoptosis induction by the synthetic triterpenoid 2-cyano-3,12-dioxooleana-1,9-dien-28-oic acid (CDDO)," *J. Biol. Chem.*, 279:11179-11187, 2004.
Han et al., "CDDO-Imidazolide inhibits growth and survival of c-Myc-induced mouse B cell and plasma cell neoplasms," *Molecular Cancer*, 5:22, 2006.
Hill et al., "Synthetical approaches to the pristimerin chromophore," *J. of the Chemical Society*, 361-375, 1965.
Hirota et al., "Total synthesis of (±)-amarolide, a quassinoid bitter principle," *J. Org. Chem.*, 56:1119-1127, 1991.
Hirota et al., "Suppression of tumor promoter-induced inflammation of mouse ear by ursolic acid and 4,4-dimethycholestane derivatives" *Agric. Biol. Chem.*, 54:1073-1075, 1990.
Honda et al., "A novel dicyanotriterpenoid, 2-cyano-3,12-dioxooleana-1,9(11)-dien-28-onitrile, active at picomolar concentrations for inhibition of nitric oxide production," *Bioorg. Med. Chem. Lett.*, 12:1027-1030, 2002.
Honda et al., "An efficient synthesis of tricyclic compounds (+)—(4aβ, 8aβ, 10aα)—1,2,3,4,4a,6,7,8,8a,9,1-,10a-Dodecahydro-1,1,4a-Trimethyl-2-Oxophenanthrene-8a-Carboxolic acid, its methyl ester, and (+)-(44,8aβ,10aα)-3,4,4a,6,7,8,8a,9,10,10a-DecahydRO-8a, hydroxymethyl-1,1,4a-trimethylphenanthren-2(1H)-one," *Org. Prep. Proced. Int.*, 37(6): 546-550, 2005.
Honda et al., "Design and synthesis of 23, 24-dinoroleanolic acid derivatives, novel triterpenoid—steroid hybrid molecules," *J. Org. Chem.*, 63:4846-4849, 1998.
Honda et al., "Design and synthesis of 2-cyano-3,12-dioxoolean-1,9-dien-28-oic acid, a novel and highly active inhibitor of nitric oxide production in mouse macrophages," *Bioorg Med Chem Lett.*, 8(19):2711-2714, 1998.
Honda et al., "Design, synthesis, and biological evaluation of biotin conjugates of 2-cyano-3,12-dioxooleana-1,9(11)-dien-28-oic acid for the isolation of the protein targets," *J. Med. Chem.*, 47 (20): 4923-4932, 2004.
Honda et al., "Efficient synthesis of (−)- and (+)-tricyclic compounds with enome functionalities in rings A and C. A novel class of orally active anti-inflammatory and cancer chemopreventive agents," *Org Biomol Chem.*, 1:4384-4391, 2003.
Honda et al., "New enone derivatives of oleanolic acid and ursolic acid as inhibitors of nitric oxide productiCon in mouse macrophages," *Bioorg. Med. Chem. Lett.*, 7:1623-1628, 1997.
Honda et al., "New synthetic oleanane and ursane triterpenoids as inhibitors of nitric oxide production in mouse macrophages," The Fifth Chemical Congress of North America, Cancun, Mexico, Abstract 552 and slides for oral presentation, Nov. 1997.
Honda et al., "Novel synthetic oleanane and ursane triterpenoids with various enone functionalities in ring A as inhibitors of nitric oxide production in mouse macrophages," *J. Med. Chem.*, 43:1866-1877, 2000.
Honda et al., "Novel synthetic oleanane triterpenoids: a series of highly active inhibitors of nitric oxide production in mouse macrophages," *Bioorg Med Chem Lett*, 9(24):3429-3434, 1999.
Honda et al., "Novel tricyclic compounds having acetylene groups at C-8a and cyano enones in rings A and C: highly potent anti-inflammatory and cytoprotective agents," *J. Med. Chem.*, 50:1731-1734, 2007.
Honda et al., "Revision and confirmation of the regiochemistry of isoxazoles derived from methyl oleanonate and lanost-8-en-3-one. Synthesis of a new lanostane triterpenoid with a cyano-enone functionality in ring A," *J. Org. Chem.*, 68:4991-4993, 2003.
Honda et al., "Synthesis of (±)-3,3-ethylenedioxy-14a-hydroxy-5-picrasene-11,16-dione, a 14aH-picrasane derivative," *Chem. Lett.*, 299-302, 1981.
Honda et al., "Synthesis of a novel dicyano abietane analogue: a potential antiinflammatory agent," *J. Org. Chem.*, 71:3314-3316, 2006.

(56) References Cited

OTHER PUBLICATIONS

Honda et al., "Synthetic oleanane and ursane triterpenoids with modified rings A and C: A series of highly active inhibitors of nitric oxide production in mouse macrophages," *J. Med. Chem.*, 43:4233-4246, 2000.

Hong et al., "Phase I trial of a novel oral NF-κB/pSTAT3 inhibitor RTA-402 in patients with solid tumors and lymphoid malignancies," 44th Annual Meeting of the American Society of Clinical Oncology, 2008.

Hyer et al., "Synthetic triterpenoids cooperate with tumor necrosis factor-related apoptosis-inducing ligand to induce apoptosis of breast cancer cells," *Cancer Res.*, 65:4799-4808, 2005.

Ikeda et al., "Induction of redox imbalance and apoptosis in multiple myeloma cells by the novel triterpenoid 2-cyano-3,12-dioxoolean-1,9-dien-28-oic acid," *Mol. Cancer Ther.*, 3:39-45, 2004.

Ikeda et al., "The novel triterpenoid CDDO and its derivatives induce apoptosis by disruption of intracellular redox balance," *Cancer Res.*, 63:5551-5558, 2003.

Ikeda et al., "Triterpenoid CDDO-Im downregulates PML/RAR αexpression in acute promyelocytic leukemia cell," *Cell Death and Differentiation*, 12 (5): 523-531, 2005.

Inoue et al., "CDDO induces apoptosis via the intrinsic pathway in lymphoid cells," *Leukemia*, 18 (5): 948-952, 2004.

Ito et al., "Involvement of caspase-8 in the induction of osteosarcoma cell apoptosis by the novel triterpenoid CDDO," 47th Annual Meeting, Orthopaedic Research Society, Feb. 25-28, 2001, San Francisco, California, p. 0863, Poster Session, 2001.

Ito et al., "The novel triterpenoid 2-cyano-3, 12-dioxoolean-1,9-dien-28-oic acid induces apoptosis of human myeloid leukemia cells by a caspase-8-dependent mechanism," *Cell Growth & Differentiation*, 11(5):261-267, 2000.

Ito et al., "The novel triterpenoid CDDO induces apoptosis and differentiation of human osteosarcoma cells by a caspase-8 dependent mechanism," *Mol. Pharmacol.*, 59:1094-1099, 2001.

Jang et al., "24-nor-ursane type triterpenoids from the stems of Rumex japonicus," *Chem. Pharm Bull* (Tokyo), 53(12): 1594-1596, 2005.

Ji et al., "The synthetic triterpenoid CDDO-imidazolide induces monocytic differentiation by activating the Smad and ERK signaling pathways in HL60 leukemia cells," *Molecular Cancer Therapeutics*, 5 (6): 1452-1458, 2006.

Johansen et al., "Pharmacology and preclinical pharmacokinetics of the triterpenoid CDDO methyl ester," *Proc. Amer. Assoc. Cancer Res.*, 44:1728, 2003.

Kahne and Collum, "Kinetic cyanations of ketone enolates," Tetrahedron Lett., 22:5011-5014, 1981.

Kamal et al., "23-oxoisopristimerin III: an new natural phenolic (9→8)-24-nor-D:A-friedo-oleanane triterpene," *Tetrahedron Letters*, 24(27):2799-2800, 1983.

Kamal et al., "Structures of two new phenolic 24-nor-D: A-friedoleananes related to zeylasterone: a partial synthesis of trimethylzeylasterone," *Tetrahetron Letters*, 24(19): 2025-2028, 1983.

Kamal et al., "The structure of zeylasterone, the first of a new series of phenolic 24-nor-D: A friedo-oleanane triterpenes," *Tetrahedron Letters*, 21(49): 4749-4752, 1980.

Kansanen et al., "Regulation of Nrf2-dependent gene expression by 15-deoxy-Delta12,14-prostaglandin J2," *Free Radic. Biol. Med.*, 47(9):1310-7, 2009.

Khalid et al., "Isolation and characterization of pristimerin as the antiplasmodial and antileishmanial agent of maytenus senegalensis (Lam.) Exell," *ARKIVOC*, 129-134, 2007.

Kim et al., "An inducible pathway for degradation of FLIP protein sensitizes tumor cells to TRAIL-induced apoptosis," *J. of Biological Chemistry*, 277 (25): 22320-22329, 2002.

Kim et al., "Capasase-3 activation is involved in apoptosis induced by a synthetic triterpenoid in Non-small cell lung cancer (NSCLC) cells," *Proc. Amer. Assoc. Cancer Res.*, 41:770, Abstract #4894, 2000.

Kim et al., "Identification of a novel synthetic triterpenoid, methyl-2-cyano-3,12-dioxooleana-1,9-dien-28-oate, that potently induces caspace-mediated apoptosis in human lung cancer cells," *Molecular Cancer Therapeutics*, 1:177-184, 2002.

Kincl et al., "Pituitary gonadotropin inhibitory action of netral steroids," *Acta. Endocrinologica*, 46: 300-306, 1964.

Kircher, "Triterpenes, in organ pipe cactus," Phytochemistry, 19:2707-2712, 1980; Database CAPLUS on STN AN:1981:550946.

Klyne et al., "The molecular rotations of polycyclic compounds. III. Polycyclic alcohols and their derivatives," *J Chem Soc.*, 1979-1988, 1954.

Kobayashi et al., "The antioxidant defense system Keapl-Nrf2 comprises a multiple sensing mechanism for responding to a wide range of chemical compounds," *Mol. Cell Biol.*, 29(2):493-502, 2009.

Kolak et al., "Antioxidant and anticholinesterase constituents of Salvia poculata," *Turkish Journal of Chemistry*, 33(6): 813-823, 2009.

Konopleva et al., "Activation of nuclear transcription factor PPARgamma by the novel triterpenoid CDDO as targeted therapy in breast cancer," 2002 Keystone Symposium, Abstract No. 539, 2002.

Konopleva et al., "Mechanisms and Activity of PPARgamma-Active Triterpenoids CDDO and CDDO-Me in Leukemias," *Blood*, 106:2460, 2005.

Konopleva et al., "Novel synthetic triterpenoid CDDO-Me: potent antiproliferative, proapoptotic and differentiating agent in AML," *Blood*, 96(11), Part 1: 121A, abstract # 522, 2000.

Konopleva et al., "Novel synthetic triterpenoid, CDDO, and its methyl ester: Potent antiproliferative, proapoptotic and differentiating agents in AML," *Blood*, 94(Suppl 1):479a, Abstract #2140, 1999.

Konopleva et al., "Novel triterpenoid CDDO-Me is a potent inducer of apoptosis and differentiation in acute myelogenous leukemia," *Blood*, 99(1):326-335, 2002.

Konopleva et al., "Peroxisome proliferator-activated receptor gamma and retinoid X receptor ligands are potent inducers of differentiation and apoptosis in leukemias," *Mol. Cancer Ther.*, 3:1249-1262, 2004.

Konopleva el al., "PPARg nuclear receptor as a novel therapeutic target in AML," *Blood*, 96(11):460a, Abstract #1982, 2000.

Konopleva et al., "PPARg nuclear receptor as a novel therapeutic target in AML," Proc. of the AACR, 42, Abstract #4458, 2001.

Konopleva et al., "PPARgamma Ligand CDDO Induces Apoptosis in Leukemias Via Multiple Apoptosis Pathways," Abstracts of the 44th Annual Meeting of the American Society of Hematology, Abstract No. 2209, 2002.

Konopleva et al., "PPARgamma Ligands Are Potent Inducers of Apoptosis in Leukemias and Lymphomas," American Society of Hematology 43rd Annual Meeting and Exposition, Abstract No. 501, 2001.

Konopleva et al., "PPARgamma Nuclear Receptor as a Novel Molecular Target in Leukemia Therapy," *Proc. Amer. Assoc. Cancer Res.*, 43:4730, 2002.

Konopleva et al., "Suppression of ERK Activation is Required for Triterpenoid Methyl-CDDO-Induced Apoptosis in AML," *Blood*, 102(11):1404, 2003.

Konopleva et al., "Synthetic triterpenoid 2-cyano-3,12-dioxooleana-1,9-dien-28-oic acid induces growth arrest in HER2-overexpressing breast cancer cells," *Mol. Cancer Ther.*, 5:317-328, 2006.

Konopleva et al., "Synthetic triterpenoid CDDO as a novel therapy for resistant breast cancer," *Proc. Amer. Assoc. Cancer Res.*, 44:2726, 2003.

Konopleva et al., "The novel triterpenoid CDDO-Me suppresses MAPK pathways and promotes p38 activation in acute myeloid leukemia cells," *Leukemia*, 19:1350-1354, 2005.

Konopleva et al., "The synthetic triterpenoid 2-cyano-3,12-dioxooleana-1,9-dien-28-oic acid induces caspase-dependent and -independent apoptosis in acute myelogenous leukemia," *Cancer Res.*, 64:7927-7935, 2004.

Korovin and Tkachev, "Synthesis of quinoxalines fused with triterpenes, ursolic acid and betulin derivatives," *Russian Chemical Bulletin*, (*Translation of* Izvestiya Akademii Nauk, Seriya Khimicheskaya), 20 (2): 304-310, 2001.

(56) References Cited

OTHER PUBLICATIONS

Koschmieder et al. "CDDO induces granulocytic differentiation of myeloid leukemic blasts through translational up-regulation of p42 CCAAT enhancer—binding protein alpha," *Blood*, 110 (10): 3695-3705, 2007.
Kress et al., "Triterpenoids display single agent activity in a mouse model of CLL/SBL," *Blood*, 108(11):2530, 2006.
Kress et al., "Triterpenoids display single agent anti-tumor activity in a transgenic mouse model of chronic lymphocytic leukemia and small B cell lymphoma," *PLOS ONE*, 6(e559):1-11, 2007.
Kurinna et al., "The novel triterpenoid CDDO-Me promotes apoptosis in Gleevec-resistant chronic myeloid leukemia cells by caspase-independent mechanisms," *Proc. Amer. Assoc. Cancer Res.*, 46:2240, 2005.
Kutschabsky et al., "Natural products from Vietnamese plants. Part XV. Molecular and crystal structure of a new 24-nor triperpenoid carboxylic acid from Acanthopanax trifoliatus," *Croatica Chemica Acta*, 58(4): 427-434, 1986.
Lapillonne et al., "Activation of peroxisome proliferator-activated receptor gamma by a novel synthetic triterpenoid 2-cyano-3,12-dioxooleana-1,9-dien-28-oic acid induces growth arrest and apoptosis in breast cancer cells," *Cancer Res.*, 63:5926-5939, 2003.
Larock et at, "Carbocycle synthesis via carbopalladation of nitriles," *J. of the American Chemical Society*, 121 (13): 3238-3239, 1999.
Lavie et al., "Studies on epoxides. IV. Rearrangements in triterpenoids," *Tetrahedron Letters*, 17: 2097-2100, 1968.
Lavie et al., "Tetranortriterpenoids from Melia azadirachta," *Chemical Communications*, 6:278-280, 1967.
Li et al., "Terpenoids from tripterygium wilfordii," *Phytochemistry*, 45(4): 791-796, 1997.
Liby et al., "A novel acetylenic tricyclic bis-(cyano enone) potently induces phase 2 cytoprotective pathways and blocks liver carcinogenesis induced by aflatoxin," *Cancer Res.*, 68:6727-6733, 2008.
Liby et al., "Novel semisynthetic analogues of betulinic acid with diverse cytoprotective, antiproliferative, and proapoptotic activities," *Mol. Cancer. Ther.*, 6(7): 2113-2119, 2007.
Liby et al., "The rexinoid LG100268 and the synthetic triterpenoid CDDO-methyl amide are more potent than erlotinib for prevention of mouse lung carcinogenesis," *Mol. Cancer Ther.*, 7:1251-1257, 2008.
Liby et al., "The synthetic triterpenoid CDDO-Imidazolide suppresses STAT phosphorylation and induces apoptosis in myeloma and lung cancer cells," *Clinical Cancer Research*, 12 (14 Part 1): 4288-4293, 2006.
Liby et al., "The synthetic triterpenoids CDDO-Methyl ester and CDDO-ethyl amide prevent lung cancer induced by vinyl carbamate in A/J mice," *Cancer Research*, 67 (6): 1-7, 2007.
Liby et al., "The synthetic triterpenoids, CDDO and CDDO-imidazolide, are potent inducers of heme oxygenase-1 and Nrf2/ARE signaling," *Cancer Res.*, 65:4789-4798, 2005.
Liby et al., "Triterpenoids and rexinoids as multifunctional agents for the prevention and treatment of cancer," *Nat. Rev. Cancer*, 7 (5): 357-369, 2007.
Ling et al., "The novel triterpenoid C-28 methyl ester of 2-cyano-3, 12-dioxoolen-1, 9-dien-28-oic acid inhibits metastatic murine breast tumor growth through inactivation of STAT3 signaling," *Cancer Res.*, 67:4210-4218, 2007.
Ling et al., "The novel triterpenoid CDDO-Me inhibits metastatic murine breast tumor through inhibition of Stat3 signaling," 2007 AACR Annual Meeting, Abstract No. 301, 2007.
Liu et al,. "New lupane-type triterpenoid saponins from leaves of Oplopanax horridus (Devil's Club)," *Nat Prod Comm.*, 5(7): 1019-1022, 2010.
Liu et al., "Chemical constituents from root of rubus irenaeus," *Zhongcaoyao*, 34 (5): 394-396, 2003.
Marples and Spilling, "Ene reactions of unsaturated acyloins," *Tetrahedron Letters*, 26 (52): 6515-6518, 1985.
Marples and Spilling, "Facile intramolecular ene reactions of steroidal unsaturated acyloins," *Tetrahedron*, 48 (19): 4017-4026, 1992.
Melichar et al., "Growth-inhibitory effect of a novel synthetic triterpenoid, 2-cyano-3,12-dioxoolean-1,9-dien-28-oic acid, on ovarian carcinoma cell lines not dependent on peroxisome proliferator-activated receptor-gamma expression," *Gynecologic Oncology*, 93:149-154, 2004.
Mencherini et al., "Triterpenoid constituents from the roots of the *Paeonia rockii* ssp. *rockii*," *J Nat Prod.*, 74(10): 2116-2121, 2011.
Minns et al., "A novel triterpenoid induces transforming growth factor beta production by intraepithelial lymphocytes to prevent ileitis," *Gastroenterology*, 127:119-126, 2004.
Mix et al., "A synthetic triterpenoid selectively inhibits the induction of matrix metalloproteinases 1 and 13 by inflammmatory cytokines," *Arthritis Rheum.*, 44:1096-1104, 2001.
Mix et al., "Peroxisome proliferator-activated receptor-gamma-independent repression of collagenase gene expression by 2-cyano-3,12-dioxooleana-1,9-dien-28-oic acid and prostaglandin 15-deoxy-delta(12,14) J2: a role for Smad signaling," *Mol. Pharmacol.*, 65(2): 309-318, 2004.
Murphy et al., "Immunomodulatory Effects of the Triterpcnoid CDDO after Allogeneic Bone Marrow Transplantation in Mice: Reduction of Acute Graft-Versus-Host Disease Lethality," *Blood*, 106:1316, 2005.
Murray and Zweifel, "Preparation of Phenyl Cyanate and Its Utilization for the Synthesis of α, β-Unsaturated Nitriles," *Synthesis*, 150-151, 1980.
Muzart, "Synthesis of unsaturated carbonyl compounds via a chromium-mediated allylic oxidation by 70% tert.butylhydroperoxide," *Tetrahedron Lett.*, 28:4665-4668, 1987.
Na and Surh et al., "Transcriptional regulation via cysteine thiol modification: a novel molecular strategy for chemoprevention and cytoprotection," *Mol. Carcinog.*,45 (6): 368-380, 2006.
Nair et al., "Triterpenes. XLVII. Oxidation rates of triterpenoid secondary alcohols with chromic acid," *Collection of Czechoslovak Chemical Communications*, 41(3): 770-779, 1976.
Nanduri et al., "Biological investigation and structure-activity relationship studies on azadirone from azadirachta indica A. juss," *Bioorganic and Medicinal Chemistry*, 13 (22): 4111-4115, 2003.
Nelson et al., "Oxidative demethylation at C-4 of a steroid via nitroxide photolysis," *J. of the American Chemical Society*, 97 (3): 648-649, 1975.
Niikura et al., "The effects of synthetic triterpenoids on superficial zone protein synthesis in articular chondrocytes," Abstract, *Orthopedic Research Society*, San Diego, 2007.
Niikura et al., "The effects of synthetic triterpenoids on szp synthesis in articular chondrocytes," Abstract P197, *Osteoarthritis and Cartilage*, 14(Suppl B):S112-S113, 2006.
Nishimura et al., "Activity-guided isolation of triterpenoid acyl CoA cholesteryl acyl transferase (ACAT) inhibitors from Ilex kudincha," *J Nat Prod.*, 62(7): 1061-1064, 1999.
Nishino et al., "Inhibition of the tumor-promoting action of 12-O tetradecanoylphorbol-13-acetate by some oleanane-type triterpenoid compounds," *Cancer Res.*, 48:5210-5215, 1988.
Osburn et al., "Genetic of pharmacologic amplification of Nrf2 signaling inhibits acute inflammatory liver injury in mice," *Toxicological Sciences*, 104:218-227, 2008.
Overnell and Whitehurts, "Reactions of steroid A-ring lactones with Grignard reagents," *J. of the Chemical Society* [*Section*] *C: Organic*, 2: 378-384, 1971.
Pappas et al., "Photoisomerization of phenalen-1-one oxide. New course of light-induced alpha beta-epoxy ketone rearrangement," *J. of the American Chemical Society*, 92 (19): 5797-5798, 1970.
Peakmen et al, "Characterization of 24-nor-triterpenoids occurring in sediments and crude oils by comparison with synthesized standards," *Tetrahedron*, 47(23): 3779-3786, 1991.
Pedersen et al., "The triterpenoid CDDO induces apoptosis in refractory CLL B cells," *Blood*, 100:2965-2972, 2002.
Place et al., "The novel synthetic triterpenoid, CDDO-imidazolide, inhibits inflammatory response and tumor growth in vivo," *Clin. Cancer Res.*, 9:2798-2806, 2003.
Rasmusson et al., "Azasteroids: structure-activity relationships for inhibition of 5 alpha-reductase and of androgen receptor binding," *J. Med. Chem.*, 29 (11): 2298-2315, 1986.

(56) References Cited

OTHER PUBLICATIONS

Ray et al., "The novel triterpenoid 2-cyano-3,12-dioxooleana-1,9-dien-28-oic acid (CDDO) induces apoptosis of human diffuse large B-cell lymphoma cells through a peroxisome proliferator-activated receptor gamma-independent pathway," *Exp. Hematology*, 34:1201-1210, 2006.
Ribo et al., "Synthesis of methyl 1, 11-dioxooleanan-2, 12-dien-30-oate and its 24-nor derivative," *Afinidad*, 38(373): 197-200, 1981.
Rossi et al., "Anti-inflammatory cyclopentenone prostaglandins are direct inhibitors of IkappaB kinase," *Nature*, 403:103-108, 2000.
Rouquette et al., "A ring-D functionalized nor-triterpenoid of the lupane series as a key intermediate in the formation of widespread hydrocarbon derivatives of higher plant origin in petroleum," *Organic Geochemistry*, 36(9): 1227-1233, 2005.
Ruvolo et al., "The novel triterpenoid methyl-CDDO inhibits Bc12 phosphorylation and potently kolls U937 cells," *Blood*, 94(10), Suppl. 1, Part 1: 280A, abstract #1251, 1999.
Samudio et al., "2, cyano-3,12 dioxoolean-1,9 diene-28-imidazolide induces apoptosis in pancreatic cancer via redox-dependent cytoplasmic stress," *Proc. Amer. Assoc. Cancer Res.*, 46: Abstract No. 5899, 2005.
Samudio et al., "2-Cyano-3,12-dioxooleana-1,9-dien-28-imidazolide (CDDO-Im) directly targets mitochondrial glutathione to induce apoptosis in pancreatic cancer," *J. Biol. Chem.*, 280:36273-36282, 2005.
Samudio et al., "A novel mechanism of action of methyl-2-cyano-3,12 dioxoolean-1,9 diene-28-oate (CDDO-Me): Direct permeabilization of the inner mitochondrial membrane to inhibit electron transport and induce apoptosis," *Proc. Am. Assoc. Cancer Res.*, 47, Abstract 4693, 2006.
Samudio et al., "A novel mechanism of action of methyl-2-cyano-3,12 dioxoolean-1,9 diene-28-oate: direct permeabilization of the inner mitochondrial membrane to inhibit electron transport and induce apoptosis," *Mol. Pharmacol.*, 69:1182-1193, 2006.
Samudio et al., "The novel triterpenoid CDDOme potently synergizes with inhibition of bcl-2 function to induce apoptosis in AML via disruption of intracellular redox homeostasis," *Proc. Amer. Assoc. Cancer Res.*, 46: Abstract No. 4955, 2005.
Satoh et al., "Activation of the Keap1/Nrf2 pathway for neuroprotection by electrophillic phase II inducers," *PNAS*, 103 (3): 768-773, 2006.
Scholz et al., "Sensitive and specific methods for the determination of CDDO methyl ester in mouse, rat, dog, monkey, and human plasma by LC-tandem mass spectrometry," *Proc. Amer. Assoc. Cancer Res.*, 4: Abstract No. 6321, 2003.
Sharpless et al., "Electrophilic and nucleophilic organoselenium reagents. New routes to alpha, beta-unsaturated carbonyl compounds," *J. Am. Chem. Soc.*, 95:6137, 1973.
Shin et al., "Inhibitory roles of NRF2 and an oleanolic triterpenoid on adipocyte differentiation and obesity," dissertation submitted to John Hopkins University in conformity with the requirements for the degree of Doctor of Philosophy, Mar. 2009.
Shin et al., "NRF2 modulates aryl hydrocarbon receptor signaling: influence on adipogenesis," *Molecular and Cellular Biology*, 27 (20): 7188-7197, 2007.
Shin et al., "Role of Nrf2 in prevention of high-fat diet-induced obesity by synthetic triterpenoid CDDO-imidazolidem" *Eur. J. Pharmacol.*, 620(1-3):138-144, 2009.
Shishodia et al., "A synthetic triterpenoid, CDDO-Me, inhibits IkappaBalpha kinase and enhances apoptosis induced by TNF and chemotherapeutic agents through down-regulation of expression of nuclear factor kappaB-regulated gene products in human leukemic cells," *Clin Cancer Research*, 12(6):1828-1838, 2006.
Siddiqui et al., "Kanerin and 12, 13-dihydroursolic acid, two new pentacyclic triterpenes from the leaves of Nerium oleander," *J Nat Prod.*, 52(1): 57-62, 1989.
Simonsen et al., "Tetracyclic hydroxy acids," In the *Terpenes*, Cambridge University, Cambridge, 5:221-285, 1957.
Singh et al., "Anti-inflammatory activity of oleanolic acid in rats and mice," *J. Pharm.Pharmacol.*, 44:456-458, 1992.
Sporn and Roberts, "Peptide growth factors and inflammation, tissue repair, and cancer," *J. Clin. Invest.*, 78:329-332, 1986.
Sporn et al., "Prospects for prevention and treatment of cancer with selective PPARg modulators (SPARMs)," *Trends in Molecular Medicine*, 7(9):395-400, 2001.
Stadheim et al., "The novel triterpenoid 2-cyano-3,12-dioxooleana-1,9-dien-28-oic acid (CDDO) potently enhances apoptosis induced by tumor necrosis factor in human leukemia cells," *J. Biol. Chem.*, 277:16448-16455, 2002.
Suh et al., "A novel synthetic oleanane triterpenoid, 2-cyano-3,12-dioxoolean-1,9-dien-28-oic acid (CDDO), induces cell differentiation in human myeloid leukemias," Proceedings of the American Association for Cancer Research Annual Meeting, 40:300, abstra.
Suh et al., "A novel synthetic oleanane triterpenoid, 2-cyano-3,12-dioxoolean-1,9-dien-28-oic acid, with potent differentiating, antiproliferative, and anti-inflammatory activity," *Cancer Res.*, 59(2):336-341, 1999.
Suh et al., "New triterpenoids as cancer preventive and anti-inflammatory agents," Proceedings of the American Association for Cancer Research, Abstract No. 1457, 38: 216, 1997.
Suh et al., "Novel triterpenoids suppress inducible nitric oxide synthase (iNOS) and inducible cyclooxygenase (COX-2) in mouse macrophages," *Cancer Res.*, 58:717-723, 1998.
Suh et al., "Novel triterpenoids suppress inducible nitric oxide synthase (iNOS) and inducible cyclooxygenase (COX-2)," Proceedings of the American Association for Cancer Research Annual Meeting, 39: Abstract No. 1821, 1998.
Suh et al., "Synthetic triterpenoids activate a pathway for apoptosis in AML cells involving downregulation of FLIP and sensitization to TRAIL," *Leukemia*, 17:2122-2129, 2003.
Suh et al., "Synthetic triterpenoids enhance transforming growth factor β/Smad signaling," *Cancer Res.*, 63:1371-1376, 2003.
Suh et al., "Triterpenoids CDDO and CDDO-Me Down-Regulate FLIP Expression and Sensitize AML Cells to Trail-Induced Apoptosis," American Society of Hematology 43rd Annual Meeting and Exposition, Abstract No. 498, 2001.
Sultana et al., "Phytochemical studies on Alstonia scholaris," *Zeitschrift für Naturforschung. B, A Journal of Chemical Sciences*, 65(2): 203-210, 2010.
Sun et al., "Structure-activity relationships of oleanan- and ursane-type triterpenoids," *Botanical Studies*, 47:339-368, 2006.
Sun et al., "The Synthetic Triterpenoid, CDDO, Suppresses Alloreactive T Cell Responses and Reduces Murine Early Acute Graft-versus-Host Disease Mortality," *Biology of Blood and Marrow Transplantation*, 13 (5): 521-529, 2007.
Tabe et al., "Chromatin-Mediated Transcriptional Activation with Novel Peroxisome Proliferator—Activated Receptor gamma(PPARgamma) Ligand 2-cyano-1,9-dien-28-oic Acid (CDDO) in Acute Promyelocytic Leukemia Cells," Abstracts of the 44th Annual Meeting of the American Society of Hematology, Abstract 2191, 2002.
Thimmulappa et al., "Nrf2 is a critical regulator of the innate immune response and survival during experimental sepsis," *J. Clinical Investigation*, 116 (4): 984-995, 2006.
Thimmulappa et al., "Nrf2-dependent protection from LPS induced inflammatory response and mortality by CDDO-imidazolide," *Biochem. Biophys. Res. Commun.*, 351:883-889, 2006.
Thimmulappa et al., "Preclinical evaluation of targeting the Nrf2 pathway by triterpenoids (CDDO-Im and CDDO-Me) for protection from LPS-induced inflammatory response and reactive oxygen species in human peripheral blood mononuclear cells and neutrophils," *Antioxidants and Redox Signalling*, 9:1-8, 2007.
Tran et al., "The synthetic triterpenoid CDDO-methyl ester modulates microglial activities, inhibits TNF production, and provides dopaminergic neuroprotection," *Journal of Neuroinflammation*, 5:1-14, 2008.
Tsao et al., "DRIP205 co-activator overexpression enhances PPARgamma-mediated differentiation of leukemia cells by CDDO," *Proc. Amer. Assoc. Cancer Res.*, 46: Abstract No. 1855, 2005.
Tsao et al., "Targeted Induction of Apoptosis in Leukemias by PPARgammma Ligation," American Society of Hematology 43rd Annual Meeting and Exposition, Abstract No. 2381, 2001.
Urban et al., "Influence of esterification and modification of A-ring in a group of lupane acids on their cytotoxicity ," *Bioorganic and Medicinal Chemistry*, 13 (19): 5527-5535, 2005.

(56) References Cited

OTHER PUBLICATIONS

Urban et al., "Synthesis of A-seco derivatives of betulinic acid with cytotoxic activity," *J. of Natural Products*, 67 (7): 1100-1105, 2004.
Uskoković et al., "D-Homosteroids. I. 3β-Hydroxy-17a,17a-dimethyl-D-homoandrostane-17-one and related compounds," *J. of the American Chemical Society*, 81: 4561-4566, 1959.
Vannini et al., "The synthetic oleanane triterpenoid, CDDO-methyl ester, is a potent antiangiogenic agent," *Molecular Cancer Therapeutics*, 6 (12 Part 1), 3139-3146, 2007.
Vilayur and Harris, "Emerging therapies for chronic kidney disease: what is their role?" *Nature Reviews*, 5: 375-383, 2009.
Vincenti et al., "The synthetic triterpenoid TP-222 inhibits RANKL induction of differentiation and MMP-9 gene expression in osteoclasts," Abstract 1385, American College of Rheumatology Annual Scientific Meeting, 2006.
Wada and Tanaka, "Synthetic lanostane-type triterpenoids as inhibitors of DNA topoisomerase 11," *Bioorganic and Medicinal Chemistry Letters*, 15 (12): 2966-2969, 2005.
Wang et al., "A novel synthetic triterpenoid, 2-cyano-3,12-dioxoolean-1,9-dien-28-oic acid (CDDO) induces adipocyte differentiation in 3T3-L1 cells," *Proceedings of the American Association for Cancer Research Annual Meeting*, 40:300, abstract # 1989, 1999.
Wang et al., "A synthetic triterpenoid, 2-cyano-3,12-dioxooleana-1,9-dien-28-oic acid (CDDO), is a ligand for the peroxisome proliferator-activated receptor g," *Mol. Endocrin.*, 14(10):1550-1556, 2000.
Wang et al., "Synthetic triterpenoid CDDO and its derivatives increase ceramides and are cytotoxic to pediatric acute lymphoblastic leukemia cell lines," *Proc. Am. Assoc. Cancer Res.*, 47: 4643, 2006.
Wen et al., "Pentacyclic triterpenes. Part 2: Synthesis and biological evaluation of maslinic acid derivatives as glycogen phosphorylase inhibitors ," *Bioorganic and Medicinal Chemistry Letters*, 16 (3): 722-726, 2006.
Yates et al., "Pharmacodynamic characterization of chemopreventive triterpenoids as exceptionally potent inducers of Nrf2-regulated genes," *Mol. Cancer Ther.*, 6:154-162, 2007.
Yates et al., "Potent protection against aflatoxin-induced tumorigenesis through induction of Nrf2-regulated pathways by the triterpenoid 1-[2-cyano-3-,12-dioxooleana-1,9(11)-dien-28-oyl]imidazole," *Cancer Res.*, 66 (4): 2488-2494, 2007.
Yore et al., "The synthetic triterpenoid 1-[2-cyano-3,12-dioxooleana-1,9(11)-dien-28-oyl]imidazole blocks nuclear factor-kappaB activation through direct inhibition of IkappaB kinase beta," *Mol. Cancer Ther.*, 5 (12): 3232-3239, 2006.
You et al., "Synthesis and cytotoxic activity of a-ring modified betulinic acid derivatives ," *Bioorganic and Medicinal Chemistry Letters*, 13 (19): 3137-3140, 2003.
Yue et al., "Depletion of intracellular glutathione contributes to JNK-mediated death receptor 5 upregulation and apoptosis induction by the novel synthetic triterpenoid methyl-2-cyano-3, 12-dioxooleana-1, 9-dien-28-oate (CDDO-Me)," *Cancer & Biology Ther.*, 5(5):492-497, 2006.
Zapata et al., "CDDO and CDDO-Im Reduce Tumor Burden in a Transgenic Mouse Model of CLL," *Blood*, 104:3477, 2004.
Zapata et al., "Triterpenoids show activity against leukemic cells in a transgenic mouse model of CLL," *Proc. Amer. Assoc. Cancer Res.*, 46: Abstract No. 5179, 2005.
Zhang et al., "Synthetic triterpenoid CDDO as effective therapy for HER2-expressing resistant breast cancer," *Proc. Amer. Assoc. Cancer Res.*, Abstract No. 3799, 2004.
Zhang et al., "The novel synthetic oleanane triterpenoid CDDO (2-cyano-3, 12-dioxoolean-1, 9-dien-28-oic acid) induces apoptosis in Mycosis fungoides/Sézary syndrome cells," *J. Invest. Dermatol.*, 123:380-387, 2004.
Zhou et al., "A new triterpenoid from the roots of Tripterygium wildfordii," *Chinese Chemical Letters*, 21(5): 600-602, 2010.
Ziegler et al., "Isolation and structure of eucosterol and 16beta-hydroxyeucosterol, two novel spirocyclic nortriterpenes, and of a new 24-nor-5alpha-chola-8, 16-diene-23-oic acid from bulbs of several Eucomis species," *Helv Chim Acta*, 59(6):1997-2011, 19.
Zou et al., "c-Jun NH2-terminal kinase-mediated up-regulation of death receptor 5 contributes to induction of apoptosis by the novel synthetic triterpenoid methyl-2-cyano-3,12-dioxooleanal, 9-dien-28-oate in human lung cancer cells," *Cancer Res.*, 64:7570-7578, 2004.
International Search Report and Written Opinion issued in PCT/US2012/028569, dated May 30, 2012.
Cheung et al., "Structures of triterpenes from *dryobalanops aromatic*," *Phytochemistry*, 11:1771-17780, 1972.
Johns et al., "Triterpense of *lantanta tiliaefolia*, 24-hydroxy-3-oxours-12-en-28-oic acid, a new triterpene," 36:2537-2547, 1983.
Peakman et al., "Characterisation of 24-nor-Triterpenoids occurring in sediments and crude oils by comparison with synthesized standards," *Tetrahedron* 47(23): 3779-3786, 1991.
Ruzieka et al., Triterpenes LXXXIX. Decomposition of hederagenin to the C26-stage, *Helvetica Chimica Acta*, 27:1185-1196, 1944.
Wolff et al., "Novel monoaromatic triterpenoid hydrocarbons occurring in sediments," *Tetrahedron*, 45(21): 6721-6728, 1989.
García-Granados, et al., "Semi-synthesis of triterpene A-ring derivatives from oleanolic and maslinic acids. Theoretical and experimental $^{13}$C chemical shifts", *J. of Chemical Research, Synopses*, 2000, 2:56-57.
Green and Long, "Compounds related to the steroid hormones. Part II. The action of hydrogen bromide on 2-bromo-3-oxo-Δ1-5α-steroids", *J of the Chemical Society*, 1961, 2532-2543.
Heiss, et al., "Active NF-E2-related factor (Nrf2) contributes to keep endothelial NO synthase (eNOS) in the coupled state: role of reactive oxygen species (ROS), eNOS, and heme oxygenase (HO-1) levels", *J. Biol. Chem.*, 2009, 284:31579-31586.
Hybertson, et al., "Oxidative stress in health and disease: The therapeutic potential of Nrf2 activation", *Molecular Aspects of Medicine*, 2011, 32:234-246.
Manzoor-I-Khuda, "Isolation techniques for active principles from plants and their composition and structure determination through spectroscopic techniques", *New Trends Nat Prod.*, 1986, 26:303-323.
Manzoor-I-Khuda and Habermehl, et al., "Chemical constituents of *corchorus capsularis* and *C. olitorium* (jute plant). III. structure of corosin", *Zeitschrift fuer Naturforschung. Teil C: Biochemie, Biophysik, Biologie, Virologie*, 1974, 29(5-6):209-221.
Marty, et al., "RTA 402 (CDDO-Me) increases survival of mice administered high doses of cytotoxic chemotherapy", *European Organization for Research and Treatment of Cancer, American Association for Cancer Research and National Cancer Institute International Conference*, Nov. 2005, Poster presentation.
Pergola, et al., "Bardoxolone Methyl and Kidney Function in CKD with Type 2 diabetes", *New England Journal of Medicine*, 2011, 365:327-336.
Saha, et al., "The triterpenoid 2-cyano-3,12-dioxooleana-1,9-dien-28-oic acid methyl ester has potent anti-diabetic effects in diet-induced diabetic mice and Lepr$^{db/db}$ mice", *J. Biol. Chem.*, 2010, 285:40581-92.
Search Report from Panama Patent Application 89604-01, issued on Apr. 8, 2013 (Spanish only).
Sussan, et al., "Targeting Nrf2 with the triterpenoid CDDO-imidazolide attenuate cigarette smoke-induced emphysema and cardiac dysfunction in mice", *Proc. Nat. Sci. Acad. USA*, 2009, 106:250-255.
Witz, et al., "Cyclic ketones. XIII. Circular dichroism of steroid and triterpene ketones. Conformation of ring A of 8-methylated 3-oxotriterpenes", *Bull. Soc. China, France* (French only, English CAPLUS database summary), 1963, 1101-1112.
Wu, et al., "Beneficial role of Nrf2 in regulating NADPH generation and consumption", *Toxicological Sciences*, 2011, 123(2):590-600.
Deeb, et al., "CDDO-Me Induces Apoptosis and Inhibits Akt, mTOR and NF-κB Signaling Proteins in Prostate Cancer Cells," *Anticancer Research*, 27:3035-3044, 2007.
Office Action and Search Report in Co-pending Taiwanese Application 098113098, dated Aug. 19, 2013. (Chinese, English translation of Search Report).
Johns, et al., "Triterpenes of Lantana tiliaefolia. 24-Hydroxy-3-oxours-12-en-28-oic Acid, a New Triterpene," *Aust. J. Chem.*, 36:2537-2547, 1983.

* cited by examiner

C4 MONOMETHYL TRITERPENOID DERIVATIVES AND METHODS OF USE THEREOF

The present application claims the benefit of priority to U.S. Provisional Application 61/452,017, filed Mar. 11, 2011, the contents of which are incorporated herein by reference.

BACKGROUND OF THE INVENTION

I. Field of the Invention

The present invention relates generally to the fields of biology and medicine. More particularly, it concerns compounds, compositions and methods for the treatment and prevention of diseases such as those associated with oxidative stress and inflammation.

II. Description of Related Art

The anti-inflammatory and anti-proliferative activity of the naturally occurring triterpenoid, oleanolic acid, has been improved by chemical modifications. For example, 2-cyano-3,12-diooxooleana-1,9(11)-dien-28-oic acid (CDDO) and related compounds have been developed (Honda et al., 1997; Honda et al., 1998; Honda et al., 1999; Honda et al., 2000a; Honda et al., 2000b; Honda, et al., 2002; Suh et al. 1998; Suh et al., 1999; Place et al., 2003; Liby et al., 2005). The methyl ester, bardoxolone methyl (CDDO-Me), is currently being evaluated in phase III clinical trials for the treatment of diabetic nephropathy and chronic kidney disease.

Synthetic triterpenoid analogs of oleanolic acid have also been shown to be inhibitors of cellular inflammatory processes, such as the induction by IFN-γ of inducible nitric oxide synthase (iNOS) and of COX-2 in mouse macrophages. See Honda et al. (2000a); Honda et al. (2000b), and Honda et al. (2002), which are all incorporated herein by reference. Synthetic derivatives of another triterpenoid, betulinic acid, have also been shown to inhibit cellular inflammatory processes, although these compounds have been less extensively characterized (Honda et al., 2006). The pharmacology of these synthetic triterpenoid molecules is complex. Compounds derived from oleanolic acid have been shown to affect the function of multiple protein targets and thereby modulate the activity of several important cellular signaling pathways related to oxidative stress, cell cycle control, and inflammation (e.g., Dinkova-Kostova et al., 2005; Ahmad et al., 2006; Ahmad et al., 2008; Liby et al., 2007a). Derivatives of betulinic acid, though they have shown comparable anti-inflammatory properties, also appear to have significant differences in their pharmacology compared to OA-derived compounds (Liby et al., 2007b). Given that the biological activity profiles of known triterpenoid derivatives vary, and in view of the wide variety of diseases that may be treated or prevented with compounds having potent antioxidant and anti-inflammatory effects, and the high degree of unmet medical need represented within this variety of diseases, it is desirable to synthesize new compounds with diverse structures that may have improved biological activity profiles for the treatment of one or more indications.

SUMMARY OF THE INVENTION

The present disclosure provides novel synthetic triterpenoid derivatives, with anti-inflammatory and/or antioxidant properties, pharmaceutical compositions, and methods for their manufacture, and methods for their use.

In one aspect, there are provided compounds of the formula:

(I)

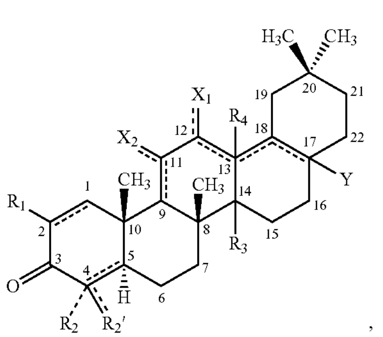

, wherein:

$X_1$ and $X_2$ are independently hydrogen, halo, hydroxy, amino or oxo, provided that $X_1$ is not oxo when carbon atoms 12 and 13 are connected to one another with a double bond, further provided that $X_2$ is not oxo when carbon atoms 9 and 11 are connected to one another with a double bond;

$R_1$ is —H, —CN, halo, —$CF_3$, or —C(O)$R_a$, wherein $R_a$ is —OH, alkoxy$_{(C1-4)}$, —$NH_2$, alkylamino$_{(C1-4)}$, or —NH—S(O)$_2$-alkyl$_{(C1-4)}$;

$R_2$ is hydrogen or $R_2$ is absent when the atom to which it is bound forms part of a double bond;

$R_2'$ is hydrogen, =$CH_2$, alkyl$_{(C\leq8)}$, or substituted alkyl$_{(C\leq8)}$;

$R_3$ and $R_4$ are each independently hydrogen, hydroxy, methyl or as defined below when either of these groups is taken together with group $R_c$; and Y is:

—H, —OH, —SH, —CN, —F, —$CF_3$, —$NH_2$ or —NCO;

alkyl$_{(C\leq8)}$, alkenyl$_{(C\leq8)}$, alkynyl$_{(C\leq8)}$, aryl$_{(C\leq12)}$, aralkyl$_{(C\leq12)}$, heteroaryl$_{(C\leq8)}$, heterocycloalkyl$_{(C\leq12)}$, alkoxy$_{(C\leq8)}$, aryloxy$_{(C\leq12)}$, acyloxy$_{(C\leq8)}$, alkylamino$_{(C\leq8)}$, dialkylamino$_{(C\leq8)}$, alkenylamino$_{(C\leq8)}$, arylamino$_{(C\leq8)}$, aralkylamino$_{(C\leq8)}$, alkylthio$_{(C\leq8)}$, acylthio$_{(C\leq8)}$, alkylsulfonylamino$_{(C\leq8)}$, or substituted versions of any of these groups;

—alkanediyl$_{(C\leq8)}$-$R_b$, -alkenediyl$_{(C\leq8)}$-$R_b$, or a substituted version of any of these groups, wherein $R_b$ is:

hydrogen, hydroxy, halo, amino or thio; or heteroaryl$_{(C\leq8)}$, alkoxy$_{(C\leq8)}$, alkenyoxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, alkylamino$_{(C\leq8)}$, dialkylamino$_{(C\leq8)}$, alkenylamino$_{(C\leq8)}$, arylamino$_{(C\leq8)}$, aralkylamino$_{(C\leq8)}$, heteroarylamino$_{(C\leq8)}$, alkylsulfonylamino$_{(C\leq8)}$, amido$_{(C\leq8)}$, —OC(O)NH-alkyl$_{(C\leq8)}$, —OC(O)$CH_2$NHC(O)O-t-butyl, —$OCH_2$-alkylthio$_{(C\leq8)}$, or a substituted version of any of these groups;

—$(CH_2)_m$C(O)$R_c$, wherein m is 0-6 and $R_c$ is:

hydrogen, hydroxy, halo, amino, —NHOH,

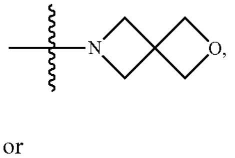

or thio; or alkyl$_{(C\leq8)}$, alkenyl$_{(C\leq8)}$, alkynyl$_{(C\leq8)}$, aryl$_{(C\leq8)}$, aralkyl$_{(C\leq8)}$, heteroaryl$_{(C\leq8)}$, heterocycloalkyl$_{(C\leq8)}$, alkoxy$_{(C\leq8)}$, alkenyloxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, alkylamino$_{(C\leq8)}$, dialkylamino$_{(C\leq8)}$, arylamino$_{(C\leq8)}$, alkylsulfonylamino$_{(C\leq8)}$, amido$_{(C\leq8)}$, —NH-alkoxy$_{(C\leq8)}$, —NH-heterocycloalkyl$_{(C\leq8)}$, —NHC(NOH)-alkyl$_{(C\leq8)}$, —NH-amido$_{(C\leq8)}$, or a substituted version of any of these groups;

$R_c$ and $R_3$, taken together, are —O— or —$NR_d$—, wherein $R_d$ is hydrogen or alkyl$_{(C\leq4)}$; or $R_c$ and $R_4$, taken together, are —O— or —$NR_d$—, wherein $R_d$ is hydrogen or alkyl$_{(C\leq4)}$; or —NHC(O)$R_e$, wherein $R_e$ is:

hydrogen, hydroxy, amino; or alkyl$_{(C\leq8)}$, alkenyl$_{(C\leq8)}$, alkynyl$_{(C\leq8)}$, aryl$_{(C\leq8)}$, aralkyl$_{(C\leq8)}$, heteroaryl$_{(C\leq8)}$, heterocycloalkyl$_{(C\leq8)}$, alkoxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, alkylamino$_{(C\leq8)}$, dialkylamino$_{(C\leq8)}$, arylamino$_{(C\leq8)}$, or a substituted version of any of these groups;

or a pharmaceutically acceptable salt or tautomer thereof.

In some embodiments, the compounds are further defined by the formula:

(II)

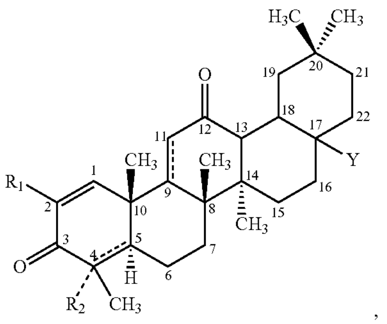

, wherein:

$R_1$ is —H, —CN, halo, —$CF_3$, or —C(O)$R_a$, wherein $R_a$ is —OH, alkoxy$_{(C1\text{-}4)}$, —$NH_2$, alkylamino$_{(C1\text{-}4)}$, or —NH—$S(O)_2$-alkyl$_{(C1\text{-}4)}$;

$R_2$ is hydrogen or $R_2$ is absent when the atom to which it is bound forms part of a double bond; and Y is:

—H, —OH, —SH, —CN, —F, —$CF_3$, —$NH_2$ or —NCO;

alkyl$_{(C\leq8)}$, alkenyl$_{(C\leq8)}$, alkynyl$_{(C\leq8)}$, aryl$_{(C\leq12)}$, aralkyl$_{(C\leq12)}$, heteroaryl$_{(C\leq8)}$, heterocycloalkyl$_{(C\leq12)}$, alkoxy$_{(C\leq8)}$, aryloxy$_{(C\leq12)}$, acyloxy$_{(C\leq8)}$, alkylamino$_{(C\leq8)}$, dialkylamino$_{(C\leq8)}$, alkenylamino$_{(C\leq8)}$, arylamino$_{(C\leq8)}$, aralkylamino$_{(C\leq8)}$, alkylthio$_{(C\leq8)}$, acylthio$_{(C\leq8)}$, alkylsulfonylamino$_{(C\leq8)}$, or substituted versions of any of these groups;

—alkanediyl$_{(C\leq8)}$-$R_b$, -alkenediyl$_{(C\leq8)}$-$R_b$, or a substituted version of any of these groups, wherein $R_b$ is:

hydrogen, hydroxy, halo, amino or thio; or heteroaryl$_{(C\leq8)}$, alkoxy$_{(C\leq8)}$, alkenyloxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, alkylamino$_{(C\leq8)}$, dialkylamino$_{(C\leq8)}$, alkenylamino$_{(C\leq8)}$, arylamino$_{(C\leq8)}$, aralkylamino$_{(C\leq8)}$, heteroarylamino$_{(C\leq8)}$, alkylsulfonylamino$_{(C\leq8)}$, amido$_{(C\leq8)}$, —OC(O)NH-alkyl$_{(C\leq8)}$, —OC(O)$CH_2$NHC(O)O-t-butyl, —$OCH_2$-alkylthio$_{(C\leq8)}$, or a substituted version of any of these groups;

—$(CH_2)_m$C(O)$R_c$, wherein m is 0-6 and $R_c$ is:

hydrogen, hydroxy, halo, amino, —NHOH,

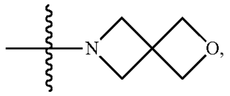 [SMILES: *N1CC2(COC2)C1]

or thio; or alkyl$_{(C\leq8)}$, alkenyl$_{(C\leq8)}$, alkynyl$_{(C\leq8)}$, aryl$_{(C\leq8)}$, aralkyl$_{(C\leq8)}$, heteroaryl$_{(C\leq8)}$, heterocycloalkyl$_{(C\leq8)}$, alkoxy$_{(C\leq8)}$, alkenyloxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, alkylamino$_{(C\leq8)}$, dialkylamino$_{(C\leq8)}$, arylamino$_{(C\leq8)}$, alkylsulfonylamino$_{(C\leq8)}$, amido$_{(C\leq8)}$, —NH-alkoxy$_{(C\leq8)}$, —NH-heterocycloalkyl$_{(C\leq8)}$, —NHC(NOH)-alkyl$_{(C\leq8)}$, —NH-amido$_{(C\leq8)}$, or a substituted version of any of these groups; or —NHC(O)$R_e$, wherein $R_e$ is:

hydrogen, hydroxy, amino; or alkyl$_{(C\leq8)}$, alkenyl$_{(C\leq8)}$, alkynyl$_{(C\leq8)}$, aryl$_{(C\leq8)}$, aralkyl$_{(C\leq8)}$, heteroaryl$_{(C\leq8)}$, heterocycloalkyl$_{(C\leq8)}$, alkoxy$_{(C\leq8)}$, aryloxy$_{(C\leq)}$, aralkoxy$_{(C\leq8)}$, heteroaryloxy$_{(C\leq8)}$, acyloxy$_{(C\leq8)}$, alkyl- or a amino$_{(C\leq8)}$, dialkylamino$_{(C\leq8)}$, arylamino$_{(C\leq8)}$, substituted version of any of these groups;

or a pharmaceutically acceptable salt or tautomer thereof.

In some embodiments, the compounds are further defined by the formula:

(III)

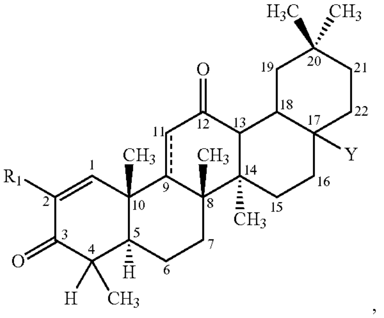

, wherein:

$R_1$ is —H, —CN, halo, —$CF_3$, or —C(O)$R_a$, wherein $R_a$ is —OH, alkoxy$_{(C1\text{-}4)}$, —$NH_2$, alkylamino$_{(C1\text{-}4)}$, or —NH—$S(O)_2$-alkyl$_{(C1\text{-}4)}$; and Y is:

—H, —OH, —F, —$CF_3$, —$NH_2$ or —NCO;

alkyl$_{(C\leq8)}$, alkenyl$_{(C\leq8)}$, alkynyl$_{(C\leq8)}$, aryl$_{(C\leq12)}$, aralkyl$_{(C\leq12)}$, heteroaryl$_{(C\leq8)}$, heterocycloalkyl$_{(C\leq12)}$, alkoxy$_{(C\leq8)}$, aryloxy$_{(C\leq12)}$, acyloxy$_{(C\leq8)}$, alkylamino$_{(C\leq8)}$, dialkylamino$_{(C\leq8)}$, alkenylamino$_{(C\leq8)}$, arylamino$_{(C\leq8)}$, aralkylamino$_{(C\leq8)}$, alkylthio$_{(C\leq8)}$, acylthio$_{(C\leq8)}$, alkylsulfonylamino$_{(C\leq8)}$, or substituted versions of any of these groups;

-alkanediyl$_{(C\leq8)}$-$R_b$, -alkenediyl$_{(C\leq8)}$-$R_b$, or a substituted version of any of these groups, wherein $R_b$ is:

hydrogen, hydroxy, halo, amino or thio; or heteroaryl$_{(C\leq8)}$, alkoxy$_{(C\leq8)}$, alkenyloxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, alkylamino$_{(C\leq8)}$, dialkylamino$_{(C\leq8)}$, alkenylamino$_{(C\leq8)}$, arylamino$_{(C\leq8)}$, aralkylamino$_{(C\leq8)}$, heteroarylamino$_{(C\leq8)}$, alkylsulfonylamino$_{(C\le8)}$, amido$_{(C\le8)}$, —OC(O)NH-alkyl$_{(C\le8)}$, —OC(O)CH$_2$NHC(O)O-t-butyl, —OCH$_2$-alkylthio$_{(C\le8)}$, or a substituted version of any of these groups;

—(CH$_2$)$_m$C(O)R$_c$, wherein m is 0-6 and R$_c$ is:

hydrogen, hydroxy, halo, amino, —NHOH,

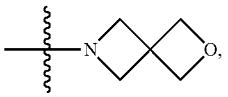 [SMILES: *N1CC2(COC2)C1]

or thio; or alkyl$_{(C\le8)}$, alkenyl$_{(C\le8)}$, alkynyl$_{(C\le8)}$, aryl$_{(C\le8)}$, aralkyl$_{(C\le8)}$, heteroaryl$_{(C\le8)}$, heterocycloalkyl$_{(C\le8)}$, alkoxy$_{(C\le8)}$, alkenyloxy$_{(C\le8)}$, aryloxy$_{(C\le8)}$, aralkoxy$_{(C\le8)}$, heteroaryloxy$_{(C\le8)}$, acyloxy$_{(C\le8)}$, alkylamino$_{(C\le8)}$, dialkylamino$_{(C\le8)}$, arylamino$_{(C\le8)}$, alkylsulfonylamino$_{(C\le8)}$, amido$_{(C\le8)}$, —NH-alkoxy$_{(C\le8)}$, —NH-heterocycloalkyl$_{(C\le8)}$, —NHC(NOH)-alkyl$_{(C\le8)}$, —NH-amido$_{(C\le8)}$, or a substituted version of any of these groups; or —NHC(O)R$_e$, wherein R$_e$ is:

hydrogen, hydroxy, amino; or alkyl$_{(C\le8)}$, alkenyl$_{(C\le8)}$, alkynyl$_{(C\le8)}$, aryl$_{(C\le8)}$, aralkyl$_{(C\le8)}$, heteroaryl$_{(C\le8)}$, heterocycloalkyl$_{(C\le8)}$, alkoxy$_{(C\le8)}$, aryloxy$_{(C\le8)}$, aralkoxy$_{(C\le8)}$, heteroaryloxy$_{(C\le8)}$, acyloxy$_{(C\le8)}$, alkylamino$_{(C\le8)}$, dialkylamino$_{(C\le8)}$, arylamino$_{(C\le8)}$, or a substituted version of any of these groups;

or a pharmaceutically acceptable salt or tautomer thereof.

In some embodiments, the compounds are further defined by the formula:

(IV)

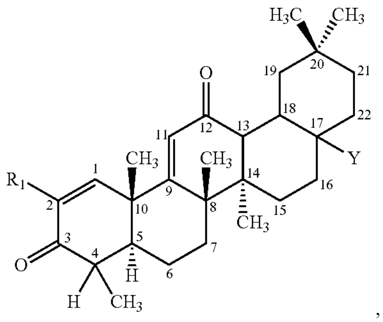

, wherein:

R$_1$ is —H, —CN, halo, —CF$_3$, or —C(O)R$_a$, wherein R$_a$ is —OH, alkoxy$_{(C1\text{-}4)}$, —NH$_2$, alkylamino$_{(C1\text{-}4)}$, or —NH—S(O)$_2$-alkyl$_{(C1\text{-}4)}$; and Y is:

—H, —OH, —SH, —F, —CF$_3$, —NH$_2$ or —NCO;

alkyl$_{(C\le8)}$, alkenyl$_{(C\le8)}$, alkynyl$_{(C\le12)}$, aryl$_{(C\le12)}$, aralkyl$_{(C\le12)}$, heteroaryl$_{(C\le8)}$, heterocycloalkyl$_{(C\le12)}$, alkoxy$_{(C\le8)}$, aryloxy$_{(C\le12)}$, acyloxy$_{(C\le8)}$, alkylamino$_{(C\le8)}$, dialkylamino$_{(C\le8)}$, alkenylamino$_{(C\le8)}$, arylamino$_{(C\le8)}$, aralkylamino$_{(C\le8)}$, amido$_{(C\le8)}$, alkylthio$_{(C\le8)}$, acylthio$_{(C\le8)}$, alkylsulfonylamino$_{(C\le8)}$, or substituted versions of any of these groups;

-alkanediyl$_{(C\le8)}$-R$_b$, -alkenediyl$_{(C\le8)}$-R$_b$, or a substituted version of any of these groups, wherein R$_b$ is:

hydrogen, hydroxy, halo, amino or thio; or heteroaryl$_{(C\le8)}$, alkoxy$_{(C\le8)}$, alkenyloxy$_{(C\le8)}$, aryloxy$_{(C\le8)}$, aralkoxy$_{(C\le8)}$, heteroaryloxy$_{(C\le8)}$, acyloxy$_{(C\le8)}$, alkylamino$_{(C\le8)}$, dialkylamino$_{(C\le8)}$, alkenylamino$_{(C\le8)}$, arylamino$_{(C\le8)}$, aralkylamino$_{(C\le8)}$, heteroarylamino$_{(C\le8)}$, alkylsulfonylamino$_{(C\le8)}$, amido$_{(C\le8)}$, —OC(O)NH-alkyl$_{(C\le8)}$, —OC(O)CH$_2$NHC(O)O-t-butyl, —OCH$_2$-alkylthio$_{(C\le8)}$, or a substituted version of any of these groups;

—(CH$_2$)$_m$C(O)R$_c$, wherein m is 0-6 and R$_c$ is:

hydrogen, hydroxy, halo, amino, —NHOH,

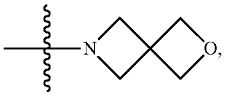

or thio; or alkyl$_{(C\le8)}$, alkenyl$_{(C\le8)}$, alkynyl$_{(C\le8)}$, aryl$_{(C\le8)}$, aralkyl$_{(C\le8)}$, heteroaryl$_{(C\le8)}$, heterocycloalkyl$_{(C\le8)}$, alkoxy$_{(C\le8)}$, alkenyloxy$_{(C\le8)}$, aryloxy$_{(C\le8)}$, aralkoxy$_{(C\le8)}$, heteroaryloxy$_{(C\le8)}$, acyloxy$_{(C\le8)}$, alkylamino$_{(C\le8)}$, dialkylamino$_{(C\le8)}$, arylamino$_{(C\le8)}$, alkylsulfonylamino$_{(C\le8)}$, amido$_{(C\le8)}$, —NH-alkoxy$_{(C\le8)}$, —NH-heterocycloalkyl$_{(C\le8)}$, —NHC(NOH)-alkyl$_{(C\le8)}$, —NH-amido$_{(C\le8)}$, or a substituted version of any of these groups; or —NHC(O)R$_e$, wherein R$_e$ is:

hydrogen, hydroxy, amino; or alkyl$_{(C\le8)}$, alkenyl$_{(C\le8)}$, alkynyl$_{(C\le8)}$, aryl$_{(C\le8)}$, aralkyl$_{(C\le8)}$, heteroaryl$_{(C\le8)}$, heterocycloalkyl$_{(C\le8)}$, alkoxy$_{(C\le8)}$, aryloxy$_{(C\le8)}$, aralkoxy$_{(C\le8)}$, heteroaryloxy$_{(C\le8)}$, acyloxy$_{(C\le8)}$, alkylamino$_{(C\le8)}$, dialkylamino$_{(C\le8)}$, arylamino$_{(C\le8)}$, or a substituted version of any of these groups;

or a pharmaceutically acceptable salt or tautomer thereof.

In some embodiments, the compounds the bond between carbon atoms 1 and 2 is a double bond. In some embodiments, the bond between carbon atoms 1 and 2 is a single bond. In some embodiments, the bond between carbon atoms 4 and 5 is a single bond. In some embodiments, the bond between carbon atoms 4 and 5 is a double bond. In some embodiments, the bond between carbon atoms 9 and 11 is a double bond.

In some embodiments, the bond between carbon atoms 9 and 11 is a single bond.

In some embodiments, X$_1$ is oxo. In some embodiments, X$_1$ is hydrogen. In some embodiments, X$_1$ is hydroxy. In some embodiments, X$_2$ is oxo. In some embodiments, X$_2$ is hydrogen.

In some embodiments, R$_1$ is —CN. In some embodiments, R$_1$ is —C(O)R$_a$, wherein R$_a$ is —OH, alkoxy$_{(C1\text{-}4)}$, —NH$_2$, alkylamino$_{(C1\text{-}4)}$, or —NH—S(O)$_2$-alkyl$_{(C1\text{-}4)}$. In some embodiments, R$_a$ is —OH. In some embodiments, R$_a$ is alkoxy$_{(C1\text{-}4)}$. In some embodiments, R$_a$ is methoxy. In some embodiments, R$_a$ is —NH$_2$. In some embodiments, R$_1$ is —H. In some embodiments, R$_1$ is halo. In some embodiments, R$_1$ is iodo.

In some embodiments, R$_2$ is hydrogen. In some embodiments, R$_2$ is absent. In some embodiments, R$_2$' is alkyl$_{(C\le8)}$. In some embodiments, R$_2$' is methyl. In some embodiments, R$_2$' is hydrogen. In some embodiments, R$_2$' is =CH$_2$.

In some embodiments, R$_3$ is methyl. In some embodiments, R$_3$ is hydrogen. In some embodiments, R$_4$ is hydrogen. In some embodiments, R$_4$ is methyl. In some embodiments, R$_4$ is hydroxy.

In some embodiments, Y is —$(CH_2)_mC(O)R_c$, wherein m is 0-6 and $R_c$ is hydrogen, hydroxy, amino, —NHOH, alkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heterocycloalkyl$_{(C\leq 8)}$, alkoxy$_{(C\leq 8)}$, alkenyloxy$_{(C\leq 8)}$, aryloxy$_{(C\leq 8)}$, aralkoxy$_{(C\leq 8)}$, acyloxy$_{(C\leq 8)}$, alkylamino$_{(C\leq 8)}$, dialkylamino$_{(C\leq 8)}$, arylamino$_{(C\leq 8)}$, alkylsulfonylamino$_{(C\leq 8)}$, amido$_{(C\leq 8)}$, —NH-alkoxy$_{(C\leq 8)}$, —NH-heterocycloalkyl$_{(C\leq 8)}$, —NHC(NOH)-alkyl$_{(C\leq 8)}$, —NH-amido$_{(C\leq 8)}$, or a substituted version of any of these groups other than hydrogen, hydroxy, amino, and —NHOH.

In some embodiments, $R_c$ is alkoxy$_{(C\leq 8)}$. In some embodiments, $R_c$ is methoxy, ethoxy or isopropoxy. In some embodiments, $R_c$ is hydroxy. In some embodiments, $R_c$ is amino. In some embodiments, $R_c$ is alkylamino$_{(C\leq 8)}$ or substituted alkylamino$_{(C\leq 8)}$. In some embodiments, $R_c$ is methylamino, ethylamino, n-butylamino or 2,2,2-trifluoroethylamino. In some embodiments, $R_c$ is heteroaryl$_{(C\leq 8)}$. In some embodiments, $R_c$ is imidazolyl or dimethylimidazolyl. In some embodiments, $R_c$ is —NHOH or —$NHOCH_3$. In some embodiments, $R_c$ is heterocycloalkyl$_{(C\leq 8)}$ or substituted heterocycloalkyl$_{(C\leq 8)}$. In some embodiments, $R_c$ is N-pyrrolidinyl, N-morpholinyl, N-piperidinyl or N-azetidinyl. In some embodiments, $R_c$ is —NH-heterocycloalkyl$_{(C\leq 8)}$. In some embodiments, $R_c$ is —NH-amido$_{(C\leq 8)}$ or a substituted version thereof. In some embodiments, $R_c$ is —NHNHC(O)H, —$NHNHC(O)CH_3$ or —$NHNHC(O)CH_2OCH_3$. In some embodiments, $R_c$ is —$NHC(NOH)CH_3$. In some embodiments, m is 0. In some embodiments, m is 2.

In some embodiments, Y is -alkanediyl$_{(C\leq 8)}$-$R_b$. In some embodiments, Y is —$CH_2$—$R_b$. In some embodiments, $R_b$ is hydroxy. In some embodiments, $R_b$ is acyloxy$_{(C\leq 8)}$ or substituted acyloxy$_{(C\leq 8)}$. In some embodiments, $R_b$ is acetyloxy, or trifluoroacetyloxy, —$OC(O)CH_2NH_2$. In some embodiments, $R_b$ is alkoxy$_{(C\leq 8)}$ or substituted alkoxy$_{(C\leq 8)}$. In some embodiments, $R_b$ is methoxy or fluoromethoxy. In some embodiments, $R_b$ is heteroaryl$_{(C\leq 8)}$. In some embodiments, $R_b$ is —OC(O)NH-alkyl$_{(C\leq 8)}$, —$OC(O)CH_2NHC(O)O$-t-butyl, or —$OCH_2$-alkylthio$_{(C\leq 8)}$.

In some embodiments, Y is —CN. In some embodiments, Y is isocyanate. In some embodiments, Y is fluoro. In some embodiments, Y is alkylsulfonylamino$_{(C\leq 8)}$ or substituted alkylsulfonylamino$_{(C\leq 8)}$. In some embodiments, Y is —$NHS(O)_2CH_3$ or —$NHS(O)_2CH_2CF_3$. In some embodiments, Y is heteroaryl$_{(C\leq 8)}$. In some embodiments, Y is oxadiazolyl, methyloxadiazolyl, or methoxymethyloxadiazolyl. In other embodiments, Y is amido$_{(C\leq 8)}$, acyl$_{(C\leq 8)}$ or substituted versions of either group.

In some embodiments, Y is —$NHC(O)R_e$, wherein $R_e$ is hydrogen, hydroxy, amino, alkyl$_{(C\leq 8)}$, aryl$_{(C\leq 8)}$, alkoxy$_{(C\leq 8)}$, acyloxy$_{(C\leq 8)}$, alkylamino$_{(C\leq 8)}$, dialkylamino$_{(C\leq 8)}$, or substituted version of any of these groups other than hydrogen, hydroxy and amino. In some embodiments, $R_e$ is hydrogen. In some embodiments, $R_e$ is amino. In some embodiments, $R_e$ is alkyl$_{(C\leq 8)}$ or substituted alkyl$_{(C\leq 8)}$. In some embodiments, $R_e$ is methyl, ethyl, cyclopropyl, cyclobutyl, n-hexyl, 1,1-difluoroethyl, or 2,2,2-trifluoroethyl. In some embodiments, $R_e$ is aryl$_{(C\leq 8)}$. In some embodiments, $R_e$ is alkoxy$_{(C\leq 8)}$. In some embodiments, $R_e$ is methoxy, ethoxy, or isopropoxy. In some embodiments, $R_e$ is alkylamino$_{(C\leq 8)}$ or dialkylamino$_{(C\leq 8)}$. In some embodiments, $R_e$ is methylamino, ethylamino, or dimethylamino.

In some embodiments, Y is —$(CH_2)_mC(O)R_c$, wherein m is 0 and wherein $R_c$ and $R_3$ are taken together and are —O—. In some embodiments, Y is —$(CH_2)_mC(O)R_c$, wherein m is 0 and wherein $R_c$ and $R_4$ are taken together and are —O—.

In embodiments having a hydrogen at carbon atom 13, the hydrogen is in the beta orientation. In others it is the alpha orientation. In some embodiments, the hydrogen at carbon atom 18 is in the beta orientation; in other embodiments, it is in the alpha orientation. For example, in some embodiments, there are hydrogen atoms at both carbon atoms 13 and 18, and they are both in the beta orientations.

In some embodiments, the invention provides compounds of the formulas:

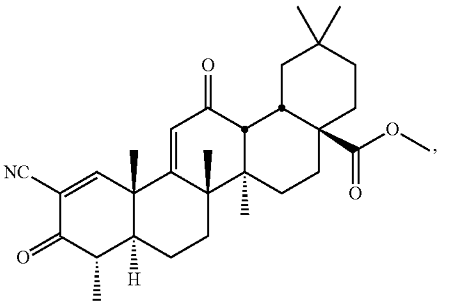

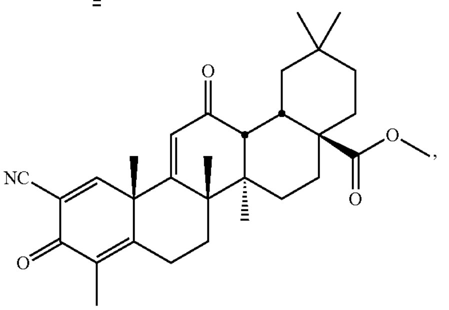

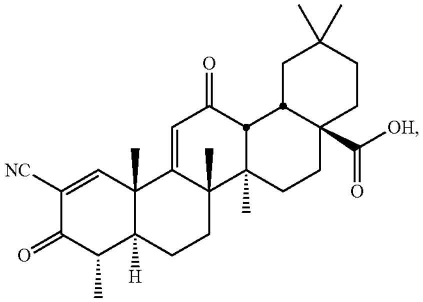

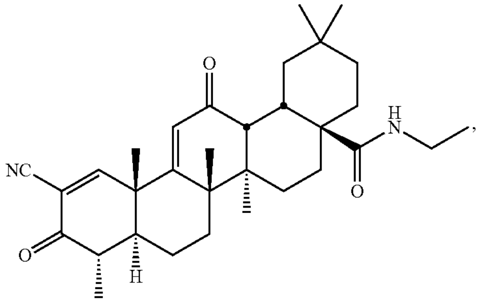

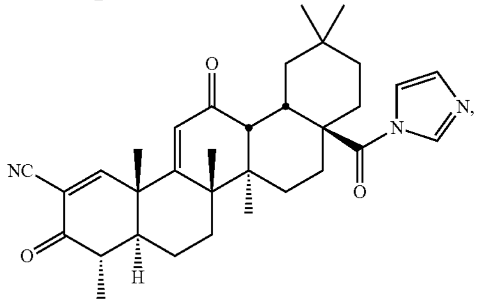

-continued
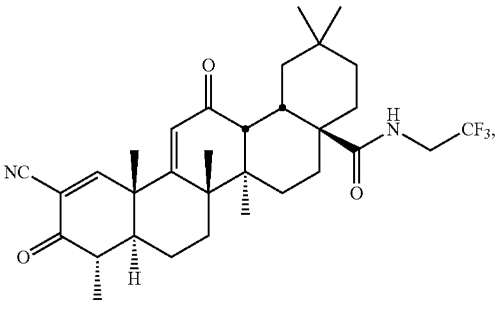
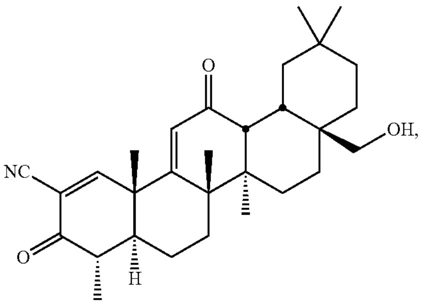
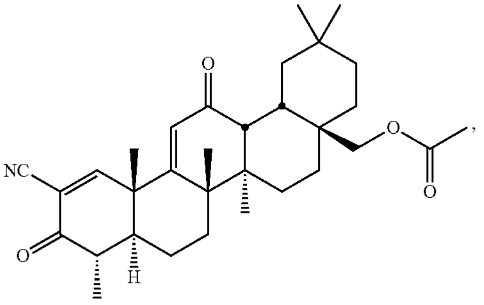
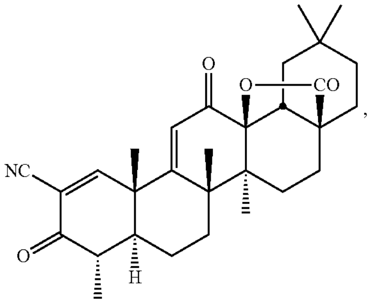
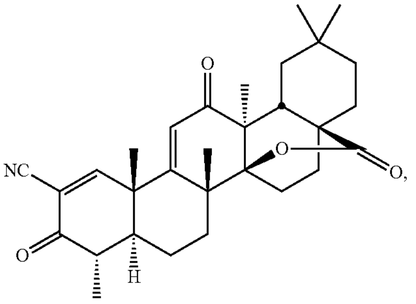
-continued
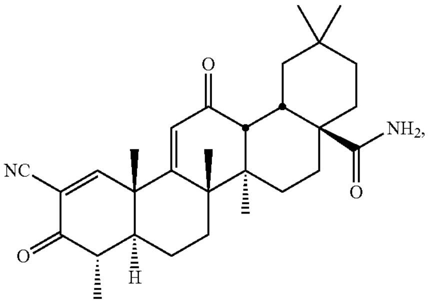
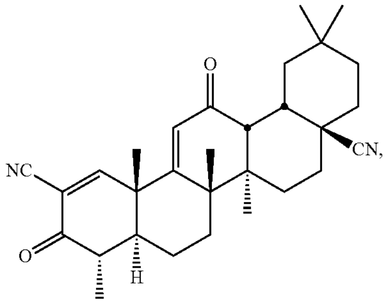
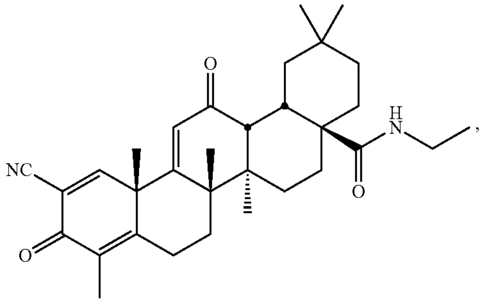
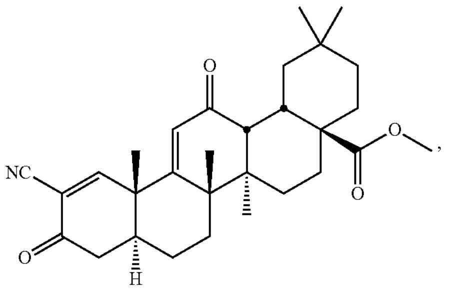
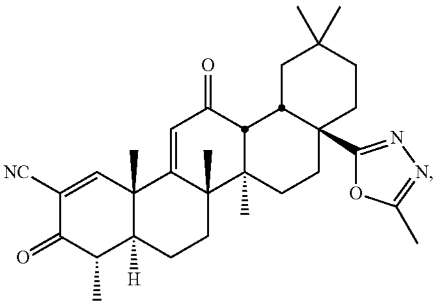

-continued
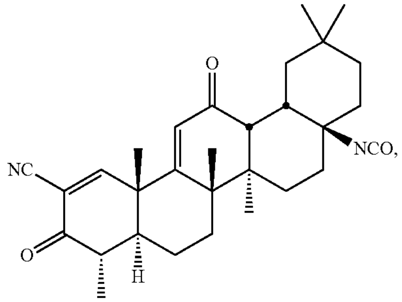
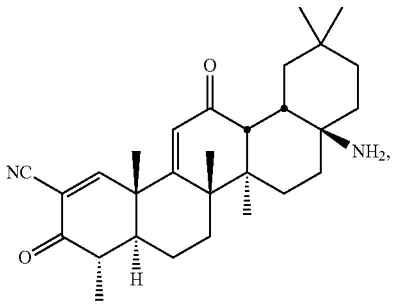
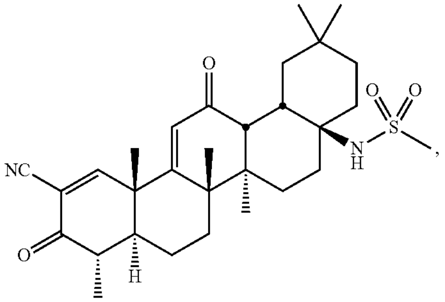
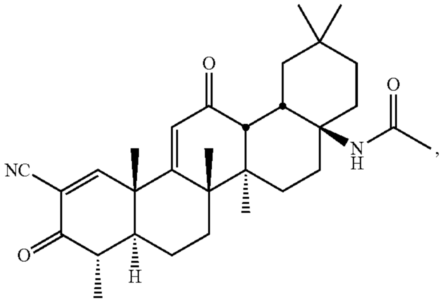
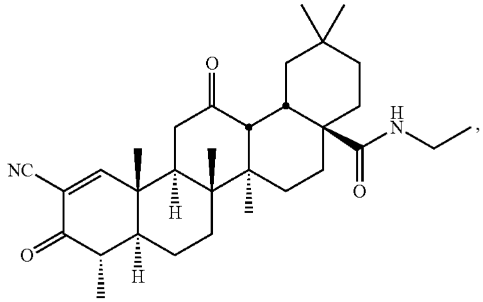
-continued
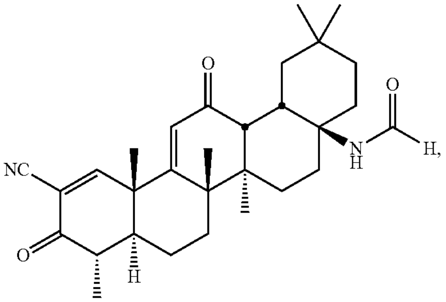
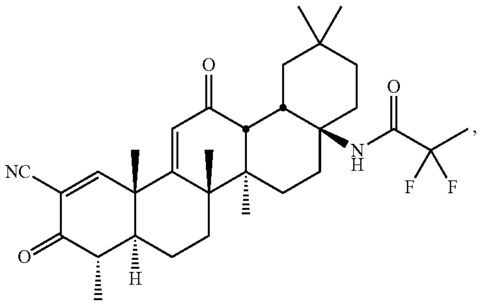
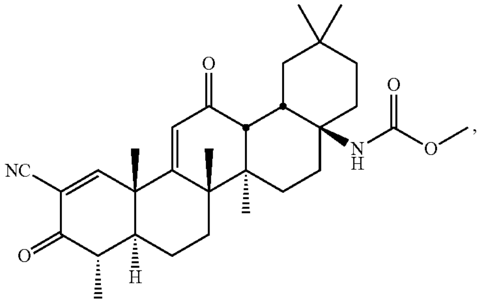
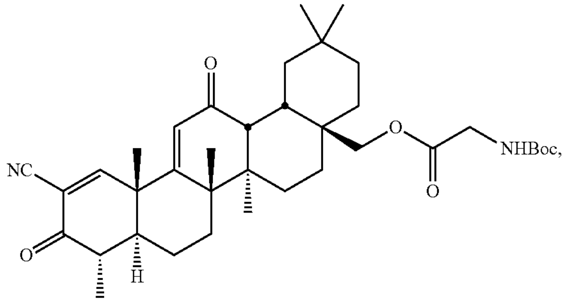
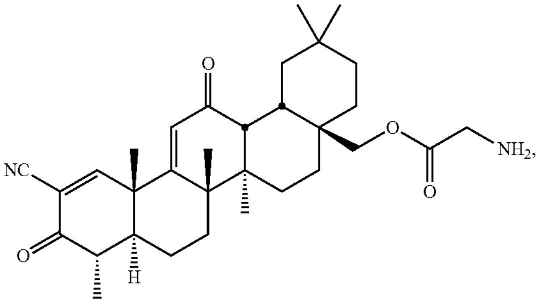

-continued
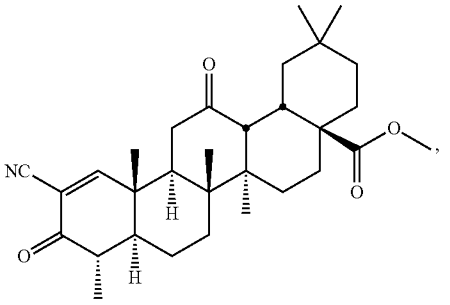
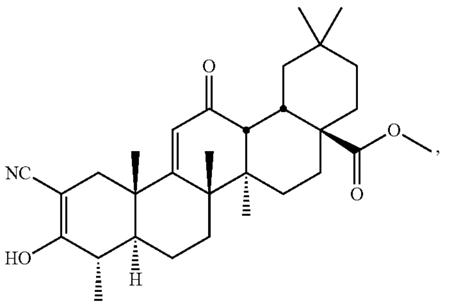
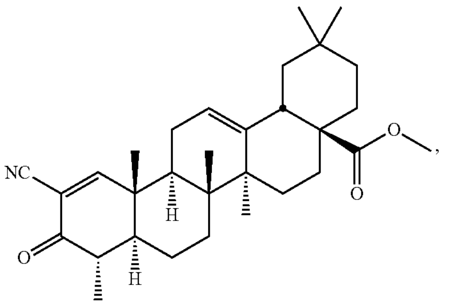
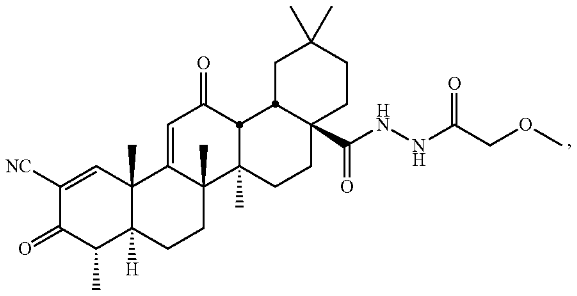
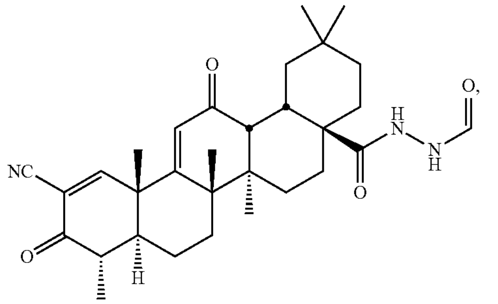
-continued
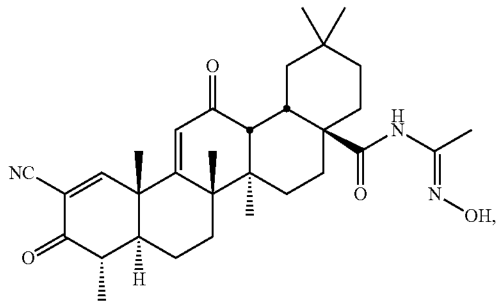
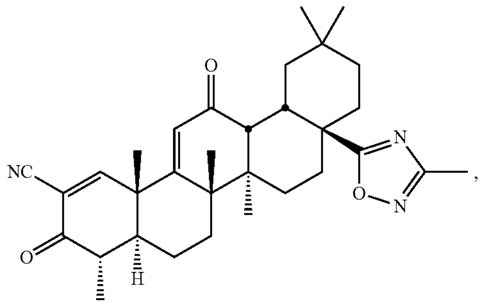
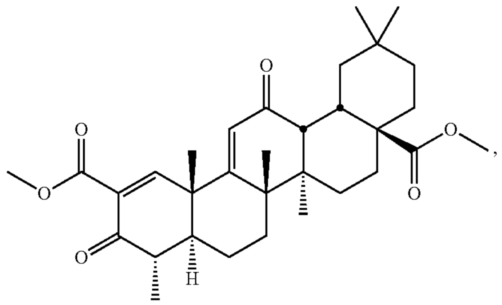
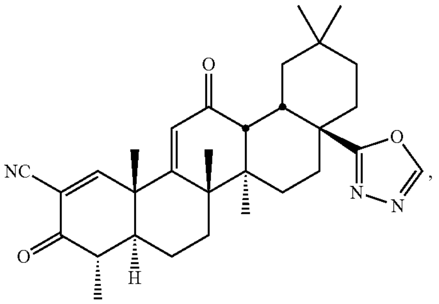
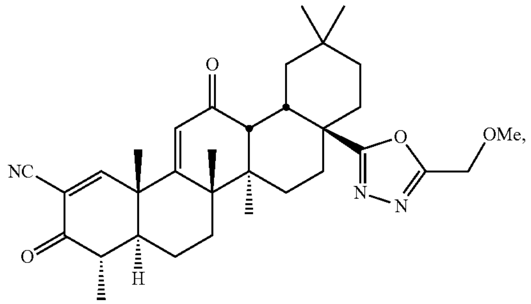

-continued
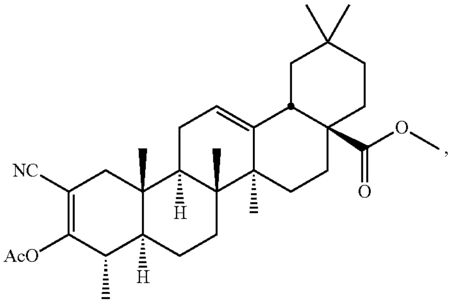
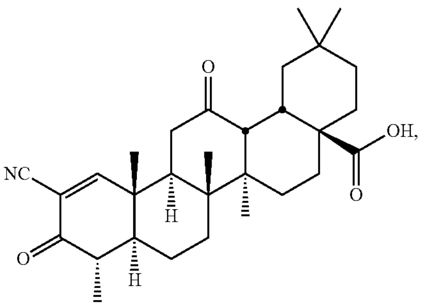
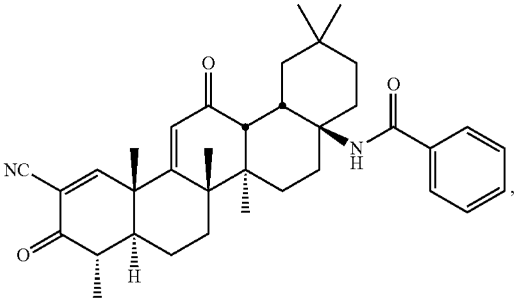
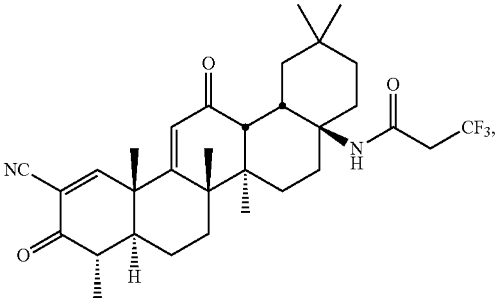
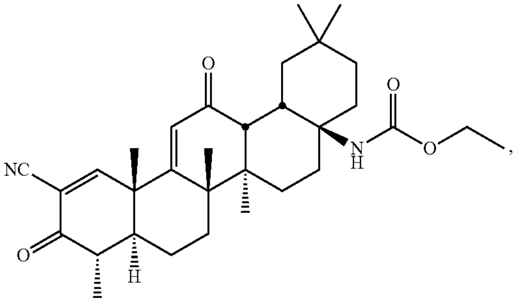
-continued
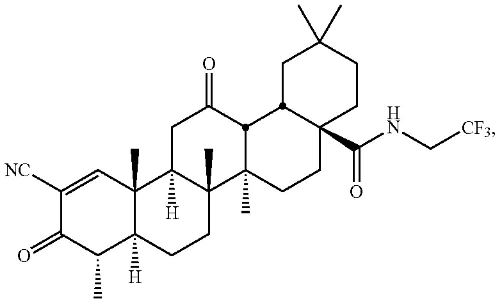
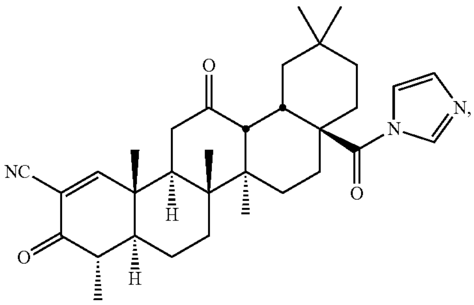
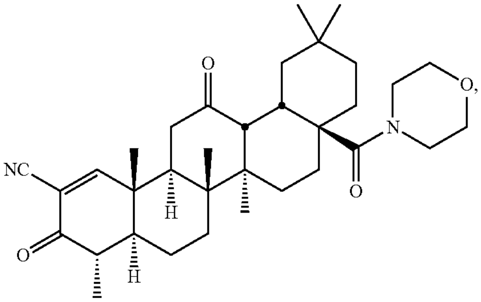
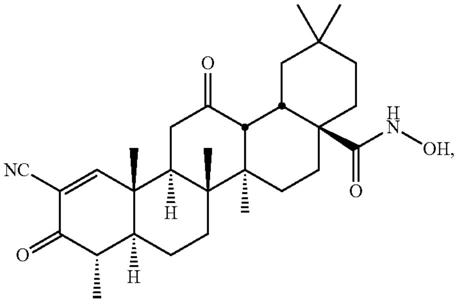
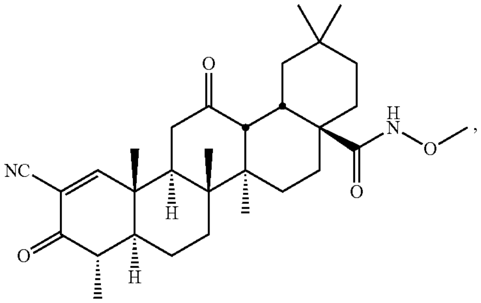

-continued
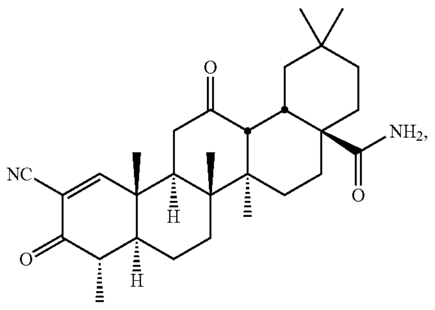
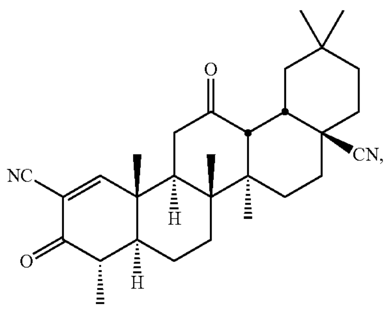
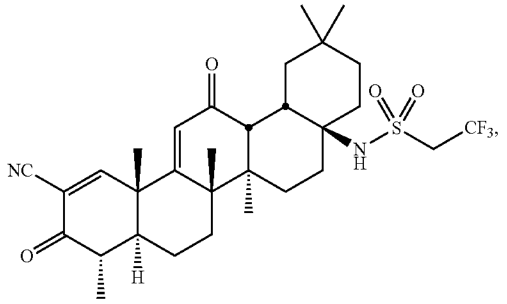
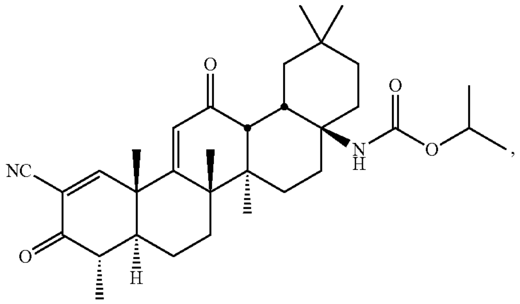
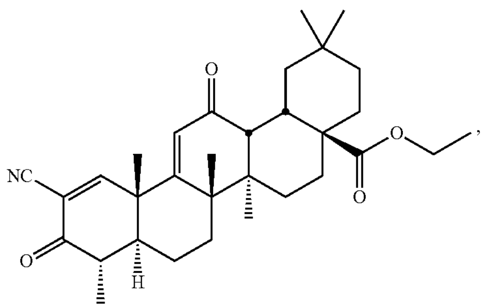
-continued
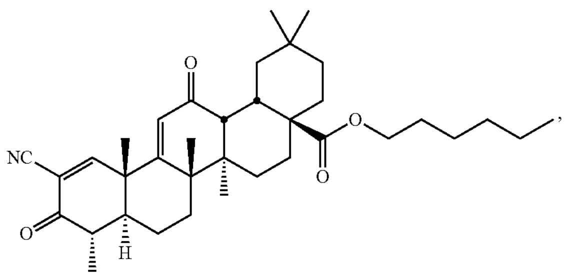
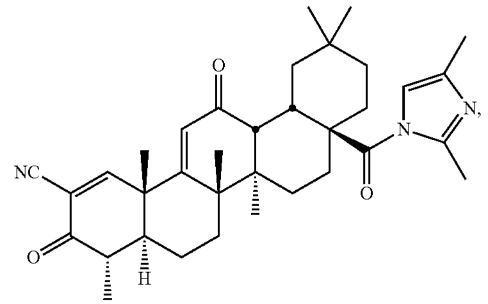
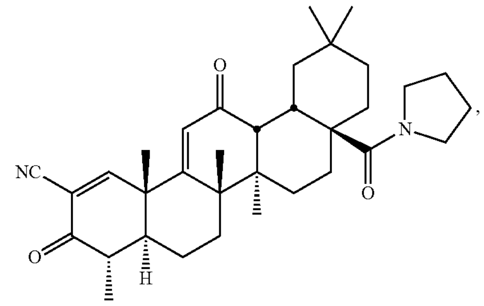
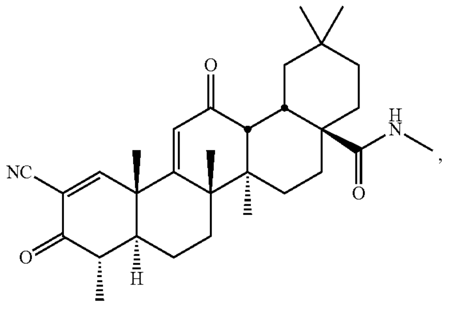
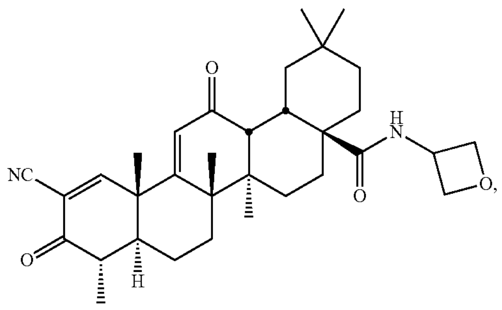

-continued
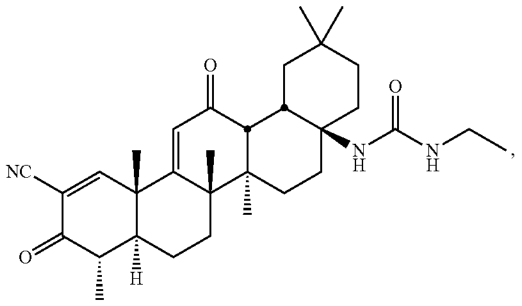
,
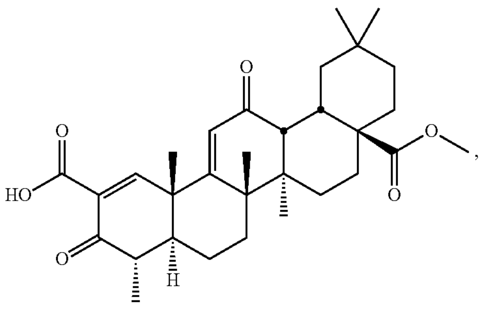
,
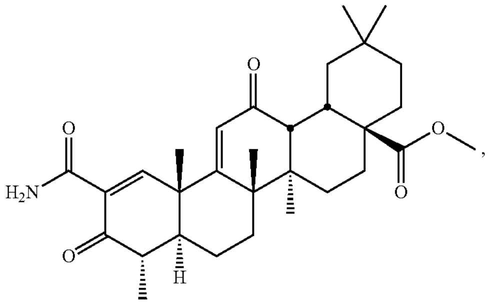
,
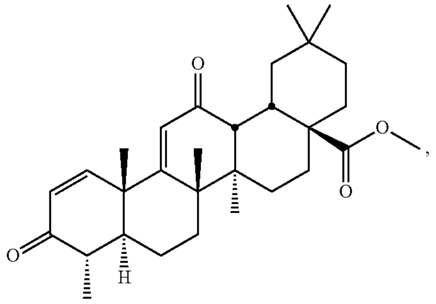
,
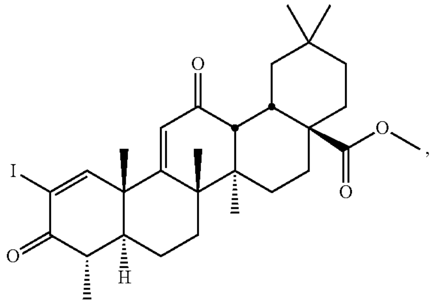
,
-continued
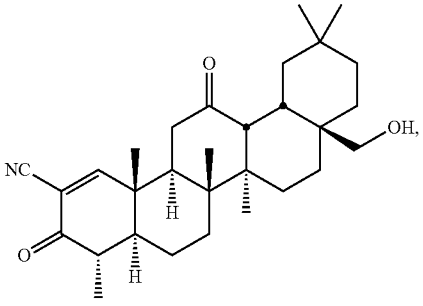
,
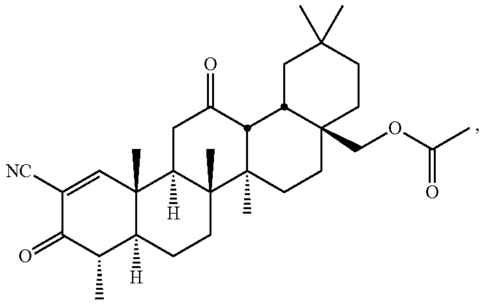
,
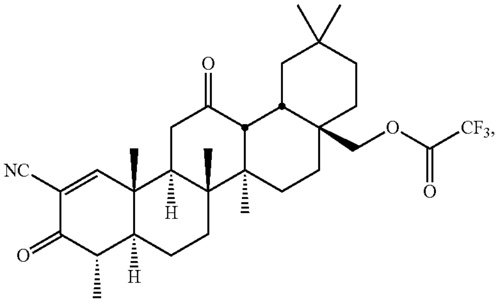
,
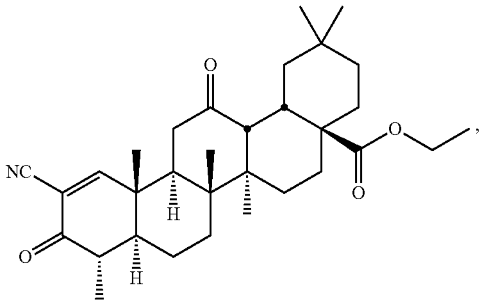
,
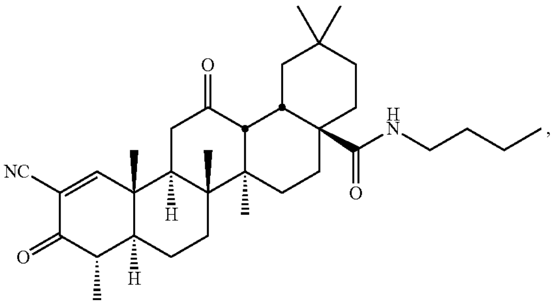
, -continued
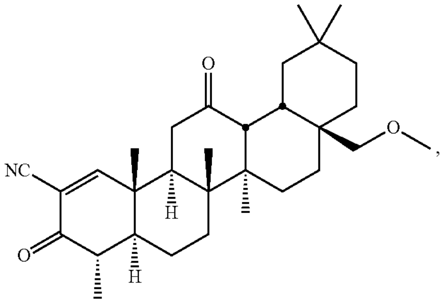
,
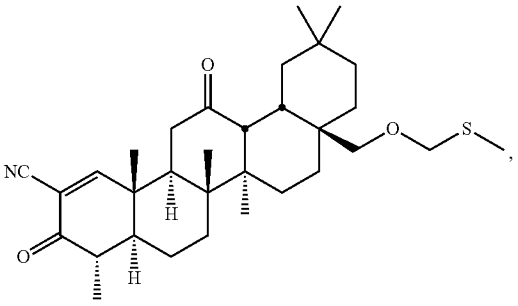
,
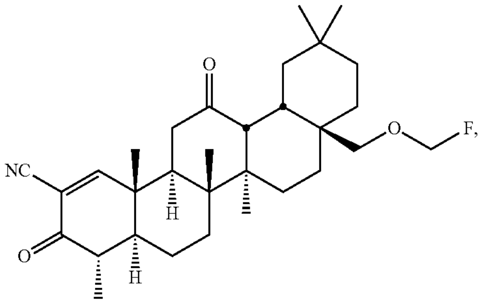
,
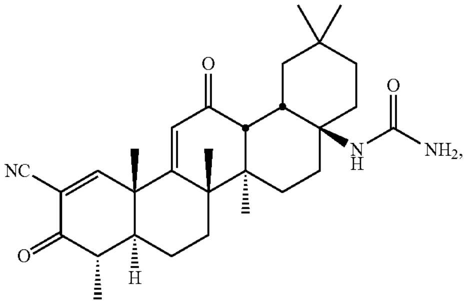
,
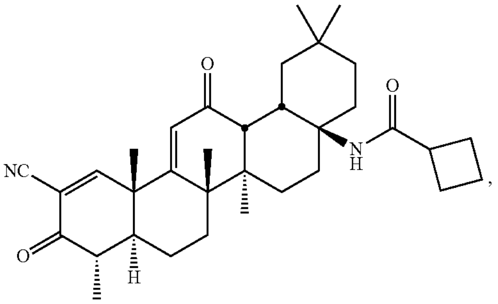
,
-continued
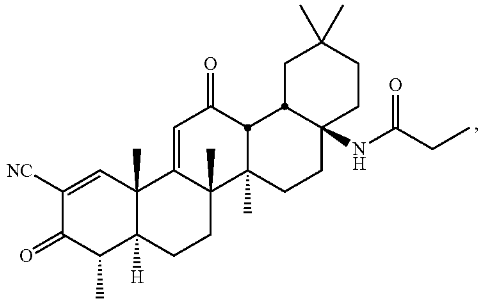
,
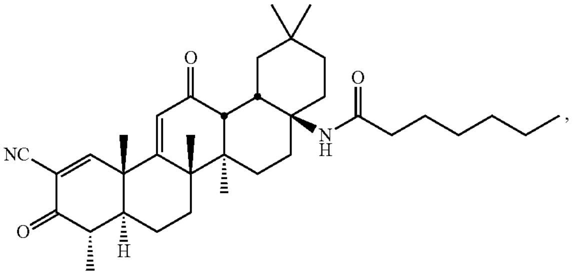
,
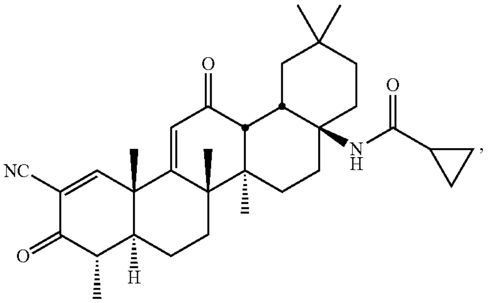
,
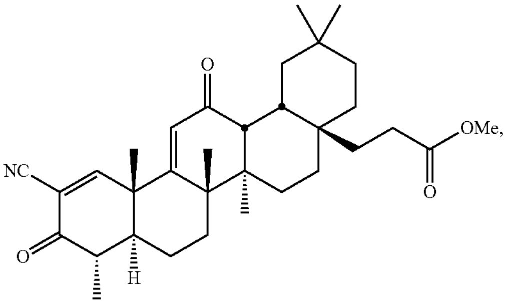
,
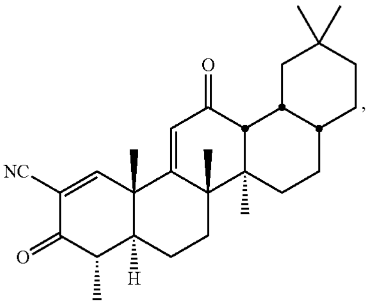
, -continued
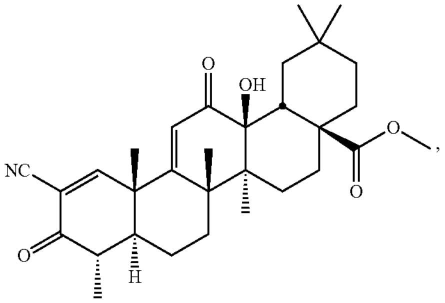
,
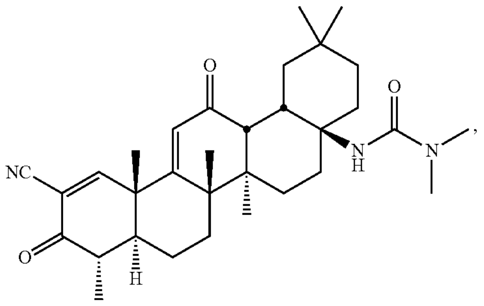
,
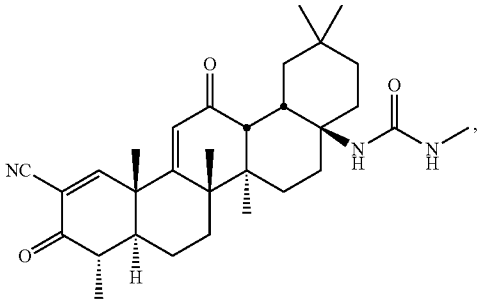
,
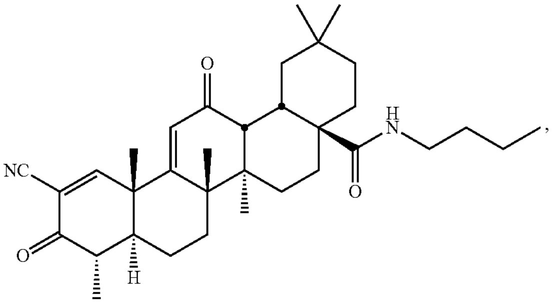
,
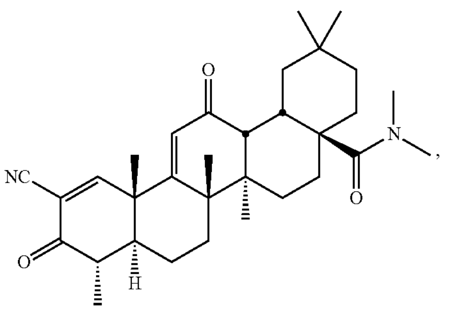
,
-continued
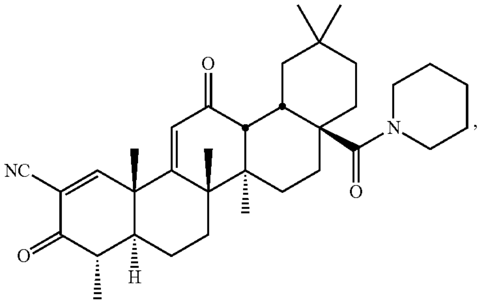
,
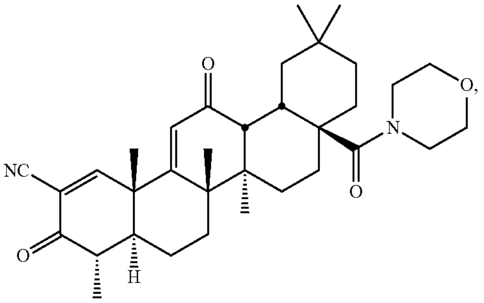
,
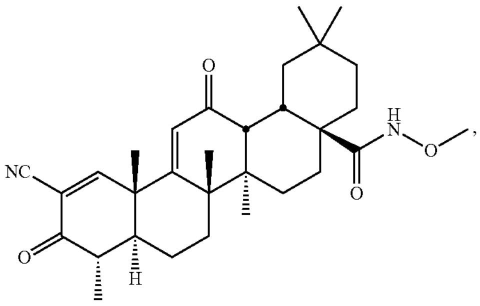
,
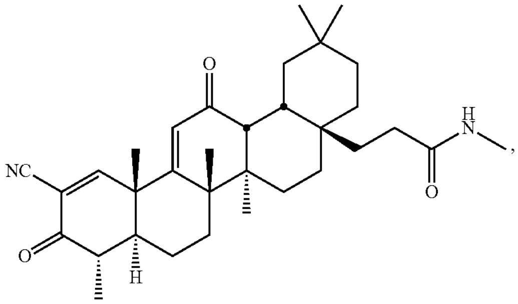
,
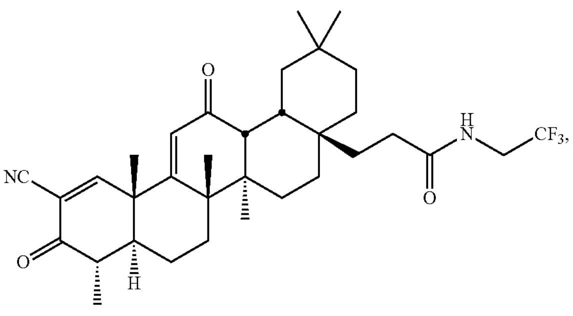
, -continued
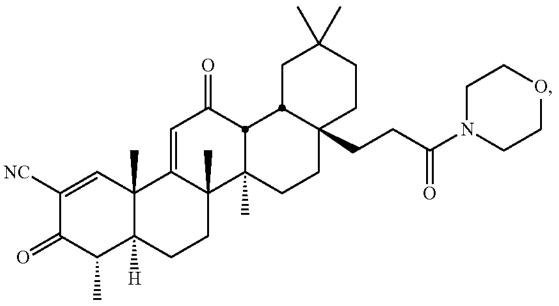
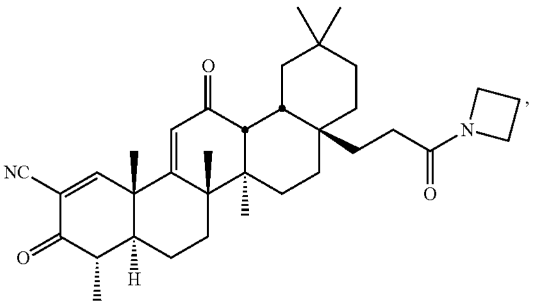
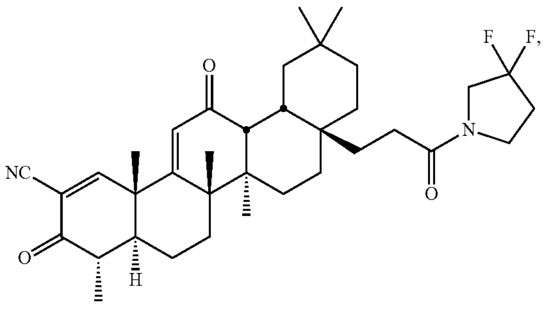
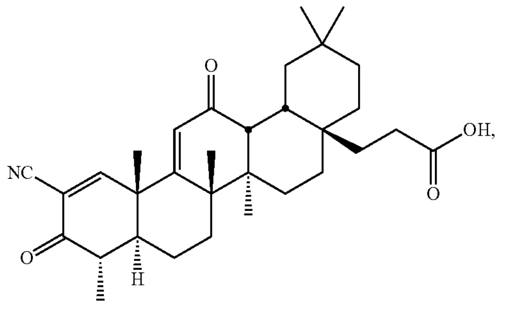
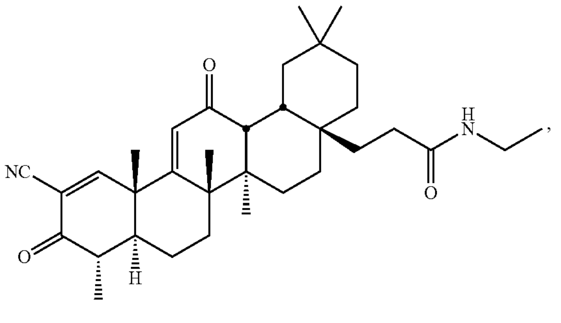
-continued
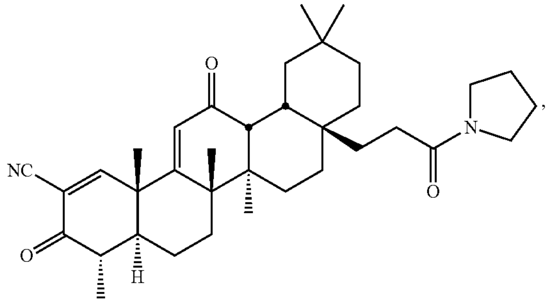
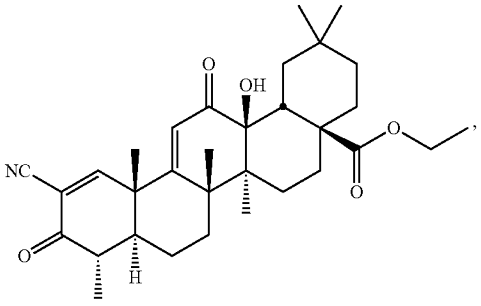
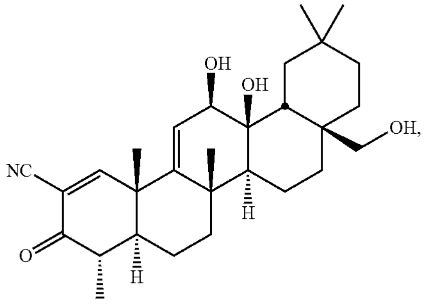
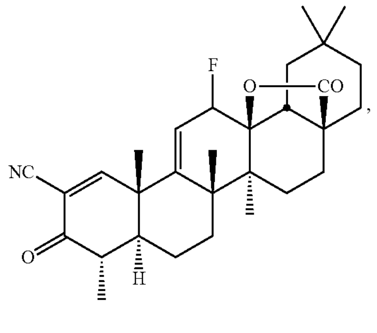
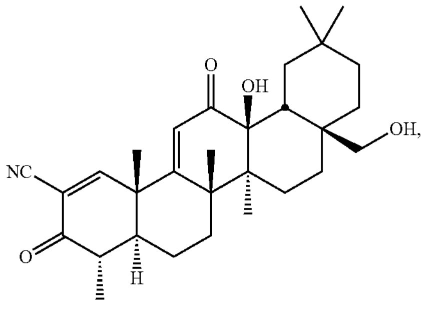

-continued
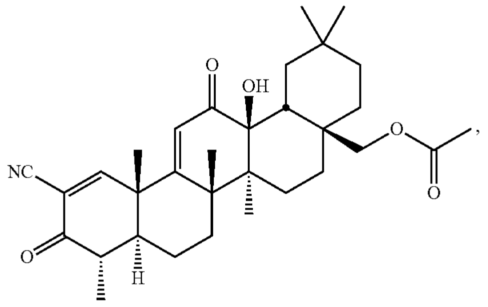
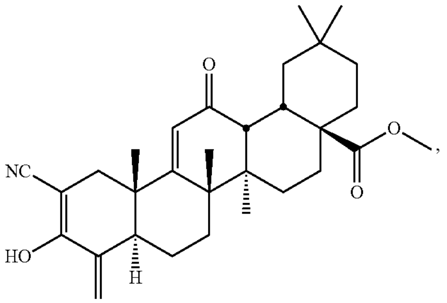
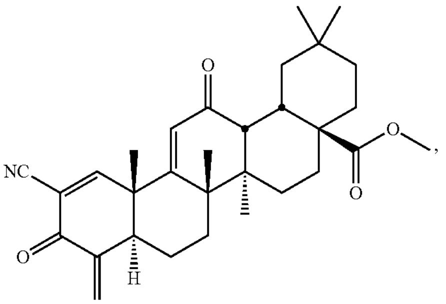
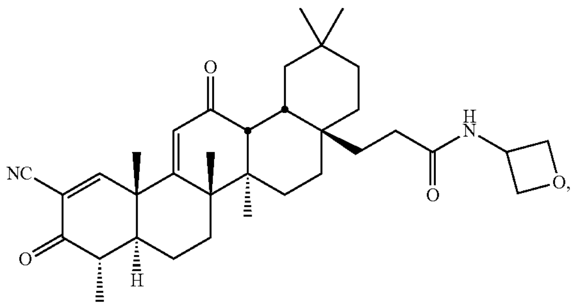
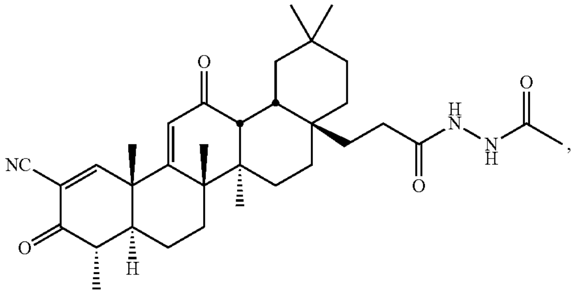
-continued
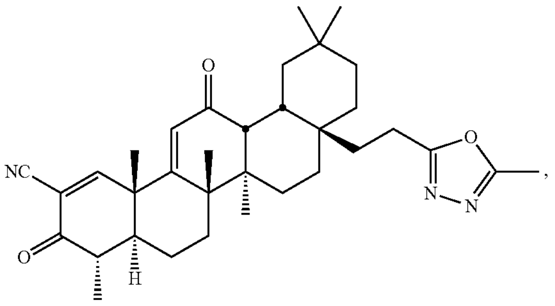
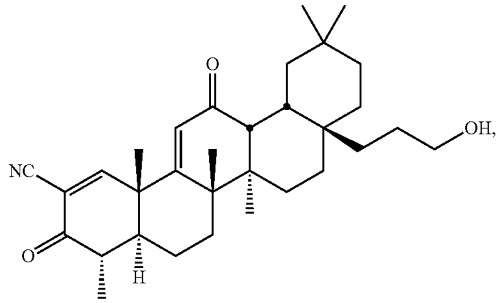
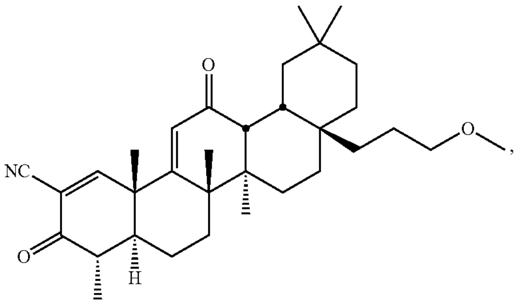
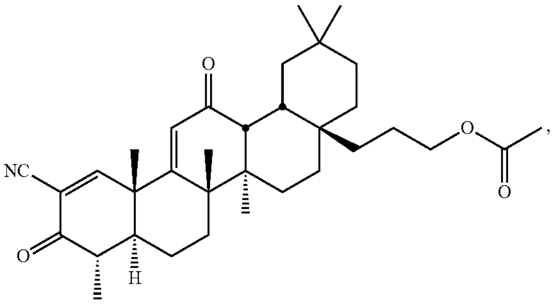
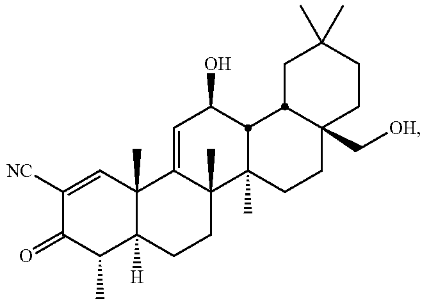

-continued

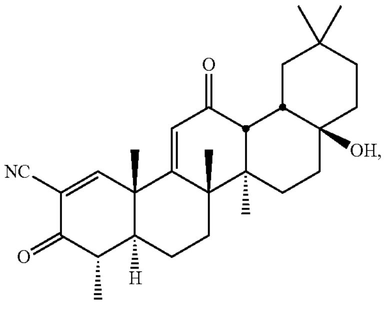

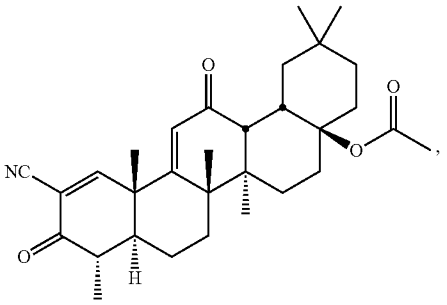

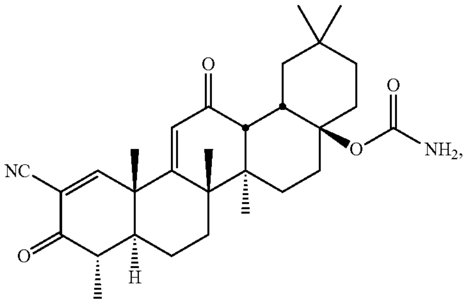

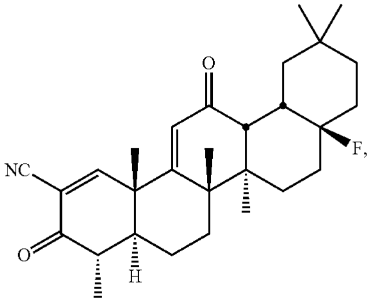

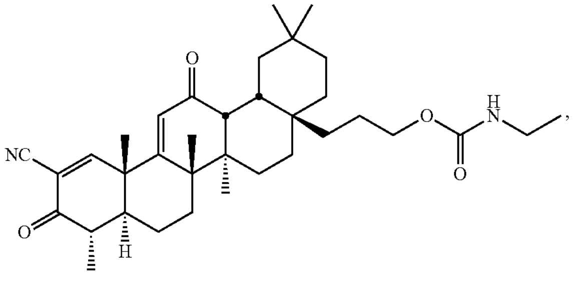

-continued

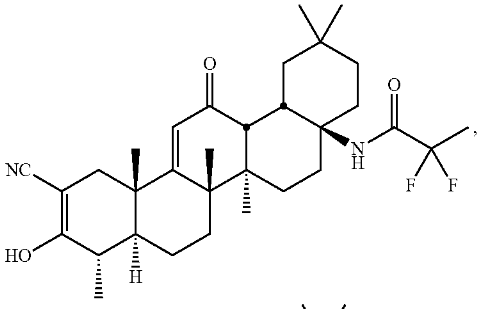

or

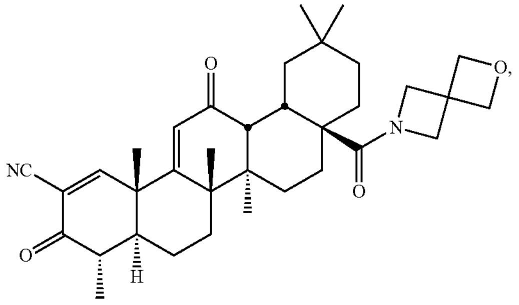

and pharmaceutically acceptable salts and tautomers thereof.

In some aspects, there are provided pharmaceutical compositions comprising one or more of the above compounds and an excipient. In other aspects there are provided methods of treating and/or preventing a disease or a disorder in patients in need thereof, comprising administering to such patients one or more of the above compounds in an amount sufficient to treat and/or prevent the disease or disorder.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

DESCRIPTION OF ILLUSTRATIVE EMBODIMENTS

Disclosed herein are new compounds and compositions with antioxidant and/or anti-inflammatory properties, methods for their manufacture, and methods for their use, including for the treatment and/or prevention of disease.

I. Definitions

When used in the context of a chemical group, "hydrogen" means —H; "hydroxy" means —OH; "oxo" means =O; "halo" means independently —F, —Cl, —Br or —I; "amino" means $—NH_2$; "hydroxyamino" means —NHOH; "nitro" means $=NO_2$; imino means =NH; "cyano" means —CN; "isocyanate" means —N=C=O; "azido" means $—N_3$; in a monovalent context "phosphate" means $—OP(O)(OH)_2$ or a deprotonated form thereof; in a divalent context "phosphate" means —OP(O)(OH)O— or a deprotonated form thereof; "mercapto" means —SH; "thio" means =S; "sulfonyl" means $—S(O)_2—$; and "sulfinyl" means —S(O)—.

In the context of chemical formulas, the symbol "—" means a single bond, "═" means a double bond; and "≡" means triple bond. The symbol "- - - " represents an optional bond, which if present is either single or double. The symbol "$\overline{\underline{----}}$" represents a single bond or a double bond. Thus, for example, the structure

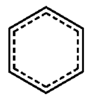

includes the structures

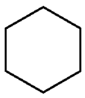, 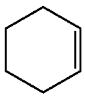, , 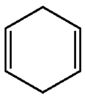, and 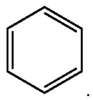.

As will be understood by a person of skill in the art, no one such ring atom forms part of more than one double bond. The symbol "∿∿", when drawn perpendicularly across a bond indicates a point of attachment of the group. It is noted that the point of attachment is typically only identified in this manner for larger groups in order to assist the reader in rapidly and unambiguously identifying a point of attachment. The symbol "◀" means a single bond where the group attached to the thick end of the wedge is "out of the page." The symbol "ıııııl" means a single bond where the group attached to the thick end of the wedge is "into the page". The symbol "∿∿" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

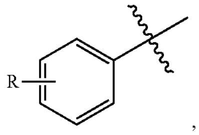, then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

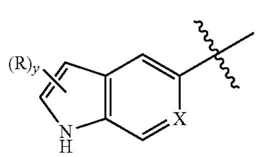, then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C\leq 8)}$" or the class "alkene$_{(C\leq 8)}$" is two. For example, "alkoxy$_{(C\leq 10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2\text{-}10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, $—NH_2$, $—NO_2$, $—CO_2H$, $—CO_2CH_3$, —CN, —SH, $—OCH_3$, $—OCH_2CH_3$, $—C(O)CH_3$, $—N(CH_3)_2$, $—C(O)NH_2$, $—OC(O)CH_3$, or $—S(O)_2NH_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups $—CH_3$ (Me), $—CH_2CH_3$ (Et), $—CH_2CH_2CH_3$ (n-Pr), $—CH(CH_3)_2$ (iso-Pr), $—CH(CH_2)_2$ (cyclopropyl), $—CH_2CH_2CH_2CH_3$ (n-Bu), $—CH(CH_3)CH_2CH_3$ (sec-butyl), $—CH_2CH(CH_3)_2$ (iso-butyl), $—C(CH_3)_3$ (tert-butyl), $—CH_2C(CH_3)_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —$CH_2$— (methylene), —$CH_2CH_2$—, $CH_2C(CH_3)_2CH_2$, $CH_2CH_2CH_2$—, and

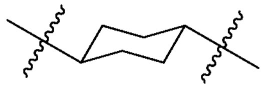, are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =$CH_2$, =$CH(CH_2CH_3)$, and =$C(CH_3)_2$. When any of these terms is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$N(CH_3)_2$, —$C(O)NH_2$, —$OC(O)CH_3$, or —$S(O)_2NH_2$. The following groups are non-limiting examples of substituted alkyl groups: —$CH_2OH$, —$CH_2Cl$, —$CF_3$, —$CH_2CN$, —$CH_2C(O)OH$, —$CH_2C(O)OCH_3$, —$CH_2C(O)NH_2$, —$CH_2C(O)CH_3$, —$CH_2OCH_3$, —$CH_2OC(O)CH_3$, —$CH_2NH_2$, —$CH_2N(CH_3)_2$, and —$CH_2CH_2Cl$. The term "haloalkyl" is a subset of substituted alkyl, in which one or more hydrogen atoms has been substituted with a halo group and no other atoms aside from carbon, hydrogen and halogen are present. The group, —$CH_2Cl$ is a non-limiting examples of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —$CH_2F$, —$CF_3$, and —$CH_2CF_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one non-aromatic carbon-carbon double bond, no carbon-carbon triple bonds, and no atoms other than carbon and hydrogen. Non-limiting examples of alkenyl groups include: —CH=$CH_2$ (vinyl), —CH=$CHCH_3$, —CH=$CHCH_2CH_3$, —$CH_2CH$=$CH_2$ (allyl), —$CH_2CH$=$CHCH_3$, and —CH=CH—$C_6H_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=$C(CH_3)CH_2$—, —CH=$CHCH_2$—, and

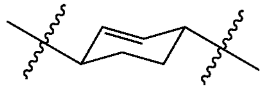, are non-limiting examples of alkenediyl groups. When these terms are used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$N(CH_3)_2$, —$C(O)NH_2$, —$OC(O)CH_3$, or —$S(O)_2NH_2$. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡$CCH_3$, and —$CH_2C$≡$CCH_3$, are non-limiting examples of alkynyl groups. When alkynyl is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$N(CH_3)_2$, —$C(O)NH_2$, —$OC(O)CH_3$, or —$S(O)_2NH_2$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —$C_6H_4CH_2CH_3$ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

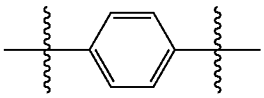, 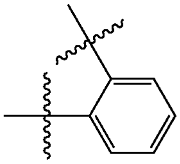,

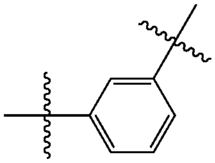,

-continued

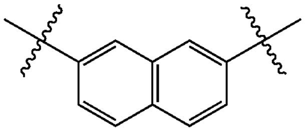

, and

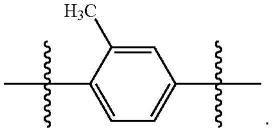

.

When these terms are used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —C(O)$CH_3$, —$N(CH_3)_2$, —C(O)$NH_2$, —OC(O)$CH_3$, or —$S(O)_2NH_2$. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —C(O)$CH_3$, —$N(CH_3)_2$, —C(O)$NH_2$, —OC(O)$CH_3$, or —$S(O)_2NH_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

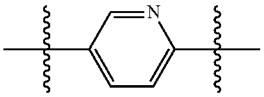

,

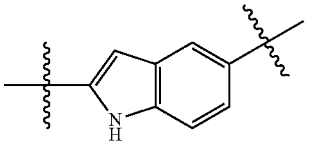

and

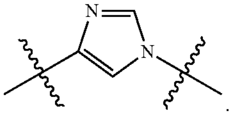

.

When these terms are used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —C(O)$CH_3$, —$N(CH_3)_2$, —C(O)$NH_2$, —OC(O)$CH_3$, or —$S(O)_2NH_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. If more than one ring is present, the rings may be fused or unfused. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, and pyranyl. When the term "heterocycloalkyl" used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —C(O)$CH_3$, —$N(CH_3)_2$, —C(O)$NH_2$, —OC(O)$CH_3$, or —$S(O)_2NH_2$.

The term "acyl" when used without the "substituted" modifier refers to the group —C(O)R, in which R is a hydrogen, alkyl, aryl, aralkyl or heteroaryl, as those terms are defined above. The groups, —CHO, —C(O)$CH_3$ (acetyl, Ac), —C(O)$CH_2CH_3$, —C(O)$CH_2CH_2CH_3$, —C(O)$CH(CH_3)_2$, —C(O)$CH(CH_2)_2$, —C(O)$C_6H_5$, —C(O)$C_6H_4$—$CH_3$, —C(O)$CH_2C_6H_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including the hydrogen atom directly attached the carbonyl or thiocarbonyl group) has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —C(O)$CH_3$, —$N(CH_3)_2$, —C(O)$NH_2$, —OC(O)$CH_3$, or —$S(O)_2NH_2$. The groups, —C(O)$CH_2CF_3$, —$CO_2H$ (carboxyl), —$CO_2CH_3$ (methylcarboxyl), —$CO_2CH_2CH_3$, —C(O)$NH_2$ (carbamoyl), and —CON$(CH_3)_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —$OCH_3$ (methoxy), —$OCH_2CH_3$ (ethoxy), —$OCH_2CH_2CH_3$, —$OCH(CH_3)_2$ (isopropoxy), —OCH $(CH_2)_2$, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. When any of these terms is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —C(O)$CH_3$, —$N(CH_3)_2$, —C(O)$NH_2$, —OC(O)$CH_3$, or —$S(O)_2NH_2$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —$NHCH_3$ and —$NHCH_2CH_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —$N(CH_3)_2$, —$N(CH_3)(CH_2CH_3)$, and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —$NHC_6H_5$. The term "amido" (acylamino), when used without the "substituted" modifier, refers to the group —NHR, in which R is acyl, as that term is defined above. A non-limiting example of an amido group is —NHC(O)$CH_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —C(O)$CH_3$, —$N(CH_3)_2$, —C(O)$NH_2$, —OC(O)$CH_3$, or —$S(O)_2NH_2$. The groups —NHC(O)$OCH_3$ and —NHC(O)$NHCH_3$ are non-limiting examples of substituted amido groups.

The terms "alkylsulfonyl" and "alkylsulfinyl" when used without the "substituted" modifier refers to the groups —$S(O)_2R$ and —S(O)R, respectively, in which R is an alkyl, as that term is defined above. The terms "alkenylsulfonyl", "alkynylsulfonyl", "arylsulfonyl", "aralkylsulfonyl", and "heteroarylsulfonyl", are defined in an analogous manner. When any of these terms is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —C(O)$CH_3$, —$N(CH_3)_2$, —C(O)$NH_2$, —OC(O)$CH_3$, or —$S(O)_2NH_2$.

As used herein, a "chiral auxiliary" refers to a removable chiral group that is capable of influencing the stereoselectivity of a reaction. Persons of skill in the art are familiar with such compounds, and many are commercially available.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts Properties, and Use* (P. H. Stahl & C. G. Wermuth eds., Verlag Helvetica Chimica Acta, 2002).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methane-sulfonates, ethanesulfonates, benzenesulfonates, p-toluenesulfonates, cyclohexyl-sulfamates, quinates, esters of amino acids, and the like. Similarly, a compound comprising an amine group may be administered as an amide that is converted by hydrolysis in vivo to the amine compound.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diasteromers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Effective amount," "Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

Other abbreviations used herein are as follows: DMSO, dimethyl sulfoxide; NO, nitric oxide; iNOS, inducible nitric oxide synthase; COX-2, cyclooxygenase-2; FBS, fetal bovine serum; IFNγ or IFN-γ, interferon-γ; TNFα or TNF-α, tumor necrosis factor-α; IL-1β, interleukin-1β; HO-1, inducible heme oxygenase.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. Compounds and Synthetic Methods

The compounds provided by the present disclosure are shown above in the summary of the invention section and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds employed in methods of the invention may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration, as defined by the IUPAC 1974 Recommendations. For example, mixtures of stereoisomers may be separated using the techniques taught in the Examples section below, as well as modifications thereof.

Atoms making up the compounds of the present invention are intended to include all isotopic forms of such atoms. Compounds of the present invention include those with one or more atoms that have been isotopically modified or enriched, in particular those with pharmaceutically acceptable isotopes or those useful for pharmaceutically research. Isotopes, as used herein, include those atoms having the same atomic number but different mass numbers. By way of general example and without limitation, isotopes of hydrogen include deuterium and tritium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Compounds of the present invention may also exist in prodrug form. Since prodrugs are known to enhance numerous desirable qualities of pharmaceuticals (e.g., solubility, bioavailability, manufacturing, etc), the compounds employed in some methods of the invention may, if desired, be delivered in prodrug form. Thus, the invention con templates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It should be further recognized that the compounds of the present invention include those that have been further modified to comprise substituents that are convertible to hydrogen in vivo. This includes those groups that may be convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydropyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl ($-C(O)OC(CH_3)_3$, Boc), benzyloxycarbonyl, p-methoxy-benzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups ($-C(O)OC(CH_3)_3$, Boc), and the like. Suitable peptide residues include peptide residues comprising two to five amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups ($-C(O)OC(CH_3)_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and β-iodoethoxycarbonyl).

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

III. Biological Activity

Assay results for the suppression of IFNγ-induced NO production are shown for several of the compounds of the present invention in Table 1 below. In the right-hand column of this table under the RAW264.7 heading, the results are compared to those of bardoxolone methyl (RTA 402, CDDO-Me). Available NQO1-ARE Luciferase reporter assay results are shown in the last column. Details regarding both assays are provided in the Examples section below.

TABLE 1
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| | Suppression of IFNγ-Induced NO Production. | | | | |
| TX63435 | 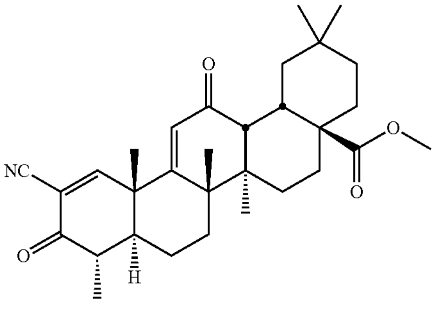 | 491.66 | 1.0 | 0.4 | 7.2 |
| TX63448 | 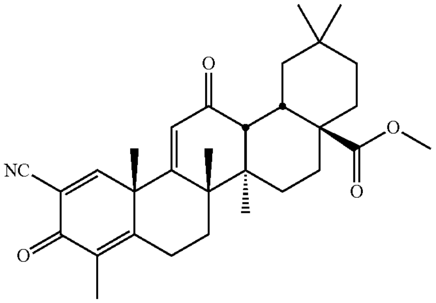 | 489.65 | 75 | 44 | |
| TX63520 | 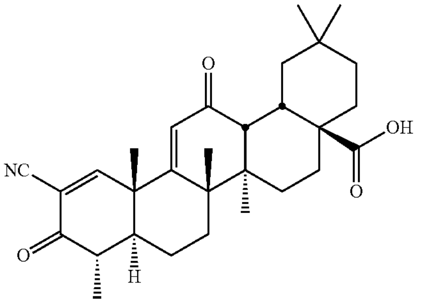 | 477.63 | 10.1 | 6.7 | 5.3 |
| TX63521 | 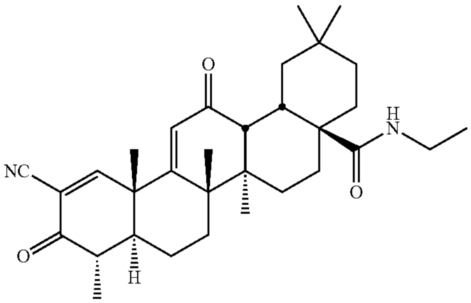 | 504.70 | 1.1 | 0.6 | |

TABLE 1-continued
Suppression of IFNγ-Induced NO Production.
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63522 | 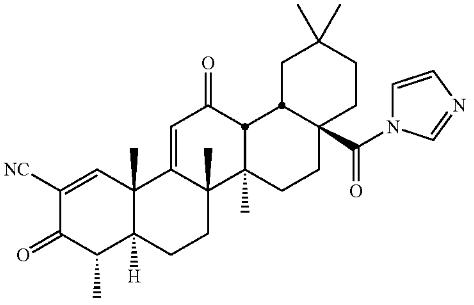 | 527.70 | 0.4 | 0.3 | 4.1 |
| TX63523 | 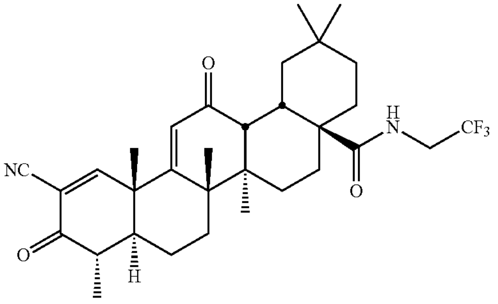 | 558.67 | 1.0 | 0.6 | 5.6 |
| TX63545 | 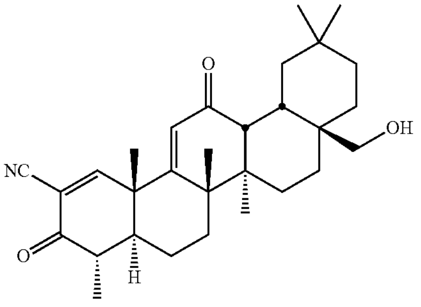 | 463.65 | 0.7 | 0.3 | 7.2 |
| TX63546 | 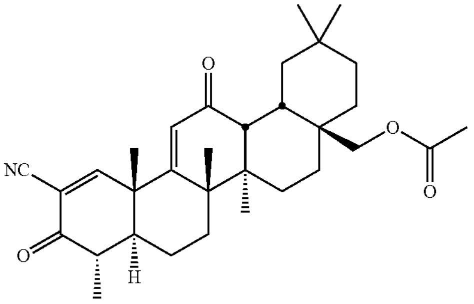 | 505.69 | 1.0 | 0.6 | |

TABLE 1-continued
| Suppression of IFNγ-Induced NO Production. | | | | | |
|---|---|---|---|---|---|
| | | | RAW264.7 | | NQO1-ARE assay |
| Compound No. | Molecular Structure | MW | NO $IC_{50}$ (nM) | Relative NO $IC_{50}$ | Fold induction at 62.5 nM |
| TX63555 | 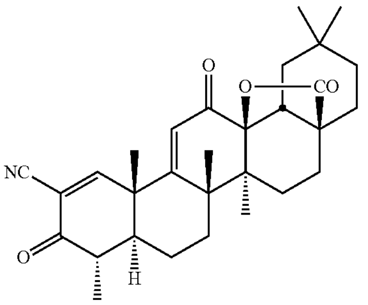 | 475.62 | 1.4 | 0.5 | 6.1 |
| TX63556 | 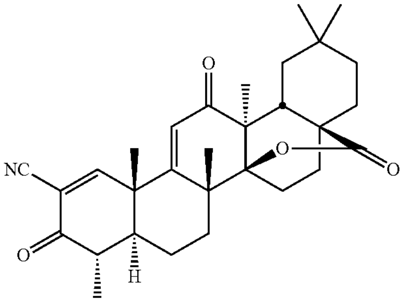 | 475.62 | 69.0 | 25.6 | |
| TX63557 | 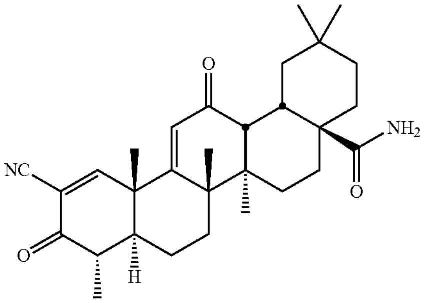 | 476.65 | 2.2 | 1.0 | |
| TX63558 | 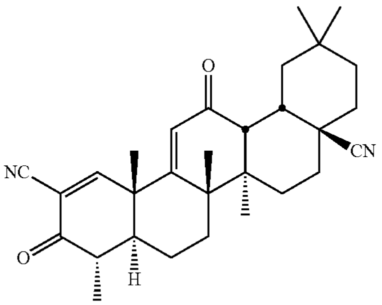 | 458.63 | 0.6 | 0.3 | |

TABLE 1-continued
Suppression of IFNγ-Induced NO Production.
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63597 | 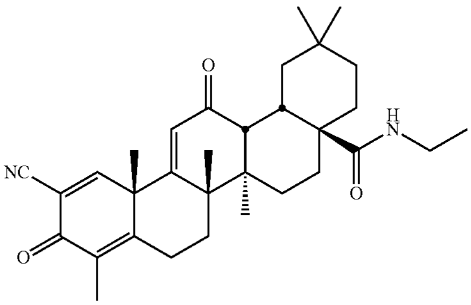 | 502.69 | >25 | >12 | |
| TX63614 | 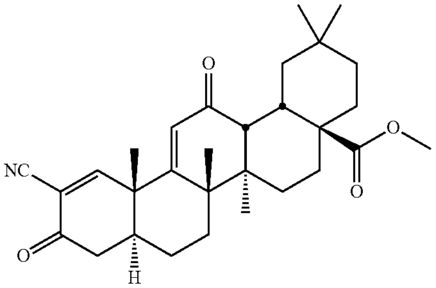 | 477.63 | 11.7 | 5.9 | |
| TX63616 | 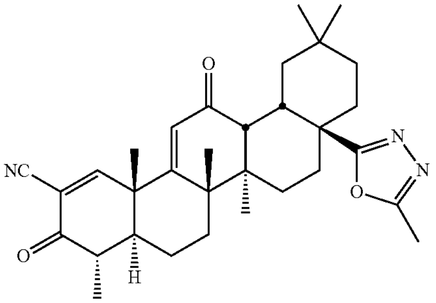 | 515.69 | 0.7 | 0.5 | 4.4 |
| TX63618 | 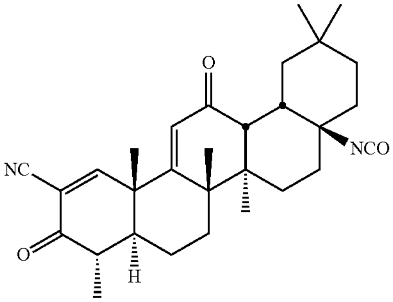 | 474.63 | 8.2 | 5.9 | |
| TX63620 | 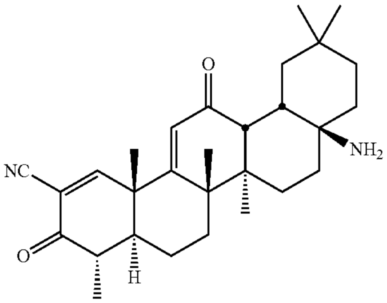 | 448.64 | 1.2 | 0.9 | |

TABLE 1-continued
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63621 | 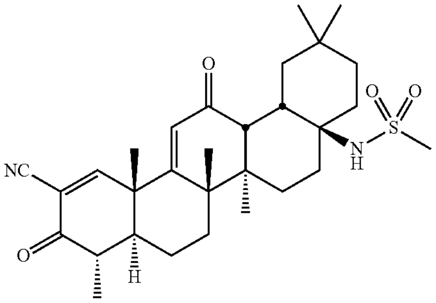 | 526.73 | 0.8 | 0.6 | |
| TX63622 | 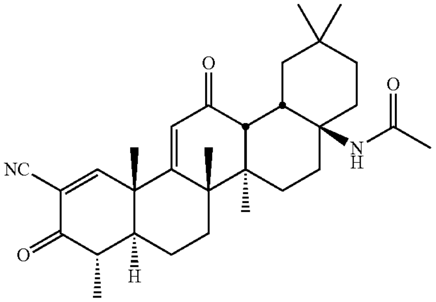 | 490.68 | 3.8 | 2.3 | |
| TX63680 | 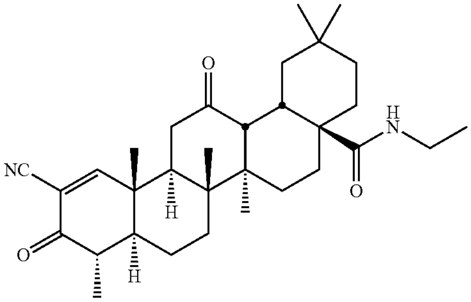 | 506.72 | 7.0 | 3.6 | |
| TX63681 | 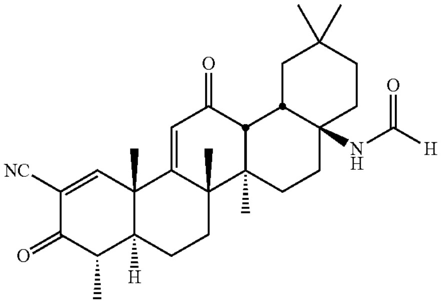 | 476.65 | 1.6 | 1.1 | |
Suppression of IFNγ-Induced NO Production.

TABLE 1-continued
Suppression of IFNγ-Induced NO Production.
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63682 | 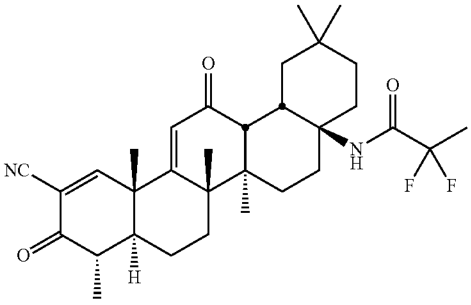 | 540.68 | 1.1 | 0.65 | 5.7 |
| TX63693 | 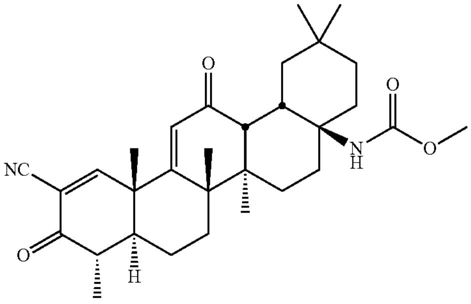 | 506.68 | 1.4 | 0.8 | |
| TX63716 | 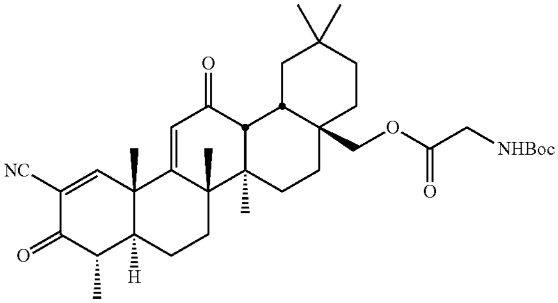 | 620.82 | 3.2 | 2.0 | |
| TX63717 | 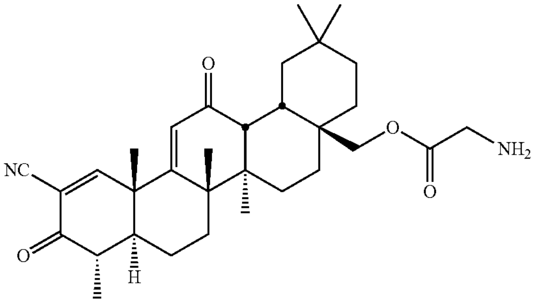 | 520.70 | 0.6 | 0.4 | |

TABLE 1-continued
Suppression of IFNγ-Induced NO Production.
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63749 | 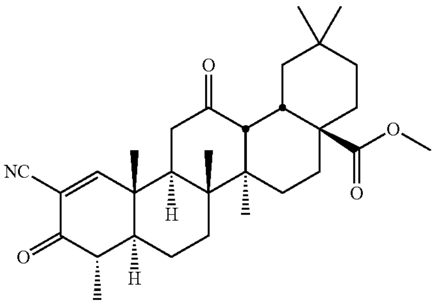 | 493.68 | 3.0 | 2.1 | 2.3 |
| TX63778 | 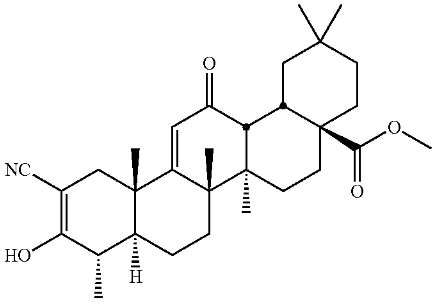 | 493.68 | 50 | 39 | |
| TX63779 | 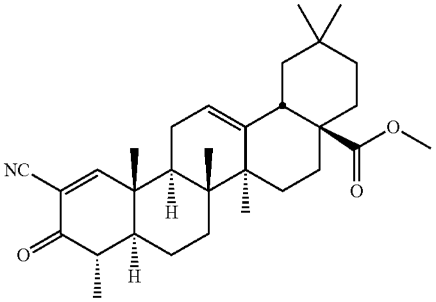 | 477.68 | 44 | 34 | |
| TX63784 | 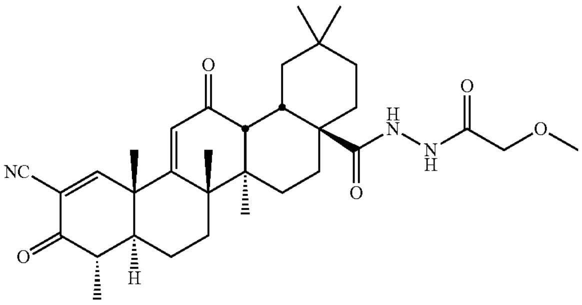 | 563.73 | 7.5 | 6.2 | |

TABLE 1-continued
| | Suppression of IFNγ-Induced NO Production. | | | | |
|---|---|---|---|---|---|
| | | | RAW264.7 | | NQO1-ARE assay |
| Compound No. | Molecular Structure | MW | NO $IC_{50}$ (nM) | Relative NO $IC_{50}$ | Fold induction at 62.5 nM |
| TX63785 | 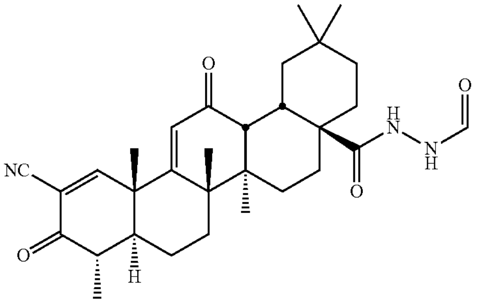 | 519.67 | 20.0 | 16.4 | |
| TX63786 | 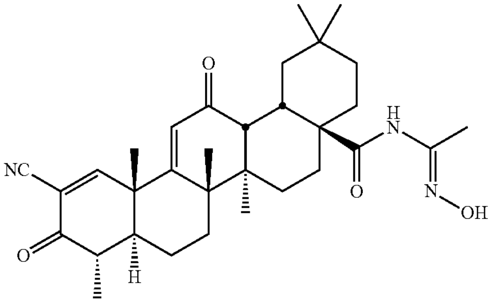 | 533.70 | 2.2 | 1.8 | |
| TX63787 | 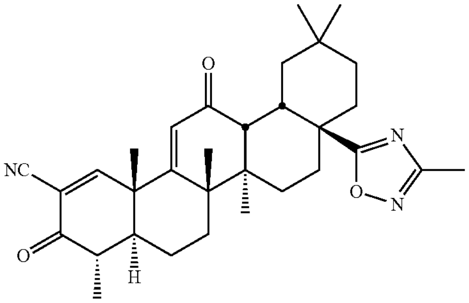 | 515.69 | 0.8 | 0.4 | |
| TX63788 | 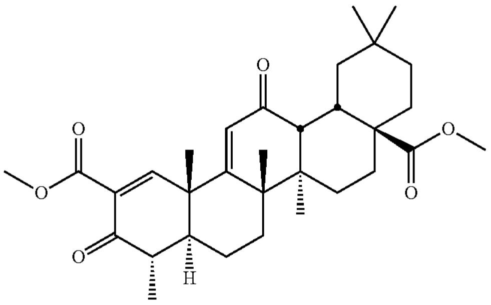 | 524.69 | 33.5 | 32 | |

TABLE 1-continued
Suppression of IFNγ-Induced NO Production.
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63789 | 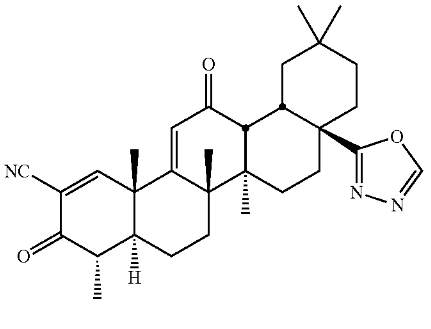 | 501.66 | 0.6 | 0.3 | |
| TX63790 | 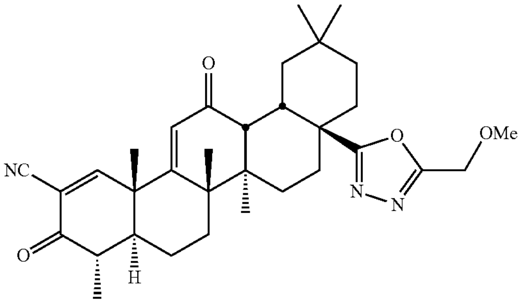 | 545.71 | 1.1 | 0.6 | |
| TX63795 | 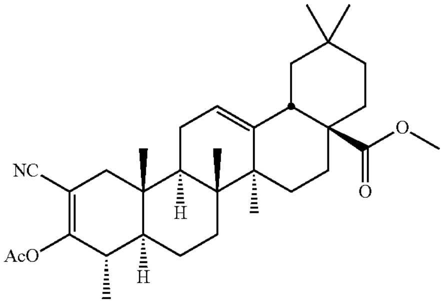 | 521.73 | >200 | NA | |
| TX63797 | 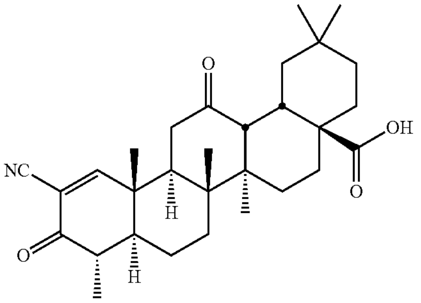 | 479.65 | 21 | 17 | |

TABLE 1-continued
Suppression of IFNγ-Induced NO Production.
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63798 | 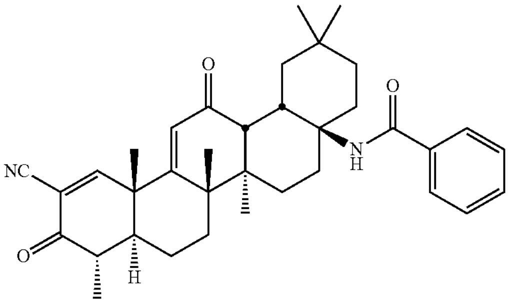 | 552.75 | 1.5 | 1.2 | |
| TX63799 | 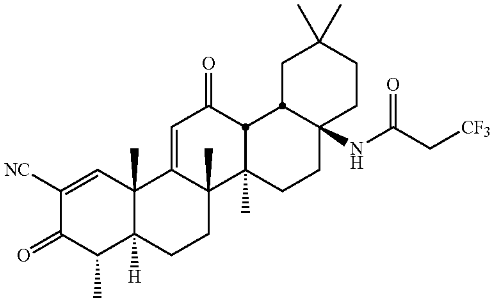 | 558.67 | 1.8 | 1.6 | |
| TX63800 | 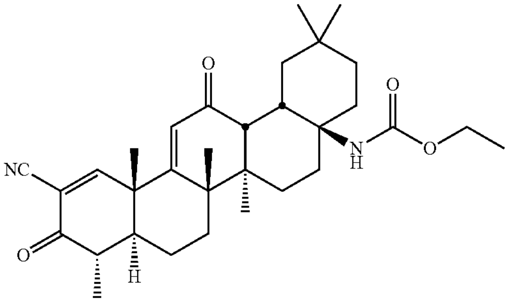 | 520.70 | 0.9 | 0.8 | |
| TX63807 | 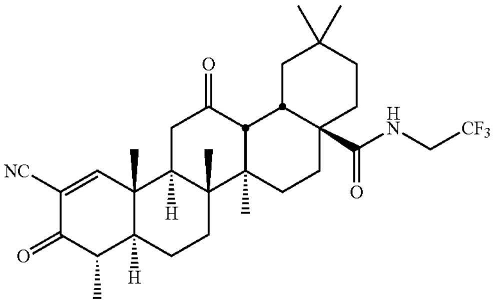 | 560.69 | 5.8 | 2.6 | |

TABLE 1-continued
Suppression of IFNγ-Induced NO Production.
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63811 | 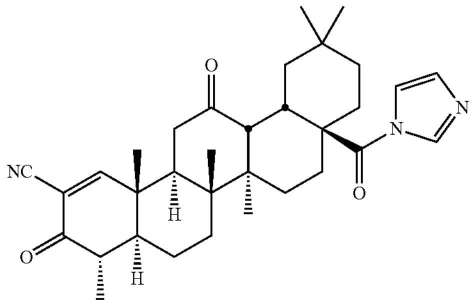 | 529.71 | 0.3 | 0.2 | |
| TX63812 | 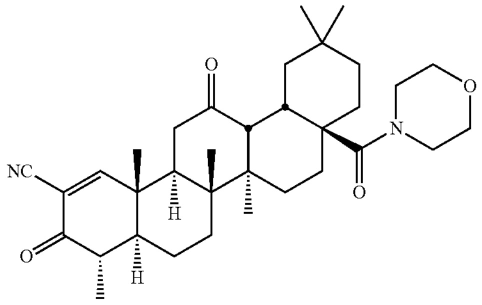 | 548.76 | 10.1 | 4.4 | |
| TX63814 | 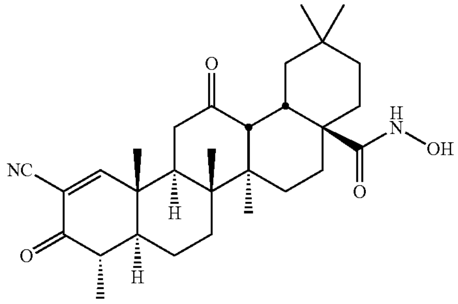 | 494.67 | 19.0 | 8.3 | |
| TX63815 | 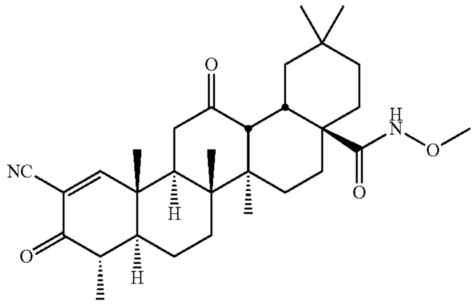 | 508.69 | 9.6 | 4.2 | |

TABLE 1-continued
Suppression of IFNγ-Induced NO Production.
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63816 | 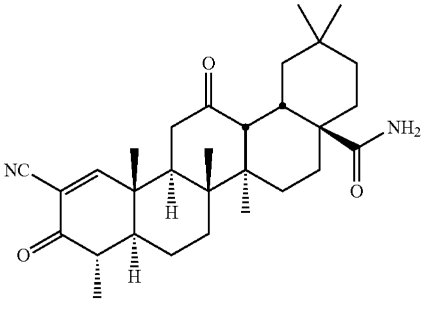 | 478.67 | 10.2 | 4.5 | |
| TX63817 | 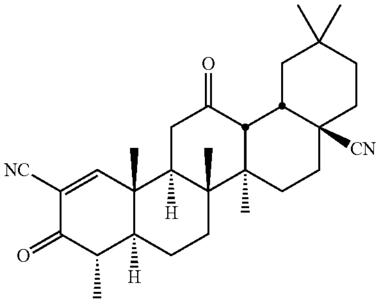 | 460.65 | 2.6 | 1.1 | |
| TX63818 | 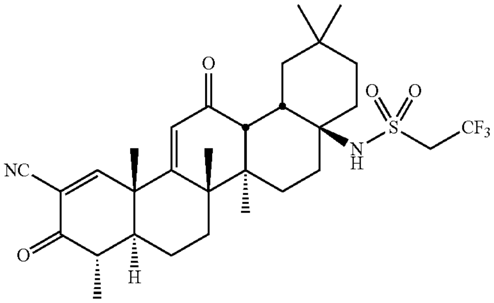 | 594.73 | 0.8 | 0.6 | |
| TX63819 | 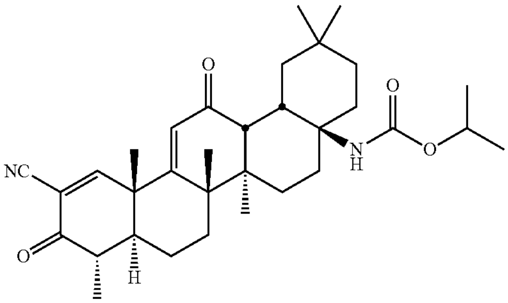 | 534.73 | 2.7 | 2.2 | |

TABLE 1-continued
Suppression of IFNγ-Induced NO Production.
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63820 | 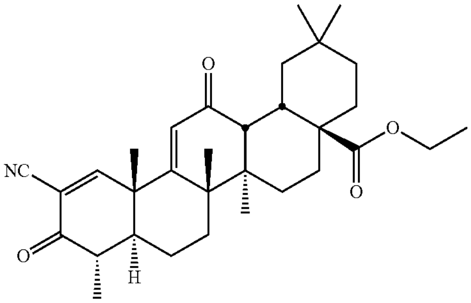 | 505.69 | 1.5 | 1.2 | |
| TX63821 | 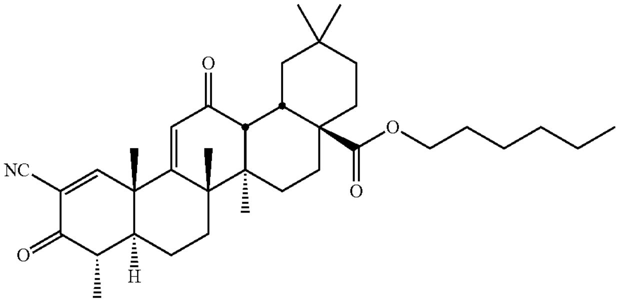 | 561.79 | 53 | 41 | |
| TX63822 | 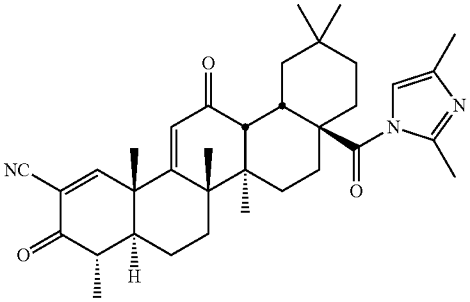 | 555.75 | 0.7 | 0.6 | |
| TX63823 | 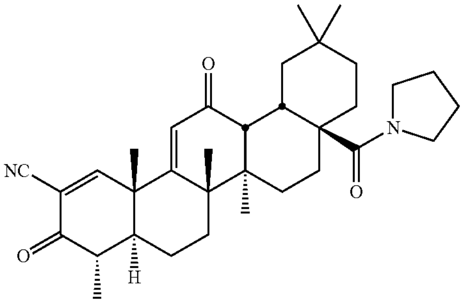 | 530.74 | 0.8 | 0.6 | |

TABLE 1-continued
Suppression of IFNγ-Induced NO Production.
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63824 | 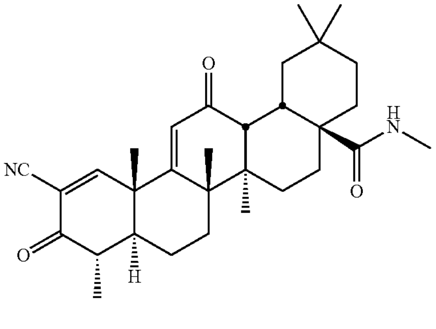 | 490.68 | 1.0 | 0.5 | |
| TX63825 | 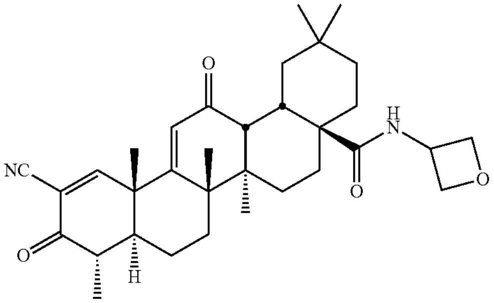 | 532.71 | 2.0 | 1.5 | |
| TX63826 | 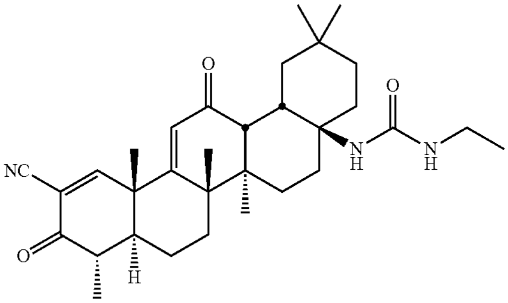 | 519.72 | 4.4 | 3.5 | |
| TX63830 | 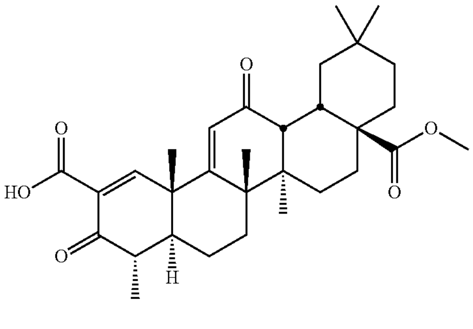 | 510.66 | 4.6 | 3.6 | |

TABLE 1-continued
Suppression of IFNγ-Induced NO Production.
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63831 | 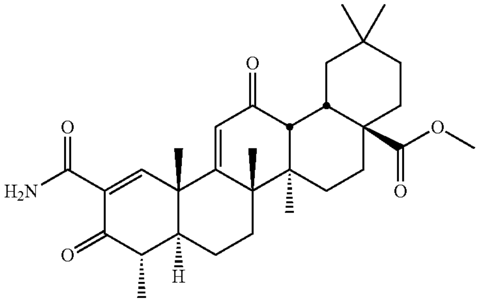 | 509.68 | 21 | 16.4 | |
| TX63832 | 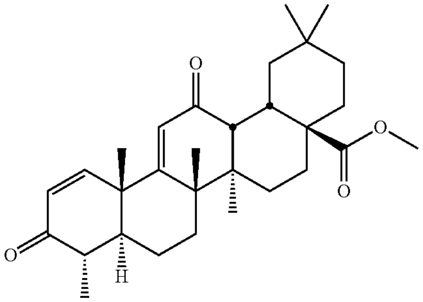 | 466.65 | 149 | 89 | |
| TX63833 | 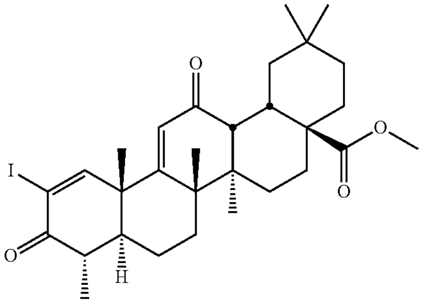 | 592.55 | 88 | 63 | |
| TX63839 | 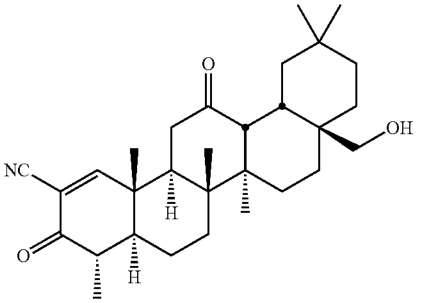 | 465.67 | 4.0 | 2.9 | |

TABLE 1-continued
Suppression of IFNγ-Induced NO Production.
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63840 | 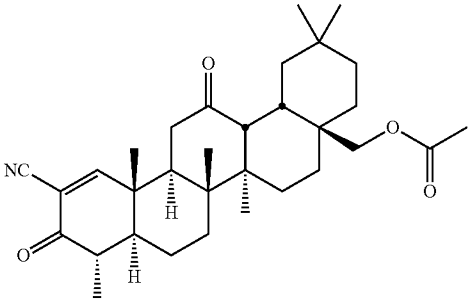 | 507.70 | 2.9 | 2.1 | |
| TX63841 | 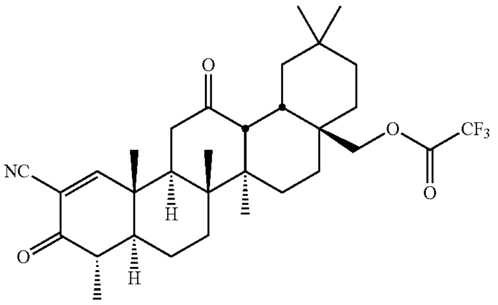 | 561.68 | 4.5 | 3.2 | |
| TX63842 | 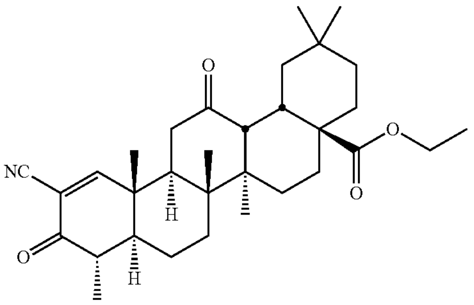 | 507.70 | 6.1 | 4.3 | |
| TX63843 | 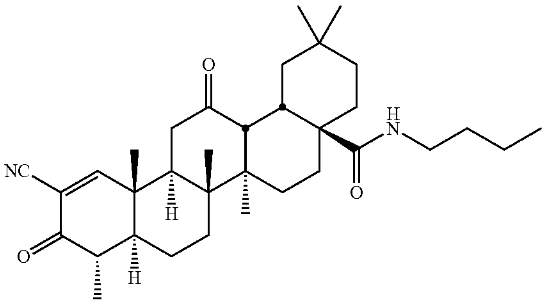 | 534.77 | 10.9 | 7.8 | |

TABLE 1-continued
Suppression of IFNγ-Induced NO Production.
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63858 | 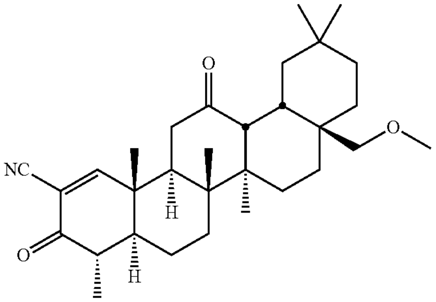 | 479.69 | 7.2 | 3.7 | |
| TX63859 | 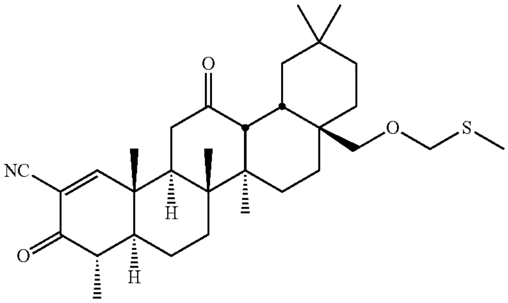 | 525.79 | 14.6 | 7.4 | |
| TX63860 | 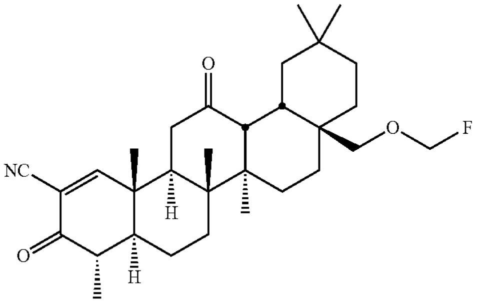 | 497.68 | 4.1 | 2.1 | |
| TX63862 | 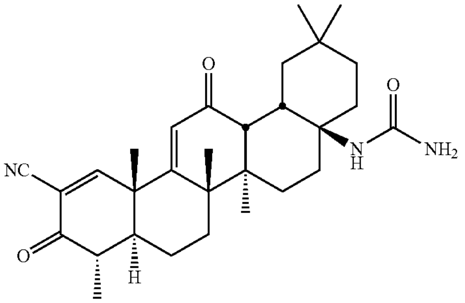 | 491.66 | 28 | 22.7 | |

TABLE 1-continued
Suppression of IFNγ-Induced NO Production.
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63863 | 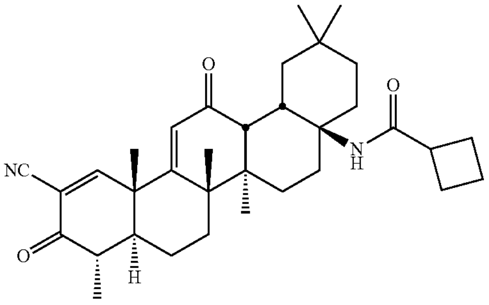 | 530.74 | 1.8 | 1.5 | |
| TX63864 | 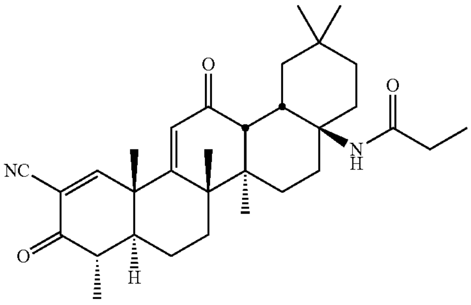 | 504.70 | 1.9 | 1.5 | |
| TX63865 | 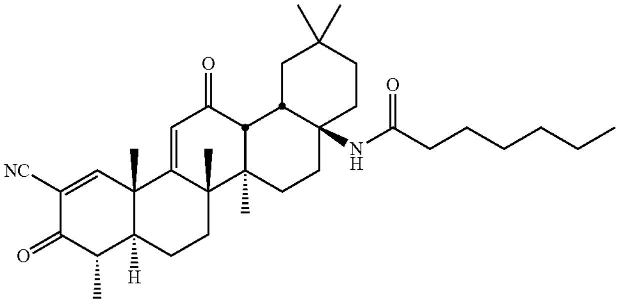 | 560.81 | 9.4 | 7.6 | |
| TX63866 | 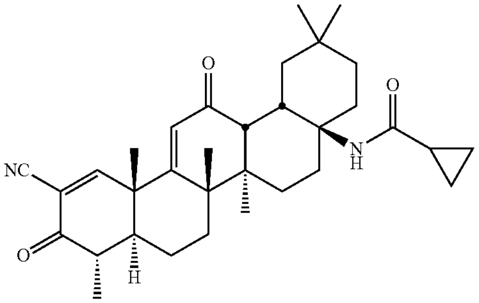 | 516.71 | 1.4 | 1.2 | |

TABLE 1-continued
Suppression of IFNγ-Induced NO Production.
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63867 | 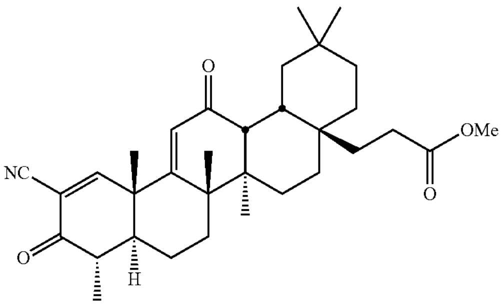 | 519.71 | 1.3 | 0.7 | |
| TX63869 | 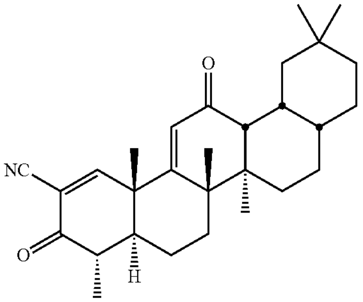 | 433.63 | 3.8 | 2.9 | |
| TX63870 | 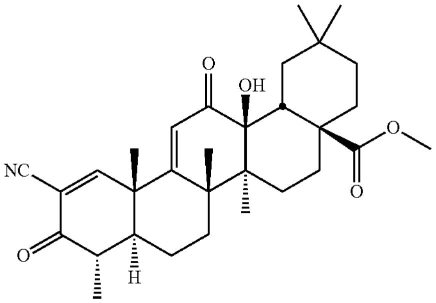 | 507.66 | 1.1 | 0.7 | |
| TX63875 | 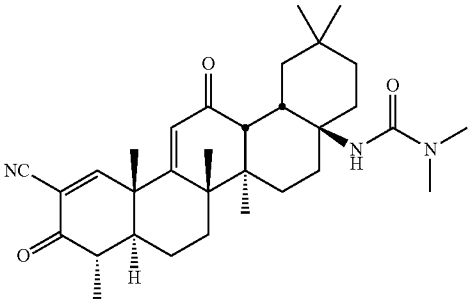 | 519.72 | 1.3 | 1.0 | |

TABLE 1-continued
Suppression of IFNγ-Induced NO Production.
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63876 | 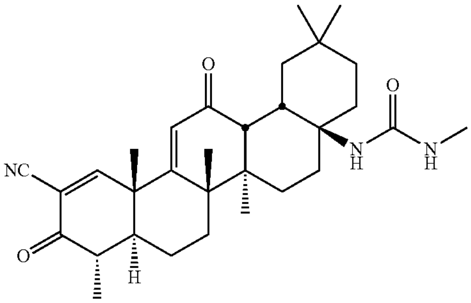 | 505.69 | 7.3 | 5.8 | |
| TX63877 | 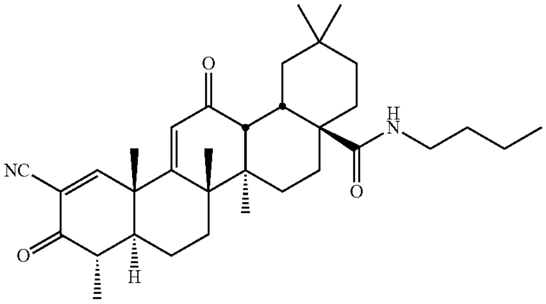 | 532.76 | 1.3 | 1.1 | |
| TX63878 | 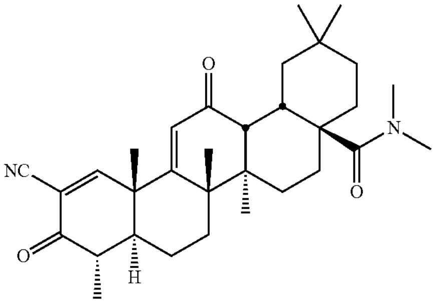 | 504.70 | 1.4 | 0.9 | |
| TX63880 | 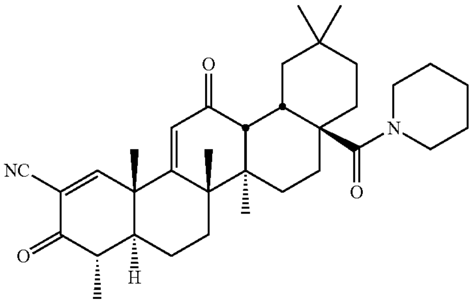 | 544.77 | 1.6 | 1.2 | |

TABLE 1-continued
Suppression of IFNγ-Induced NO Production.
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63881 | 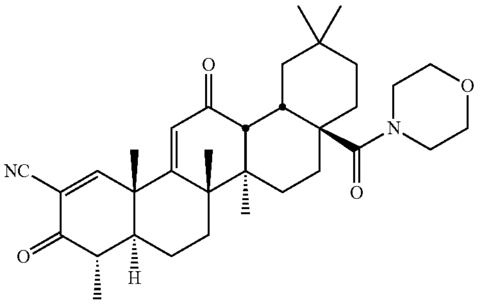 | 546.74 | 0.9 | 0.7 | |
| TX63882 | 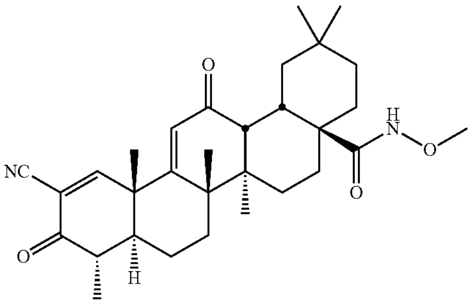 | 506.68 | 1.6 | 1.2 | |
| TX63886 | 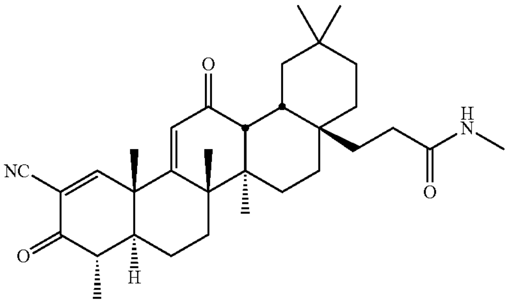 | 518.73 | 0.3 | 0.2 | |
| TX63887 | 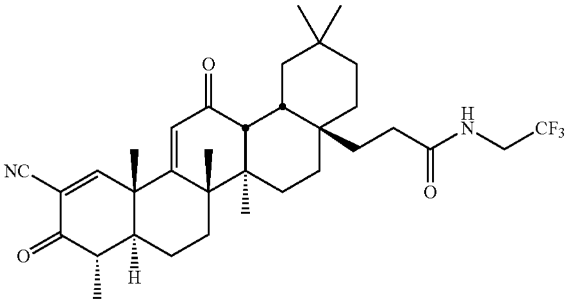 | 586.73 | 0.8 | 0.6 | |

TABLE 1-continued
Suppression of IFNγ-Induced NO Production.
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63888 | 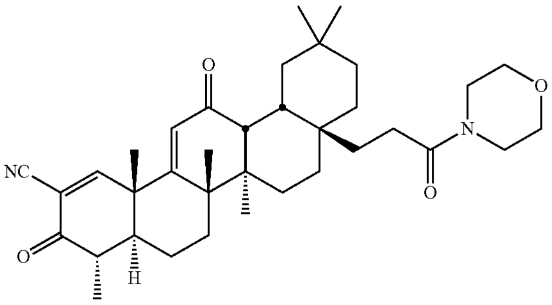 | 574.79 | 0.3 | 0.3 | |
| TX63889 | 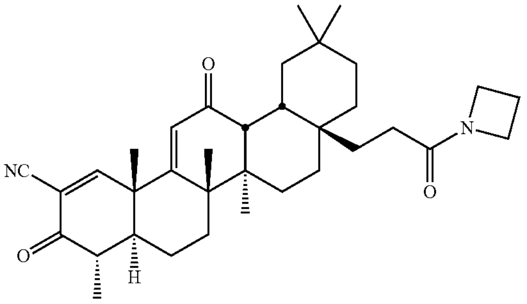 | 544.77 | 0.4 | 0.3 | |
| TX63890 | 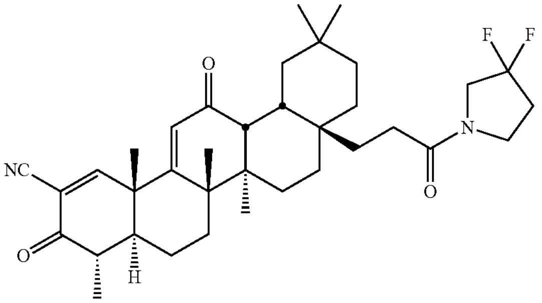 | 594.77 | 0.8 | 0.6 | |
| TX63891 | 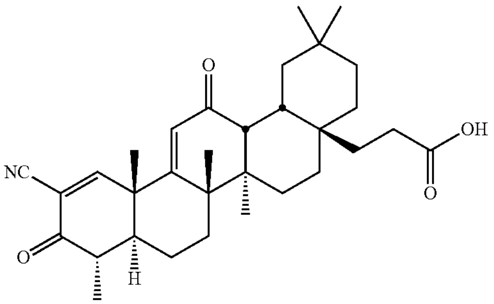 | 505.69 | 1.3 | 1.1 | |

TABLE 1-continued
Suppression of IFNγ-Induced NO Production.
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63892 | 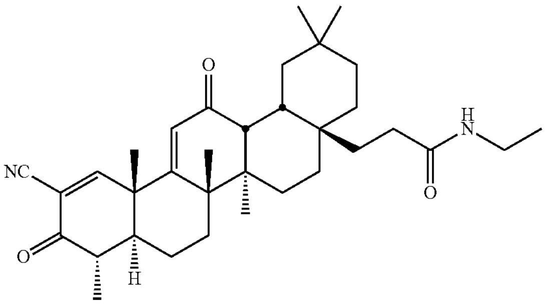 | 532.76 | 0.3 | 0.2 | |
| TX63893 | 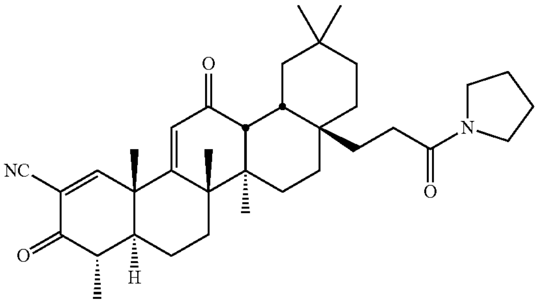 | 558.79 | 0.5 | 0.4 | |
| TX63901 | 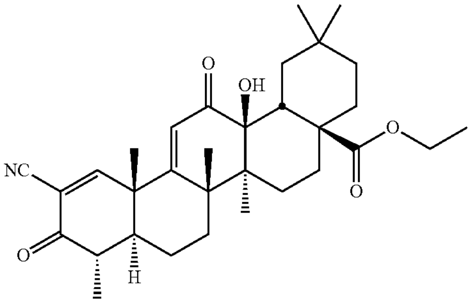 | 521.69 | 1.3 | 0.8 | |
| TX63904 | 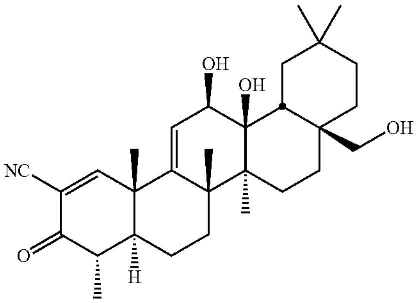 | 481.67 | 10.4 | 6.3 | |

TABLE 1-continued
Suppression of IFNγ-Induced NO Production.
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63907 | 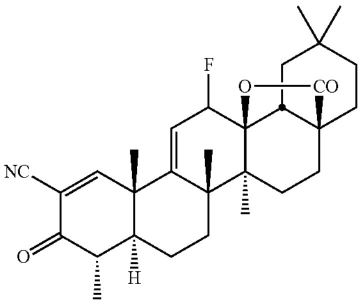 | 479.63 | 1.6 | 1.0 | |
| TX63908 | 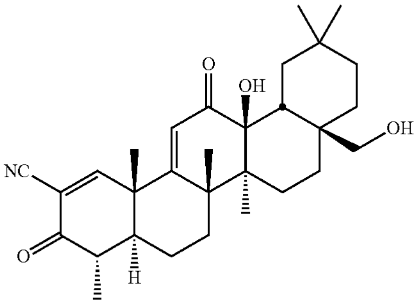 | 479.65 | 0.6 | 0.4 | |
| TX63909 | 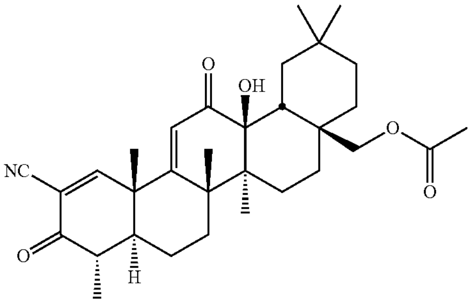 | 521.69 | 1.4 | 0.8 | |
| TX63910 | 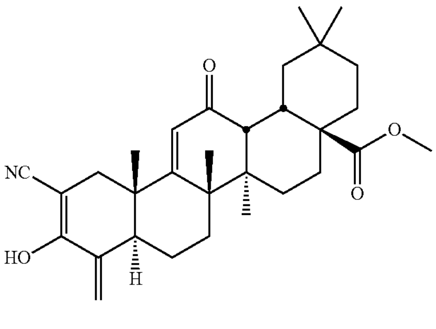 | 491.66 | 304 | 230 | |

TABLE 1-continued
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| | Suppression of IFNγ-Induced NO Production. | | | | |
| TX63911 | 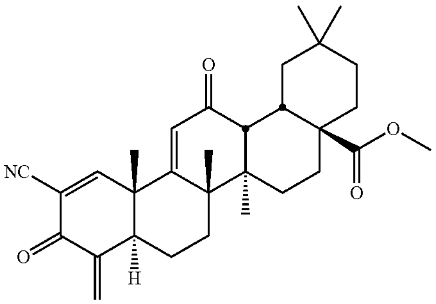 | 489.65 | 10.0 | 7.6 | |
| TX63914 | 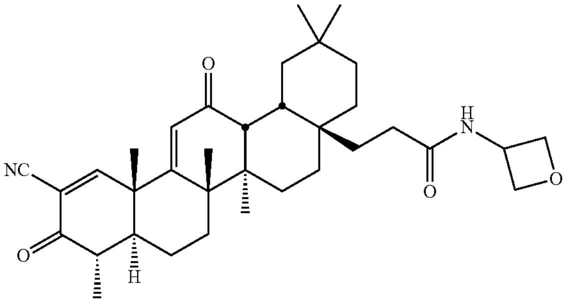 | 560.77 | 0.4 | 0.3 | |
| TX63915 | 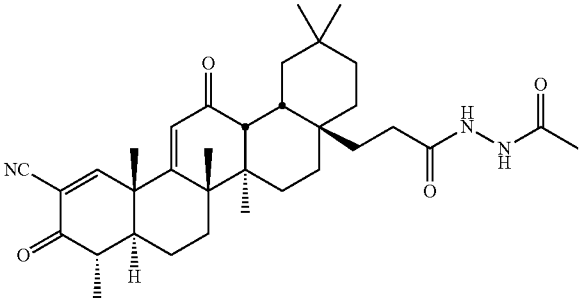 | 561.75 | 4.0 | 3.1 | |
| TX63916 | 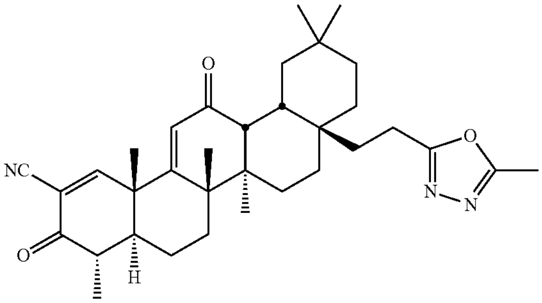 | 543.74 | 0.4 | 0.3 | |

TABLE 1-continued
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63918 | 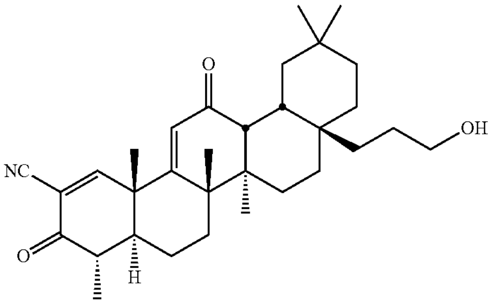 | 491.70 | 0.5 | 0.5 | |
| TX63919 | 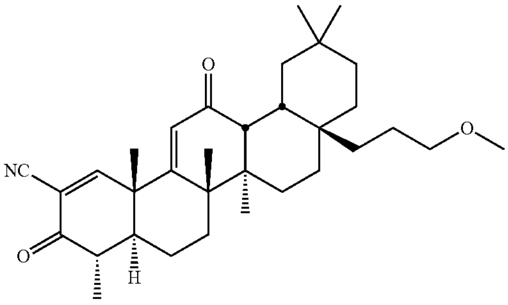 | 505.73 | 1.4 | 1.2 | |
| TX63920 | 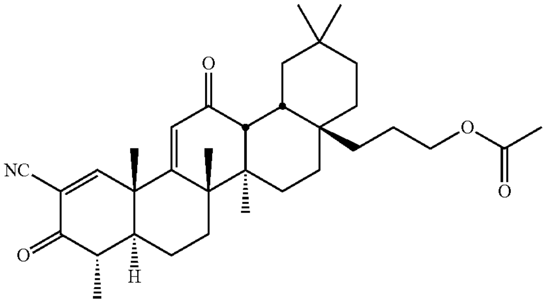 | 533.74 | 0.9 | 0.8 | |
| TX63923 | 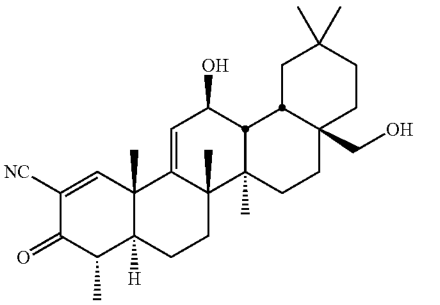 | 465.67 | 2.5 | 1.8 | |
Suppression of IFNγ-Induced NO Production.

TABLE 1-continued
Suppression of IFNγ-Induced NO Production.
| Compound No. | Molecular Structure | MW | RAW264.7 NO $IC_{50}$ (nM) | RAW264.7 Relative NO $IC_{50}$ | NQO1-ARE assay Fold induction at 62.5 nM |
|---|---|---|---|---|---|
| TX63925 | 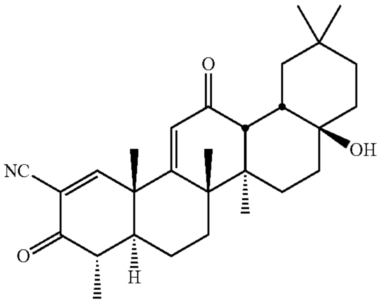 | 449.62 | 0.4 | 0.3 | |
| TX63928 | 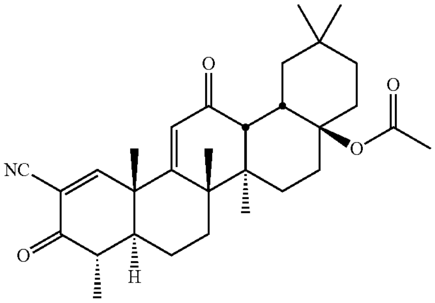 | 491.66 | 0.6 | 0.4 | |
| TX63929 | 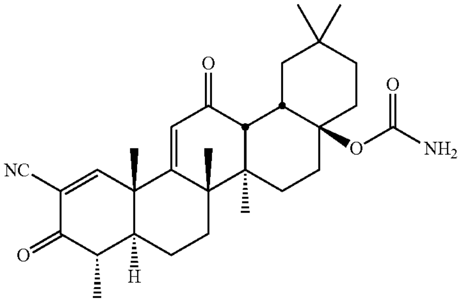 | 492.65 | 0.5 | 0.3 | |
| TX63936 | 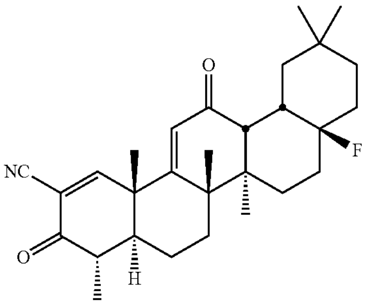 | 451.62 | 1.1 | 0.7 | |

TABLE 1-continued

| Suppression of IFNγ-Induced NO Production. | | | RAW264.7 | | NQO1-ARE assay |
|---|---|---|---|---|---|
| Compound No. | Molecular Structure | MW | NO $IC_{50}$ (nM) | Relative NO $IC_{50}$ | Fold induction at 62.5 nM |
| TX63982 | 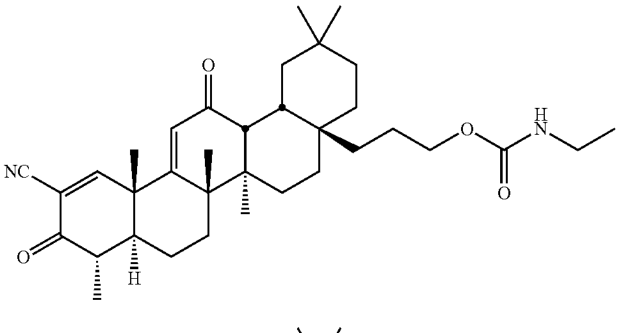 | 562.78 | 3.5 | 1.4 | |
| TX63984 | 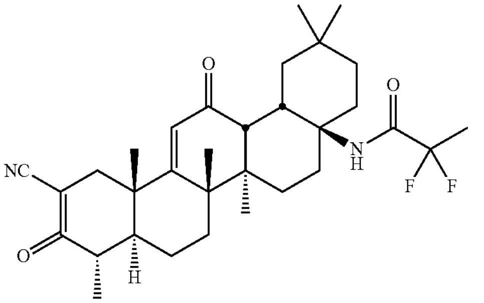 | 542.70 | 48 | 18 | |

IV. Diseases Associated with Inflammation and/or Oxidative Stress

Inflammation is a biological process that provides resistance to infectious or parasitic organisms and the repair of damaged tissue. Inflammation is commonly characterized by localized vasodilation, redness, swelling, and pain, the recruitment of leukocytes to the site of infection or injury, production of inflammatory cytokines such as TNF-α and IL-1, and production of reactive oxygen or nitrogen species such as hydrogen peroxide, superoxide and peroxynitrite. In later stages of inflammation, tissue remodeling, angiogenesis, and scar formation (fibrosis) may occur as part of the wound healing process. Under normal circumstances, the inflammatory response is regulated and temporary and is resolved in an orchestrated fashion once the infection or injury has been dealt with adequately. However, acute inflammation can become excessive and life-threatening if regulatory mechanisms fail. Alternatively, inflammation can become chronic and cause cumulative tissue damage or systemic complications. Based at least on the evidence presented above, the compounds of this invention may be used in the treatment or prevention of inflammation or diseases associated with inflammation.

Many serious and intractable human diseases involve dysregulation of inflammatory processes, including diseases such as cancer, atherosclerosis, and diabetes, which were not traditionally viewed as inflammatory conditions. In the case of cancer, the inflammatory processes are associated with tumor formation, progression, metastasis, and resistance to therapy. Atherosclerosis, long viewed as a disorder of lipid metabolism, is now understood to be primarily an inflammatory condition, with activated macrophages playing an important role in the formation and eventual rupture of atherosclerotic plaques. Activation of inflammatory signaling pathways has also been shown to play a role in the development of insulin resistance, as well as in the peripheral tissue damage associated with diabetic hyperglycemia. Excessive production of reactive oxygen species and reactive nitrogen species such as superoxide, hydrogen peroxide, nitric oxide, and peroxynitrite is a hallmark of inflammatory conditions. Evidence of dysregulated peroxynitrite production has been reported in a wide variety of diseases (Szabo et al., 2007; Schulz et al., 2008; Forstermann, 2006; Pall, 2007).

Autoimmune diseases such as rheumatoid arthritis, lupus, psoriasis, and multiple sclerosis involve inappropriate and chronic activation of inflammatory processes in affected tissues, arising from dysfunction of self vs. non-self recognition and response mechanisms in the immune system. In neurodegenerative diseases such as Alzheimer's and Parkinson's diseases, neural damage is correlated with activation of microglia and elevated levels of pro-inflammatory proteins such as inducible nitric oxide synthase (iNOS). Chronic organ failure such as renal failure, heart failure, liver failure, and chronic obstructive pulmonary disease is closely associated with the presence of chronic oxidative stress and inflammation, leading to the development of fibrosis and eventual loss of organ function. Oxidative stress in vascular endothelial cells, which line major and minor blood vessels, can lead to endothelial dysfunction and is believed to be an important contributing factor in the development of systemic cardiovascular disease, complications of diabetes, chronic kidney disease and other forms of organ failure, and a number of other aging-related diseases including degenerative diseases of the central nervous system and the retina.

Many other disorders involve oxidative stress and inflammation in affected tissues, including inflammatory bowel disease; inflammatory skin diseases; mucositis related to radiation therapy and chemotherapy; eye diseases such as uveitis, glaucoma, macular degeneration, and various forms of retinopathy; transplant failure and rejection; ischemia-reperfusion injury; chronic pain; degenerative conditions of the bones and joints including osteoarthritis and osteoporosis; asthma and cystic fibrosis; seizure disorders; and neuropsychiatric conditions including schizophrenia, depression, bipolar disorder, post-traumatic stress disorder, attention deficit disorders, autism-spectrum disorders, and eating disorders such as anorexia nervosa. Dysregulation of inflammatory signaling pathways is believed to be a major factor in the pathology of muscle wasting diseases including muscular dystrophy and various forms of cachexia.

A variety of life-threatening acute disorders also involve dysregulated inflammatory signaling, including acute organ failure involving the pancreas, kidneys, liver, or lungs, myocardial infarction or acute coronary syndrome, stroke, septic shock, trauma, severe burns, and anaphylaxis.

Many complications of infectious diseases also involve dysregulation of inflammatory responses. Although an inflammatory response can kill invading pathogens, an excessive inflammatory response can also be quite destructive and in some cases can be a primary source of damage in infected tissues. Furthermore, an excessive inflammatory response can also lead to systemic complications due to overproduction of inflammatory cytokines such as TNF-$\alpha$ and IL-1. This is believed to be a factor in mortality arising from severe influenza, severe acute respiratory syndrome, and sepsis.

The aberrant or excessive expression of either iNOS or cyclooxygenase-2 (COX-2) has been implicated in the pathogenesis of many disease processes. For example, it is clear that NO is a potent mutagen (Tamir and Tannebaum, 1996), and that nitric oxide can also activate COX-2 (Salvemini et al., 1994). Furthermore, there is a marked increase in iNOS in rat colon tumors induced by the carcinogen, azoxymethane (Takahashi et al., 1997). A series of synthetic triterpenoid analogs of oleanolic acid have been shown to be powerful inhibitors of cellular inflammatory processes, such as the induction by IFN-$\gamma$ of inducible nitric oxide synthase (iNOS) and of COX-2 in mouse macrophages. See Honda et al. (2000a); Honda et al. (2000b), and Honda et al. (2002), which are all incorporated herein by reference.

In one aspect, compounds disclosed herein are characterized by their ability to inhibit the production of nitric oxide in macrophage-derived RAW 264.7 cells induced by exposure to $\gamma$-interferon. They are further characterized by their ability to induce the expression of antioxidant proteins such as NQO1 and reduce the expression of pro-inflammatory proteins such as COX-2 and inducible nitric oxide synthase (iNOS). These properties are relevant to the treatment of a wide array of diseases and disorders involving oxidative stress and dysregulation of inflammatory processes including cancer, complications from localized or total-body exposure to ionizing radiation, mucositis resulting from radiation therapy or chemotherapy, autoimmune diseases, cardiovascular diseases including atherosclerosis, ischemia-reperfusion injury, acute and chronic organ failure including renal failure and heart failure, respiratory diseases, diabetes and complications of diabetes, severe allergies, transplant rejection, graft-versus-host disease, neurodegenerative diseases, diseases of the eye and retina, acute and chronic pain, degenerative bone diseases including osteoarthritis and osteoporosis, inflammatory bowel diseases, dermatitis and other skin diseases, sepsis, burns, seizure disorders, and neuropsychiatric disorders.

Without being bound by theory, the activation of the antioxidant/anti-inflammatory Keap1/Nrf2/ARE pathway is believed to be implicated in both the anti-inflammatory and anti-carcinogenic properties of the compounds disclosed herein.

In another aspect, compounds disclosed herein may be used for treating a subject having a condition caused by elevated levels of oxidative stress in one or more tissues. Oxidative stress results from abnormally high or prolonged levels of reactive oxygen species such as superoxide, hydrogen peroxide, nitric oxide, and peroxynitrite (formed by the reaction of nitric oxide and superoxide). The oxidative stress may be accompanied by either acute or chronic inflammation. The oxidative stress may be caused by mitochondrial dysfunction, by activation of immune cells such as macrophages and neutrophils, by acute exposure to an external agent such as ionizing radiation or a cytotoxic chemotherapy agent (e.g., doxorubicin), by trauma or other acute tissue injury, by ischemia/reperfusion, by poor circulation or anemia, by localized or systemic hypoxia or hyperoxia, by elevated levels of inflammatory cytokines and other inflammation-related proteins, and/or by other abnormal physiological states such as hyperglycemia or hypoglycemia.

In animal models of many such conditions, stimulating expression of inducible heme oxygenase (HO-1), a target gene of the Nrf2 pathway, has been shown to have a significant therapeutic effect including models of myocardial infarction, renal failure, transplant failure and rejection, stroke, cardiovascular disease, and autoimmune disease (e.g., Sacerdoti et al., 2005; Abraham & Kappas, 2005; Bach, 2006; Araujo et al., 2003; Liu et al., 2006; Ishikawa et al., 2001; Kruger et al., 2006; Satoh et al., 2006; Zhou et al., 2005; Morse and Choi, 2005; Morse and Choi, 2002). This enzyme breaks free heme down into iron, carbon monoxide (CO), and biliverdin (which is subsequently converted to the potent antioxidant molecule, bilirubin).

In another aspect, compounds of this invention may be used in preventing or treating tissue damage or organ failure, acute and chronic, resulting from oxidative stress exacerbated by inflammation. Examples of diseases that fall in this category include: heart failure, liver failure, transplant failure and rejection, renal failure, pancreatitis, fibrotic lung diseases (cystic fibrosis, COPD, and idiopathic pulmonary fibrosis, among others), diabetes (including complications), atherosclerosis, ischemia-reperfusion injury, glaucoma, stroke, autoimmune disease, autism, macular degeneration, and muscular dystrophy. For example, in the case of autism, studies suggest that increased oxidative stress in the central nervous system may contribute to the development of the disease (Chauhan and Chauhan, 2006).

Evidence also links oxidative stress and inflammation to the development and pathology of many other disorders of the central nervous system, including psychiatric disorders such as psychosis, major depression, and bipolar disorder; seizure disorders such as epilepsy; pain and sensory syndromes such as migraine, neuropathic pain or tinnitus; and behavioral syndromes such as the attention deficit disorders. See, e.g., Dickerson et al., 2007; Hanson et al., 2005; Kendall-Tackett, 2007; Lencz et al., 2007; Dudhgaonkar et al., 2006; Lee et al., 2007; Morris et al., 2002; Ruster et al., 2005; McIver et al., 2005; Sarchielli et al., 2006; Kawakami et al., 2006; Ross et al., 2003, which are all incorporated by reference herein. For example, elevated levels of inflammatory cytokines, including TNF, interferon-$\gamma$, and IL-6, are associated with major mental illness (Dickerson et al., 2007). Microglial activation has also been linked to major mental illness. Therefore, downregulating inflammatory cytokines and inhibiting excessive activation of microglia could be beneficial in patients with schizophrenia, major depression, bipolar disorder, autism-spectrum disorders, and other neuropsychiatric disorders.

Accordingly, in pathologies involving oxidative stress alone or oxidative stress exacerbated by inflammation, treatment may comprise administering to a subject a therapeutically effective amount of a compound of this invention, such as those described above or throughout this specification. Treatment may be administered preventively, in advance of a predictable state of oxidative stress (e.g., organ transplantation or the administration of radiation therapy to a cancer patient), or it may be administered therapeutically in settings involving established oxidative stress and inflammation.

The compounds disclosed herein may be generally applied to the treatment of inflammatory conditions, such as sepsis, dermatitis, autoimmune disease and osteoarthritis. In one aspect, the compounds of this invention may be used to treat inflammatory pain and/or neuropathic pain, for example, by inducing Nrf2 and/or inhibiting NF-κB.

In some embodiments, the compounds disclosed herein may be used in the treatment and prevention of diseases such as cancer, inflammation, Alzheimer's disease, Parkinson's disease, multiple sclerosis, autism, amyotrophic lateral sclerosis, Huntington's disease, autoimmune diseases such as rheumatoid arthritis, lupus, Crohn's disease and psoriasis, inflammatory bowel disease, all other diseases whose pathogenesis is believed to involve excessive production of either nitric oxide or prostaglandins, and pathologies involving oxidative stress alone or oxidative stress exacerbated by inflammation.

Another aspect of inflammation is the production of inflammatory prostaglandins such as prostaglandin E. These molecules promote vasodilation, plasma extravasation, localized pain, elevated temperature, and other symptoms of inflammation. The inducible form of the enzyme COX-2 is associated with their production, and high levels of COX-2 are found in inflamed tissues. Consequently, inhibition of COX-2 may relieve many symptoms of inflammation and a number of important anti-inflammatory drugs (e.g., ibuprofen and celecoxib) act by inhibiting COX-2 activity. Recent research, however, has demonstrated that a class of cyclopentenone prostaglandins (cyPGs) (e.g., 15-deoxy prostaglandin J2, a.k.a. PGJ2) plays a role in stimulating the orchestrated resolution of inflammation (e.g., Rajakariar et al., 2007). COX-2 is also associated with the production of cyclopentenone prostaglandins. Consequently, inhibition of COX-2 may interfere with the full resolution of inflammation, potentially promoting the persistence of activated immune cells in tissues and leading to chronic, "smoldering" inflammation. This effect may be responsible for the increased incidence of cardiovascular disease in patients using selective COX-2 inhibitors for long periods of time.

In one aspect, the compounds disclosed herein may be used to control the production of pro-inflammatory cytokines within the cell by selectively activating regulatory cysteine residues (RCRs) on proteins that regulate the activity of redox-sensitive transcription factors. Activation of RCRs by cyPGs has been shown to initiate a pro-resolution program in which the activity of the antioxidant and cytoprotective transcription factor Nrf2 is potently induced and the activities of the pro-oxidant and pro-inflammatory transcription factors NF-κB and the STATs are suppressed. In some embodiments, this increases the production of antioxidant and reductive molecules (NQO1, HO-1, SOD1, γ-GCS) and decreases oxidative stress and the production of pro-oxidant and pro-inflammatory molecules (iNOS, COX-2, TNF-α). In some embodiments, the compounds of this invention may cause the cells that host the inflammatory event to revert to a non-inflammatory state by promoting the resolution of inflammation and limiting excessive tissue damage to the host.

V. Pharmaceutical Formulations and Routes of Administration

The compounds of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. See for example U.S. patent application by J. Zhang, entitled "Amorphous Solid Dispersions of CDDO-Me for Delayed Release Oral Dosage Compositions," filed Feb. 13, 2009, which is incorporated herein by reference. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is ±10% of the blood glucose level of a non-diabetic subject.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milli-gram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

VI. Combination Therapy

In addition to being used as a monotherapy, the compounds of the present invention may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Non-limiting examples of such combination therapy include combination of one or more compounds of the invention with another anti-inflammatory agent, a chemotherapeutic agent, radiation therapy, an antidepressant, an antipsychotic agent, an anticonvulsant, a mood stabilizer, an anti-infective agent, an antihypertensive agent, a cholesterol-lowering agent or other modulator of blood lipids, an agent for promoting weight loss, an antithrombotic agent, an agent for treating or preventing cardiovascular events such as myocardial infarction or stroke, an antidiabetic agent, an agent for reducing transplant rejection or graft-versus-host disease, an anti-arthritic agent, an analgesic agent, an anti-asthmatic agent or other treatment for respiratory diseases, or an agent for treatment or prevention of skin disorders. Compounds of the invention may be combined with agents designed to improve a patient's immune response to cancer, including (but not limited to) cancer vaccines. See Lu et al. (2011), which is incorporated herein by reference.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Methods and Materials

Nitric Oxide Production and Cell Viability.

RAW264.7 mouse macrophages were plated in 96-well plates at 30,000 cells/well in triplicate in RPMI1640+0.5% FBS and incubated at 37° C. with 5% $CO_2$. On the next day, cells were pre-treated with DMSO or drug (0-200 nM dose range) for 2 hours, and then treated with recombinant mouse IFNγ (R&D Systems) for 24 hours. Nitric Oxide concentration in media was determined using the Griess reagent system (Promega). Cell viability was determined using WST-1 reagent (Roche). $IC_{50}$ values were determined based on the suppression of IFNγ induced Nitric Oxide production normalized to cell viability.

NQO1-ARE Luciferase Reporter Assay.

This assay allows for quantitative assessment of the endogenous activity of the Nrf2 transcription factor in cultured mammalian cells. Expression of Firefly luciferase from NQO1-ARE luciferase reporter plasmid is controlled by binding of Nrf2 to a specific enhancer sequence corresponding to the antioxidant response element (ARE) that was identified in the promoter region of the human NADPH:quinone oxidoreductase 1 (NQO1) gene (Xie et al., 1995). The plasmid was constructed by inserting a sequence:

```
                                   (SEQ ID NO: 1)
5'-CAGTCACAGTGACTCAGCAGAATCTG-3'
```

encompassing the human NQO1-ARE into the pLuc-MCS vector using HindIII/XhoI cloning sites (GenScript Corp., Piscataway, N.J.). The assay is performed in HuH7 cells maintained in DMEM (Invitrogen) supplemented with 10% FBS and 100 U/ml (each) of penicillin and streptomycin. For the assay, cells are plated in 96-well plates at 17,000 cells per well. Twenty four hours later, the cells are co-transfected with 50 ng each of NQO1-ARE reporter plasmid and pRL-TK plasmid using Lipofectamine 2000 transfection reagent (Invitrogen). pRL-TK plasmid constitutively expresses *Renilla luciferase* and is used as an internal control for normalization of transfection levels. Thirty hours after transfection, the cells are treated with compounds (at concentrations ranging from 0 to 1 μM) for eighteen hours. Firefly and *Renilla luciferase* activity is assayed by Dual-Glo Luciferase Assay (Promega Corp., Madison, Wis.), the luminescence signal is measured on an L-Max II luminometer (Molecular Devices). Firefly luciferase activity is normalized to the *Renilla* activity, and fold induction over a vehicle control (DMSO) of normalized Firefly activity is calculated. The fold induction at 62.5 nM concentration is used for comparing relative potencies of compounds to induce Nrf2 transcriptional activity. See Xie et al., 1995, which is incorporated herein by reference.

Synthetic Schemes, Reagents and Yields

Scheme 1

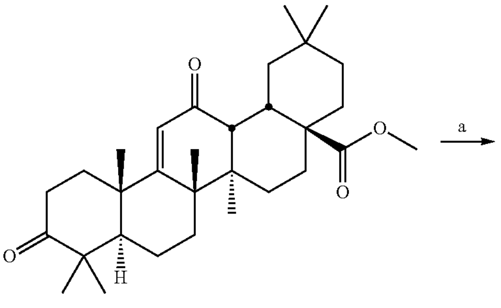

1

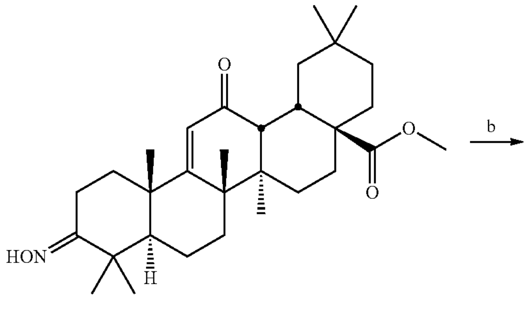

2

-continued
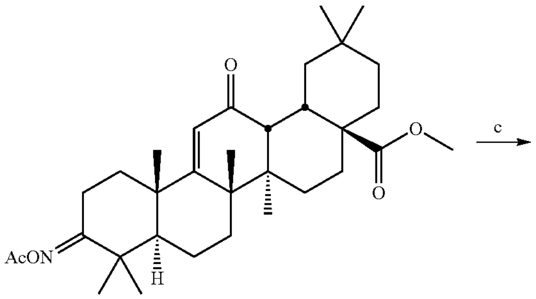
3
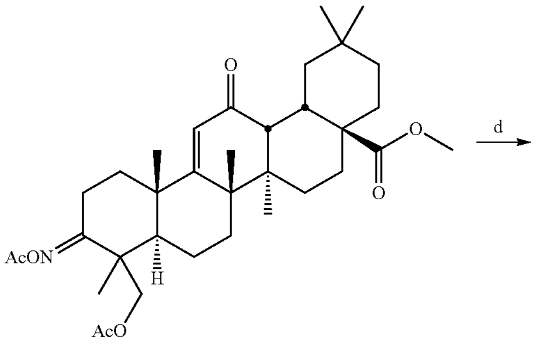
4
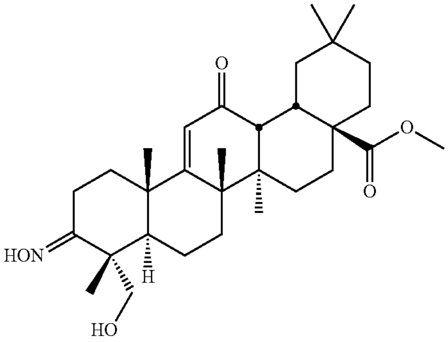
+
5
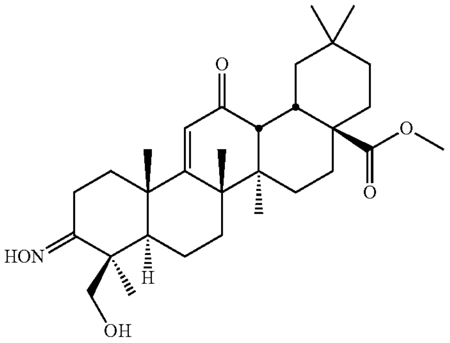
6
Reagents and conditions: a) $NH_2OH$—HCl, NaOAc, $CH_2Cl_2$, MeOH, 70° C., 1.5 h; b) AcOH, $Ac_2O$, rt, 2 h; c) $PhI(OAc)_2$, $Pd(OAc)_2$, 60° C., 24 h, 48% from 1; d) $K_2CO_3$, MeOH, 0° C.-rt, 1 h, 75% for 5, 11% for 6.
Scheme 2
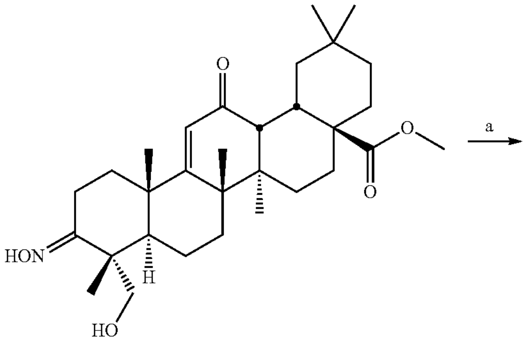
5
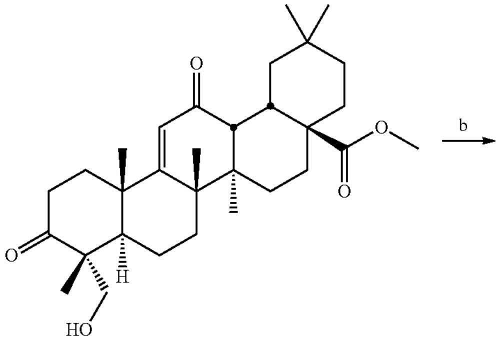
7
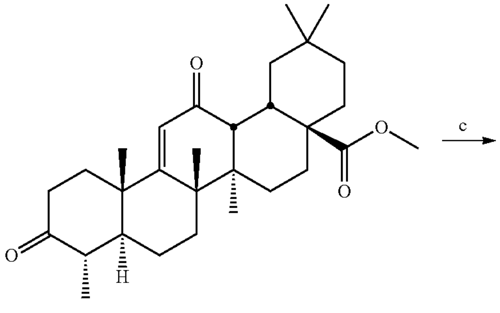
8
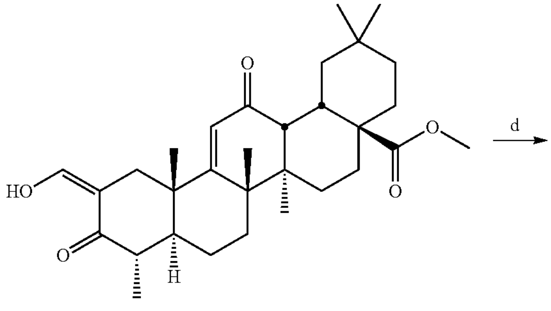
9

-continued
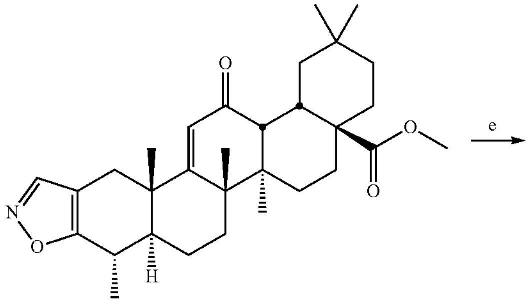
10
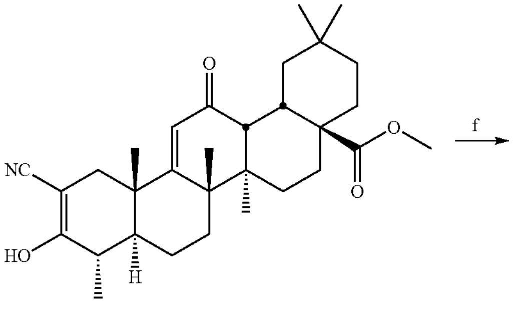
TX63778
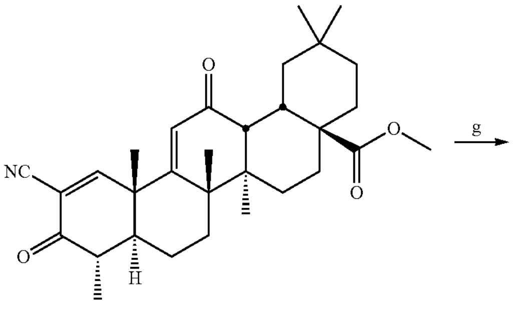
TX63435
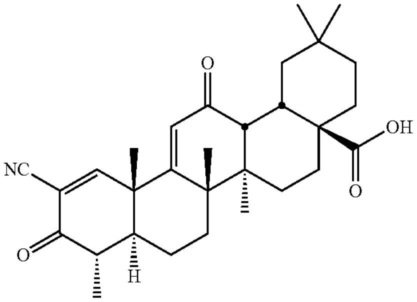
TX63520
Reagents and conditions: a) $NaHSO_3$, aq. EtOH, reflux, 3 h, 85%; b) xylene, reflux, 28 h, 85%; c) $HCO_2Et$, NaOMe, 0° C.-rt, 2.5 h; d) $NH_2OH$—HCl, aq. EtOH, 55° C., 3 h, 76% from 7; e) NaOMe, MeOH, 55° C., 2 h; f) (i) DBDMH, DMF, 0° C., 1 h; (ii) Py, 55° C., 3.5 h, 85% from 9; g) LiI, DMF, 150° C., 4 h, 64%.
Scheme 3
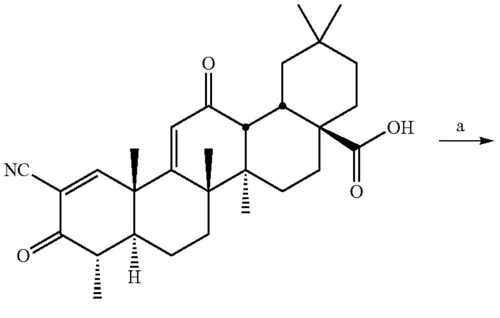
TX63520
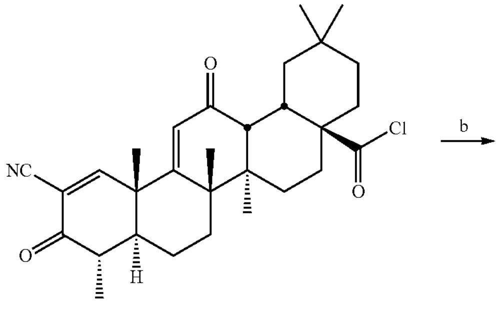
11
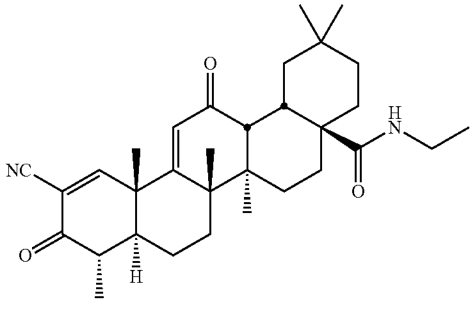
TX63521
Reagents and conditions: a) oxalyl chloride, DMF (cat.) $CH_2Cl_2$, 0° C.-rt, 2 h; b) $EtNH_2$, $CH_2Cl_2$, THF, 0° C., 30 min, 100%.
Scheme 4. Alternative synthetic route to TX63521
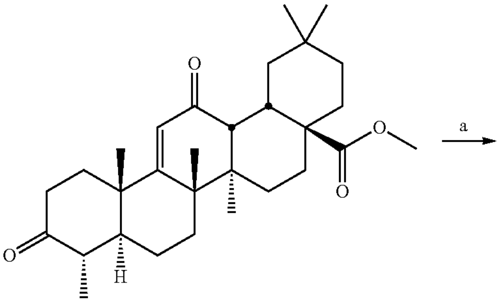
7

-continued
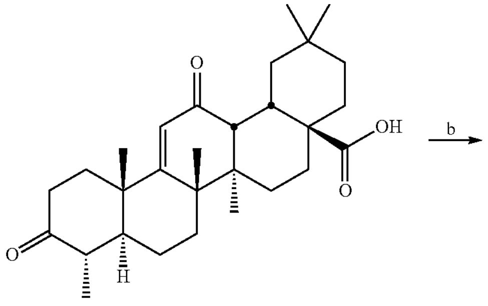
12
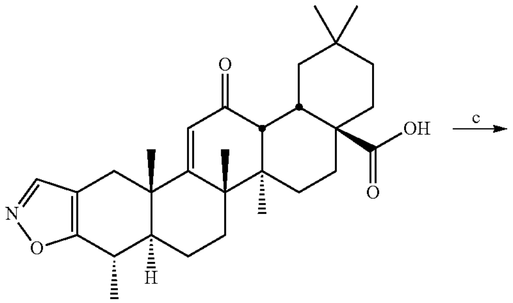
13
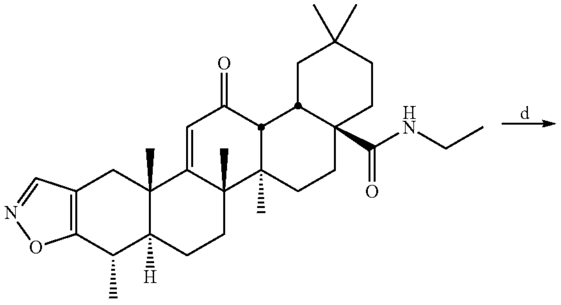
14
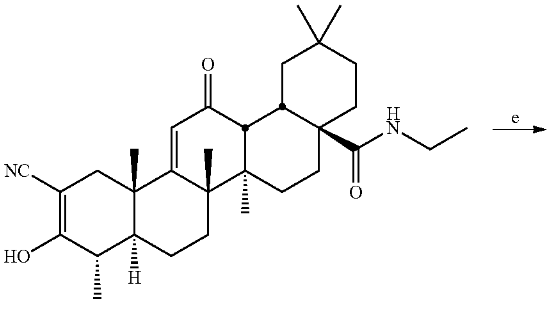
15
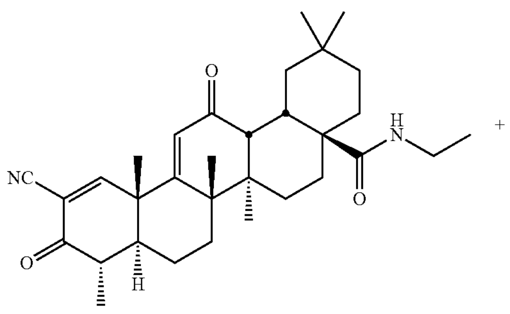
TX63521
-continued
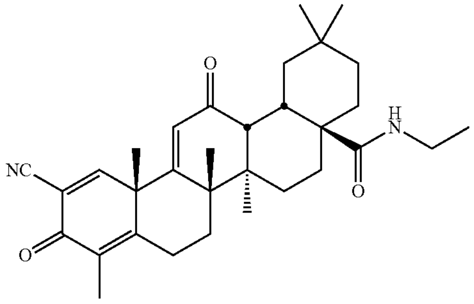
TX63597
Reagents and conditions: a) LiI, DMF, 150° C., 5-8 h, 93%; b) (i) HCOOEt, NaOMe, MeOH, 0° C. to rt, 1 h; (ii) $NH_2OH$—HCl, 55° C., 3 h, 80%; c) (i) $(COCl)_2$, $CH_2Cl_2$, DMF, 0° C. to rt, 2 h; (ii) $EtNH_2$, $CH_2Cl_2$,THF, 0° C., 40 min, 86%; d) NaOMe, MeOH, 55° C., 2 h, 92%; e) (i) DBDMH, DMF, 0° C., 1 h; (ii) Py, 55° C., 3 h, 82%.
Scheme 5
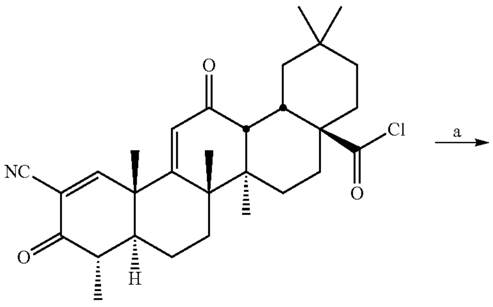
11
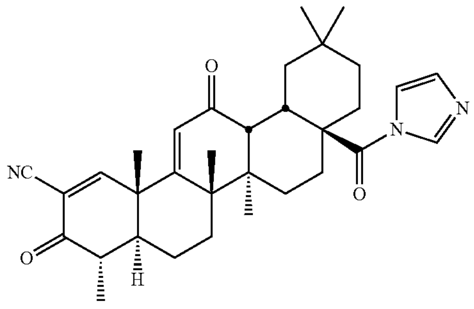
TX635522
Reagents and conditions: a) imidazole, benzene, 10° C., 70 min, 77%.

Scheme 6
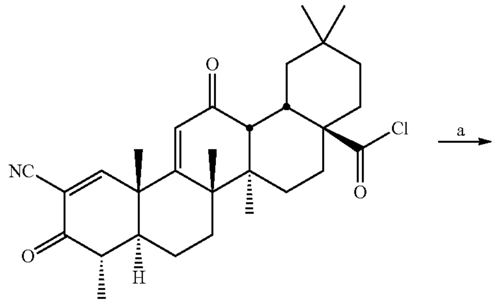
11
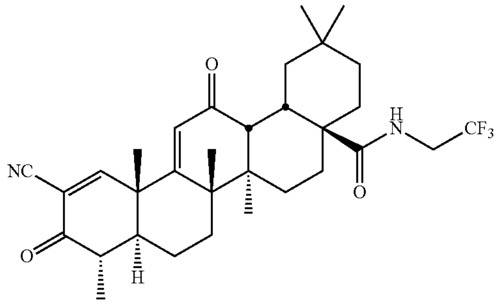
TX635523
Reagents and conditions: a) $CF_3CH_2NH_2$, $CH_2Cl_2$, rt, 1 h, 82%.
Scheme 7. Alternative synthetic route to TX63523
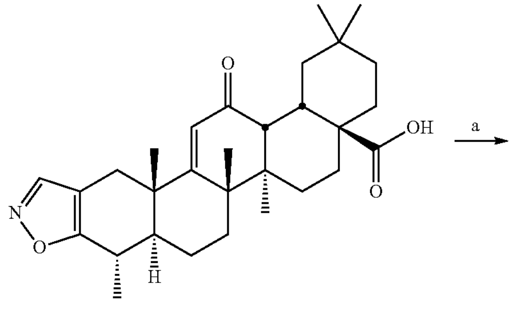
13
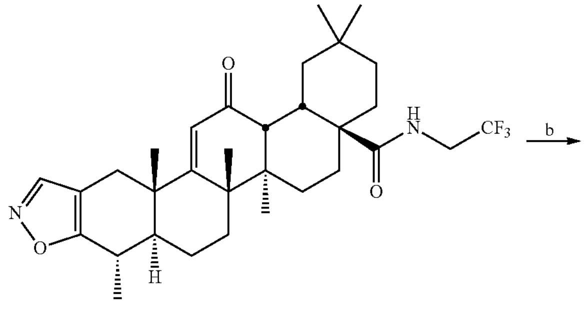
16
-continued
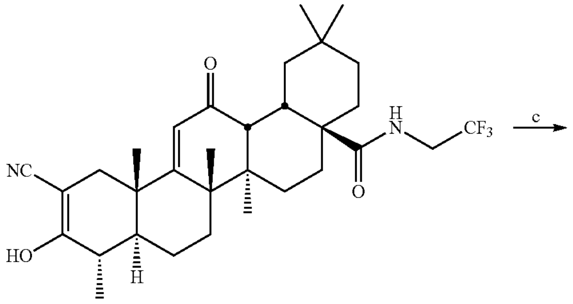
17
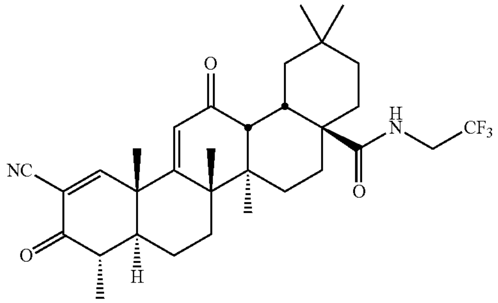
TX63523
Reagents and conditions: a) (i) $(COCl)_2$, $CH_2Cl_2$, DMF, 0° C. to rt, 2 h; (ii) $CF_3CH_2NH_2$, $CH_2Cl_2$, 0° C., 90 min, 85%; d) NaOMe, MeOH, 55° C., 2 h, 81%; e) (i) DBDMH, DMF, 0° C., 1 h; (ii) Pyridine, 55° C., 3 h, 86%.
Scheme 8
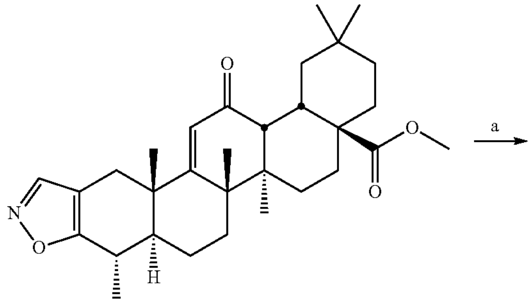
9
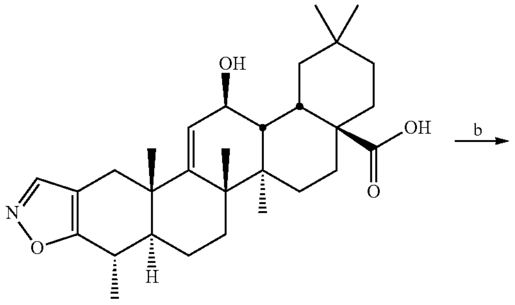
18

-continued
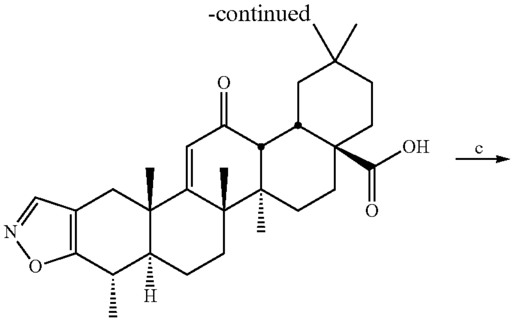
19
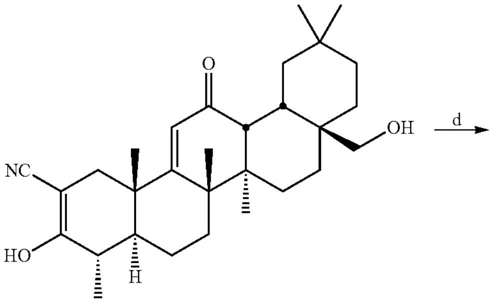
20
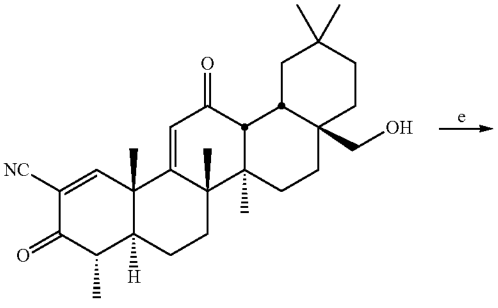
TX63545
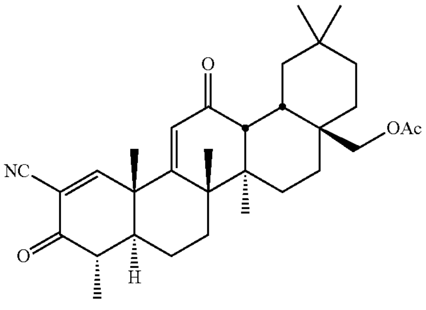
TX63546
Reagents and conditions: a) $LiAlH_4$, THF, 0° C., 7 h, 59%; b) NBS, DME, $H_2O$, rt, 30 min, 94%; c) NaOMe, MeOH, 55° C., 1 h, 94%; d) (i) DBDMH, DMF, 0° C., 1 h; (ii) Pyridine, 55° C., 3 h, 80%; e) $Ac_2O$, Pyridine, $CH_2Cl_2$, rt, 3 h, 77%.
Scheme 9
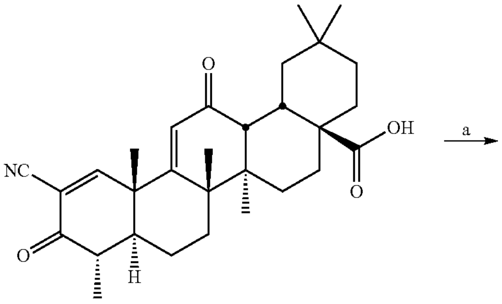
TX63520
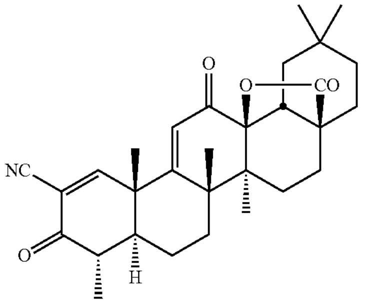
+
TX63555
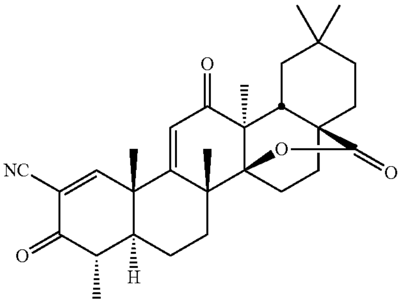
TX63556
Reagents and conditions: a) IPh(OH)OTs, $CH_2Cl_2$, reflux, 1 h, 53% for TX63555, 37% for TX63556.
Scheme 10
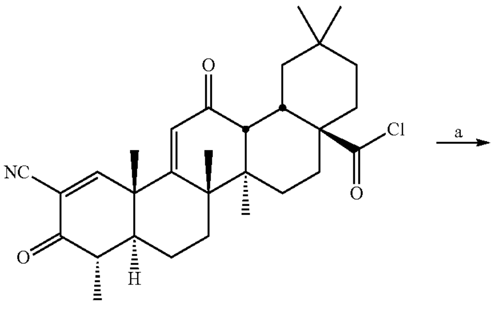
11

-continued
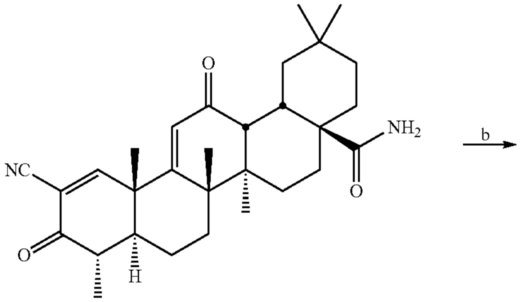
TX63557
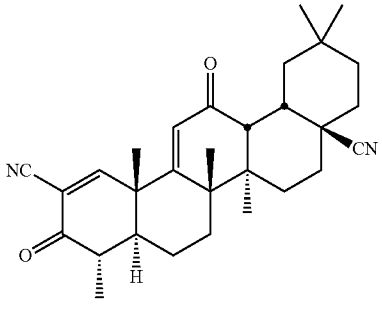
TX63558
Reagents and conditions: a) $NH_3$ in MeOH, 0° C., 30 min, 95%; b) TFAA, $Et_3N$, $CH_2Cl_2$, 0° C., 15 min, 83%.
Scheme 11
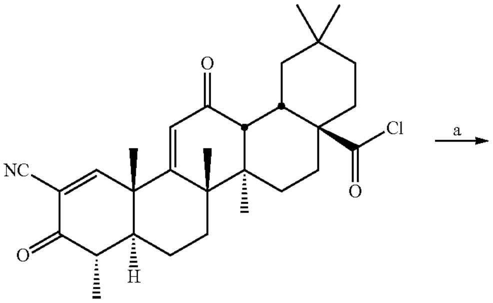
11
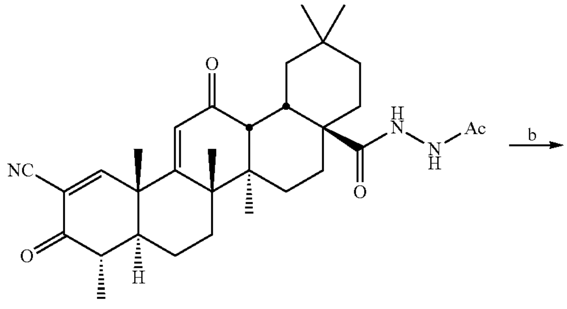
21
-continued
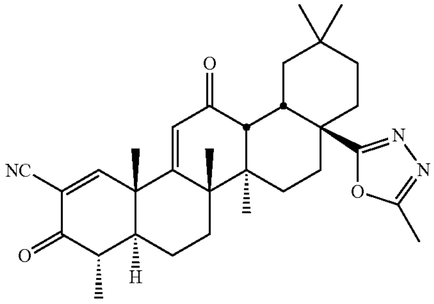
TX63616
Reagents and conditions: a) $AcNHNH_2$, $Et_3N$, $Et_2O$, $CH_2Cl_2$, 0° to rt, 2.5 h, 68%; b) TsOH, toluene, reflux, 2 h, 74%.
Scheme 12
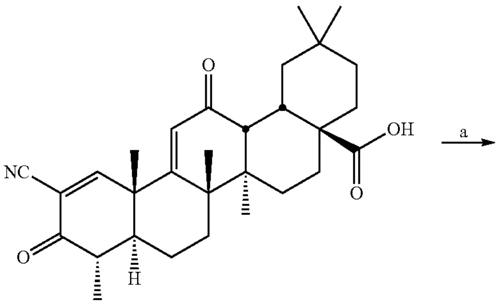
TX63520
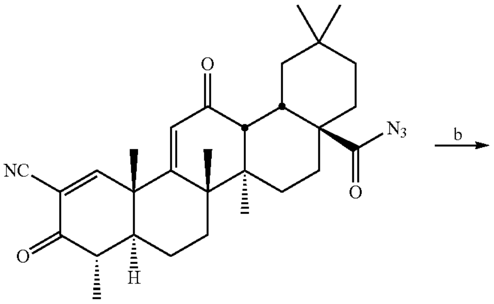
22
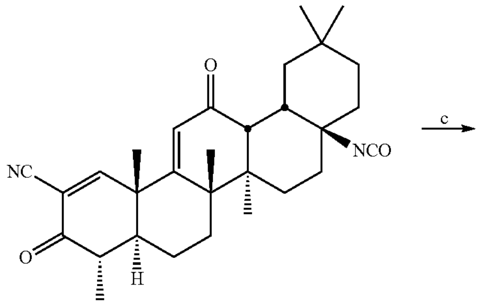
TX63618

-continued
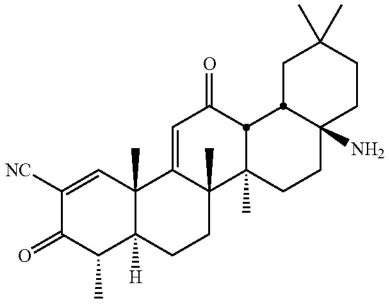
TX63620
Reagents and conditions: a) DPPA, $Et_3N$, toluene, 0° C. to rt, 4 h, 79%; b) toluene, 80° C., 3 hr, 91%; c) MeCN, 12N HCl, 0° C.~rt, 1 h, 97%.
Scheme 13
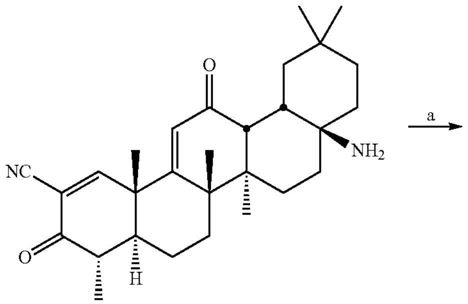
TX63620
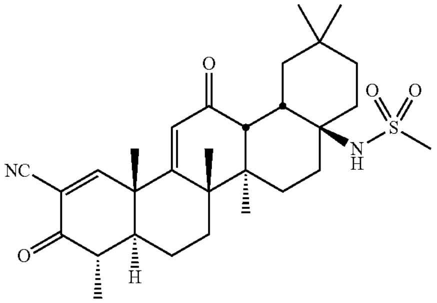
TX63621
Reagents and conditions: a) $CH_3SO_2Cl$, $Et_3N$, $CH_2Cl_2$, 0° C., 1 h, 36%.
Scheme 14
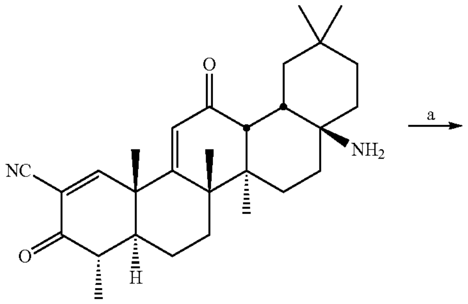
TX63620
-continued
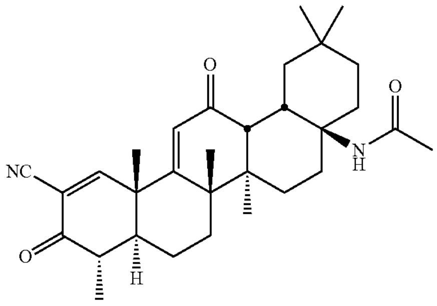
TX63622
Reagents and conditions: a) $CH_3COCl$, $Et_3N$, $CH_2Cl_2$, 0° C., 30 min, 96%.
Scheme 15
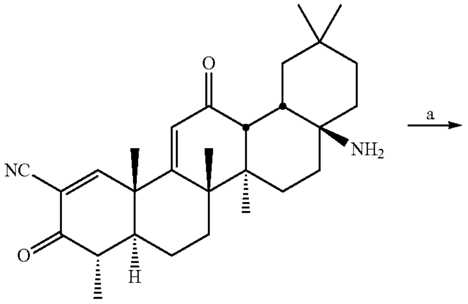
TX63620
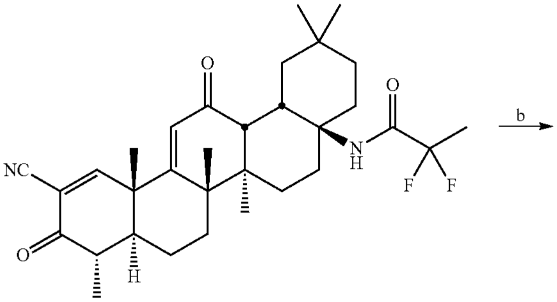
TX63682
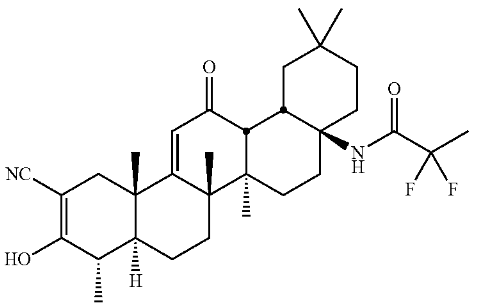
TX63984
Reagents and conditions: a) $CH_3CF_2COOH$, DCC, DMAP, $CH_2Cl_2$, rt, 16 h, 81%; b) $H_2$, EtOAc, rt, 2 h, 85%.

Scheme 16
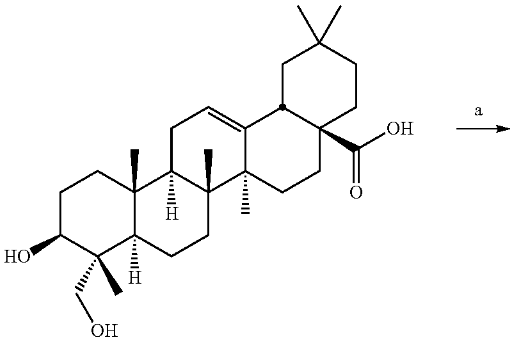
23
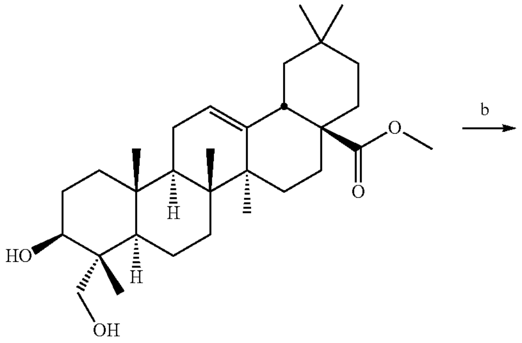
24
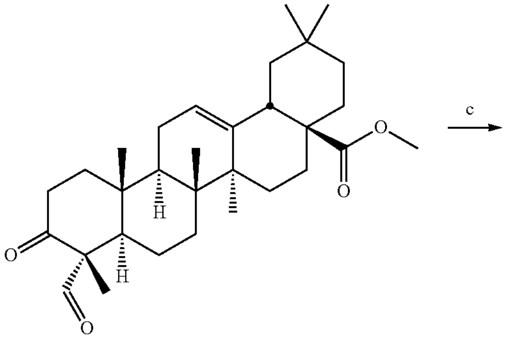
25
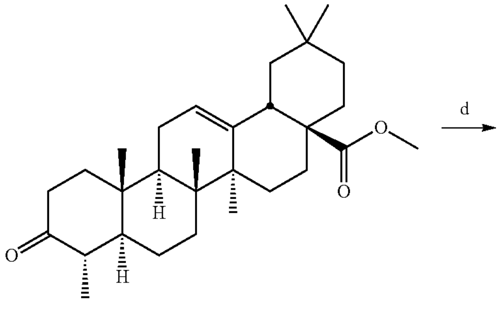
26
-continued
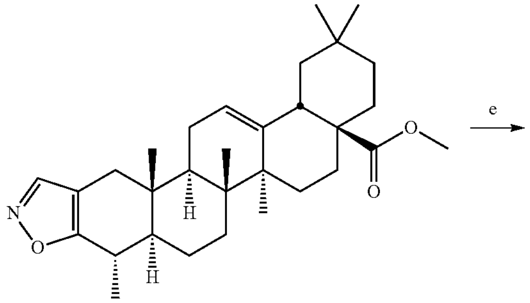
27
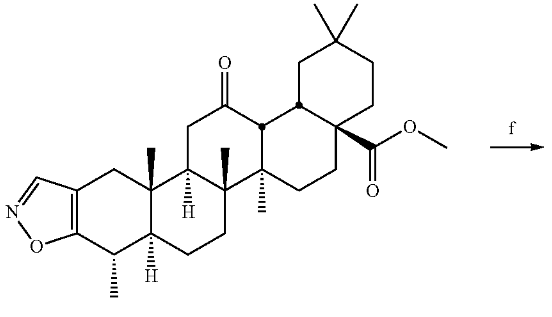
28
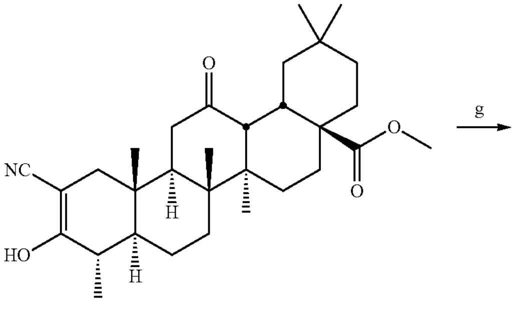
29
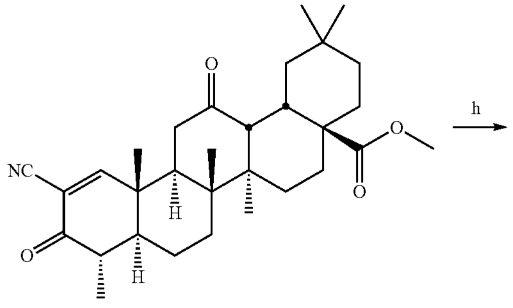
TX63749

-continued

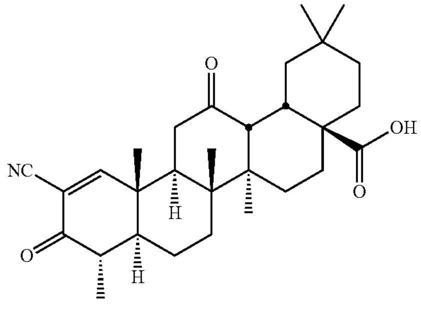

TX63797

Reagents and conditions: a) TMSCHN$_2$, MeOH, toluene, 0° C., 1 h, 96%; b) (i) (COCl)$_2$, DMSO, -78° C., 1.5 h; (ii) Et$_3$N, rt, 1 h; c) NaOMe, MeOH, rt, 30 min, 76% yield from 24; d) (i) NaOMe, MeOH, 0° C. to rt, 6 h; (ii) NH$_2$OH—HCl, 55° C., 16 h, 83%; e) 39% AcOOH in AcOH, AcOH, 55° C, 18 h, 80%; f) HCOOEt, NaOMe, MeOH, 55° C., 1 h; g) (i) DBDMH, DMF, 0° C., 1 h; (ii) Pyridine, 55° C., 3 h, 90% from 28; h) LiBr, NaOAc, DMAc, 150° C., 6 h, 61%.

Scheme 17

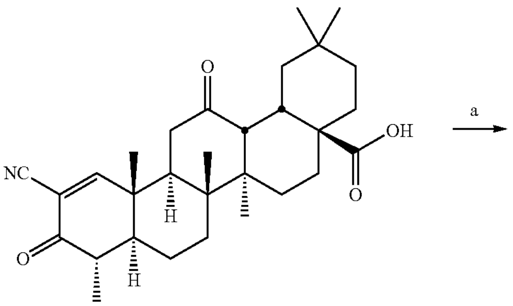

TX63797

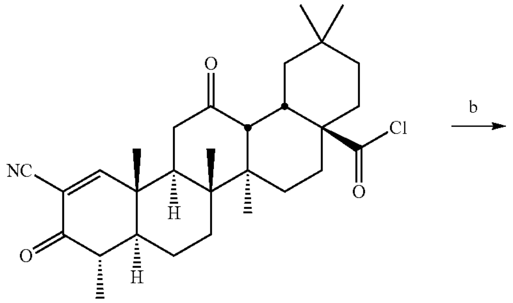

30

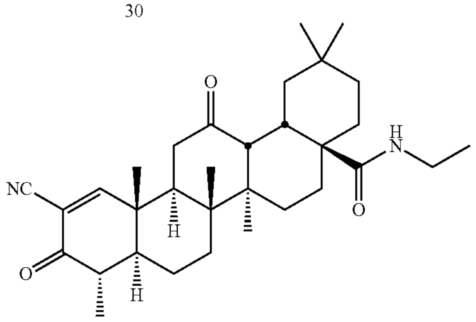

TX63680

Reagents and conditions: a) (COCl)$_2$, CH$_2$Cl$_2$, DMF, 0° C. to rt, 2 h; b) EtNH$_2$, CH$_2$Cl$_2$, THF, 0° C., 30 min, 88%.

Scheme 18

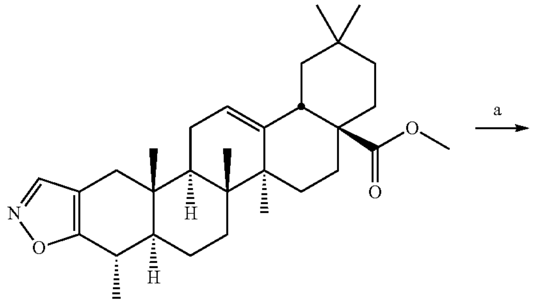

27

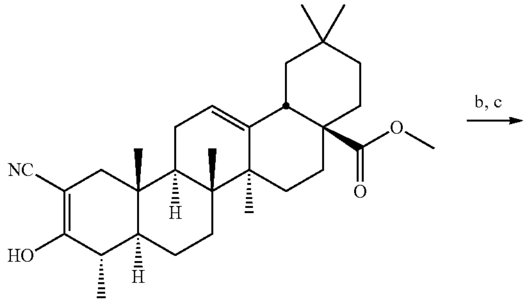

31

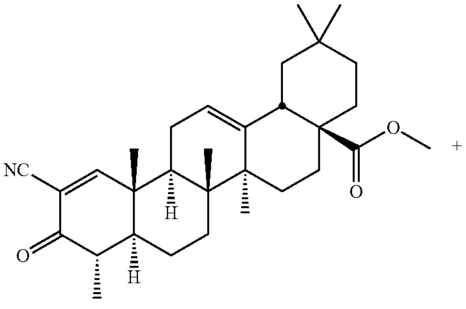

TX63779

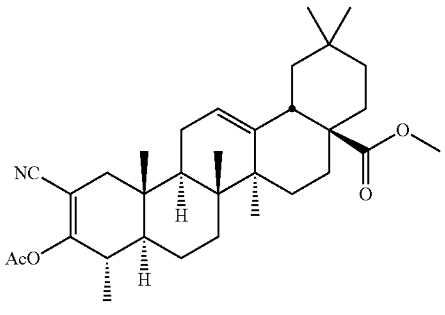

TX63795

Reagents and conditions: a) NaOMe, MeOH, THF, 55° C., 2 h, 95%; b) DDQ, benzene; c) Ac$_2$O, pyridine, DMAP, CH$_2$Cl$_2$, rt, 20 min, 27% for TX63779 from 27, 43% for TX63795 from 27.

Scheme 19
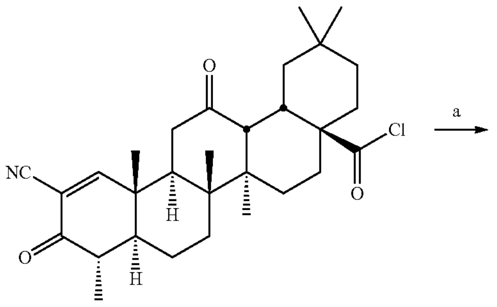
30
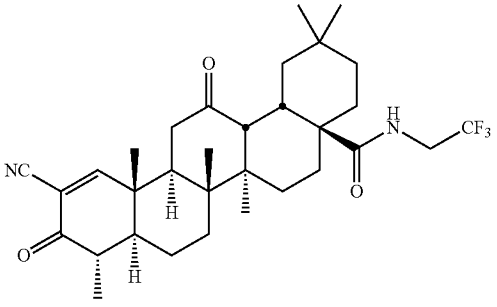
TX63807
Reagents and conditions: a) $CF_3CH_2NH_2$, $CH_2Cl_2$, 0° C.-rt, 2 h, 62%.
Scheme 20
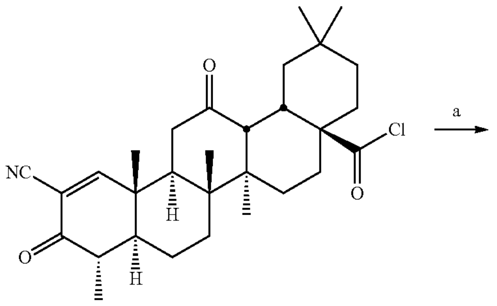
30
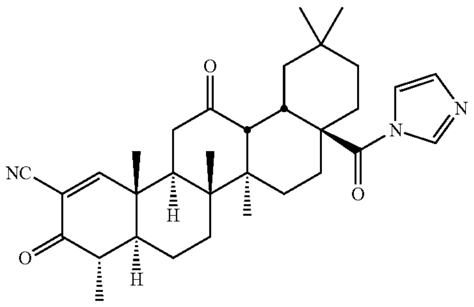
TX63811
Reagents and conditions: a) imidazole, benzene, 0° C.-rt, 2 h, 80%.
Scheme 21
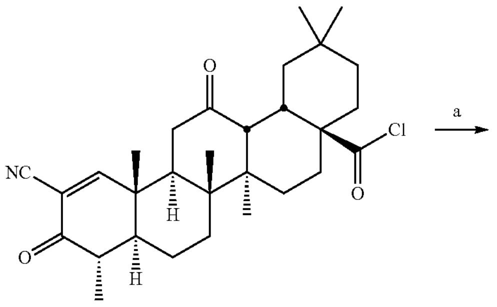
30
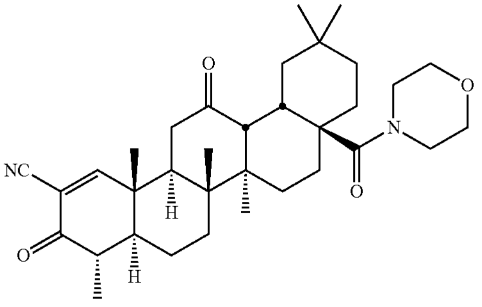
TX63812
Reagents and conditions: a) morpholine, $CH_2Cl_2$, 0° C.-rt, 1 h, 68%.
Scheme 22
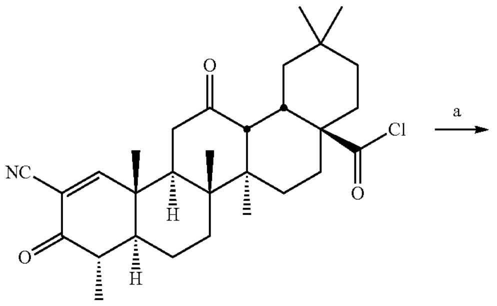
30
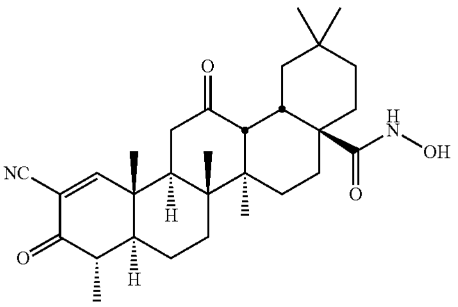
TX63814
Reagents and conditions: a) $NH_2OH$—HCl, THF, $H_2O$, $Et_3N$, rt, 1 h, 48%.

Scheme 23
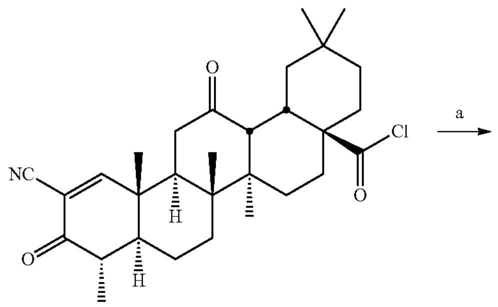
30
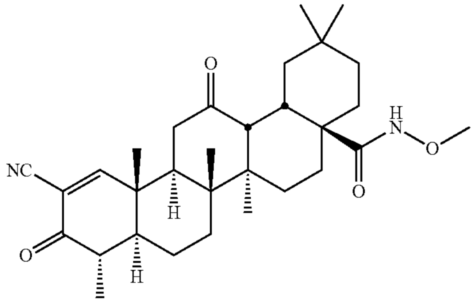
TX63815
Reagents and conditions: a) $NH_2OMe$—HCl, THF, $H_2O$, $Et_3N$, rt, 1 h, 61%.
Scheme 24
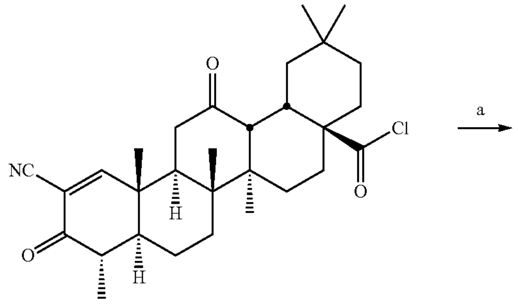
30
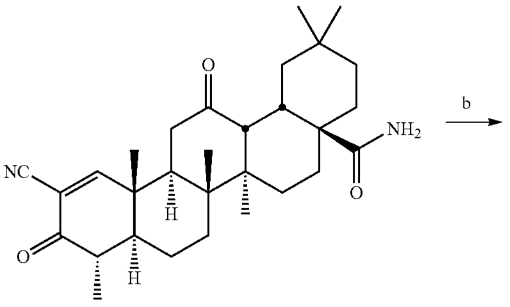
TX63816
-continued
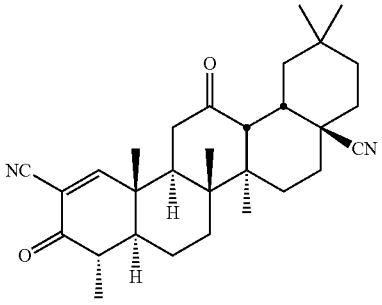
TX63817
Reagents and conditions: a) $NH_3$ in MeOH, MTBE, $CH_2Cl_2$, 0° C.-rt, 1 h, 83%; b) TFFA, $Et_3N$, $CH_2Cl_2$, 0° C., 30 min, 75%.
Scheme 25
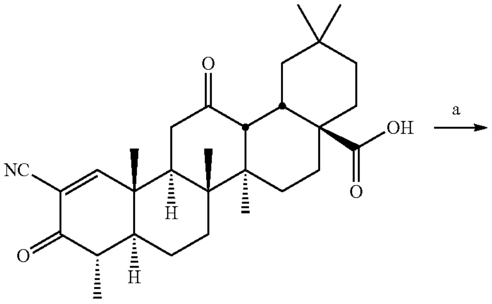
TX63797
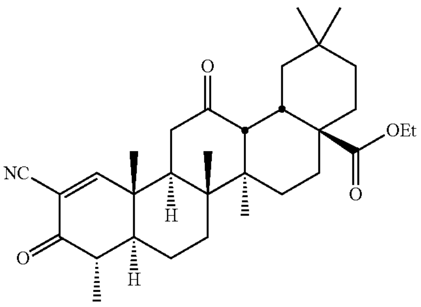
TX63842
Reagents and conditions: a) EtI, DBU, toluene, 50° C., 2 h, 61%.

Scheme 26
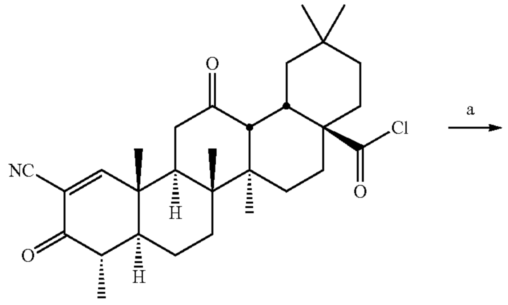
30
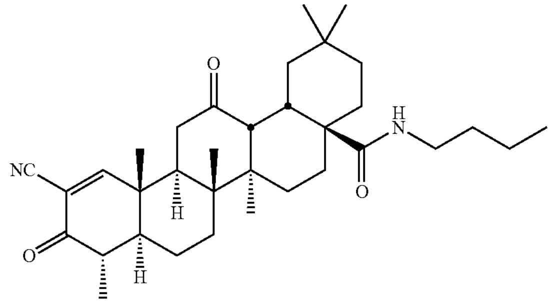
TX63843
Reagents and conditions: a) n-BuNH$_2$, CH$_2$Cl$_2$, 0° C., 30 min, 69%.
Scheme 27
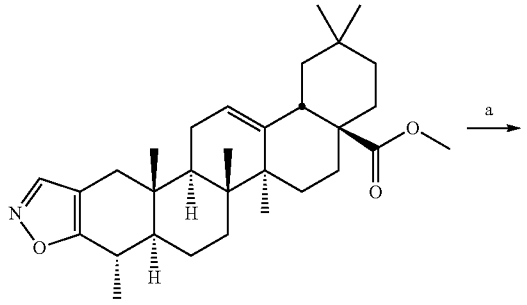
27
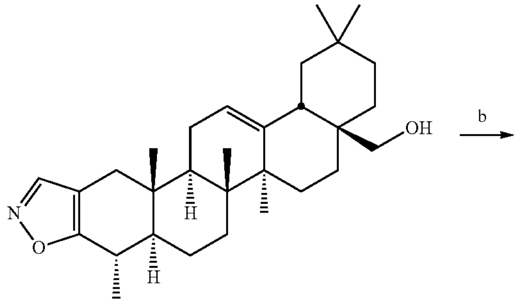
32
-continued
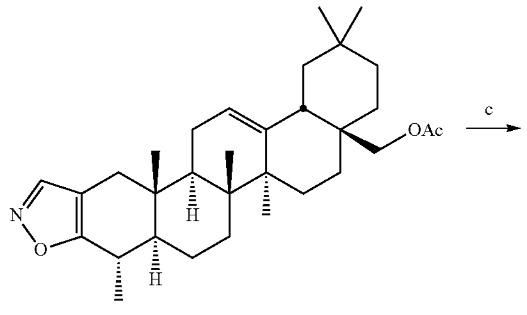
33
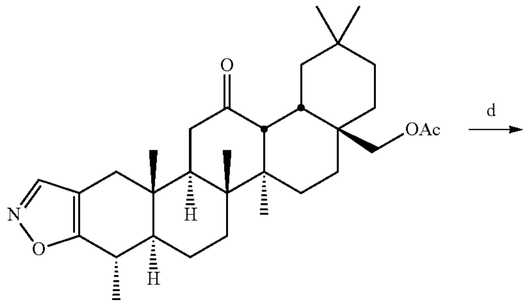
34
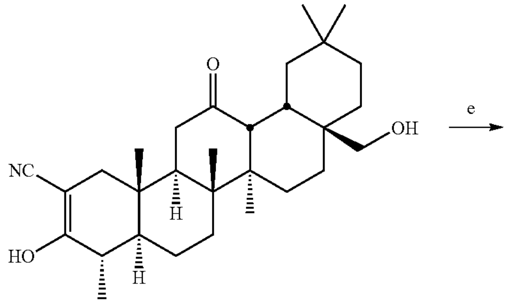
35
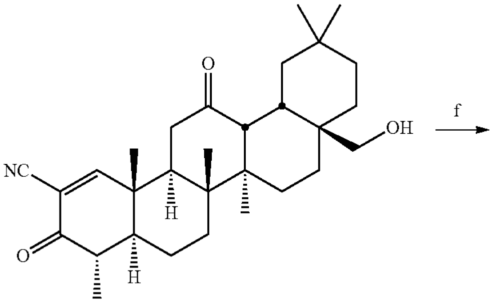
TX63839

-continued
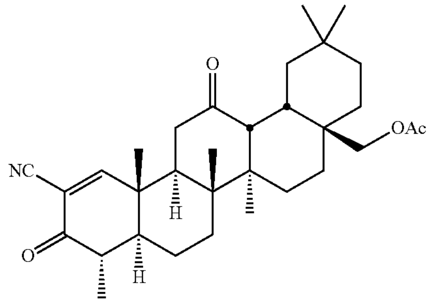
TX63840
Reagents and conditions: a) DIBAL—H, THF, 0° C., 2 h, 96%; b) $Ac_2O$, Pyridine, DMAP, rt, 10 min, 96%; c) AcOOH, AcOH, 55° C., 20 h, 80%; d) NaOMe, MeOH, 55° C. 1 h, 99%; e) (i) DBDMH, DMF, 0° C, 1.5 h; (ii) pyridine, 55° C., 1.5 h, 81%; f) $Ac_2O$, Pyridine, DMAP, $CH_2Cl_2$, rt, 10 min, 99%.
Scheme 28
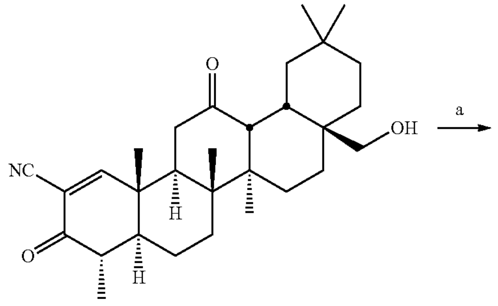
TX63839
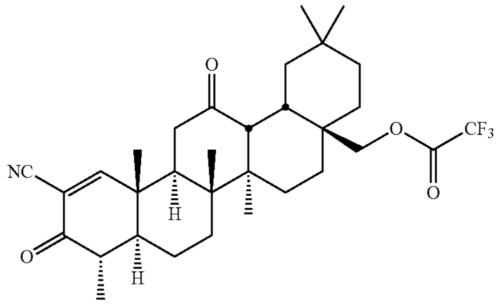
TX63841
Reagents and conditions: a) TFAA, $Et_3N$, $CH_2Cl_2$, 0° C., 1 h, 87%.
Scheme 29
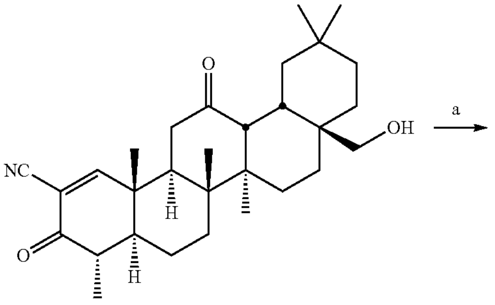
TX63839
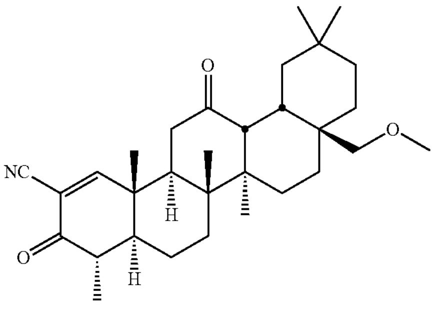
TX63858
Reagents and conditions: a) MeOTf, 2,6-di-t-butyl-4-methylpyridine, $CH_2Cl_2$, rt, 16 h, 75%.
Scheme 30
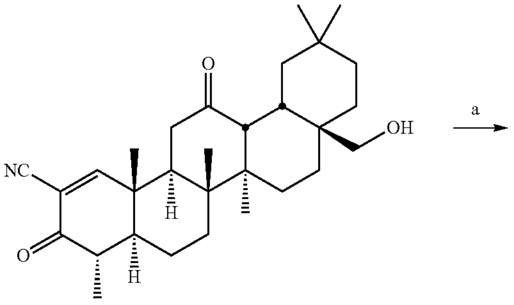
TX63839
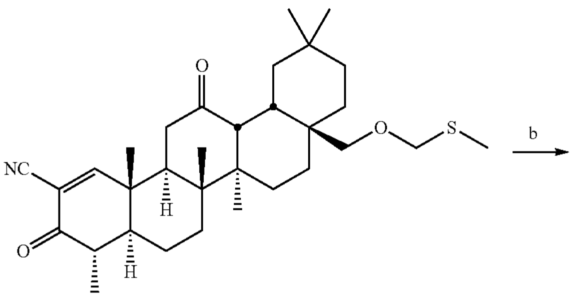
TX63859

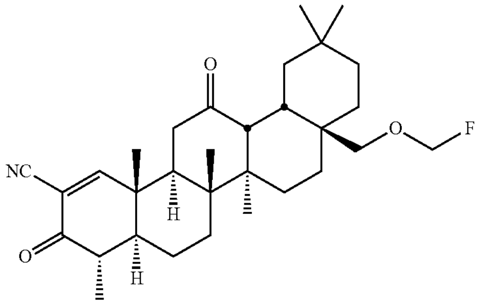
TX63860
Reagents and conditions: a) DMSO, AcOH, $Ac_2O$, rt, 20 h, 80%; b) DAST, NBS, 4 Å MS, $CH_2Cl_2$, 0° C., 50 min, 52%.
Scheme 31
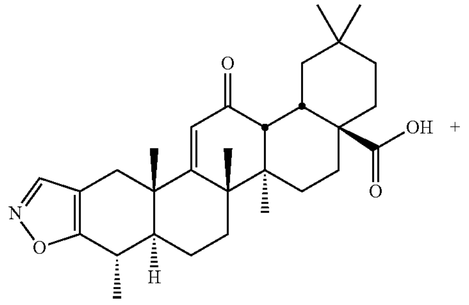
13
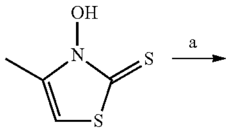
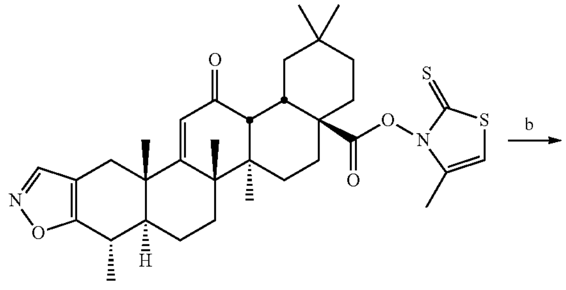
36
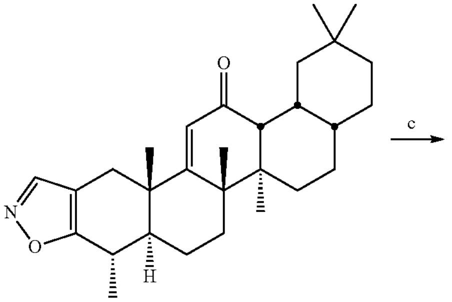
37
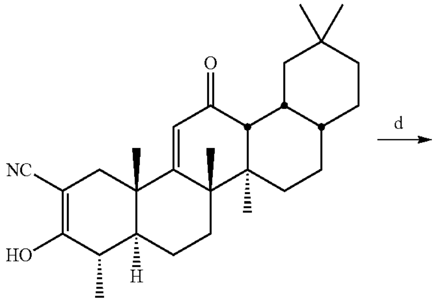
38
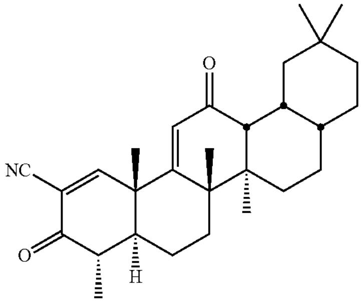
TX63869
Reagents and conditions:
a) DCC, DMAP, $CH_2Cl_2$, rt, 5 h, 80%;
b) $Bu_3SnH$, AIBN, benzene, reflux, 25 min, 89%;
c) NaOMe, MeOH, 55° C., 2 h, 99%;
d) (i) DBDMH, DMF, 0° C., 1 h; (ii) Pyridine, 55° C., 2 h, 84%.
Scheme 32
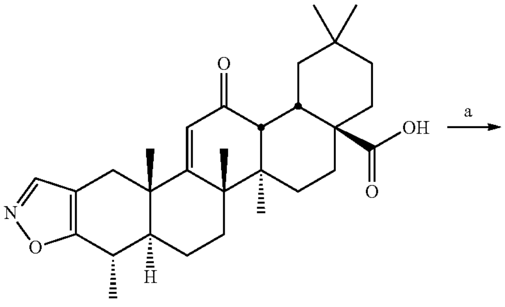
13
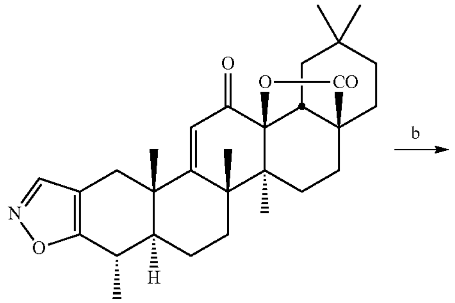
39

-continued
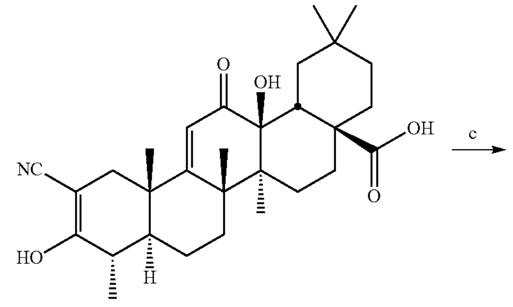
40
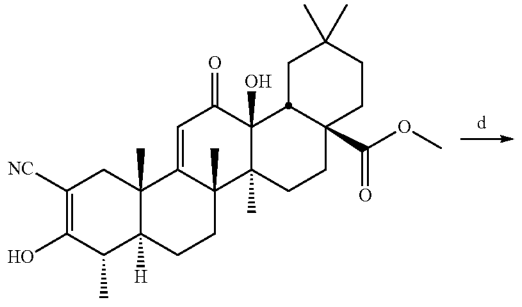
41
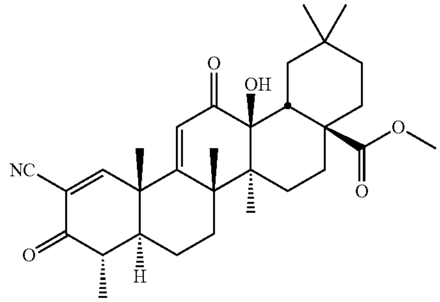
TX63870
Reagents and conditions:
a) DDQ, toluene, microwave, 115° C., 3 h, 47%;
b) NaOH, THF, EtOH, $H_2O$, rt, 6 h;
c) $TMSCHN_2$, toluene, MeOH, -20° C., 15 min, 42% for 2 steps;
d) (i) DBDMH, DMF, 0° C., 1 h; (ii) Pyridine, 55° C., 2 h, 72%.
Scheme 33
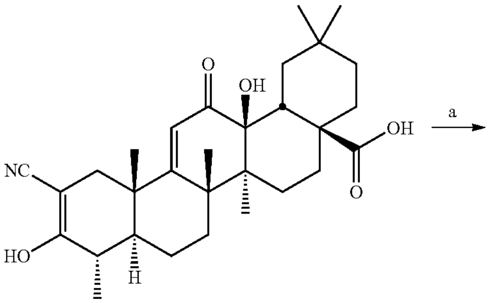
40
-continued
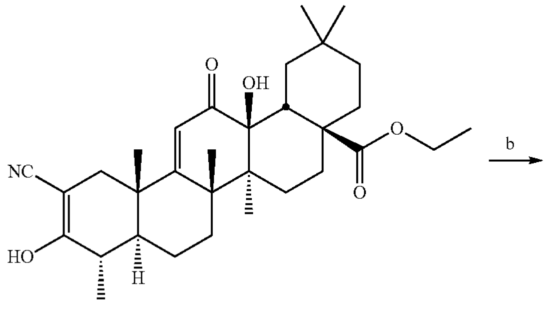
42
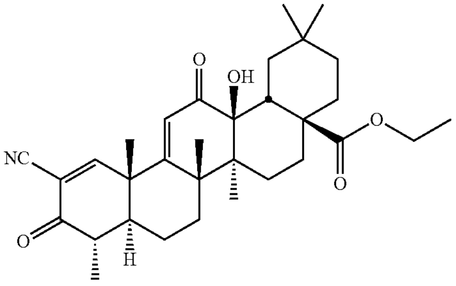
TX63901
Reagents and conditions:
a) $CH_3CHN_2$, $CHCl_3$, MTBE, 0° C., 15 min, 18%;
b) (i) DBDMH, DMF, 0° C., 1 h: (ii) Pyridine, 55° C., 2 h, 68%.
Scheme 34
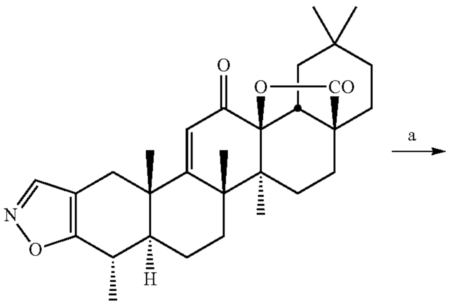
39
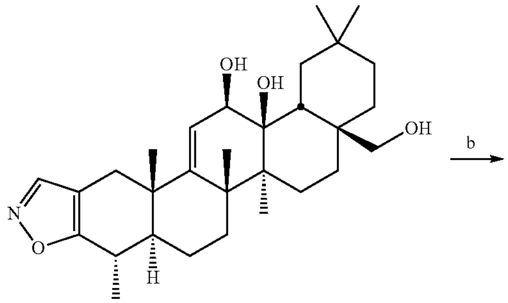
43

-continued
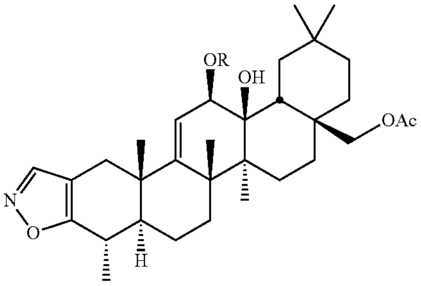
44 R = H
45 R = Ac
Reagents and conditions:
a) $LiAlH_4$, THF, 0° C., 3 h, 47%;
b) $Ac_2O$, Pyridine, DMAP, $CH_2Cl_2$, 0° C., 1 h, 75% for 44.
Scheme 35
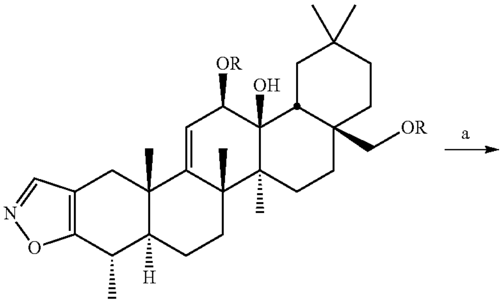
43 R = H
45 R = Ac
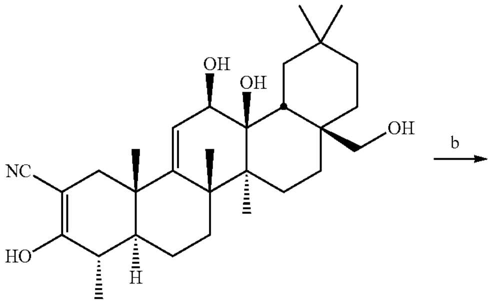
46
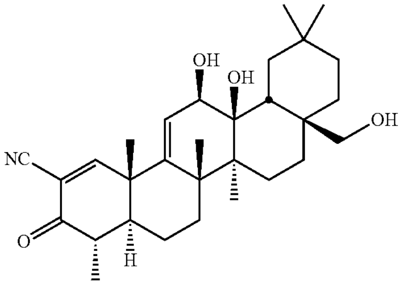
TX63904
Reagents and conditions:
a) NaOMe, MeOH, 55° C., 1 h, 60%;
b) (i) DBDMH, DMF, 0° C., 1 h; (ii) Pyridine, 55° C., 2 h, 88%.
Scheme 36
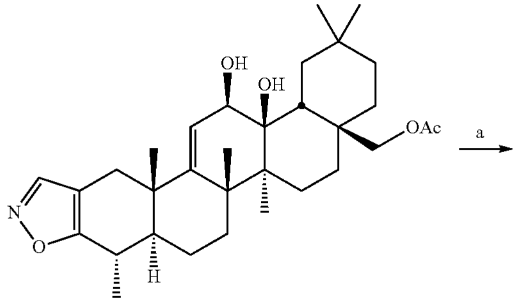
44
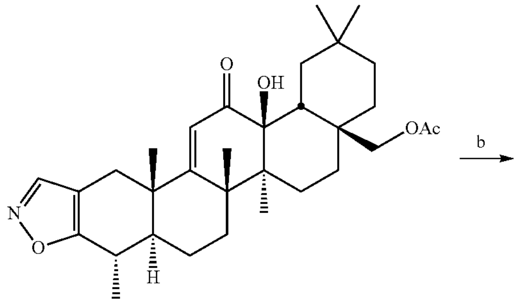
47
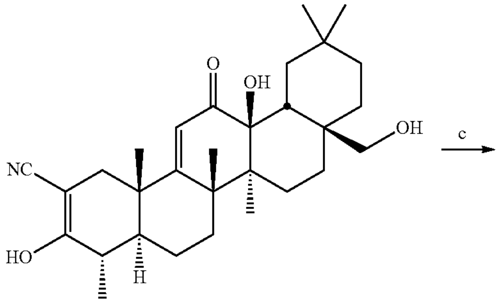
48
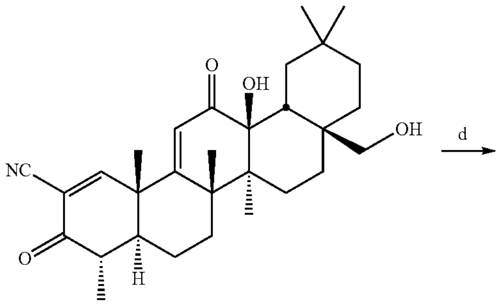
TX63908

-continued
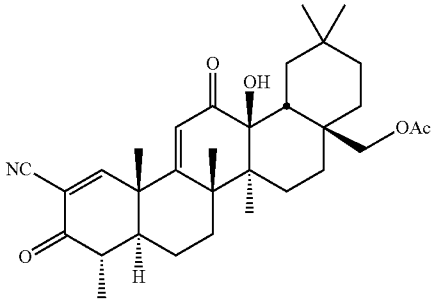
TX63909
Reagents and conditions:
a) NMO, TPAP, 4Å MS, $CH_2Cl_2$, rt, 3 h, 72%;
b) NaOMe, MeOH, 55° C., 2 h, 89%;
c) (i) DBDMH, DMF, 0° C., 1 h; (ii) Pyridine, 55° C., 1.5 h, 86%;
d) $Ac_2O$, Pyridine, DMAP, rt, 30 min, 94%.
Scheme 37
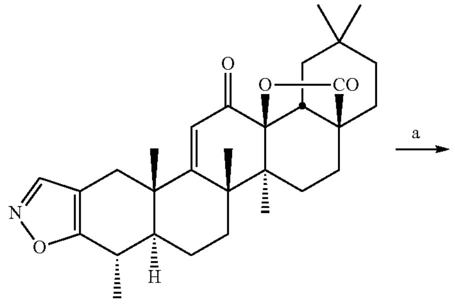
39
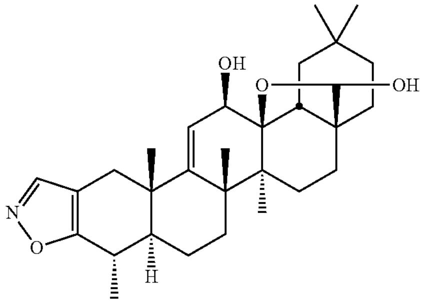
49
+
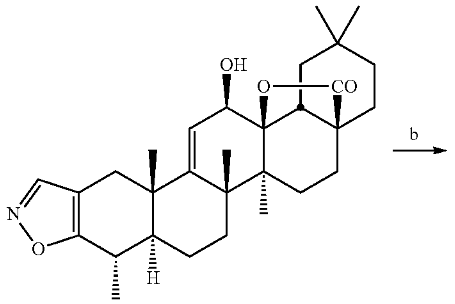
50
-continued
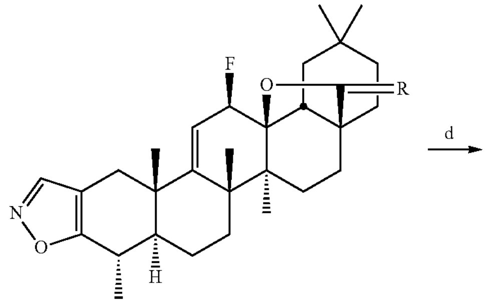
c 51 R = H, OH
52 R = O
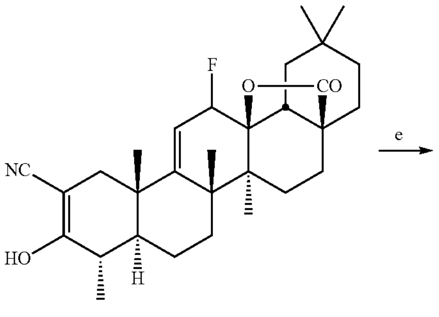
53
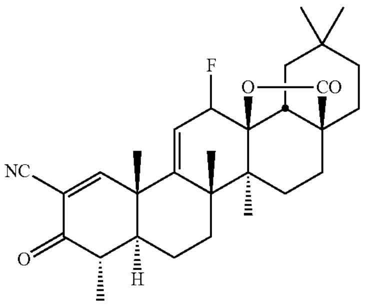
TX63907
Reagents and conditions:
a) $LiAlH_4$, THF, 0° C., 1 h, 72%;
b) (i) DAST, $CH_2Cl_2$, 0° C., 20 min; (ii) silica gel;
c) Jones' reagent, acetone, 0° C., 10 min, 39% from 49 and 50;
d) NaOMe, MeOH, 55° C., 2 h;
e) (i) DBDMH, DMF, 0° C., 1 h; (ii) Pyridine, 55° C., 1.5 h, 81% from 52.
Scheme 38
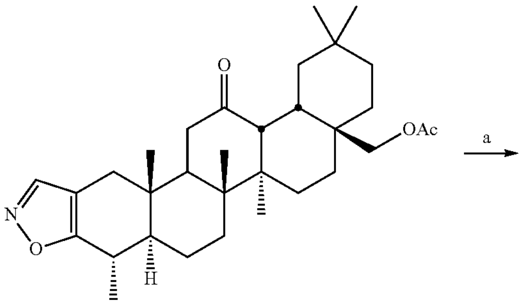
34

-continued
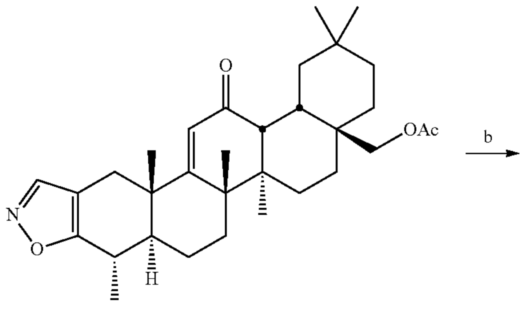
54
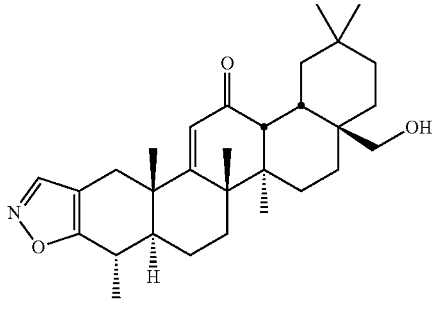
+
55
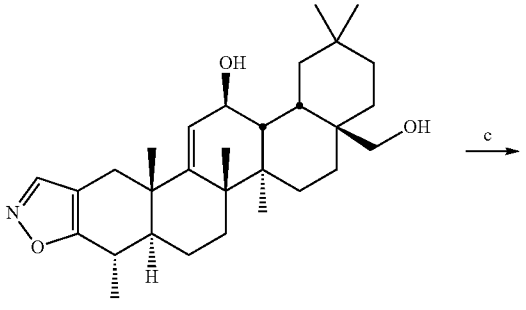
56
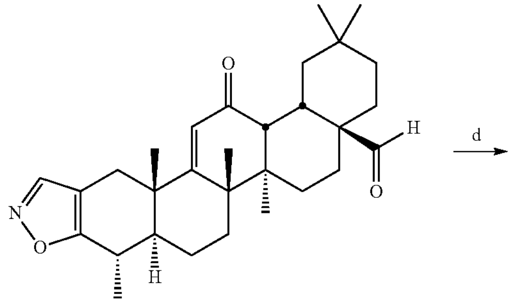
57
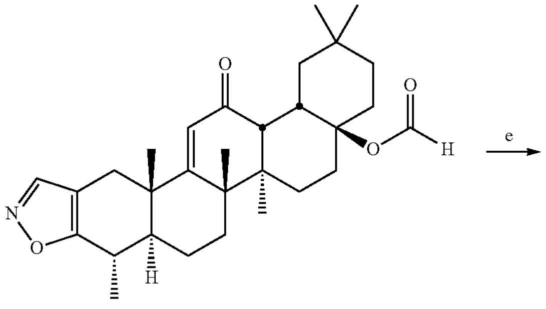
58
-continued
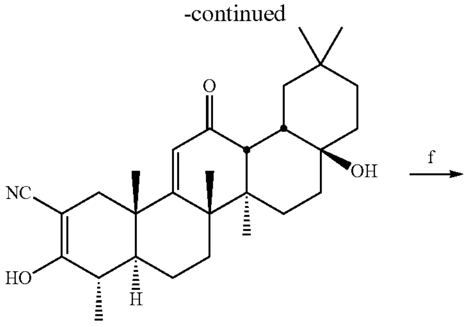
59
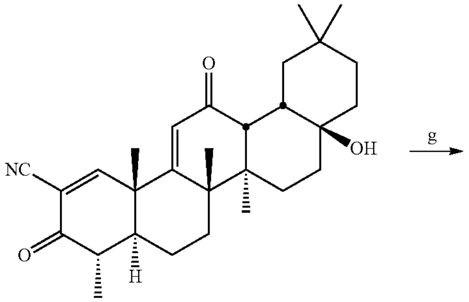
TX63925
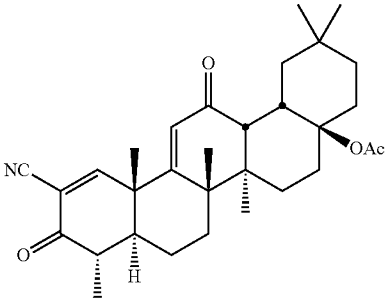
TX63928
Reagents and conditions: a) $PyH^+Br_3^-$, MeCN, rt, 3 h, 66%; b) $LiAlH_4$, THF, 0° C., 1 h, 46% for 55, 46% for 56; c) NMO, TPAP, 4 Å MS, $CH_2Cl_2$, rt, 1 h, 86%; d) m-CPBA, $Na_2HPO_4$, $CH_2Cl_2$, rt, 6 h, 85%; e) NaOMe, MeOH, 55° C., 1 h, 90%; f) (i) DBDMH, DMF, 0° C., 1 h; (ii) Pyridine, 55° C., 3 h, 94%; g) $Ac_2O$, $BF_3$—$OEt_2$, $CH_2Cl_2$, 0° C., 10 min, 34%.
Scheme 39
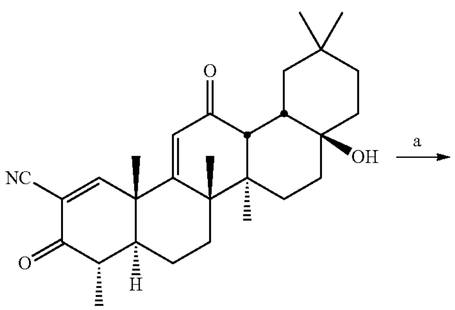
TX63925

-continued
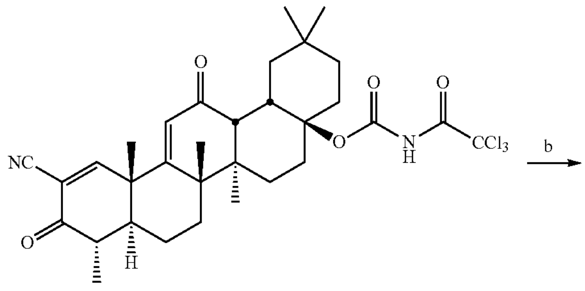
60
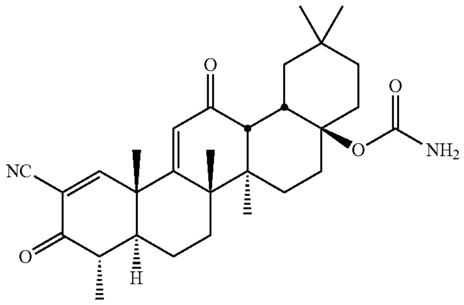
TX63929
Reagents and conditions:
a) $Cl_3CCONCO$, $CH_2Cl_2$, rt, 2 h;
b) $K_2CO_3$, MeOH, rt, 1 h, 61% for 2 steps.
Scheme 40
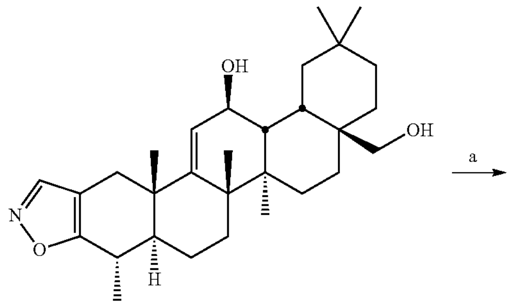
55
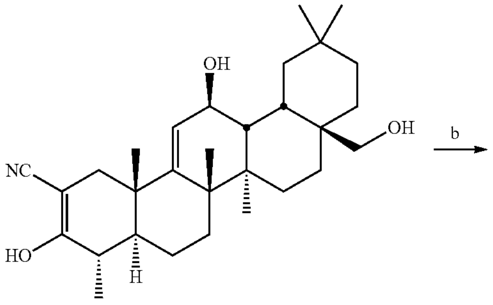
61
-continued
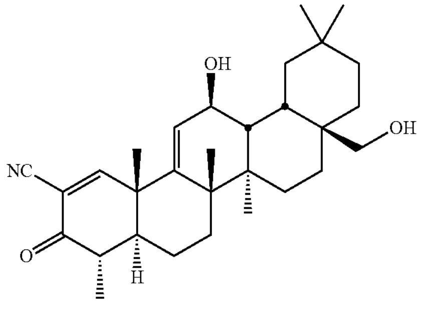
TX63923
Reagents and conditions:
a) NaOMe, MeOH, 55° C., 1 h, 81%;
b) (i) DBDMH, DMF, 0° C., 1 h; (ii) Pyridine, 55° C., 3 h, 80%.
Scheme 41
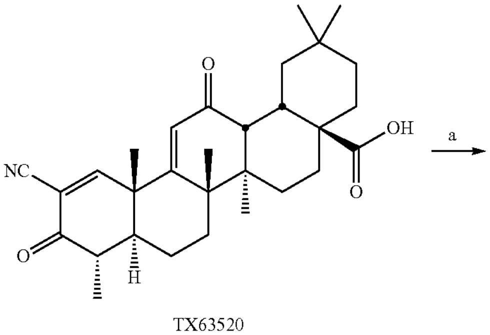
TX63520
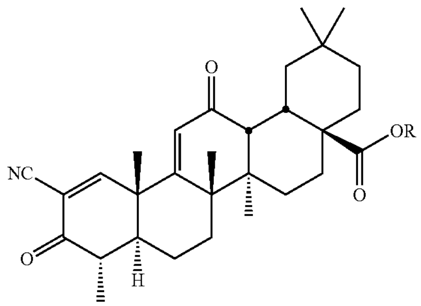
a-b
a: TX63820 R = Et
b: TX63821 R = n-$C_6H_{13}$
Reagents and conditions:
a) alkyl iodide (RI), DBU, Toluene, TX63820: rt, 21 h, 18.4%; TX63821: rt, 18 h, then 80° C., 2 h, 75%.

Scheme 42

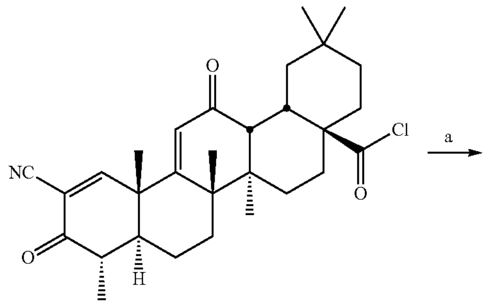

11

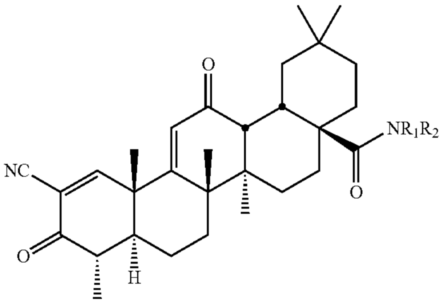

a-l a: TX63878 $NR_1R_2 = NMe_2$
b: TX63824 $NR_1R_2$ = NHMe
c: TX63877 $NR_1R_2 = NH\text{-}n\text{-}C_4H_9$
d: TX63823 $NR_1R_2$ = 1-pyrrolidinyl
e: TX63880 $NR_1R_2$ = 1-piperidinyl
f: TX63881 $NR_1R_2$ = 4-morpholinyl
g: TX63822 $NR_1R_2$ = 2,4-dimethyl-1H-imidazol-1-yl
h: TX64005 $NR_1R_2$ = methyl 5-carboxylate-1H-imidazol-1-yl
i: TX63882 $NR_1R_2$ = NHOMe
j: TX64006 $NR_1R_2$ = NHOH
k: TX63825 $NR_1R_2$ = N-3-oxetanyl
l: TX64007 $NR_1R_2$ = 2-oxa-6-azaspiro[3.3]hept-6-yl Reagents and conditions:
a) $(COCl)_2$, DMF (cat.), $CH_2Cl_2$, rt, 2 h;
(b) $R_1R_2NH$, reaction conditions: see experimental for details.

Scheme 43

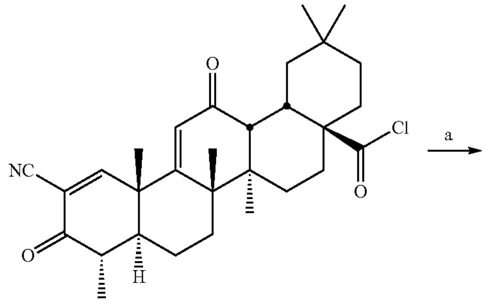

11

-continued

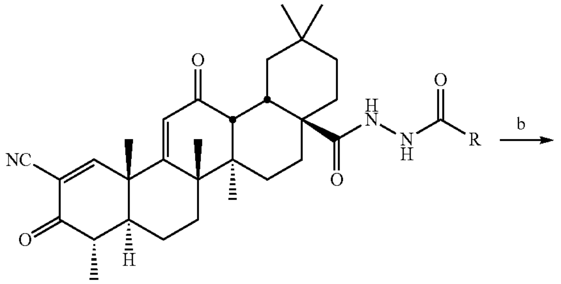

TX63784: R = $CH_2OCH_3$
TX63785: R = H

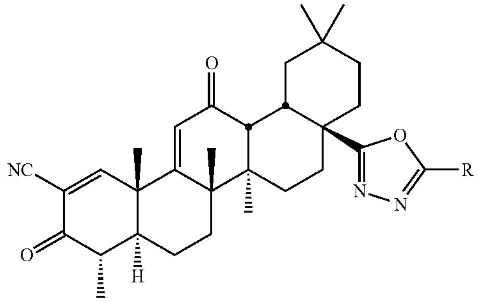

TX63790: R = $CH_2OCH_3$
TX63789: R = H

Reagents and conditions:
a) $H_2NNHOR$, DCM, TEA, rt, TX63784: 72%, TX63785: 47%;
b) TsOH—$H_2O$, Toluene, reflux, —$H_2O$,TX63789: 34%, TX63790: 51%.

Scheme 44

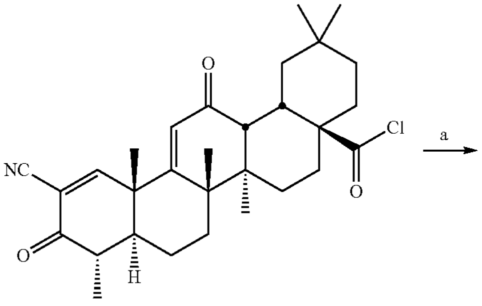

11

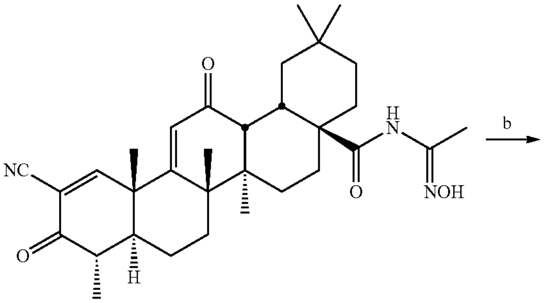

TX63786

-continued
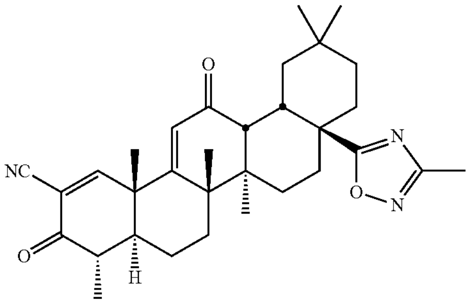
TX63787
Reagents and conditions:
a) Acetamide oxime, DCM, TEA, rt, 61%;
b) EtOAc, Toluene, 200° C., microwave, 20 min, 24%.
Scheme 45
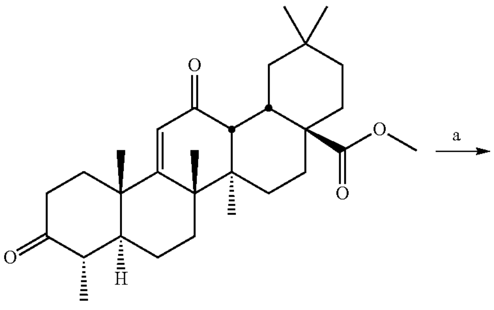
7
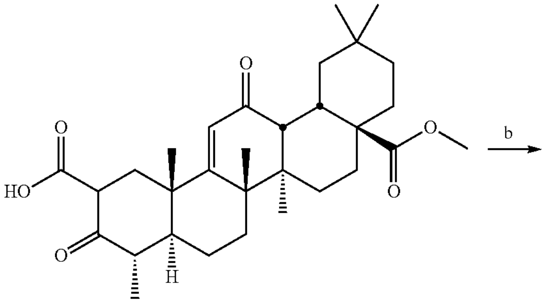
62
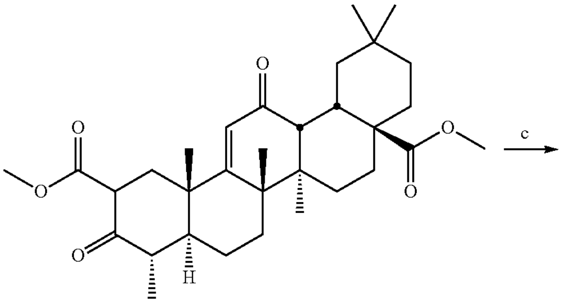
63
-continued
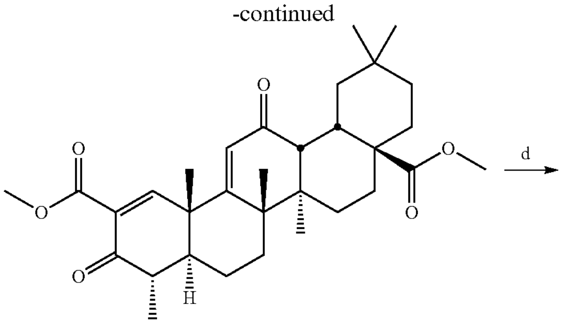
TX63788
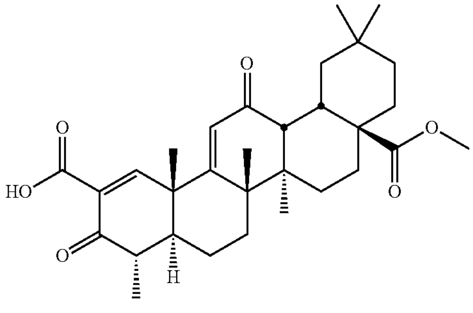
TX63830
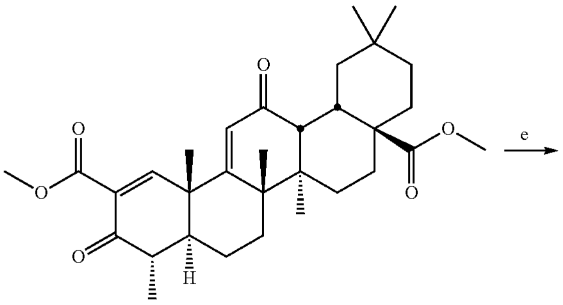
TX63788
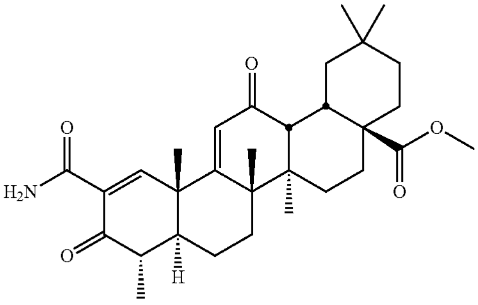
TX63831
Reagents and conditions:
a) MMC, DMF, 110° C., $N_2$ sparge, 99%;
b) $TMSCHN_2$, THF, MeOH, 0° C.;
c) (i) PhSeCl, pyridine, DCM, 0° C.; (ii) $H_2O_2$, 0° C., 67%;
d) KOH, $H_2O$, MeOH, reflux, 61%;
e) $NH_3$, MeOH, rt, 40%.

Scheme 46
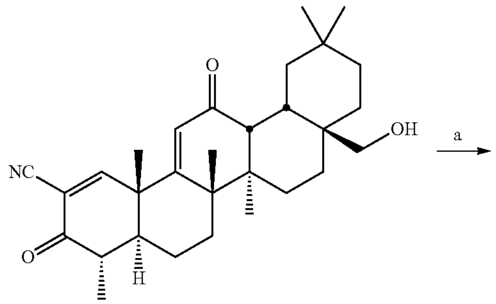
TX63545
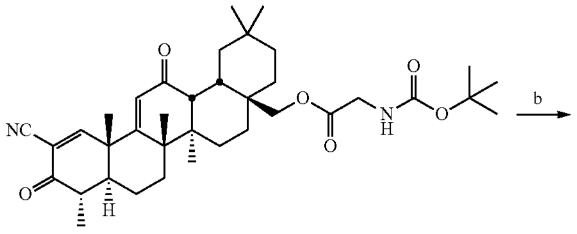
TX63716
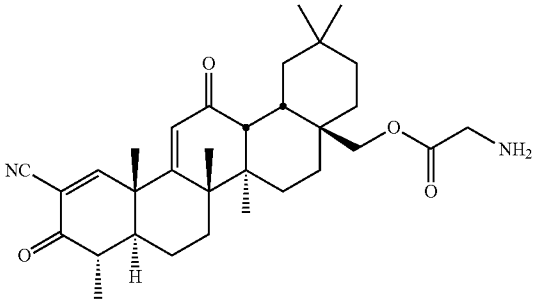
TX63717
Reagents and conditions:
a) N-Boc-Gly-OH, EDC, DMAP, DCM, rt, 85%;
b) HCl, DCM, 1,4-dioxane, rt, 85%.
Scheme 47
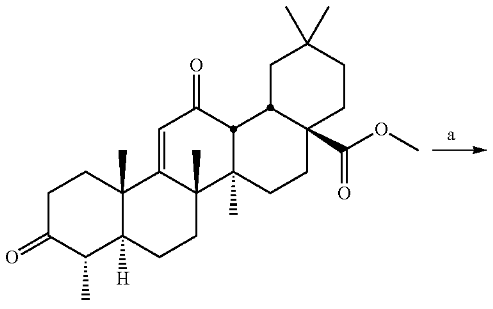
7
-continued
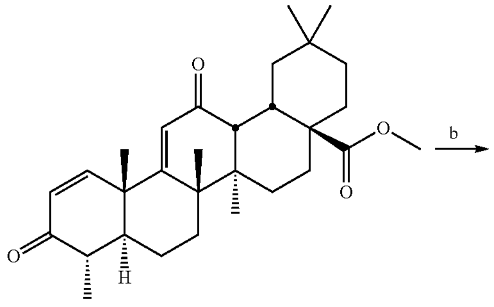
TX63832
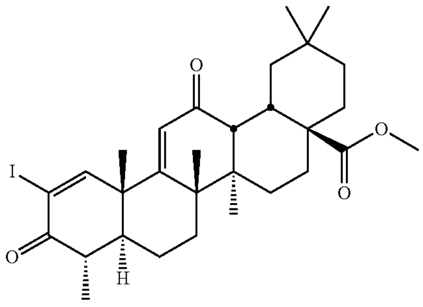
TX63833
Reagents and conditions: a) (i) PhSeCl, EtOAc, rt to -20° C.; (ii) $H_2O_2$, THF, rt, 55%; b) $I_2$, pyridine THF, reflux, 60%.
Scheme 48 (a)
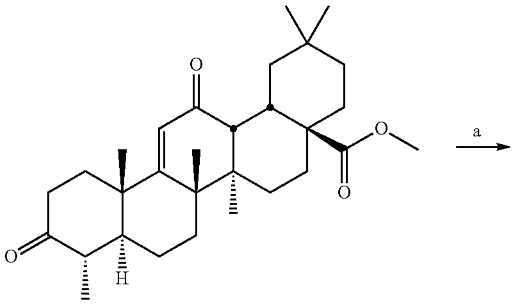
7
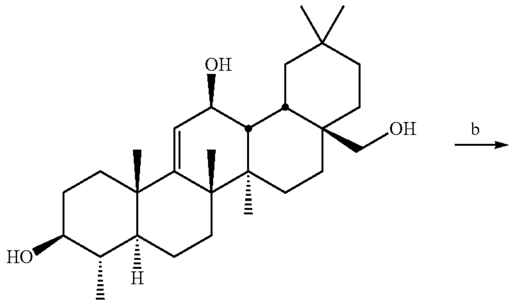
64

-continued
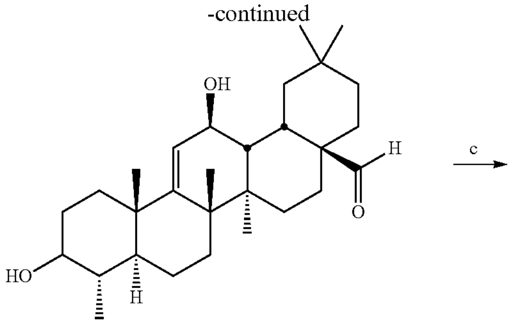
65
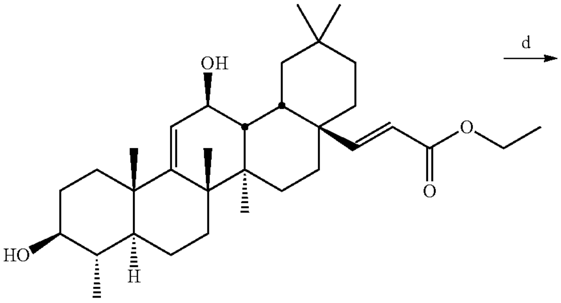
66
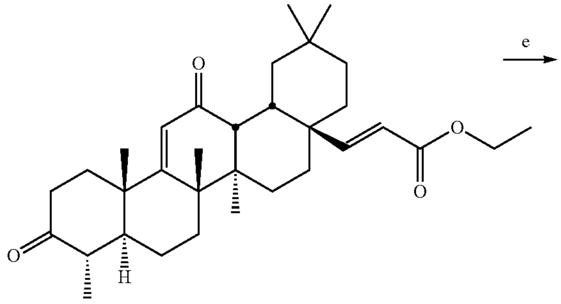
67
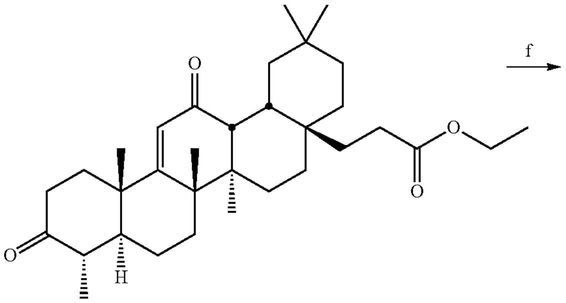
68
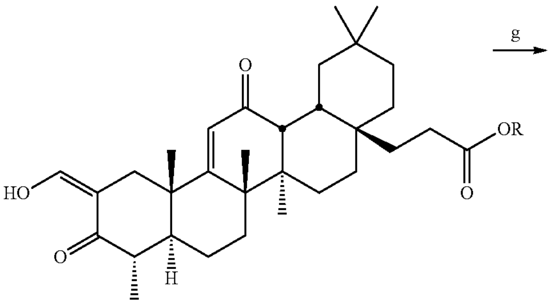
69
(R = Me/Et)
-continued
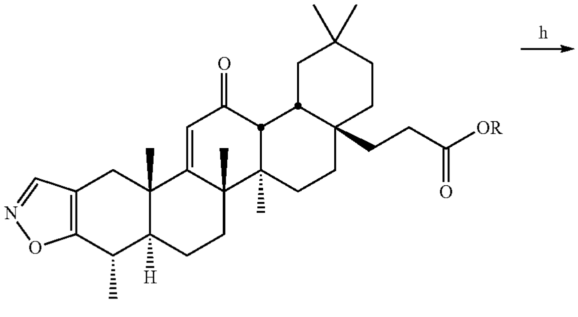
70 (R = Me/Et)
Scheme 48 (b)
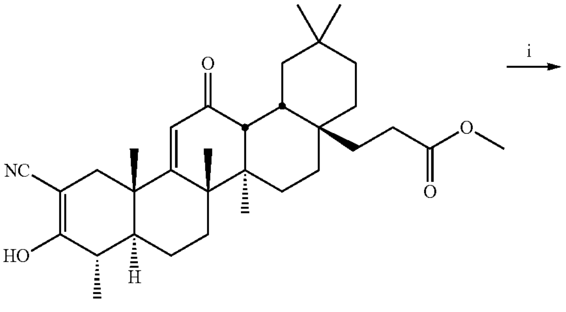
71
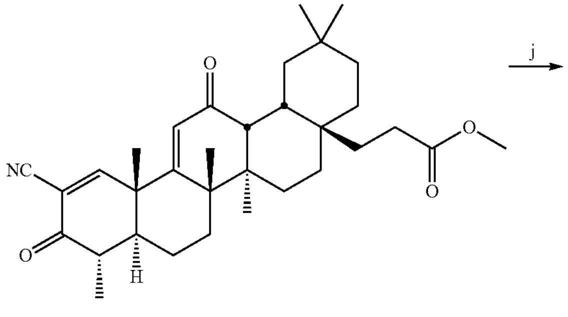
TX63867
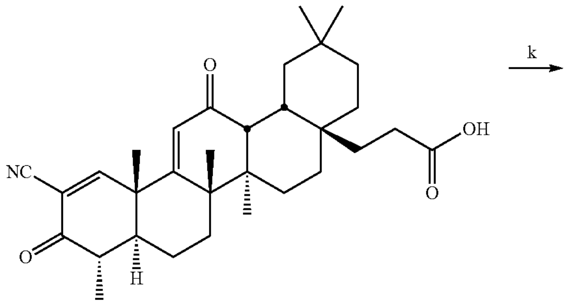
TX63891

-continued

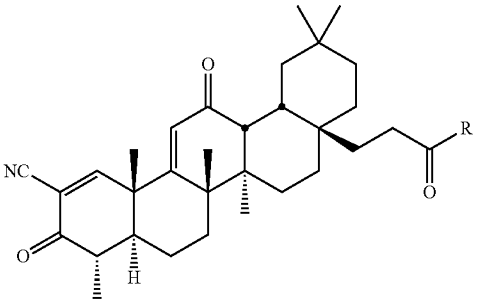

a-h a: TX63886 R = NHMe
b: TX63892 R = NHEt
c: TX63887 R = $NHCH_2CF_3$
d: TX63888 R = Morpholine
e: TX63889 R = Azetidine
f: TX63893 R = Pyrrolidine g: TX63890 R = 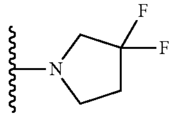

h: TX63914 R = 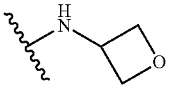

Reagents and conditions: a) LAH, THF, 0° C. to rt; b) TEMPO, $PhI(OAc)_2$, $CH_2Cl_2$, $H_2O$, rt 27%; c) Triethyl phosphonoacetate, NaH, 0° C. to rt, 67%; d) TPAP, NMO, $CH_2Cl_2$, 4 AMS, rt, 88%; e) Pd/C, $H_2$, THF, rt; f) EtOCHO, NaOMe, MeOH, rt; g) (i) $NH_2OH$•HCl, EtOH, $H_2O$, 55° C., (ii) HCl, MeOH, rt, 80%; h) NaOMe, MeOH, 55° C.; (i) DBDMH, DMF, 0° C., (ii) pyridine, 55° C., 82%; j) HCl, $H_2O$, MeCN, 65° C., 93%; k) amine or amine-HCl, EDCI, TEA, DMAP, $CH_2Cl_2$, rt, TX63888: 69%, TX63893: 74%, TX63886: 76%, TX63887: 77%, TX63889: 84%, TX63890: 79%, TX63892: 85%, TX63914: 75%.

Scheme 49

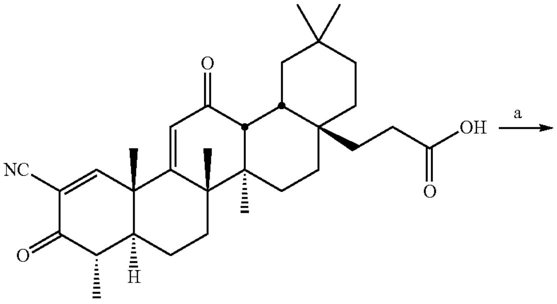

TX63891

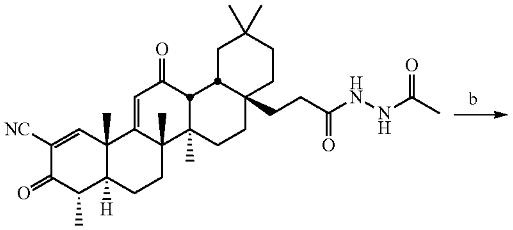

TX63915

-continued

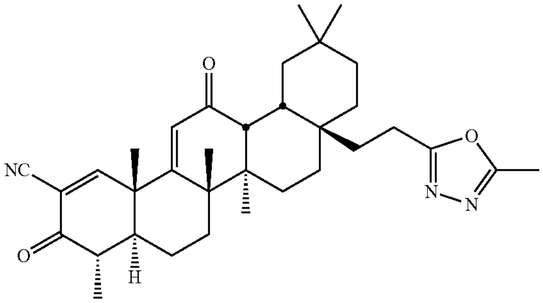

TX63916

Reagents and conditions: a) $AcNHNH_2$, EDC, TEA, DMAP, DCM, rt, 74%; b) TsOH—$H_2O$, toluene, reflux, —$H_2O$, 73%.

Scheme 50

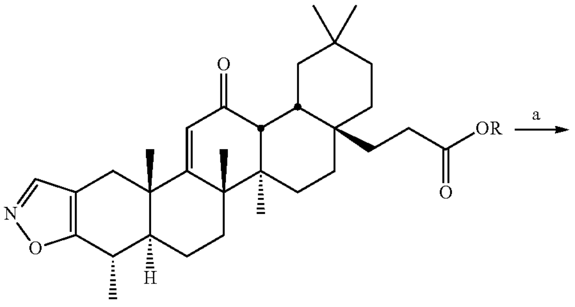

8 (R = Me/Et)

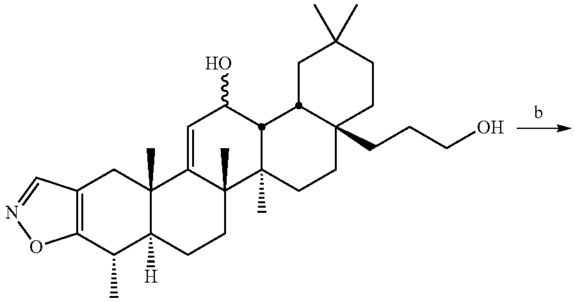

72

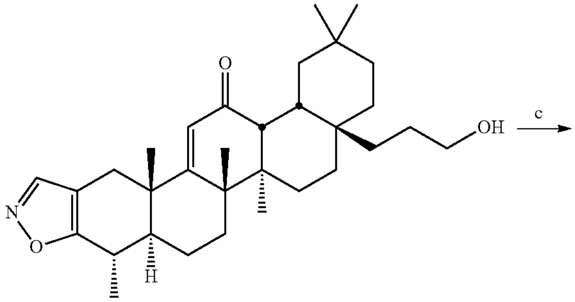

73

-continued
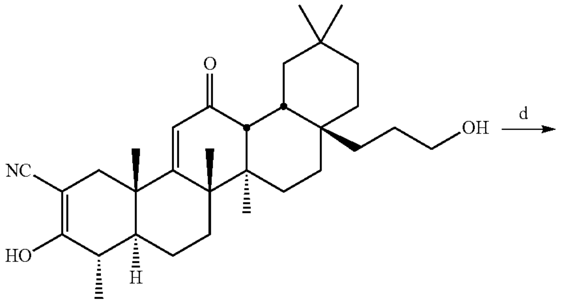
74
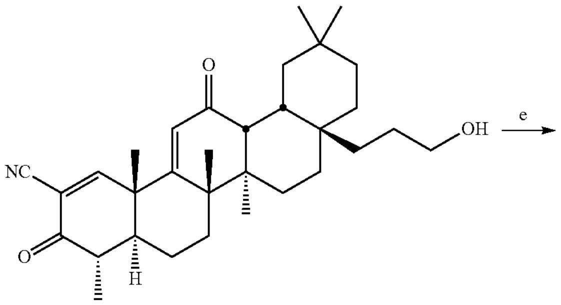
TX63918
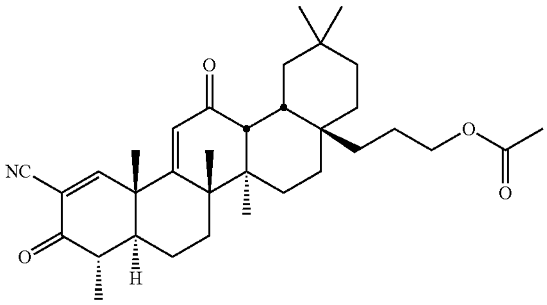
TX63920
Reagents and conditions: a) DIBAL—H, THF, 0° C. to rt; b) NBS, DME, H2O, rt, 81%; c) NaOMe, MeOH, rt, 67%; d) DBDMH, DMF, 0° C.; then Pyridine, 55° C., 83%; e) $Ac_2O$, TEA, DMAP, DCM, rt, 95%
Scheme 51
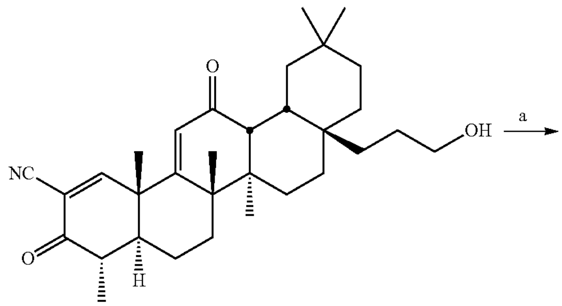
TX63918
-continued
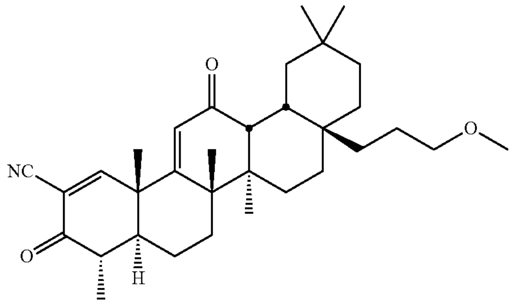
TX63919
Reagents and conditions: a) MePTF, 2,6-tBu-4-Me-Pyridine, DCM, rt, 73%.
Scheme 52
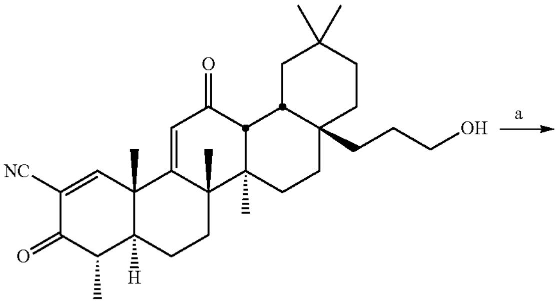
TX63918
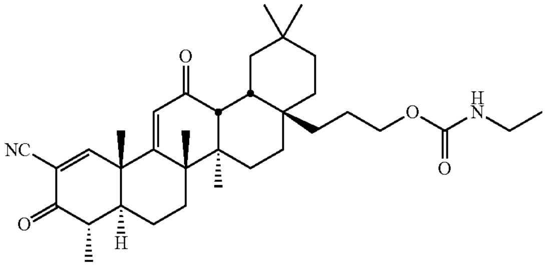
TX63982
Reagents and conditions: a) EtNCO, toluene, rt, 73%.
Scheme 53
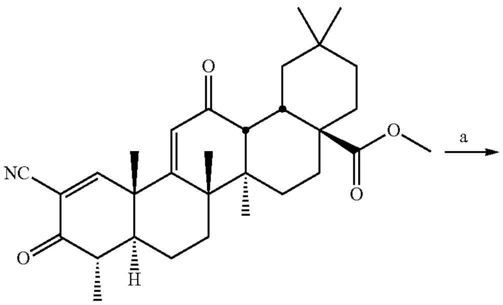
TX63435

-continued
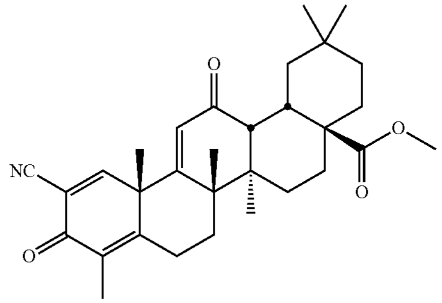
TX63448
Reagents and conditions: a) $SeO_2$, 1,4-dioxane, 12%.
Scheme 54
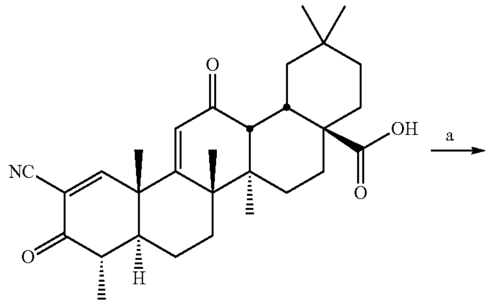
TX63520
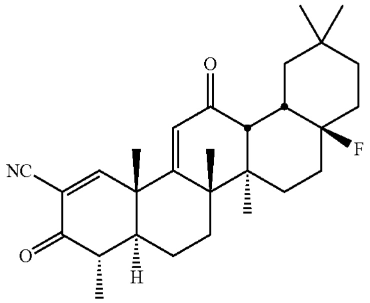
TX63936
Reagents and conditions: a) $XeF_2$, $CH_2Cl_2$, rt, 16 h, 9%.
Scheme 55
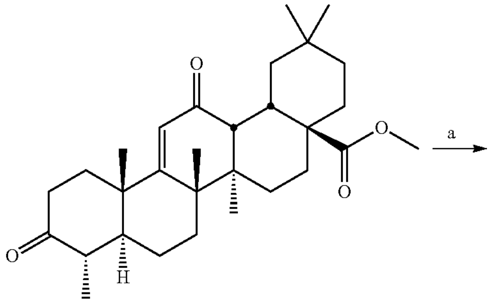
7
-continued
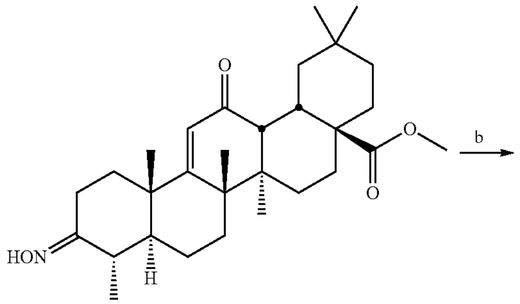
75
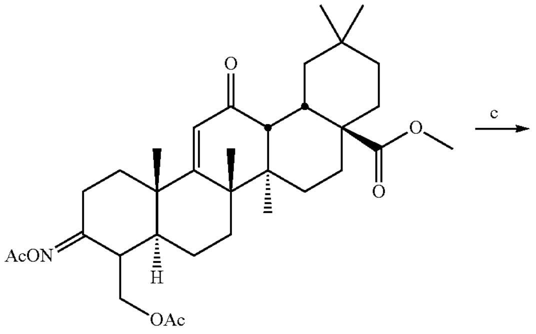
76
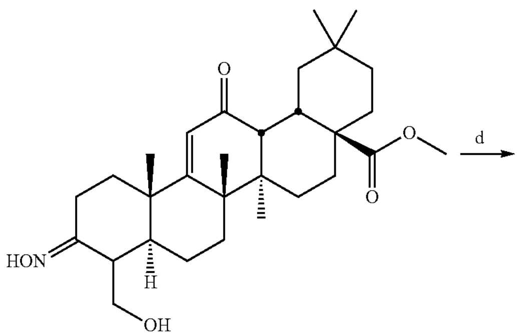
77
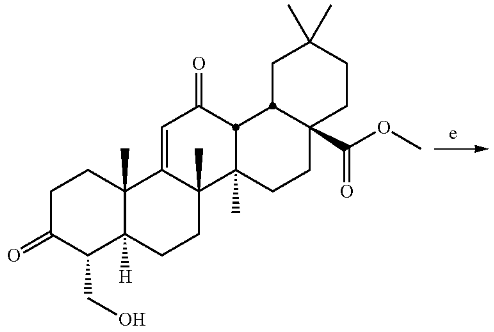
78

-continued

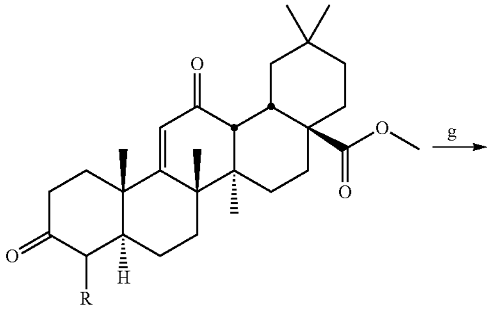

f 79 R = $CO_2H$
80 R = H

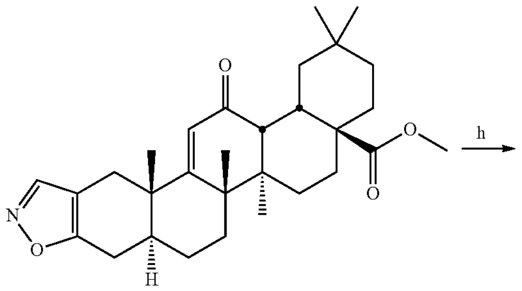

81

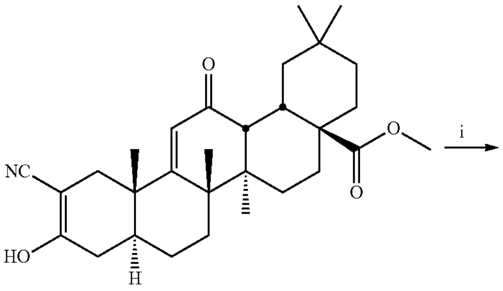

82

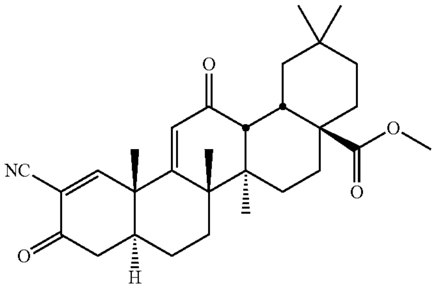

TX63614

Reagents and conditions: a) $NH_2OH$—HCl, $CH_2Cl_2$, MeOH, 60° C., 1.5 h; b) i) AcOH, $Ac_2O$, rt, 1 h; ii) $PhI(OAc)_2$, $Pd(OAc)_2$, $ClCH_2CH_2Cl$, 60° C., 15 h, then 80° C., 6 h, 44% from 7; c) $K_2CO_3$, MeOH, 0° C.-rt, 1.5 h; d) $NaHSO_3$, aq. EtOH, 80° C., 4 h, 73% from 78; e) Jones' reagent, 0° C.; f) 80° C., 2 h, then, 120° C., 30 min, vacuum, 80% from 81; g) i) $HCO_2Et$, NaOMe, 0° C.-rt, 5 h; ii) $NH_2OH$—HCl, aq. 55° C., 18 h, 45%; h) NaOMe, MeOH, 55° C., 3.5 h, 51%; i) DBDMH, DMF, 0° C., 1 h; Py, 55° C., 3 h, 81%

Scheme 56

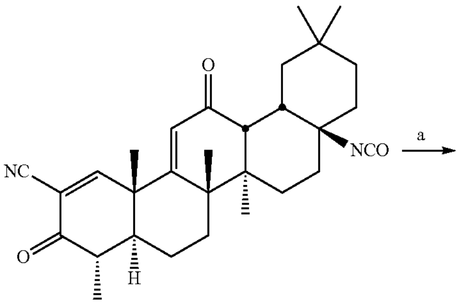

TX63618

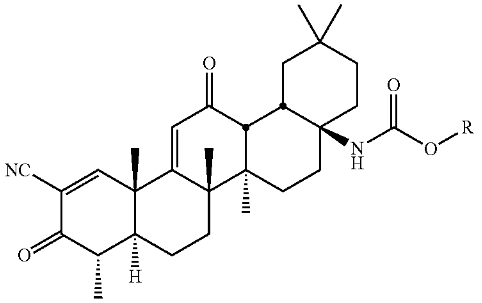

a-c

Reagents and conditions: a) ROH, Benzene, 85° C., 20 hr.

a: TX63693 R = $CH_3$
b: TX63800 R = $CH_2CH_3$
c: TX63819 R = $CH(CH_3)_2$,

Scheme 57

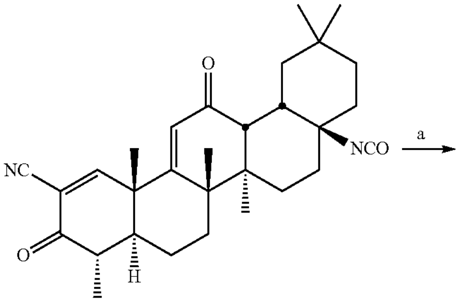

TX63618

-continued

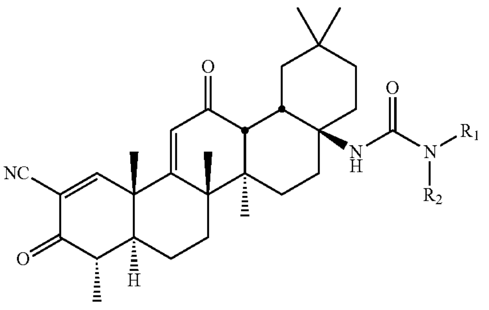

a-d

Reagents and conditions: a) $R_1R_2NH$, THF, 0° C., to rt, 2-20 h.

a: TX63862 R1 = R2 = H
b: TX63876 R1 = H, R2 = $CH_3$
c: TX63826 R1 = H, R2 = $CH_2CH_3$
d: TX63875 R1 = R2 = $CH_3$

Scheme 58

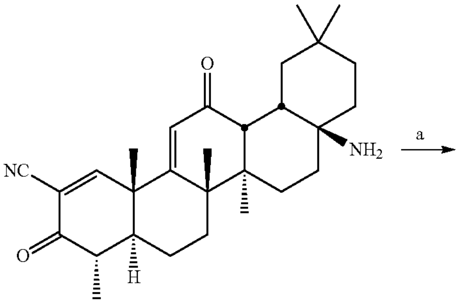

TX63620

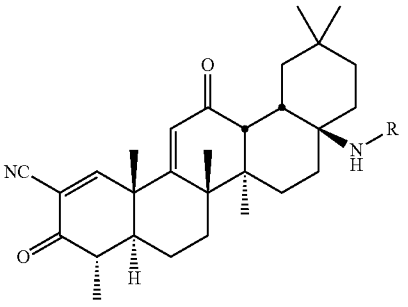

a-e

Reagents and conditions: a) RCl, TEA, DCM, 0° C., or rt, 1-2 hr.

a: TX63798 R = $COC_6H_5$
b: TX63818 R = $SO_2CH_2CF_3$
c: TX63863 R = $COCH(CH_2)_3$
d: TX63864 R = $COCH_2CH_3$
e: TX63865 R = $CO(CH_2)_5CH_3$

Scheme 59

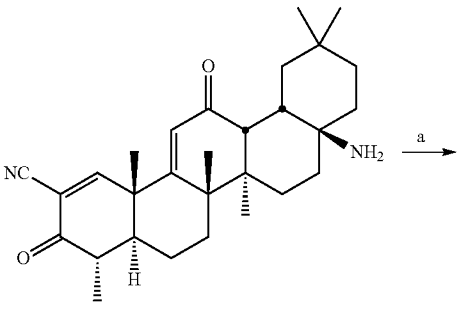

TX63620

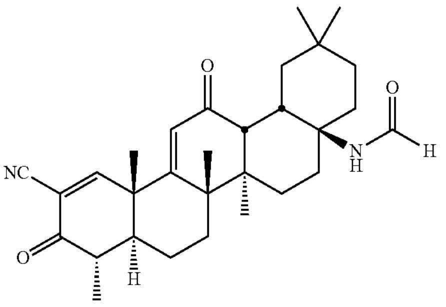

TX63681

Reagents and conditions: a) HCOOAc, TEA, DCM, 0° C., 1 hr, 68%

Scheme 60

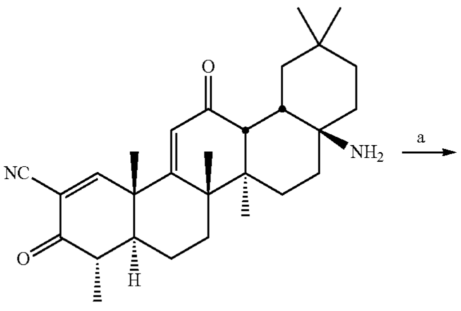

TX63620

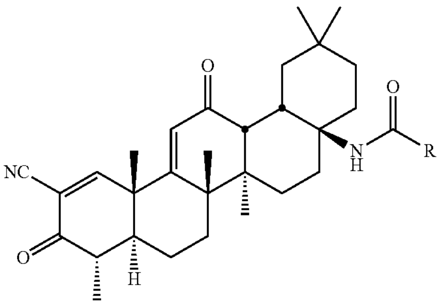

a-b

Reagents and conditions: a) T3P, TEA, DCM, RCOOH, rt, 2 h, TX63799: 20%, TX63866: 42%.

a: TX63799 R = $CH_2CF_3$
b: TX63866 R = cyclopropyl

Synthesis and Characterization of Compounds and Intermediates

Compound 2:

Compound 1 (40 g, 83.0 mmol), $NH_2OH$—HCl (13.33 g, 191.8 mmol), NaOAc (15.60 g, 190.2 mmol), $CH_2Cl_2$ (400 mL) and MeOH (400 mL) were mixed in a 2 L flask. The heterogeneous reaction mixture was stirred at 70° C. (oil bath temperature) for 1.5 hrs, and then, was cooled to room temperature. The solvent was removed on a rotary evaporator. The residue was dissolved in $CH_2Cl_2$, and was washed with water. The organic extract was dried with $MgSO_4$, and concentrated to give the crude product as a white foam solid. The crude product was dissolved in $CH_2Cl_2$, and the solution was filtered through a 2-inch pad of silica gel eluting with $CH_2Cl_2$/EtOAc (1:1, 1 L). The filtrate and washes were combined, and concentrated to give oxime 2 (43.44 g) as a white foam solid: m/z 498.3 (M+1).

Compound 3:

Compound 2 (43.44 g, 87.22 mmol) obtained above was dissolved in AcOH (217 mL) and $Ac_2O$ (217 mL), and the reaction was stirred at room temperature for 2 h. $PhI(OAc)_2$ (42.13 g, 131 mmol) and $Pd(OAc)_2$ (0.98 g, 4.37 mmol, 0.05 eq.) were added. The flask was sealed, and the mixture was heated in a 60° C. oil bath for 24 hrs. After cooling to room temperature, toluene was added, and most of the AcOH was removed by azeotropic evaporation with toluene on a rotary evaporator. The red oil obtained was slowly poured into a suspension of $NaHCO_3$ (150 g) in water (500 mL). After the mixture was stirred at room temperature for 15 min, it was extracted with $CH_2Cl_2$. The combined organic extracts was washed with aq. $NaHCO_3$, dried with $MgSO_4$, and concentrated. The residue was purified by column chromatography (silica gel, eluting with 0% to 50% EtOAc in hexanes) to give product 3 (23.56 g, 47.5% yield from 1) as a yellow foam solid. Compound 3 is a 4.4:1 mixture of C4-diastereomers: m/z 598.4 (M+1), 538.4 (M-OAc).

Compounds 4 and 5:

$K_2CO_3$ (27.38 g, 197.1 mmol) was added to a solution of compound 3 (23.56 g, 39.4 mmol) in MeOH (390 mL) at 0° C. After the reaction was stirred at room temperature for 1 hr, the solvent was removed on a rotary evaporator. The residue was treated with $CH_2Cl_2$ and 12 N HCl (33 mL, 396 mmol). After the mixture was stirred for 5 min, it was transferred to a separatory funnel, which was extracted with $CH_2Cl_2$. The combined organic extracts was washed with water, dried with $MgSO_4$, and concentrated. The crude product was purified by column chromatography (silica gel, eluting with 0% to 70% EtOAc in hexanes) to give product 4 (15.25 g, 75% yield) as a light yellow solid: m/z 514.1 (M+1). From the column, also get product 5 (2.20 g, 11% yield) as a yellow foam: m/z 514.1 (M+1).

Compound 6:

Compound 4 (17.25 g, 33.6 mmol), $NaHSO_3$ (12.21 g, 117.4 mmol), EtOH (135 mL) and water (68 mL) were mixed, and heated in an 80° C. oil bath for 3 hrs. Additional amount of $NaHSO_3$ (3.49 g, 33.6 mmol) was added, and the reaction was heated for another 1 hr. After EtOH was removed on a rotary evaporator, the residue was extracted with EtOAc. The combined organic extracts was washed with water, dried with $MgSO_4$, and concentrated to give the crude product, which was dissolved in $CH_2Cl_2$, and was filtered through a 1-inch pad of silica gel, eluting with $CH_2Cl_2$/EtOAc (1:1, 800 mL). The filtrate was concentrated to give Compound 6 (14.20 g, 85% yield) as a white solid: m/z 499.3 (M+1).

Compound 7:

Compound 6 (14.20 g, 28.5 mmol) was dissolved in xylene (600 mL), and was heated at reflux for 28 hrs. After the reaction was cooled to room temperature, the solvent was removed on a rotary evaporator to give the crude product 7 as a yellow solid. Crude 7 was dissolved in $CH_2Cl_2$ (50 mL) and EtOH (50 mL), and the solution was evaporated on a rotary evaporator until most of $CH_2Cl_2$ was removed. Additional amount of EtOH (25 mL) was added. The heterogeneous mixture was heated at reflux for 10 min, after which, it was allowed to stand at room temperature for 1 hr. The precipitate was collected by filtration, washed with EtOH, and dried under vacuum for 16 hrs to give compound 7 (11.40 g, 85% yield) as a white solid. Compound 7 is a 15:1 mixture of the two C4-epimers: m/z 469.3 (M+1).

Compound 8:

NaOMe (29.40 mL, 128.6 mmol) was added to a solution of compound 7 (4.02 g, 8.57 mmol) in THF (8.6 mL) at 0° C. After the reaction was stirred for 10 min, it was treated with $HCO_2Et$ (20.70 mL, 257.4 mmol), and was stirred at ambient temperature for 2.5 hrs. After the mixture was cooled to 0° C., MTBE (90 mL) and 12 N HCl (11 mL) were added. The mixture was stirred for 2 min, and was partitioned between water and EtOAc. The organic extract was washed with water, dried with $MgSO_4$, and concentrated to give compound 8 as a pink foam solid: m/z 497.3 (M+1).

Compound 9:

Compound 8 obtained above, $NH_2OH$—HCl (900 mg, 12.9 mmol), EtOH (86 mL) and water (8.6 mL) were mixed and heated at 55° C. for 3 hrs. After EtOH was removed on a rotary evaporator, the residue was extracted with $CH_2Cl_2$. The combined organic extracts was washed with water, dried with $MgSO_4$, and concentrated. The crude product was triturated with EtOH (20 mL) at reflux for 20 min, and the mixture was allowed to stand at room temperature for 2 hrs. The precipitate was collected by filtration, washed with EtOH, and dried under vacuum for 16 hrs to give compound 9 (2.40 g, 57% yield from 7) as a white solid. The mother liquor was concentrated, and the residue was purified by column chromatography (silica gel, eluting with 0% to 25% EtOAc in hexanes) to give a second crop of product 9 (820 mg, 19% yield from 7) as a white solid. Compound 9: m/z 494.3 (M+1).

Compound 10 (TX63778):

NaOMe (2.05 mL, 8.96 mmol) was added to a suspension of compound 9 (3.195 g, 6.47 mmol) in MeOH (65 mL) at room temperature. After the reaction was heated at 55° C. for 2 hrs, it was cooled to room temperature. MTBE was added, and the mixture was transferred to a separatory funnel, which was washed with 1 N aq. HCl, and water. The organic extract was dried with $MgSO_4$, and concentrated to give compound 10 as an off-white solid: m/z 494.3 (M+1); $^1H$ NMR (500 MHz, $CDCl_3$) δ 5.82 (s, 1H), 3.72 (dd, 1H, J=5.7, 13.6 Hz), 3.69 (s, 3H), 3.03 (m, 1H), 2.91 (d, 1H, J=4.5 Hz), 2.68 (dd, 1H, J=5.6, 13.1 Hz), 2.43 (m, 1H), 2.01 (dd, 1H, J=13.2, 13.4 Hz), 1.41 (s, 3H), 1.31 (s, 3H), 1.13 (d, 3H, J=6.4 Hz), 1.10-1.95 (m, 15H), 1.00 (s, 3H), 1.00 (s, 3H), 0.90 (s, 3H).

Compound TX63435:

A solution of 1,3-dibromo-5,5-dimethylhydantoin (939 mg, 3.28 mmol) in DMF (10 mL) was added to a solution of compound 10 obtained above in DMF (25 mL) at 0° C. After the reaction was stirred at 0° C. for 1 hr, pyridine (1.68 mL, 20.8 mmol) was added. The reaction was heated at 55° C. for 3.5 hrs, and was cooled to room temperature. The mixture was diluted with EtOAc, and was transferred to a separatory funnel, which was washed with 1 N aq. HCl, aq. $Na_2SO_3$ solution, and water. The organic extract was dried with $MgSO_4$ and concentrated. The residue was purified by column chromatography (silica gel, eluting with 0% to 30% EtOAc in hexanes) to give TX63435 (2.727 g, 85% yield from 9) as a white solid: $^1H$ NMR (500 MHz, $CDCl_3$) δ 8.03 (s, 1H), 6.026 (s, 1H), 3.71 (s, 3H), 3.05 (m, 1H), 2.96 (d, 1H, J=4.5 Hz), 2.48 (m, 1H), 1.45 (s, 3H), 1.33 (s, 3H), 1.26 (d, 3H, J=6.5 Hz), 1.20-1.95 (m, 15H), 1.02 (s, 3H), 1.01 (s, 3H), 0.91 (s, 3H); m/z 492.3 (M+1).

Compound TX63520:

LiI (14.85 g, 110.8 mmol) was added to a solution of compound 10 (2.727 g, 5.54 mmol) in DMF (40 mL) at room temperature. After the reaction was heated at 150° C. with $N_2$ bubbled through for 4 hrs, it was cooled, and was diluted with EtOAc. The mixture was washed with 1 N aq. HCl, and water. The aq. washes were extracted again with EtOAc. The combined EtOAc extracts was washed with aq. $Na_2SO_3$, and water, dried with $Na_2SO_4$, and concentrated. The residue was purified by column chromatography (silica gel, eluting with 0% to 10% MeOH on $CH_2Cl_2$) to give TX63520 (1.700 g, 64% yield) as a white solid: $^1H$ NMR (400 MHz, $CDCl_3$) δ 8.02 (s, 1H), 6.03 (s, 1H), 3.01-3.05 (m, 2H), 2.47 (m, 1H), 1.44 (s, 3H), 1.35 (s, 3H), 1.25 (d, 3H, J=6.8 Hz), 1.18-1.97 (m, 15H), 1.02 (s, 3H), 1.00 (s, 3H), 0.90 (s, 3H); m/z 478.3 (M+1).

Compound TX63521:

Oxalyl chloride (0.35 mL, 4.13 mmol) and DMF (11 μL, 0.14 mmol) were added sequentially to a solution of TX63520 (660 mg, 1.38 mmol) in $CH_2Cl_2$ (28 mL) at 0° C. After the reaction was stirred at ambient temperature for 2 hrs, it was concentrated on a rotary evaporator. The residue was co-evaporated with toluene (3×10 mL) to remove residual oxalyl chloride. Compound 11 was obtained as a light yellow foam solid.

The acid chloride 11 was dissolved in $CH_2Cl_2$ (14 mL), and was cooled to 0° C. $EtNH_2$ (2.0 M solution in THF, 2.07 mL, 4.14 mmol) was added. After the reaction was stirred at 0° C. for 30 min, it was transferred to a reparatory funnel, which was washed with water. The organic extract was dried with $Na_2SO_4$, and concentrated. The residue was purified by column chromatography (silica gel, eluting with 0% to 100% EtOAc in hexanes) to give TX63521 (704 mg, 100% yield) as a white solid, which was contaminated with a small amount of impurities. The TX63521 obtained was further purified by triturated with EtOH (5 mL) at 55° C. for 10 min. After the mixture was allowed to stand at room temperature for 1 hr, the white precipitate was collected by filtration, washed with EtOH, and dried under vacuum for 16 hrs to give TX63521 (504 mg) as a white solid: $^1H$ NMR (600 MHz, $CDCl_3$) δ 8.01 (s, 1H), 6.01 (s, 1H), 5.74 (t, 1H, J=5.4 Hz), 3.30 (m, 2H), 3.06 (d, 1H, J=4.2 Hz), 2.84 (m, 1H), 2.46 (m, 1H), 1.43 (s, 3H), 1.32 (s, 3H), 1.24 (d, 3H, J=6.6 Hz), 1.14-1.96 (m, 15H), 1.12 (t, 3H, J=7.2 Hz), 1.01 (s, 3H), 0.99 (s, 3H), 0.89 (s, 3H); m/z 505.3 (M+1).

Compound 12:

LiI (67.89 g, 506.6 mmol) was added to a solution of compound 7 (11.88 g, 25.3 mmol) in DMF (180 mL) at room temperature. The mixture was heated at 150° C. with $N_2$ bubbled through for 7.5 h. After the reaction was cooled, it was diluted with EtOAc, and was washed with 1 N aq. HCl, and water. The aqueous washes were extracted again with EtOAc. The combined EtOAc extracts was washed with aq. $Na_2SO_3$, and water, dried over $Na_2SO_4$, and concentrated on a rotary evaporator to approximately 40 mL. The yellow heterogeneous mixture was refluxed for 20 min, after which, it was allowed to stand at room temperature for 5 h. The precipitate was collected by filtration, washed with EtOAc/hexane (1:1), and dried under vacuum for 16 h to give compound 12 (9.15 g, 79% yield) as a white solid. The mother liquor was concentrated, and the residue was purified by column chromatography (silica gel, eluting with 0% to 35% EtOAc in $CH_2Cl_2$) to give a second crop of compound 12 (1.65 g, 14% yield) as a white solid. Compound 12: m/z 455.3 (M+1).

Compound 13:

NaOMe (87 mL, 380.5 mmol) was added to a suspension of compound 12 (11.54 g, 25.4 mmol) in $HCO_2Et$ (61 mL, 758.4 mmol) at 0° C. After the reaction was stirred at ambient temperature for 1 h, it was cooled to 0° C. MTBE (250 mL) and 6 N aq. HCl (67.6 mL, 405.6 mmol) were added sequentially. After stirring for 5 min, the mixture was transferred to a reparatory funnel, and was extracted with EtOAc. The combined organic extracts was washed with 1 N aq. HCl, and water, dried with $Na_2SO_4$, and concentrated.

The residue was mixed with $NH_2OH$—HCl (2.66 g, 38.3 mmol), EtOH (250 mL) and water (25 mL), and was heated at 55° C. for 3 h. After EtOH was removed on a rotary evaporator, the residue was extracted with $CH_2Cl_2$. The combined organic extracts was washed with water, dried with $Na_2SO_4$, and concentrated to give the crude product as a pink solid. Crude 7 was triturated with EtOAc (25 mL) at reflux for 10 min, and the mixture was allowed to stand at room temperature for 2 h. The precipitate was collected by filtration, washed with EtOAc/hexane (1:1), and dried under vacuum for 16 h to give compound 13 (9.70 g, 80% yield) as a light pink solid: m/z 480.3 (M+1).

Compound 14:

Oxalyl chloride (3.31 mL, 39.0 mmol) and DMF (0.10 mL, 1.29 mmol) were added sequentially to a solution of compound 13 (6.25 g, 13.0 mmol) in $CH_2Cl_2$ (130 mL) at 0° C. After the reaction was stirred at ambient temperature for 2 h, it was concentrated on a rotary evaporator. The residue was co-evaporated with toluene (3×50 mL) to remove residual oxalyl chloride. Crude acid chloride was obtained as a light brown solid.

The acid chloride was dissolved in $CH_2Cl_2$ (130 mL), and was cooled to 0° C. $EtNH_2$ (2.0 M solution in THF, 19.5 mL, 39.0 mmol) was added, and the reaction was stirred at 0° C. for 40 min. The mixture was transferred to a separatory funnel, which was washed with water. The organic extract was dried with $Na_2SO_4$, and concentrated. The crude product was dissolved in minimal amount of $CH_2Cl_2$, and EtOH (10 mL) was added. After the mixture was heated at reflux for 10 min to evaporate the $CH_2Cl_2$, it was allowed to stand at 4° C. for 16 h. The precipitate was collected by filtration, washed with EtOH, and dried under vacuum for 16 h to give compound 14 (5.66 g, 86% yield) as a white solid: m/z 507.3 (M+1).

Compound 15:

NaOMe (5.11 mL, 22.3 mmol) was added to a solution of compound 14 (5.66 g, 11.2 mmol) in MeOH (112 mL) at room temperature. After the reaction was heated at 55° C. for 2 h, it was cooled to room temperature. MTBE (200 mL) was added, and the mixture was transferred to a separatory funnel, which was washed with 1 N aq. HCl, and water. The aqueous washes were extracted again with EtOAc. The combined organic extracts was dried with $Na_2SO_4$, and concentrated to give crude product 15 as a white solid. Crude 15 was triturated with EtOAc (20 mL) at reflux for 5 min, and was allowed to stand at room temperature for 2 h. The precipitate was collected by filtration, washed with EtOAc, and dried under vacuum for 16 h to give compound 15 (5.22 g, 92% yield) as a white solid. Compound 15 is a 1.75:1 mixture of A-ring enol and ketone isomers: m/z 507.3 (M+1).

Compounds TX63521 and TX63597:

A solution of 1,3-dibromo-5,5-dimethylhydantoin (1.472 g, 5.15 mmol) in DMF (26 mL) was added to a solution of compound 15 (5.218 g, 10.3 mmol) in DMF (25 mL) at 0° C. After the reaction was stirred at 0° C. for 1 h, pyridine (2.50 mL, 31.0 mmol) was added, and the mixture was heated at 55° C. for 3 h. After cooling to room temperature, the reaction was diluted with EtOAc (300 mL), and was transferred to a separatory funnel, which was washed with 1 N aq. HCl, aq. $Na_2SO_3$, and water. The organic extract was dried with $Na_2SO_4$ and concentrated. The residue was filtered through a pad of silica gel, eluting with 1:1 EtOAc:$CH_2Cl_2$ (400 mL). The filtrate was concentrated to give the crude product, which was triturated from $CH_2Cl_2$/EtOH to give TX63521 (4.37 g, 84% yield) as a white solid: m/z 505.3 (M+1). The mother liquor was concentrated. The residue was purified by column chromatography (silica gel, eluting with 0% to 100% EtOAc in (10:1 hexanes:$CH_2Cl_2$)) to give a second crop of TX63521 (0.67 g, 12% yield) as a white solid. From the mother liquor, compound TX63597 (12 mg, 2% yield) was also obtained as a white solid: m/z=503.3 (M+1); $^1$H NMR (500 MHz, $CDCl_3$) δ 7.85 (s, 1H), 5.95 (s, 1H), 5.76 (t, 1H, J=5.3 Hz), 3.33 (m, 2H), 3.13 (d, 1H, J=4.5 Hz), 2.94 (m, 1H), 2.86 (m, 1H), 2.60 (m, 1H), 2.01 (s, 3H), 1.95 (m, 1H), 1.65 (s, 3H), 1.50 (s, 3H), 1.15-1.85 (m, 11H), 1.15 (t, 3H, J=7.2 Hz), 1.00 (s, 3H), 0.90 (s, 3H), 0.86 (s, 3H).

Compound TX63522:

Imidazole (75 mg, 1.10 mmol) was added to a solution of compound 11 (184 mg, 0.37 mmol)) in benzene (3.7 mL) at 10° C. After the reaction was stirred for 40 min, additional amount of imidazole (25 mg, 0.37 mmol) was added. After the reaction was continued to stir for another 30 min, it was diluted with EtOAc. The mixture was transferred to a separatory funnel, which was washed with water. The organic extract was dried with $Na_2SO_4$, and concentrated. The residue was purified by column chromatography (silica gel, eluting with 0% to 100% EtOAc in $CH_2Cl_2$) to give TX63522 (150 mg, 77% yield) as a white foam solid: $^1$H NMR (600 MHz, $CDCl_3$) δ 8.32 (s, 1H), 8.00 (s, 1H), 7.61 (s, 1H), 7.08 (s, 1H), 6.02 (s, 1H), 3.19-3.22 (m, 2H), 2.45 (m, 1H), 2.23 (m, 1H), 1.43 (s, 3H), 1.27 (s, 3H), 1.23 (d, 3H, J=7.2 Hz), 1.20-2.04 (m, 14H), 1.04 (s, 6H), 0.95 (s, 3H); m/z 528.3 (M+1).

Compound TX63523:

$CF_3CH_2NH_2$ (359 mg, 3.62 mmol) was added to a solution of compound 11 (600 mg, 1.21 mmol) in $CH_2Cl_2$ (12 mL) at room temperature. After the reaction was stirred for 1 hr, it was diluted with EtOAc, transferred to a separatory funnel, which was washed with water. The organic extract was dried with $Na_2SO_4$, and concentrated. The residue was triturated with EtOH at 55° C. for 10 min. After the mixture was allowed to stand at room temperature for 1 hr, the white precipitate was collected by filtration, washed with EtOH, and dried under vacuum for 16 hrs to give TX63523 (320 mg, 47% yield) as a white solid. The mother liquor was concentrated, and the residue was purified by column chromatography (silica gel, eluting with 0% to 100% EtOAc in hexanes) to give a second crop of TX63523 (235 mg, 35% yield) as a white solid. Compound TX63523: $^1$H NMR (600 MHz, $CDCl_3$) δ 8.01 (s, 1H), 6.02 (s, 1H), 5.99 (t, 1H, J=6.6 Hz), 3.88-4.05 (m, 2H), 3.05 (d, 1H, J=4.8 Hz), 2.92 (m, 1H), 2.46 (m, 1H), 2.03 (m, 1H), 1.43 (s, 3H), 1.30 (s, 3H), 1.24 (d, 3H, J=6.0 Hz), 1.18-1.89 (m, 14H), 1.02 (s, 3H), 0.99 (s, 3H), 0.90 (s, 3H); m/z 559.3 (M+1).

Compound 16:

Oxalyl chloride (2.10 mL, 24.8 mmol) and catalytic amount of DMF were added sequentially to a solution of compound 13 (3.99 g, 8.32 mmol) in $CH_2Cl_2$ (83 mL) at 0° C. After the reaction was stirred at ambient temperature for 2 h, it was concentrated on a rotary evaporator. The residue was co-evaporated with toluene (3×30 mL) to remove residual oxalyl chloride. Crude acid chloride was obtained as a light brown solid.

The acid chloride was dissolved in $CH_2Cl_2$ (83 mL), and was cooled to 0° C. $CF_3CH_2NH_2$ (1.90 mL, 24.9 mmol) was added, and the reaction was stirred at 0° C. for 90 min. The mixture was transferred to a separatory funnel, which was washed with water. The organic extract was dried with $Na_2SO_4$, and concentrated. The residue was purified by column chromatography (silica gel, eluting with 0% to 50% EtOAc in hexane) to give compound 16 (3.95 g, 85% yield) as a white solid: m/z 561.3 (M+1).

Compound 17:

NaOMe (2.30 mL, 10.1 mmol) was added to a solution of compound 16 (3.95 g, 7.04 mmol) in MeOH (70 mL) at room temperature. After the reaction was heated at 55° C. for 2 h, it was cooled to room temperature. MTBE (200 mL) was added, and the mixture was transferred to a separatory funnel, which was washed with 1 N aq. HCl, and water. The organic extract was dried with $Na_2SO_4$, and concentrated. The residue was purified by column chromatography (silica gel, eluting with 0% to 60% EtOAc in hexane) to give compound 17 (3.18 g, 81% yield) as a white solid: m/z 561.3 (M+1).

Compound TX63523:

A solution of 1,3-dibromo-5,5-dimethylhydantoin (1.22 g, 4.27 mmol) in DMF (15 mL) was added to a solution of compound 17 (4.80 g, 8.55 mmol) in DMF (20 mL) at 0° C. via syringe. The syringe was rinsed with DMF (8 mL), and was added to the reaction mixture. After the reaction was stirred at 0° C. for 1 h, pyridine (2.07 mL, 25.7 mmol) was added, and the mixture was heated at 55° C. for 3 h. After cooling to room temperature, the reaction was diluted with EtOAc, and was transferred to a separatory funnel, which was washed with 1 N aq. HCl, aq. $Na_2SO_3$, and water. The organic extract was dried with $Na_2SO_4$ and concentrated to give crude compound TX63523 (4.70 g, 98% yield) as a light yellow solid. Crude compound TX63523 was dissolved in $CH_2Cl_2$ (30 mL) and EtOH (15 mL). The solution was evaporated on a rotary evaporator until most of $CH_2Cl_2$ was removed. The heterogeneous mixture was heated at reflux for 20 min, and was allowed to stand at room temperature for 1 h. The precipitate was collected by filtration, washed with EtOH, and dried under vacuum for 16 h to give compound TX63523 (4.04 g, 86% yield) as a white solid: m/z 559.2 (M+1).

Compound 18:

$LiAlH_4$ (2.0 M in THF, 0.30 mL, 0.60 mmol) was added to a solution of compound 9 (100 mg, 0.20 mmol) in THF (4.0 mL) at 0° C. After the reaction was stirred at 0° C. for 4 hrs, additional amount of $LiAlH_4$ (2.0 M in THF, 0.10 mL, 0.20 mmol) was added. After the reaction was stirred for another 2 hrs, it was quenched by the addition of EtOH. EtOAc was added, and the mixture was washed with 1N aq. HCl and water. The organic extract was dried with $MgSO_4$, and concentrated. The residue was purified by column chromatography (silica gel, eluting with 0% to 80% EtOAc in hexane) to give compound 18 (56 mg, 59% yield) as a white foam solid: m/z 468.3 (M+1).

Compound 19:

NBS (30 mg, 0.17 mmol) was added to a solution of compound 18 (53 mg, 0.11 mmol) in DME (1 mL) and water (0.1 mL) at room temperature. After the reaction was stirred at room temperature while shielded from light for 25 min, aq. $Na_2SO_3$ was added. The mixture was transferred to a separatory funnel, which was extracted with EtOAc. The organic extract was dried with $MgSO_4$, and concentrated. The residue was purified by column chromatography (silica gel, eluting with 0% to 60% EtOAc in hexane) to give compound 19 (50 mg, 94% yield) as a white foam solid: m/z 466.3 (M+1).

Compound 20:

NaOMe (37 μL, 0.16 mmol) was added to a solution of compound 19 (50 mg, 0.11 mmol) in MeOH (1.1 mL) at room temperature. After the reaction was heated at 55° C. for 1 hr, it was cooled to room temperature. MTBE was added, and the mixture was transferred to a separatory funnel, which was washed with 1 N aq. HCl, and water. The organic extract was dried with $MgSO_4$, and concentrated. The residue was purified by column chromatography (silica gel, eluting with 0% to 80% EtOAc in hexane) to give compound 20 (47 mg, 94% yield) as a white foam solid: m/z 466.3 (M+1).

Compound TX63545:

A solution of 1,3-dibromo-5,5-dimethylhydantoin (14 mg, 0.049 mmol) in DMF (0.2 mL) was added to a solution of compound 20 (46 mg, 0.099 mmol) in DMF (0.3 mL) at 0° C. After the reaction was stirred at 0° C. for 1 hr, pyridine (24 μL, 0.30 mmol) was added. The reaction was heated at 55° C. for 3 hrs, and was cooled to room temperature. The mixture was diluted with EtOAc, and was washed with 1 N aq. HCl, aq. $Na_2SO_3$ solution, and water. The organic extract was dried with $MgSO_4$ and concentrated. The residue was purified by column chromatography (silica gel, eluting with 0% to 80% EtOAc in hexanes) to give TX63545 (37 mg, 80% yield) as a white solid: $^1$H NMR (500 MHz, $CDCl_3$) δ 8.04 (s, 1H), 6.05 (s, 1H), 3.63 (dd, 1H, J=6.5, 10.8 Hz), 3.54 (dd, 1H, J=4.6, 10.8 Hz), 2.97 (d, 1H, J=4.6 Hz), 2.50 (m, 1H), 2.38 (m, 1H), 1.47 (s, 6H), 1.27 (d, 3H, J=6.7 Hz), 1.10-1.93 (m, 16H), 1.04 (s, 3H), 0.96 (s, 3H), 0.90 (s, 3H); m/z 464.3 (M+1).

Compound TX63546:

$Ac_2O$ (11 μL, 0.12 mmol) was added to a solution of compound TX63545 (10.7 mg, 0.023 mmol) and pyridine (19 μL, 0.23 mmol) in $CH_2Cl_2$ (0.23 mL) at room temperature. After the reaction was stirred at room temperature for 3 hrs, aq. $NaHCO_3$ was added. The mixture was transferred to a separatory funnel, which was extracted with EtOAc. The organic extract was washed with 1 N aq. HCl, and water, dried with $MgSO_4$ and concentrated. The residue was purified by column chromatography (silica gel, eluting with 0% to 80% EtOAc in hexanes) to give TX63546 (9 mg, 77% yield) as a white foam solid: $^1$H NMR (500 MHz, $CDCl_3$) δ 8.02 (s, 1H), 6.03 (s, 1H), 4.11 (d, 1H, J=11.2 Hz), 4.01 (d, 1H, J=11.2 Hz), 3.00 (d, 1H, J=4.6 Hz), 2.48 (m, 1H), 2.38 (m, 1H), 2.09 (s, 3H), 1.51 (s, 3H), 1.46 (s, 3H), 1.25 (d, 3H, J=6.8 Hz), 1.10-1.91 (m, 15H), 1.02 (s, 3H), 0.94 (s, 3H), 0.88 (s, 3H); m/z 506.3 (M+1).

Compound TX63555 and TX63556:

TX63520 (65 mg, 0.14 mmol), IPh(OH)(OTs) (64 mg, 0.16 mmol) and $CH_2Cl_2$ (2.7 mL) were mixed and heated at reflux for 1 hr. After cooling to room temperature, the mixture was purified by column chromatography (silica gel, eluting with 0% to 70% EtOAc in hexanes) to give TX63555 (34 mg, 53% yield) as a white solid: $^1$H NMR (500 MHz, $CDCl_3$) δ 7.99 (s, 1H), 6.25 (s, 1H), 2.98 (m, 1H), 2.52 (m, 1H), 2.11 (m, 1H), 1.53 (s, 3H), 1.53 (s, 3H), 1.27 (d, 3H, J=6.8 Hz), 1.22-1.93 (m, 14H), 1.02 (s, 3H), 0.97 (s, 6H); m/z 476.2 (M+1).

From the column, TX63556 (24 mg, 37%) was also obtained as a white solid: $^1$H NMR (500 MHz, $CDCl_3$) δ 7.95 (s, 1H), 5.92 (s, 1H), 2.97 (t, 1H, J=8.4 Hz), 2.49 (m, 1H), 2.37 (m, 1H), 1.56 (s, 3H), 1.47 (s, 3H), 1.22-2.02 (m, 14H), 1.20 (d, 3H, J=6.8 Hz), 1.17 (s, 3H), 1.02 (s, 3H), 0.99 (s, 3H); m/z 476.3 (M+1).

Compound TX63557:

$NH_3$ (2.0 M in MeOH, 0.50 mL, 1.00 mmol) was added to a solution of compound 11 (104 mg, 0.21 mmol) in THF (2.1 mL) at 0° C. After the reaction was stirred at 0° C. for 30 min, EtOAc was added. The mixture was transferred to a separatory funnel, which was washed with water. The organic extract was dried with $MgSO_4$, and concentrated. The residue was purified by column chromatography (silica gel, eluting with 0% to 100% EtOAc in hexanes) to give TX63557 (95 mg, 95% yield) as a white solid: $^1$H NMR (500 MHz, $CDCl_3$) δ 8.04 (s, 1H), 6.04 (s, 1H), 5.74 (bs, 1H), 5.31 (bs, 1H), 3.15 (d, 1H, J=4.5 Hz), 2.88 (m, 1H), 2.48 (m, 1H), 1.46 (s, 3H), 1.38 (s, 3H), 1.27 (d, 3H, J=6.7 Hz), 1.19-2.04 (m, 15H), 1.04 (s, 3H), 1.02 (s, 3H), 0.92 (s, 3H); m/z 477.3 (M+1).

Compound TX63558:

$Et_3N$ (51 μL, 0.37 mmol) and TFAA (30 μL, 0.22 mmol) were added sequentially to a solution of TX63557 (70 mg, 0.15 mmol) in $CH_2Cl_2$ at 0° C. After the reaction was stirred at 0° C. for 15 min, aq. $NaHCO_3$ was added. The mixture was transferred to a separatory funnel, which was extracted with $CH_2Cl_2$. The combined organic extracts was washed with water, dried with $MgSO_4$, and concentrated. The residue was purified by column chromatography (silica gel, eluting with 0% to 35% EtOAc in hexanes) to give TX63558 (51 mg, 83% yield) as a white solid: $^1$H NMR (500 MHz, $CDCl_3$) δ 8.03 (s, 1H), 6.07 (s, 1H), 3.29 (d, 1H, J=4.7 Hz), 2.80 (m, 1H), 2.50 (m, 1H), 2.21 (m, 1H), 1.57 (s, 3H), 1.50 (s, 3H), 1.27 (d, 3H, J=6.9 Hz), 1.18-2.08 (m, 14H), 1.03 (s, 3H), 1.02 (s, 3H), 0.92 (s, 3H); m/z 459.2 (M+1).

Compound 21:

A mixture of Compound 11 (176 mg, 0.35 mmol) in ether (3.0 mL) was cooled to 0° C. $Et_3N$ (99 μL, 0.71 mmol) and $AcNHNH_2$ (40 mg, 0.53 mmol) in $CH_2Cl_2$ (8 mL) were added sequentially. The reaction was stirred at room temperature for 30 min, after which, additional amount of $AcNHNH_2$ (40 mg, 0.53 mmol) was added. After stirring for another 2 h, the mixture was diluted with EtOAc, and was transferred to a separatory funnel, which was washed with 1N aq. HCl and water. The organic extract was dried with $MgSO_4$, and concentrated. The residue was purified by column chromatography (silica gel, eluting with 0% to 100% EtOAc in hexanes) to give compound 21 (130 mg, 68% yield) as a white foam solid: m/z 534.2 (M+1).

Compound TX63616:

A mixture of compound 21 (28 mg, 0.052 mmol), $TsOH.H_2O$ (5 mg, 0.026 mmol) and toluene (2 mL) was heated at reflux with a dean-stark apparatus for 2 hrs. The mixture was transferred to a separatory funnel, which was washed with aq. $NaHCO_3$ and water. The organic extract was dried with $MgSO_4$, and concentrated. The residue was purified by column chromatography (silica gel, eluting with 0% to 65% EtOAc in hexanes) to give compound TX63616 (20 mg, 74% yield) as a white foam solid: $^1$H NMR (500 MHz, $CDCl_3$) δ 8.02 (s, 1H), 6.02 (s, 1H), 3.15 (m, 1H), 2.97 (d, 1H, J=4.6 Hz), 2.54 (s, 3H), 2.47 (m, 1H), 2.19 (m, 1H), 1.42 (s, 3H), 1.26 (d, 3H, J=6.7 Hz), 1.20-2.03 (m, 14H), 1.20 (s, 3H), 1.07 (s, 3H), 1.06 (s, 3H), 0.96 (s, 3H); m/z 516.2 (M+1).

Compound 22:

$Et_3N$ (0.44 mL, 3.16 mmol) and DPPA (103 μL, 0.48 mmol) were added sequentially to a solution of compound TX63520 (76 mg, 0.16 mmol) in toluene (1.6 mL) at 0° C. After the reaction was stirred at room temperature for 4 h, the solvent was removed by evaporation. The residue was purified by column chromatography (silica gel, 0 to 30% EtOAc in hexanes) to give azide 22 (63 mg, 79%) as white foam solid: m/z 503.2 (M+1).

Compound TX63618:

A solution of compound 22 (63 mg, 0.13 mmol) in toluene (5 mL) was heated at 80° C. for 3 h. The solvent was removed, and the residue was purified by column chromatography (silica gel, 0 to 3% EtOAc in $CH_2Cl_2$) to give compound TX63618 (54 mg, 91%) as white foam solid: $^1$H NMR (500 MHz, $CDCl_3$) δ 8.03 (s, 1H), 6.06 (s, 1H), 3.30 (d, 1H, J=4.7 Hz), 2.54 (m, 1H), 2.50 (m, 1H), 1.53 (s, 3H), 1.49 (s, 3H), 1.28 (d, 3H, J=6.7 Hz), 1.15-2.14 (m, 15H), 1.04 (s, 3H), 1.01 (s, 3H), 0.92 (s, 3H); m/z 475.2 (M+1).

Compound TX63620:

12 N aq. HCl (0.5 mL, 6.00 mmol) was added to a solution of compound TX63618 (49 mg, 0.10 mmol) in MeCN (0.5 mL) at 0° C., and the reaction was stirred at room temperature for 1 hr. $CH_2Cl_2$ and 10% aq. NaOH (2.4 mL, 6.00 mmol) were added. The mixture was transferred to a separatory funnel, which was washed with aq. $NaHCO_3$ and water. The organic extract was dried with $MgSO_4$, and concentrated to give compound TX63620 (45 mg, 97% yield) as an off-white foam solid: $^1$H NMR (500 MHz, $CDCl_3$) δ 8.05 (s, 1H), 6.04 (s, 1H), 3.65 (d, 1H, J=4.4 Hz), 2.50 (m, 1H), 2.23 (m, 1H), 1.52 (s, 3H), 1.48 (s, 3H), 1.28 (d, 3H, J=6.7 Hz), 1.00 (s, 6H), 0.98-2.14 (m, 15H), 0.90 (s, 3H); m/z 449.2 (M+1).

Compound TX63621:

$Et_3N$ (59 μL, 0.42 mmol) and $MeSO_2Cl$ (5 μL, 0.064 mmol) were added sequentially to a solution of compound TX63620 (19 mg, 0.042 mmol) in $CH_2Cl_2$ (0.42 mL) at 0° C. After the reaction was stirred at 0° C. for 1 hr, aq. $NaHCO_3$ was added. The mixture was transferred to a separatory funnel, which was extracted with EtOAc. The organic extract was washed with water, dried with $MgSO_4$, and concentrated. The residue was purified by column chromatography (silica gel, 0 to 70% EtOAc in hexanes) to give compound TX63621 (8 mg, 36%) as white foam solid: $^1$H NMR (500 MHz, $CDCl_3$) δ 8.05 (s, 1H), 6.15 (s, 1H), 4.27 (s, 1H), 3.22 (d, 1H, J=4.4 Hz), 3.11 (s, 3H), 2.54 (m, 1H), 2.50 (m, 1H), 1.51 (s, 3H), 1.46 (s, 3H), 1.27 (d, 3H, J=6.7 Hz), 1.05 (s, 3H), 1.03 (s, 3H), 0.95-2.18 (m, 15H), 0.93 (s, 3H); m/z 432.2 (M-$MeSO_2$).

Compound TX63622:

$Et_3N$ (18 μL, 0.13 mmol) and AcCl (6 μL, 0.085 mmol) were added sequentially to a solution of compound TX63620 (19 mg, 0.042 mmol) in $CH_2Cl_2$ (0.42 mL) at 0° C. After the reaction was stirred at 0° C. for 30 min, aq. $NaHCO_3$ was added. The mixture was transferred to a separatory funnel, which was extracted with EtOAc. The organic extract was washed with water, dried with $MgSO_4$, and concentrated. The residue was purified by column chromatography (silica gel, 0 to 70% EtOAc in hexanes) to give compound TX63622 (20 mg, 96%) as white foam solid: $^1$H NMR (500 MHz, $CDCl_3$) δ 8.03 (s, 1H), 6.06 (s, 1H), 5.00 (s, 1H), 3.10 (d, 1H, J=4.7 Hz), 2.60 (m, 1H), 2.49 (m, 1H), 2.29 (m, 1H), 1.97 (s, 3H), 1.47 (s, 3H), 1.45 (s, 3H), 1.28 (d, 3H, J=6.5 Hz), 1.15-2.15 (m, 14H), 1.04 (s, 6H), 0.91 (s, 3H); m/z 491.2 (M+1).

Compound TX63682:

TX63620: (77 mg, 0.17 mmol), $CH_3CF_2CO_2H$ (22.7 mg, 0.21 mmol) were dissolved in $CH_2Cl_2$ (2 mL). DCC (53 mg, 0.26 mmol) and DMAP (8.4 mg, 0.069 mmol) were added. The reaction was stirred at room temperature for 16 h. The reaction mixture was filtered. The filtrate was purified by column chromatography (silica gel, eluting with 0-40% EtOAc in hexanes) to give TX63682 (75 mg, 81% yield) as a white solid: $^1$H NMR (600 MHz, $CDCl_3$) δ 8.02 (s, 1H), 6.05 (s, 1H), 5.92 (s, 1H), 3.02 (d, 1H, J=4.2 Hz), 2.79 (m, 1H), 2.48 (m, 1H), 1.78 (t, 3H, J=19.3 Hz), 1.46 (s, 3H), 1.42 (s, 3H), 1.27 (d, 3H, J=6.5 Hz), 1.17-2.35 (m, 15H), 1.06 (s, 3H), 1.04 (s, 3H), 0.91 (s, 3H); m/z=541.3 (M+1).

Compound TX63984:

10% Pd/C (30 mg) was added to a solution of TX63682 (100 mg, 0.18 mmol) in EtOAc (2 mL). After the mixture was hydrogenated (balloon) for 2 h at room temperature, the catalyst was removed by filtered through a pad of silica gel. The filtrate was concentrated. The residue was purified by column chromatography (silica gel, eluting with 0-30% EtOAc in hexanes) to give TX63984 (85 mg, 85% yield) as a white solid: 3:1 mixture of ketone:enol isomers, m/z=543.3 (M+1); Ketone isomer: $^1$H NMR (400 MHz, $CDCl_3$) δ 5.89 (bs, 1H), 5.84 (s, 1H), 3.72 (dd, 1H, J=5.8, 13.6 Hz), 2.97 (d, 1H, J=4.6 Hz), 2.74 (m, 1H), 2.67 (dd, 1H, J=5.9, 13.2 Hz), 2.46 (m, 1H), 1.76 (t, 3H, J=19.3 Hz), 1.41 (s, 3H), 1.39 (s, 3H), 1.12 (d, 3H, J=6.6 Hz), 1.10-2.15 (m, 16H), 1.04 (s, 3H), 1.00 (s, 3H), 0.89 (s, 3H).

Compound 24:

$TMSCHN_2$ (2.0 M solution in ether, 10.60 mL, 21.20 mmol) was added to a mixture of compound 23 (10.00 g, 21.16 mmol) in toluene (150 mL) and MeOH (50 mL) at 0° C. After the heterogeneous reaction mixture was stirred at 0-10° C. for 1 h, additional amount of $TMSCHN_2$ (2.0 M solution in ether, 5.30 mL, 10.60 mmol) was added. After another 1 h, the reaction was quenched by AcOH. EtOAc was added. The mixture was transferred to a seperatory funnel, which was washed with aq. $NaHCO_3$ and water. The organic extract was separated, dried with $MgSO_4$, filtered, and concentrated. The residue was recrystallized with EtOH to give compound 24 (5.20 g, 51% yield) as a white solid. The mother liquor was concentrated, and the residue was purified by column chromatography (silica gel, 0 to 70% EtOAc in hexanes) to give a second crop of compound 24 (4.60 g, 45% yield) as a white solid: m/z 487.3 (M+1), 451.4.

Compound 25:

DMSO (6.75 mL, 95.03 mmol) was added drop wise to a solution of oxalyl chloride (4.02 mL, 47.51 mmol) in $CH_2Cl_2$ (50 mL) at −78° C. After stirring for 30 min, compound 24 (4.63 g, 9.51 mmol) in $CH_2Cl_2$ (45 mL) was added at −78° C. After stirring for another 1 h, the reaction was treated with $Et_3N$ (26.5 mL, 190.2 mmol), and continued stirring for 30 min at ambient temperature. EtOAc was added. The mixture was transferred to a separatory funnel, which was washed with aq. $NaHCO_3$ and water. The organic extract was separated, dried with $MgSO_4$, and concentrated to give compound 25: m/z=483.3 (M+1). Compound 25 was used in the next step without further purification.

Compound 26:

NaOMe (3.30 mL, 14.43 mmol) was added to a mixture of compound 25 in MeOH (95 mL) at room temperature. After stirring for 30 min, the reaction was cooled to 0° C. MTBE and 6 N aq. HCl (2.50 mL, 15.00 mmol) were added. The mixture was transferred to a separatory funnel, which was washed with water. The aqueous wash was extracted with EtOAc. The combined organic extracts were dried with $MgSO_4$, filtered, and concentrated. The residue was dissolved in $CH_2Cl_2$ (30 mL) and EtOH (30 mL). The solution was evaporated on a rotary evaporator to remove $CH_2Cl_2$. After the white slurry was allowed to stand at room temperature for 60 h, the precipitate was collected by filtration, and was washed with EtOH to give compound 26 (3.29 g, 76% yield from 24) as a white solid: m/z=455.3 (M+1).

Compound 27:

NaOMe (24.80 mL, 108.5 mmol) was added to a mixture of compound 26 (3.29 g, 7.24 mmol) and $HCO_2Et$ (17.4 mL, 216.3 mmol) at 0° C. After the reaction was stirred at room temperature for 1 h, THF (5 mL) was added. After another 2 h, THF (5 mL) was added again, and the reaction was stirred for another 3 h. The reaction was cooled to 0° C. MTBE and 6 N HCl (19 mL, 114 mmol) were added. The mixture was transferred to a separatory funnel, which was extracted with EtOAc. The organic extract was washed with water, dried with $MgSO_4$, and concentrated. The residue was mixed with $NH_2OH$—HCl (760 mg, 10.94 mmol), EtOH (162 mL) and water (8 mL), and the reaction was stirred at 55° C. for 16 h. After EtOH was removed on a rotary evaporator, the residue was extracted with EtOAc. The combined organic extracts were washed with water, dried with $MgSO_4$, and concentrated. The crude product was triturated with MeOH (10 mL) at reflux for 10 min, and the mixture was allowed to stand at room temperature for 1 h. The precipitate was collected by filtration, washed with MeOH, and dried under vacuum for 16 h to give compound 27 (2.87 g, 83% yield) as an off-white solid: m/z 480.3 (M+1).

Compound 28:

$AcO_2H$ (39% in AcOH, 410 μL, 3.15 mmol) was added to a solution of compound 27 (1.00 g, 2.08 mmol) in AcOH (10.4 mL) at room temperature. After heated at 55° C. for 18 h, the reaction was cooled to room temperature, and was treated with aq. $Na_2SO_3$. The product was extracted with $CH_2Cl_2$. The combined organic extracts were washed with aq. $Na_2SO_3$, and aq. $NaHCO_3$, dried with $MgSO_4$, and concentrated. The residue was purified by column chromatography (silica gel, eluting with 0-25% EtOAc in hexanes) to give compound 28 (825 mg, 80% yield) as a white solid: m/z=496.3 (M+1).

Compound 29:

NaOMe (570 μL, 2.49 mmol) was added to a mixture of compound 28 (823 mg, 1.67 mmol) and MeOH (17 mL) at room temperature. After the reaction was heated at 55° C. for 1 h, MTBE was added. The mixture was transferred to a separatory funnel, which was washed with 1N aq. HCl and water. The organic extract was dried with $MgSO_4$, and concentrated to give compound 29 as a white solid: m/z=496.3 (M+1). Compound 29 was used in the next step without further purification.

Compound TX63749:

A solution of DBDMH (236 mg, 0.83 mmol) in DMF (4 mL) was added to a solution of cyanoketone 29 in DMF (4.25 mL) at 0° C. After stirring at 0° C. for 1 h, pyridine (0.40 mL, 4.96 mmol) was added. After the reaction was heated at 55° C. for 3 h, EtOAc was added. The mixture was transferred to a separatory funnel, which was washed with 1N aq. HCl, aq. $Na_2SO_3$ and water. The organic extract was separated, dried with $MgSO_4$, filtered, and concentrated. The residue was triturated with $CH_2Cl_2$/EtOH to give compound TX63749 (744 mg, 90% yield from 28) as a white solid: m/z 494.3 (M+1), 434.3 (M-$CO_2$Me); $^1$H NMR (600 MHz, $CDCl_3$) δ 7.63 (s, 1H), 3.68 (s, 3H), 2.81 (m, 1H), 2.68 (d, 1H, J=3.8 Hz), 2.48 (dd, 1H, J=4.4, 16.3 Hz), 2.33-2.46 (m, 2H), 1.21 (d, 3H, J=6.7 Hz), 1.14 (s, 3H), 1.09-2.00 (m, 16H), 1.07 (s, 3H), 0.97 (s, 3H), 0.95 (s, 3H), 0.90 (s, 3H).

Compound TX63797:

LiBr (1.20 g, 13.82 mmol) was added to a mixture of TX63749 (684 mg, 1.39 mmol), NaOAc (280 mg, 3.41 mmol) and DMAc (14 mL) at room temperature. The heterogeneous mixture was heated at 150° C. with $N_2$ bubbled through for 6 h. The reaction was cooled, and was diluted with EtOAc. The mixture was transferred to a seperatory funnel, which was washed with 1N aq. HCl, and water. The organic extract was separated, dried with $MgSO_4$, filtered, and concentrated. The residue was purified by column chromatography (silica gel, eluting with 0-30% EtOAc in hexanes, and then, 0-5% MeOH in $CH_2Cl_2$) to give compound TX63797 (404 mg, 61% yield) as a white solid: m/z=480.3 (M+1); $^1$H NMR (500 MHz, $CDCl_3$) δ 7.65 (s, 1H), 2.80 (m, 1H), 2.76 (d, 1H, J=3.9 Hz), 2.51 (dd, 1H, J=4.5, 16.4 Hz), 2.35-2.47 (m, 2H), 1.20 (d, 3H, J=6.7 Hz), 1.15-2.05 (m, 16H), 1.15 (s, 3H), 1.12 (s, 3H), 0.99 (s, 3H), 0.97 (s, 3H), 0.92 (s, 3H).

Compound 30:

Oxalyl chloride (0.22 mL, 2.60 mmol) and catalytic amount of DMF were added sequentially to a solution of TX63797 (407 mg, 0.85 mmol) in $CH_2Cl_2$ (17 mL) at 0° C. After the reaction was stirred at ambient temperature for 2 h, it was concentrated on a rotary evaporator. The residue was azeotroped with toluene (3×10 mL) to remove residual oxalyl chloride. Compound 30 (490 mg) was obtained as a light yellow foam solid. Compound 30 was used in the next steps without further purification.

Compound TX63680:

$EtNH_2$ (2.0 M solution in THF, mL, mmol) was added to a solution of compound 30 (mg, mmol) in $CH_2Cl_2$ (mL) at 0° C. After stirring at 0° C. for 30 min, the reaction was transferred to a separatory funnel, which was washed with water. The organic extract was dried with $Na_2SO_4$, filtered, and concentrated. The residue was purified by column chromatography (silica gel, eluting with 0% to 70% EtOAc in hexanes) to give TX63680 (18 mg, 88% yield) as a white solid: m/z=507.3 (M+1); $^1$H NMR (500 MHz, $CDCl_3$) δ 7.66 (s, 1H), 5.66 (t, 1H, J=5.4 Hz), 3.33 (m, 2H), 2.87 (d, 1H, J=3.9 Hz), 2.75 (m, 1H), 2.50 (dd, 1H, J=4.5, 16.2 Hz), 2.34-2.47 (m, 2H), 1.94-2.10 (m, 3H), 1.72-1.84 (m, 3H), 1.14-1.65 (m, 13H), 1.21 (d, 3H, J=6.7 Hz), 1.16 (s, 3H), 1.11 (s, 3H), 1.00 (s, 3H), 0.98 (s, 3H), 0.93 (s, 3H).

Compound 31:

NaOMe (71 μL, 0.31 mmol) was added to a mixture of compound 27 (100 mg, 0.21 mmol) and MeOH (2.1 mL) at room temperature. After the reaction was heated at 55° C. for 10 min, THF (0.4 mL) was added. The reaction was heated for another 2 h, and was cooled to room temperature. MTBE was added. The mixture was transferred to a separatory funnel, which was washed with 1N aq. HCl and water. The organic extract was dried with $MgSO_4$, and concentrated. The residue was purified by column chromatography (silica gel, eluting with 0-30% EtOAc in hexanes) to give compound 31 (95 mg, 95% yield) as a white solid: m/z=480.3 (M+1).

Compounds TX63779 and TX63795:

DDQ (47 mg, 0.21 mmol) was added to a solution of compound 31 (95 mg, 19.8 mmol) in benzene (2 mL) at room temperature. After the reaction was refluxed for 20 min, it was cooled to room temperature. MTBE was added. The mixture was transferred to a seperatory funnel, which was washed with aq. $NaHCO_3$ until the organic layer was almost colorless. The organic extract was separated, dried with $MgSO_4$, and filtered through a pad of silica gel, which was eluted with EtOAc/hexanes (1/1). The filtrate was concentrated. The residue was dissolved in $CH_2Cl_2$ (0.5 mL), and was treated with $Ac_2O$ (0.1 mL, 1.06 mmol), pyridine (0.2 mL, 2.48 mmol) and catalytic amount of DMAP. After the reaction was stirred at room temperature for 20 min, aq. $NaHCO_3$ was added. The mixture was transferred to a reparatory funnel, which was washed with 1N aq. HCl, aq. $NaHCO_3$, and water. The organic extract was dried with $MgSO_4$, and concentrated. The residue was purified by column chromatography (silica gel, eluting with 0-25% EtOAc in hexanes) to give compound TX63779 (26 mg, 27% yield) as a white solid: m/z=478.3 (M+1); $^1$H NMR (500 MHz, $CDCl_3$) δ 7.75 (s, 1H), 5.36 (t, 1H, J=3.4 Hz), 3.64 (s, 3H), 2.91 (m, 1H), 2.44 (m, 1H), 1.87-2.18 (m, 4H), 1.07-1.75 (m, 14H), 1.21 (s, 3H), 1.20 (d, 3H, J=6.8 Hz), 1.14 (s, 3H), 0.94 (s, 3H), 0.91 (s, 3H), 0.85 (s, 3H).

From the column, also get compound TX63795 (44 mg, 43% yield) as a white solid: m/z=522.3 (M+1); $^1$H NMR (500 MHz, $CDCl_3$) δ 5.33 (t, 1H, J=3.4 Hz), 3.63 (s, 1H), 2.89 (m, 1H), 2.25 (s, 3H), 2.22 (m, 1H), 1.86-2.08 (m, 4H), 1.00-1.74 (m, 18H), 1.13 (s, 3H), 1.06 (d, 3H, J=6.8 Hz), 0.96 (s, 3H), 0.94 (s, 3H), 0.91 (s, 3H), 0.78 (s, 3H).

Compound TX63807:

$CF_3CH_2NH_2$ (19 μL, 0.24 mmol) was added to a solution of compound 30 (40 mg, 0.08 mmol) in $CH_2Cl_2$ (0.80 mL) at 0° C. After stirring at ambient temperature for 2 h, the reaction mixture was purified by column chromatography (silica gel, eluting with 0% to 15% EtOAc in $CH_2Cl_2$) to give TX63807 (28 mg, 62% yield) as a white solid: m/z=561.3 (M+1); $^1H$ NMR (500 MHz, $CDCl_3$) δ 7.65 (s, 1H), 5.93 (t, 1H, J=6.3 Hz), 4.08 (m, 1H), 3.84 (m, 1H), 2.84 (d, 1H, J=4.1 Hz), 2.78 (m, 1H), 2.49 (dd, 1H, J=4.6, 16.3 Hz), 2.34-2.47 (m, 2H), 2.11 (ddd, 1H, J=4.0, 14.2, 14.2 Hz), 1.98 (m, 2H), 1.22-1.85 (m, 13H), 1.21 (d, 3H, J=6.8 Hz), 1.15 (s, 3H), 1.07 (s, 3H), 0.99 (s, 3H), 0.98 (s, 3H), 0.93 (s, 3H).

Compound TX63811:

Imidazole (16 mg, 0.24 mmol) was added to a solution of compound 30 (40 mg, 0.08 mmol) in benzene (0.80 mL) at 0° C. After stirring at ambient temperature for 2 h, the reaction mixture was purified by column chromatography (silica gel, eluting with 0% to 65% EtOAc in hexanes) to give TX63811 (34 mg, 80% yield) as a white solid: m/z=530.3 (M+1); $^1H$ NMR (500 MHz, $CDCl_3$) δ 8.32 (s, 1H), 7.64 (s, 1H), 7.60 (s, 1H), 7.09 (s, 1H), 2.99 (m, 1H), 2.95 (d, 1H, J=4.1 Hz), 2.51 (dd, 1H, J=4.6, 16.4 Hz), 2.34-2.47 (m, 2H), 2.26 (ddd, 1H, J=3.6, 14.3, 14.3 Hz), 2.10 (m, 1H), 1.93-2.03 (m, 3H), 1.72-1.92 (m, 3H), 1.30-1.62 (m, 8H), 1.19 (d, 3H, J=6.7 Hz), 1.15 (s, 3H), 1.04 (s, 3H), 1.04 (s, 3H), 1.00 (s, 3H), 0.98 (s, 3H).

Compound TX63812:

Morpholine (27 μL, 0.25 mmol) was added to a solution of compound 30 (40 mg, 0.08 mmol) in $CH_2Cl_2$ (0.80 mL) at 0° C. After stirring at ambient temperature for 1 h, the reaction mixture was purified by column chromatography (silica gel, eluting with 0% to 60% EtOAc in hexanes) to give TX63812 (30 mg, 68% yield) as a white solid: m/z=549.3 (M+1); $^1H$ NMR (500 MHz, $CDCl_3$) δ 7.66 (s, 1H), 3.61-3.77 (m, 8H), 3.16 (bs, 1H), 2.92 (m, 1H), 2.34-2.50 (m, 3H), 1.95-2.10 (m, 3H), 1.12-1.85 (m, 13H), 1.21 (d, 3H, J=6.7 Hz), 1.15 (s, 3H), 1.08 (s, 3H), 0.99 (s, 3H), 0.97 (s, 3H), 0.92 (s, 3H).

Compound TX63814:

$Et_3N$ (56 μL, 0.40 mmol) and $NH_2OH$—HCl (21 mg, 0.30 mmol) were added sequentially to a solution of compound 30 (50 mg, 0.10 mmol) in THF (1 mL) and water (0.1 mL) at room temperature. After the reaction was stirred for 1 h, EtOAc was added. The mixture was transferred to a reparatory funnel, which was washed with 1 N aq. HCl and water. The organic extract was dried with $MgSO_4$, and concentrated. The residue was purified by column chromatography (silica gel, eluting with 0% to 100% EtOAc in hexanes) to give TX63814 which was contaminated with some impurities. The compound was purified again by column chromatography (silica gel, eluting with 0% to 5% MeOH in $CH_2Cl_2$) to give TX63814 (24 mg, 48% yield) as a white solid: m/z=495.2 (M+1); $^1H$ NMR (500 MHz, $CDCl_3$) δ 8.53 (s, 1H), 7.65 (s, 1H), 7.42 (bs, 1H), 2.79 (d, 1H, J=4.1 Hz), 2.75 (m, 1H), 2.52 (dd, 1H, J=4.5, 16.4 Hz), 2.35-2.48 (m, 2H), 1.72-2.14 (m, 6H), 1.21-1.63 (m, 10H), 1.21 (d, 3H, J=6.7 Hz), 1.15 (s, 3H), 1.11 (s, 3H), 0.99 (s, 3H), 0.98 (s, 3H), 0.93 (s, 3H).

Compound TX63815:

$Et_3N$ (56 μL, 0.40 mmol) and $NH_2OMe$-HCl (25 mg, 0.30 mmol) were added sequentially to a solution of compound 30 (50 mg, 0.10 mmol) in THF (1 mL) and water (0.1 mL) at room temperature. After the reaction was stirred for 1 h, EtOAc was added. The mixture was transferred to a separatory funnel, which was washed with 1 N aq. HCl and water. The organic extract was dried with $MgSO_4$, and concentrated. The residue was purified by column chromatography (silica gel, eluting with 0% to 65% EtOAc in hexanes) to give TX63815 (31 mg, 61% yield) as a white solid: m/z=509.3 (M+1); $^1H$ NMR (500 MHz, $CDCl_3$) δ 8.39 (s, 1H), 7.65 (s, 1H), 3.77 (s, 3H), 2.87 (d, 1H, J=4.1 Hz), 2.73 (m, 1H), 2.35-2.53 (m, 3H), 1.75-2.10 (m, 6H), 1.22-1.63 (m, 10H), 1.21 (d, 3H, J=6.7 Hz), 1.15 (s, 3H), 1.14 (s, 3H), 0.99 (s, 3H), 0.97 (s, 3H), 0.92 (s, 3H).

Compound TX63816:

$NH_3$ (2.0 M in MeOH, 0.45 mL, 0.90 mmol) was added to a solution of compound 30 (150 mg, 0.30 mmol) in MTBE (3 mL) and $CH_2Cl_2$ (3 mL) at 0° C. The reaction was stirred at 0° C., and then, at room temperature for 1 h. EtOAc was added. The mixture was transferred to a separatory funnel, which was washed with water, 1 N aq. HCl, and water. The organic extract was dried with $MgSO_4$, and concentrated. The residue was purified by column chromatography (silica gel, eluting with 0% to 100% EtOAc in hexanes) to give TX63816 (120 mg, 83% yield) as a white solid: m/z=479.3 (M+1); $^1H$ NMR (500 MHz, $CDCl_3$) δ 7.65 (s, 1H), 5.64 (bs, 1H), 5.30 (bs, 1H), 2.91 (d, 1H, J=4.1 Hz), 2.72 (m, 1H), 2.35-2.53 (m, 3H), 1.76-2.10 (m, 6H), 1.22-1.63 (m, 10H), 1.21 (d, 3H, J=6.7 Hz), 1.16 (s, 3H), 1.14 (s, 3H), 0.99 (s, 3H), 0.98 (s, 3H), 0.93 (s, 3H).

Compound TX63817:

$Et_3N$ (65 μL, 0.47 mmol) and TFAA (39 μL, 0.28 mmol) were added sequentially to a solution of TX63816 (90 mg, 0.19 mmol) in $CH_2Cl_2$ (1.9 mL) at 0° C. After the reaction was stirred at 0° C. for 30 min, aq. $NaHCO_3$ was added. The mixture was transferred to a separatory funnel, which was extracted with $CH_2Cl_2$. The combined organic extracts were dried with $MgSO_4$, and concentrated. The residue was purified by column chromatography (silica gel, eluting with 0% to 35% EtOAc in hexanes) to give TX63817 (65 mg, 75% yield) as a white solid: m/z=461.3 (M+1); $^1H$ NMR (600 MHz, $CDCl_3$) δ 7.65 (s, 1H), 3.05 (d, 1H, J=4.2 Hz), 2.42-2.59 (m, 4H), 1.98-2.21 (m, 4H), 1.94 (m, 1H), 1.74-1.86 (m, 2H), 1.45-1.65 (m, 5H), 1.34 (s, 3H), 1.15-1.32 (m, 4H), 1.22 (d, 3H, J=6.7 Hz), 1.20 (s, 3H), 1.00 (s, 3H), 0.96 (s, 3H), 0.93 (s, 3H).

Compound TX63842:

A mixture of DBU (14 μL, 0.09 mmol), EtI (6.7 μL, 0.08 mmol), compound TX63797 (40 mg, 0.083 mmol) and toluene (0.83 mL) was heated at 50° C. for 2 h. After cooling to room temperature, the reaction mixture was purified by column chromatography (silica gel, eluting with 0% to 25% EtOAc in hexanes) to give TX63842 (26 mg, 61% yield) as a white solid: m/z=508.4 (M+1), 434.2 (M-$CO_2$Et); $^1H$ NMR (600 MHz, $CDCl_3$) δ 7.65 (s, 1H), 4.17 (m, 2H), 2.82 (m, 1H), 2.72 (d, 1H, J=4.2 Hz), 2.49 (dd, 1H, J=4.7, 16.3 Hz), 2.43 (m, 1H), 2.37 (dd, 1H, J=13.5, 16.0 Hz), 1.99 (dd, 1H, J=4.5, 13.4 Hz), 1.87-1.96 (m, 2H), 1.76-1.83 (m, 2H), 1.40-1.72 (m, 7H), 1.33 (ddd, 1H, J=4.4, 13.9, 13.9 Hz), 1.26 (t, 3H, J=7.1 Hz), 1.20 (d, 3H, J=6.8 Hz), 1.15 (s, 3H), 1.10-1.26 (m, 3H), 1.09 (s, 3H), 0.98 (s, 3H), 0.96 (s, 3H), 0.91 (s, 3H).

Compound TX63843:

n-$BuNH_2$ (30 μL, 0.30 mmol) was added to a solution of compound 30 (50 mg, 0.10 mmol) in $CH_2Cl_2$ (1.0 mL) at 0° C. After the reaction was stirred at 0° C. for 30 min, EtOAc was added. The mixture was transferred to a separatory funnel, which was washed with 1 N aq. HCl, and water. The organic extract was dried with $MgSO_4$, and concentrated. The residue was purified by column chromatography (silica gel, eluting with 0% to 40% EtOAc in hexanes) to give TX63843 (37 mg, 69% yield) as a white solid: m/z=535.3 (M+1); $^1H$ NMR (600 MHz, $CDCl_3$) δ 7.64 (s, 1H), 5.65 (t, 1H, J=5.7 Hz), 3.25 (m, 2H), 2.86 (d, 1H, J=4.2 Hz), 2.75 (m, 1H), 2.48 (dd, 1H, J=4.6, 16.3 Hz), 2.43 (m, 1H), 2.37 (dd, 1H, J=13.6, 16.2 Hz), 1.92-2.08 (m, 3H), 1.71-1.82 (m, 3H), 1.20 (d, 3H, J=6.8 Hz), 1.15 (s, 3H), 1.10-1.62 (m, 14H), 1.09 (s, 3H), 0.98 (s, 3H), 0.97 (s, 3H), 0.93 (t, 3H, J=7.4 Hz), 0.92 (s, 3H).

Compound 32:

DIBAL-H (1.0 M solution in toluene, 7.3 mL, 7.30 mmol) was added to a solution of compound 27 (1.00 g, 2.08 mmol) in THF (20 mL) at 0° C. After the reaction was stirred at 0° C. for 2 h, water (1 mL) and 1 N aq. HCl (50 mL) were added sequentially. The mixture was transferred to a separatory funnel, which extracted with EtOAc. The organic extract was washed with water, dried with $MgSO_4$, and concentrated. The residue was purified by column chromatography (silica gel, eluting with 0% to 30% EtOAc in hexanes) to give compound 32 (0.90 g, 96% yield) as a white solid: m/z=452.3 (M+1).

Compound 33:

$Ac_2O$ (0.8 mL, 8.47 mmol) and DMAP (10 mg, 0.08 mmol) were added to a solution of compound 32 (400 mg, 0.88 mmol) in pyridine (1.6 mL) at room temperature. After the reaction was stirred at room temperature for 10 min, aq. $NaHCO_3$ was added. The mixture was transferred to a separatory funnel, which was extracted with EtOAc. The organic extract was washed with 1N aq. HCl, aq. $NaHCO_3$, water, and was dried with $MgSO_4$. The solution was filtered through a pad of silica gel, and was concentrated to give compound 33 (420 mg, 96% yield) as a white solid: m/z=494.3 (M+1).

Compound 34:

$AcO_2H$ (39% in AcOH, 210 μL, 1.62 mmol) was added to a solution of compound 33 (533 mg, 1.08 mmol) in AcOH (5.4 mL) at room temperature. After heated at 55° C. for 7 h, additional amount of $AcO_2H$ (39% in AcOH, 100 μL, 0.77 mmol) was added. After another 13 h, the reaction was cooled to room temperature, and was treated with aq. $Na_2SO_3$. The product was extracted with $CH_2Cl_2$. The combined organic extracts were washed with aq. $Na_2SO_3$, and aq. $NaHCO_3$, dried with $MgSO_4$, and concentrated. The residue was purified by column chromatography (silica gel, eluting with 0-40% EtOAc in hexanes) to give compound 34 (440 mg, 80% yield) as a white solid: m/z=510.3 (M+1).

Compound 35:

NaOMe (0.35 mL, 1.53 mmol) was added to a mixture of compound 34 (315 mg, 0.62 mmol) and MeOH (6 mL) at room temperature. After heated at 55° C. for 2 h, the reaction was cooled to room temperature. MTBE was added. The mixture was transferred to a separatory funnel, which was washed with 1N aq. HCl and water. The organic extract was dried with $MgSO_4$, and concentrated. The residue was purified by column chromatography (silica gel, eluting with 0-70% EtOAc in hexanes) to give compound 35 (290 mg, 99% yield) as a white solid: m/z=468.3 (M+1).

Compound TX63839:

A solution of 1,3-dibromo-5,5-dimethylhydantoin (81 mg, 0.28 mmol) in DMF (1.5 mL) was added to a solution of compound 35 (290 mg, 0.62 mmol) in DMF (1.5 mL) at 0° C. After the reaction was stirred at 0° C. for 1 h, pyridine (200 μL, 2.48 mmol) was added. The reaction was heated at 55° C. for another 1.5 h. EtOAc was added. The mixture was transferred to a separatory funnel, which was washed with 1 N aq. HCl, aq. $Na_2SO_3$, and water. The organic extract was dried with $MgSO_4$ and concentrated. The residue was purified by column chromatography (silica gel, eluting with 0% to 65% EtOAc in hexanes) to give TX63839 (235 mg, 81% yield) as a white solid: m/z=466.3 (M+1); $^1H$ NMR (600 MHz, $CDCl_3$) δ 7.65 (s, 1H), 3.51 (d, 2H, J=6.0 Hz), 2.71 (d, 1H, J=4.2 Hz), 2.52 (dd, 1H, J=4.6, 16.6 Hz), 2.45 (m, 1H), 2.39 (dd, 1H, J=13.5, 16.4 Hz), 2.21 (m, 1H), 2.03 (dd, 1H, J=4.7, 13.6 Hz), 1.43-1.90 (m, 8H), 1.24 (s, 3H), 1.21 (d, 3H, J=6.7 Hz), 1.22-1.34 (m, 6H), 1.17 (s, 3H), 1.14 (m, 1H), 1.05 (m, 1H), 0.99 (s, 3H), 0.94 (s, 3H), 0.90 (s, 3H).

Compound TX63840:

$Ac_2O$ (50 μL, 0.47 mmol) and catalytic amount of DMAP were added to a solution of compound TX63839 (25 mg, 0.05 mmol) and pyridine (0.2 mL) in $CH_2Cl_2$ (0.5 mL) at room temperature. After the reaction was stirred at room temperature for 10 min, aq. $NaHCO_3$ was added. The mixture was transferred to a separatory funnel, which was extracted with EtOAc. The organic extract was washed with 1N aq. HCl, aq. $NaHCO_3$, water, dried with $MgSO_4$, and concentrated. The residue was purified by column chromatography (silica gel, eluting with 0% to 10% EtOAc in $CH_2Cl_2$) to give TX63840 (28 mg, 99% yield) as a white solid: m/z=508.3 (M+1), 448.2 (M-OAc); $^1H$ NMR (600 MHz, $CDCl_3$) δ 7.65 (s, 1H), 4.13 (d, 1H, J=11.1 Hz), 3.88 (d, 1H, J=11.1 Hz), 2.79 (d, 1H, J=4.3 Hz), 2.51 (dd, 1H, J=4.6, 16.5 Hz), 2.37-2.48 (m, 2H), 2.19 (m, 1H), 2.08 (s, 3H), 2.02 (dd, 1H, J=4.7, 13.3 Hz), 1.94 (m, 1H), 1.73-1.85 (m, 4H), 1.43-1.64 (m, 4H), 1.28 (s, 3H), 1.21 (d, 3H, J=6.7 Hz), 1.18-1.33 (m, 4H), 1.17 (s, 3H), 1.03-1.08 (m, 2H), 0.98 (s, 3H), 0.93 (s, 3H), 0.90 (s, 3H).

Compound TX63841:

TFAA (26 μL, 0.18 mmol) was added to a solution of compound TX63839 (43 mg, 0.09 mmol) and $Et_3N$ (39 μL, 0.28 mmol) in $CH_2Cl_2$ (1 mL) at 0° C. After the reaction was stirred at 0° C. for 1 h, aq. $NaHCO_3$ was added. The mixture was transferred to a separatory funnel, which was extracted with EtOAc. The organic extract was washed with aq. $NaHCO_3$, and water, dried with $MgSO_4$, and concentrated. The residue was purified by column chromatography (silica gel, eluting with 0% to 25% EtOAc in hexanes) to give TX63841 (45 mg, 87% yield) as a white solid: m/z=562.3 (M+1); $^1H$ NMR (600 MHz, $CDCl_3$) δ 7.64 (s, 1H), 4.29 (s, 2H), 2.71 (d, 1H, J=4.3 Hz), 2.53 (dd, 1H, J=4.6, 16.6 Hz), 2.38-2.48 (m, 2H), 2.18 (m, 1H), 1.94-2.05 (m, 2H), 1.69-1.89 (m, 4H), 1.45-1.65 (m, 4H), 1.28 (s, 3H), 1.22 (d, 3H, J=6.7 Hz), 1.18 (s, 3H), 1.09-1.33 (m, 6H), 1.00 (s, 3H), 0.93 (s, 3H), 0.91 (s, 3H).

Compound TX63858:

Methyl triflate (17 μL, 0.15 mmol) was added to a solution of compound TX63839 (40 mg, 0.09 mmol) and 2,6-di-t-butyl-4-methylpyridine (35 mg, 0.17 mmol) in $CH_2Cl_2$ (1 mL) at 0° C. After stirring at ambient temperature for 16 h, the reaction was quenched with the addition of aq. $NaHCO_3$. The mixture was transferred to a separatory funnel, which was extracted with EtOAc. The organic extract was washed with 1 N aq. HCl, aq. $NaHCO_3$, and water, dried with $MgSO_4$, and concentrated. The residue was purified by column chromatography (silica gel, eluting with 0% to 40% EtOAc in hexanes) to give TX63858 (31 mg, 75% yield) as a white solid: m/z=480.3 (M+1); $^1H$ NMR (500 MHz, $CDCl_3$) δ 7.68 (s, 1H), 3.34 (s, 3H), 3.24 (d, 1H, J=9.1 Hz), 3.20 (d, 1H, J=9.1 Hz), 2.80 (d, 1H, J=4.1 Hz), 2.38-2.56 (m, 3H), 2.27 (m, 1H), 2.06 (dd, 1H, J=4.6, 13.1 Hz), 1.72-1.92 (m, 5H), 1.46-1.68 (m, 4H), 1.28 (s, 3H), 1.24 (d, 3H, J=6.8 Hz), 1.02-1.34 (m, 6H), 1.20 (s, 3H), 1.00 (s, 3H), 0.95 (s, 3H), 0.91 (s, 3H).

Compound TX63859:

A mixture of compound TX63839 (85 mg, 0.18 mmol), DMSO (2.2 mL), AcOH (2.2 mL) and $Ac_2O$ (1.1 mL) was stirred at room temperature for 2 h. The reaction mixture was added slowly to a solution of saturated aq. $NaHCO_3$ (80 mL) at room temperature. After stirring for 40 min, the mixture was transferred to a separatory funnel, which was extracted with $CH_2Cl_2$. The organic extract was washed with water, dried with $MgSO_4$, and concentrated. The residue was purified by column chromatography (silica gel, eluting with 0% to 30% EtOAc in hexanes) to give TX63859 (77 mg, 80% yield) as a white solid: m/z=478.3 (M-MeS); $^1H$ NMR (500 MHz, $CDCl_3$) δ 7.68 (s, 1H), 4.67 (d, 1H, J=11.4 Hz), 4.61 (d, 1H, J=11.4 Hz), 3.45 (d, 1H, J=9.0 Hz), 3.31 (d, 1H, J=9.0 Hz), 2.88 (d, 1H, J=4.1 Hz), 2.30-2.56 (m, 4H), 2.13 (s, 3H), 2.06 (m, 1H), 1.76-1.96 (m, 5H), 1.46-1.67 (m, 4H), 1.32 (s, 3H), 1.24 (d, 3H, J=6.8 Hz), 1.03-1.35 (m, 6H), 1.21 (s, 3H), 1.01 (s, 3H), 0.96 (s, 3H), 0.91 (s, 3H).

Compound TX63860:

DAST (24 μL, 0.18 mmol) was added to a mixture of compound TX63859 (63 mg, 0.12 mmol), NBS (32 mg, 0.18 mmol) and 4 Å MS in $CH_2Cl_2$ (1.5 mL) at 0° C. After stirring for 50 min, aq. $NaHCO_3$ was added. The mixture was transferred to a separatory funnel, which was extracted with EtOAc. The organic extract was washed with aq. $Na_2SO_3$, aq. $NaHCO_3$, and water, dried with $MgSO_4$, and concentrated. The residue was purified by column chromatography (silica gel, eluting with 0% to 35% EtOAc in hexanes) to give TX63860 (31 mg, 52% yield) as a white solid: m/z=478.3 (M-F); $^1$H NMR (500 MHz, $CDCl_3$) δ 7.68 (s, 1H), 5.28 (m, 2H), 3.65 (d, 1H, J=8.8 Hz), 3.52 (d, 1H, J=8.7 Hz), 2.75 (d, 1H, J=4.3 Hz), 2.37-2.58 (m, 3H), 2.32 (m, 1H), 2.05 (dd, 1H, J=4.7, 13.2 Hz), 1.93 (ddd, 1H, J=4.8, 13.9, 13.9 Hz), 1.74-1.87 (m, 4H), 1.46-1.67 (m, 4H), 1.27 (s, 3H), 1.24 (d, 3H, J=6.7 Hz), 1.05-1.35 (m, 6H), 1.20 (s, 3H), 1.01 (s, 3H), 0.96 (s, 3H), 0.92 (s, 3H).

Compound 36:

DCC (171 mg, 0.83 mmol) and DMAP (26 mg, 0.21 mmol) were added to a solution of compound 13 (300 mg, 0.63 mmol) and 3-hydroxy-4-methyl-2(3H)-thiazolethione (123 mg, 0.84 mmol) in $CH_2Cl_2$ successively at room temperature. After stirring for 5 h, hexanes (2 mL) was added. The mixture was filtered. The precipitate was washed with $CH_2Cl_2$/hexanes (1:1, 10 mL). The combined filtrate and washes were concentrated. The residue was purified by column chromatography (silica gel, eluting with 0% to 50% EtOAc in hexanes) to give compound 36 (305 mg, 80% yield) as a white solid: m/z=434.2 (M-$C_5H_4NO_2S_2$). Compound 36 was contaminated with some N,N'-dicyclohexylurea, and was used in the next step without further purification.

Compound 37:

$Bu_3SnH$ (0.33 mL, 1.24 mmol) and AIBN (9 mg, 0.05 mmol) were added to a solution of compound 36 (305 mg, 0.50 mmol) in benzene (20 mL) at room temperature. The reaction was heated at reflux for 25 min. After the reaction was cooled to room temperature, the mixture was purified by column chromatography (silica gel, eluting with 0% to 20% EtOAc in hexanes) to give purified compound 37 (84 mg, 38% yield) as a white solid. From the column, also get a second crop of compound 37 (111 mg, 51% yield) which was contaminated with some impurities. Compound 37: m/z=436.3 (M+1).

Compound 38:

NaOMe (66 μL, 0.29 mmol) was added to a mixture of compound 37 (84 mg, 0.19 mmol) and MeOH (1.9 mL) at room temperature. After the reaction was heated at 55° C. for 1 h, MTBE was added. The mixture was transferred to a reparatory funnel, which was washed with 1N aq. HCl and water. The organic extract was dried with $MgSO_4$, and concentrated. The residue was purified by column chromatography (silica gel, eluting with 0% to 30% EtOAc in hexanes) to give compound 38 (86 mg, 99% yield) as a white solid: m/z=436.3 (M+1).

Compound TX63869:

A solution of DBDMH (28 mg, 0.10 mmol) in DMF (0.5 mL) was added to a solution of cyanoketone 38 (86 mg, 0.20 mmol) in DMF (0.5 mL) at 0° C. After stirring at 0° C. for 1 h, pyridine (48 μL, 0.59 mmol) was added. The reaction was heated at 55° C. for 2 h. EtOAc was added. The mixture was transferred to a separatory funnel, which was washed with 1N aq. HCl, aq. $Na_2SO_3$ and water. The organic extract was separated, dried with $MgSO_4$, filtered, and concentrated. The residue was purified by column chromatography (silica gel, eluting with 0% to 25% EtOAc in hexanes) to give compound TX63869 (72 mg, 84% yield) as a white solid: m/z=434.3 (M+1); $^1$H NMR (500 MHz, $CDCl_3$) δ 8.04 (s, 1H), 6.04 (s, 1H), 2.75 (d, 1H, J=4.7 Hz), 2.57 (m, 1H), 2.48 (m, 1H), 1.46 (s, 3H), 1.42 (s, 3H), 1.26 (d, 3H, J=6.7 Hz), 1.10-1.92 (m, 16H), 1.00 (s, 3H), 0.96 (s, 3H), 0.87 (s, 3H).

Compound 39:

A mixture of compound 13 (600 mg, 1.21 mmol), DDQ (305 mg, 1.34 mmol) and toluene (12 mL) was heated at 115° C. in a Biotage microwave reactor for 3 h. $CH_2Cl_2$ was added. The mixture was transferred to a separatory funnel, which was washed with aq. $NaHCO_3$. The organic extract was dried with $MgSO_4$, and concentrated. The residue was purified by column chromatography (silica gel, eluting with 0% to 40% EtOAc in hexanes) to give compound 39 (272 mg, 47% yield) as a white solid: m/z=478.3 (M+1).

Compound 40:

Compound 39 (180 mg, 0.38 mmol) was dissolved in EtOH (4.8 mL), THF (2.4 mL) and water (0.6 mL). NaOH (2.5 N aq. solution, 0.75 mL, 1.88 mmol) was added at room temperature. After stirring for 6 h, MTBE was added. The mixture was transferred to a separatory funnel, which was washed with 1 N aq. HCl and water. The organic extract was dried with $MgSO_4$, and concentrated to give compound 40 (180 mg) as a white solid: m/z=478.3 (M−17). Compound 40 was used in the next steps without further purification.

Compound 41:

Compound 40 (80 mg, 0.16 mmol) was dissolved in toluene (1.2 mL) and MeOH (0.4 mL), and the mixture was cooled to −20° C. $TMSCHN_2$ (2.0 M solution in ether, 96 μL, 0.19 mmol) was added dropwise. After stirring for 10 min, AcOH and EtOAc were added successively. The mixture was transferred to a separatory funnel, which was washed with aq. $NaHCO_3$. The organic extract was dried with $MgSO_4$, and concentrated. The residue was purified by column chromatography (silica gel, eluting with 0% to 40% EtOAc in hexanes) to give compound 41 (36 mg, 42% yield from 39) as a white solid: m/z=492.3 (M−17).

Compound TX63870:

A solution of DBDMH (10 mg, 0.035 mmol) in DMF (0.17 mL) was added to a solution of compound 41 (36 mg, 0.07 mmol) in DMF (0.18 mL) at 0° C. After stirring at 0° C. for 1 h, pyridine (17 μL, 0.21 mmol) was added. The reaction was heated at 55° C. for 2 h. EtOAc was added. The mixture was transferred to a separatory funnel, which was washed with 1N aq. HCl, aq. $Na_2SO_3$ and water. The organic extract was separated, dried with $MgSO_4$, filtered, and concentrated. The residue was purified by column chromatography (silica gel, eluting with 0% to 40% EtOAc in hexanes) to give compound TX63870, which was contaminated with some impurities. The product was purified again by PTLC (silica gel, eluting with 40% EtOAc in hexanes) to give purified TX63870 (26 mg, 72% yield) as a white solid: m/z=490.3 (M−17); $^1$H NMR (500 MHz, $CDCl_3$) δ 8.05 (s, 1H), 6.05 (s, 1H), 3.70 (s, 3H), 2.90 (m, 1H), 2.47 (m, 1H), 2.23 (m, 1H), 1.67-2.00 (m, 7H), 1.55 (m, 1H), 1.49 (s, 3H), 1.47 (s, 3H), 1.25 (d, 3H, J=6.8 Hz), 1.04 (s, 3H), 0.99 (s, 3H), 0.95-1.45 (m, 7H), 0.89 (s, 3H).

Compound 42:

Compound 40 (100 mg, 0.20 mmol) was dissolved in MTBE (2 mL) and $CHCl_3$ (2 mL), and the solution was cooled to 0° C. $CH_3CHN_2$ (1.0 M solution in MTBE, prepared in situ from N-nitroso-N-ethylurea and KOH) was added dropwise until compound 40 was completely consumed.

Nitrogen was bubbled through the reaction for 5 min to blow out the excess $CH_3CHN_2$. The mixture was filtered, and the filtrate was concentrated. The residue was purified by column chromatography (silica gel, eluting with 0% to 35% EtOAc in hexanes) to give compound 42 (19 mg, 18% yield from 39) as a white solid: m/z=506.3 (M−17).

Compound TX63901:

A solution of DBDMH (5.2 mg, 0.018 mmol) in DMF (0.09 mL) was added to a solution of compound 42 (19 mg, 0.036 mmol) in DMF (0.09 mL) at 0° C. After stirring at 0° C. for 1 h, pyridine (9 μL, 0.11 mmol) was added. The reaction was heated at 55° C. for 2 h. EtOAc was added. The mixture was transferred to a separatory funnel, which was washed with 1N aq. HCl, aq. $Na_2SO_3$ and water. The organic extract was separated, dried with $MgSO_4$, filtered, and concentrated. The residue was purified by PTLC (silica gel, eluting with 33% EtOAc in hexanes) to give compound TX63901 (13 mg, 68% yield) as a white solid: m/z=504.3 (M−17); $^1$H NMR (500 MHz, $CDCl_3$) δ 8.06 (s, 1H), 6.05 (s, 1H), 4.25 (m, 1H), 4.11 (m, 1H), 2.90 (m, 1H), 2.47 (m, 1H), 2.24 (m, 1H), 1.97 (m, 1H), 1.67-1.89 (m, 6H), 1.55 (m, 1H), 1.50 (s, 3H), 1.47 (s, 3H), 1.27 (t, 3H, J=7.1 Hz), 1.25 (d, 3H, J=6.8 Hz), 1.04 (s, 3H), 0.99 (s, 3H), 0.95-1.47 (m, 7H), 0.89 (s, 3H).

Compound 43:

$LiAlH_4$ (2.0 M in THF, 0.73 mL, 1.46 mmol) was added to a solution of compound 39 (350 mg, 0.73 mmol) in THF (7 mL) at 0° C. After stirring at 0° C. for 3 h, the reaction was quenched by water. EtOAc and 1 N aq. HCl were added. After stirring at room temperature for 10 min, the mixture was transferred to a separatory funnel. The organic extract was separated, washed with water, dried with $MgSO_4$, filtered, and concentrated. The residue was purified by column chromatography (silica gel, eluting with 0% to 70% EtOAc in hexanes) to give compound 43 (165 mg, 47% yield) as a white solid: m/z=484.3 (M+1).

Compounds 44 and 45:

$Ac_2O$ (40 μL, 0.42 mmol) was added to a solution of compound 43 (163 mg, 0.34 mmol), pyridine (136 μL, 1.68 mmol) and DMAP (4 mg, 0.03 mmol) in $CH_2Cl_2$ (3.3 mL) at 0° C. After the reaction was stirred at 0° C. for 1 h, aq. $NaHCO_3$ was added. The mixture was transferred to a separatory funnel, which was extracted with EtOAc. The organic extract was washed with 1N aq. HCl, aq. $NaHCO_3$ and water, dried with $MgSO_4$, and concentrated. The residue was purified by column chromatography (silica gel, eluting with 0% to 50% EtOAc in hexanes) to give compound 44 (133 mg, 75% yield) as a white solid: m/z=526.3 (M+1). From the column, also get some compound 43 and 45 (overall 58 mg).

Compound 46:

NaOMe (82 μL, 0.36 mmol) was added to a solution of compound 43 and 45 (58 mg) obtained from the last reaction in MeOH (1.2 mL) at room temperature. After the reaction was heated at 55° C. for 1 h, MTBE was added. The mixture was transferred to a separatory funnel, which was washed with 1N aq. HCl and water. The organic extract was dried with $MgSO_4$, and concentrated. The residue was purified by column chromatography (silica gel, eluting with 0% to 60% EtOAc in hexanes) to give compound 46 (33 mg, 60%) as a white solid: m/z=466.3 (M−17), 448.3.

Compound TX63904:

A solution of DBDMH (9.5 mg, 0.033 mmol) in DMF (0.16 mL) was added to a solution of compound 46 (32 mg, 0.066 mmol) in DMF (0.17 mL) at 0° C. After Stirring at 0° C. for 1 h, pyridine (16 μL, 0.20 mmol) was added. The reaction was heated at 55° C. for 3 h. EtOAc was added. The mixture was transferred to a separatory funnel, which was washed with 1N aq. HCl, aq. $Na_2SO_3$ and water. The organic extract was separated, dried with $MgSO_4$, filtered, and concentrated. The residue was purified by column chromatography (silica gel, eluting with 0% to 50% EtOAc in hexanes) to give compound TX63904 (28 mg, 88% yield) as a white solid: m/z=446.3 (M−35); $^1$H NMR (500 MHz, $CDCl_3$) δ 8.16 (s, 1H), 5.50 (d, 1H, J=2.2 Hz), 4.28 (dd, 1H, J=2.1, 8.4 Hz), 3.92 (d, 1H, J=10.6 Hz), 3.55 (d, 1H, J=10.6 Hz), 3.13 (b, 1H), 2.40 (m, 1H), 2.29 (m, 1H), 2.13 (d, 1H, J=8.5 Hz), 1.89 (m, 1H), 1.46 (s, 6H), 1.19 (d, 3H, J=6.7 Hz), 1.00-1.80 (m, 15H), 1.02 (s, 3H), 0.92 (s, 3H), 0.92 (s, 3H).

Compound 47:

A mixture of compound 44 (132 mg, 0.25 mmol), NMO (45 mg, 0.38 mmol) and 4 Å MS in $CH_2Cl_2$ (5 mL) was stirred at room temperature for 10 min. TPAP (9 mg, 0.025 mmol) was added. After the reaction was stirred at room temperature for 3 h, aq. $Na_2SO_3$ was added. The mixture was transferred to a separatory funnel, which was extracted with EtOAc. The organic extract was washed with water, and was filtered through a pad of celite. The filtrate was dried with $MgSO_4$, and was concentrated. The residue was purified by column chromatography (silica gel, eluting with 0% to 10% EtOAc in $CH_2Cl_2$) to give compound 47 (95 mg, 72% yield) as a white solid: m/z=524.3 (M+1), 508.3.

Compound 48:

NaOMe (103 μL, 0.45 mmol) was added to a solution of compound 47 (94 mg, 0.18 mmol) in MeOH (1.8 mL) at room temperature. After the reaction was heated at 55° C. for 2 h, MTBE was added. The mixture was transferred to a separatory funnel, which was washed with 1N aq. HCl and water. The organic extract was dried with $MgSO_4$, and concentrated. The residue was purified by column chromatography (silica gel, eluting with 0% to 50% EtOAc in hexanes) to give compound 48 (77 mg, 89% yield) as a white solid: m/z=464.3 (M−17).

Compound TX63908:

A solution of DBDMH (23 mg, 0.080 mmol) in DMF (0.4 mL) was added to a solution of compound 48 (77 mg, 0.16 mmol) in DMF (0.4 mL) at 0° C. After Stirring at 0° C. for 1 h, pyridine (39 μL, 0.48 mmol) was added. The reaction was heated at 55° C. for 1.5 h. EtOAc was added. The mixture was transferred to a separatory funnel, which was washed with 1N aq. HCl, aq. $Na_2SO_3$ and water. The organic extract was separated, dried with $MgSO_4$, filtered, and concentrated. The residue was purified by column chromatography (silica gel, eluting with 0% to 50% EtOAc in hexanes) to give compound TX63908 (66 mg, 86% yield) as a white solid: m/z=462.2 (M−17); $^1$H NMR (500 MHz, $CDCl_3$) δ 8.08 (s, 1H), 6.04 (s, 1H), 4.12 (d, 1H, J=9.9 Hz), 3.40 (d, 1H, J=9.9 Hz), 2.89 (bs, 1H), 2.47 (m, 1H), 2.34 (m, 1H), 2.12 (m, 1H), 1.69-1.88 (m, 7H), 1.58 (s, 3H), 1.49 (s, 3H), 1.48 (m, 1H), 1.25 (d, 3H, J=6.7 Hz), 1.05-1.35 (m, 6H), 1.01 (s, 3H), 0.96 (s, 3H), 0.87 (s, 3H).

Compound TX63909:

$Ac_2O$ (26 μL, 0.28 mmol) and DMAP (1 mg, 0.008 mmol) were added to a solution of compound TX63908 (32 mg, 0.067 mmol) and pyridine (54 μL, 0.67 mmol) in $CH_2Cl_2$ (1 mL) at room temperature. After the reaction was stirred at room temperature for 30 min, aq. $NaHCO_3$ was added. The mixture was transferred to a separatory funnel, which was extracted with EtOAc. The organic extract was washed with 1N aq. HCl, aq. $NaHCO_3$, and water, dried with $MgSO_4$, and concentrated. The residue was purified by column chromatography (silica gel, eluting with 0% to 30% EtOAc in hexanes) to give compound TX63909 (30 mg, 94% yield) as a white solid: m/z=504.3 (M−17); $^1$H NMR (500 MHz, $CDCl_3$) δ 8.08 (s, 1H), 6.06 (s, 1H), 4.39 (d, 1H, J=10.7 Hz), 4.32 (d, 1H, J=10.7 Hz), 2.48 (m, 1H), 2.11 (s, 3H), 2.08-2.15 (m, 2H), 1.88 (m, 1H), 1.70-1.82 (m, 6H), 1.58 (m, 1H), 1.56 (s, 3H), 1.50 (s, 3H), 1.44 (m, 1H), 1.26 (d, 3H, J=6.7 Hz), 1.10-1.39 (m, 6H), 1.04 (s, 3H), 0.97 (s, 3H), 0.88 (s, 3H).

Compounds 49 and 50:

$LiAlH_4$ (2.0 M in THF, 0.10 mL, 0.20 mmol) was added to a solution of compound 39 (200 mg, 0.42 mmol) in THF (4 mL) at 0° C. After stirring at 0° C. for 1 h, the reaction was quenched by water. EtOAc and 1 N aq. HCl were added. After stirring at room temperature for 10 min, the mixture was transferred to a separatory funnel. The organic extract was washed with water, dried with $MgSO_4$, filtered, and concentrated. The residue was purified by column chromatography (silica gel, eluting with 0% to 50% EtOAc in hexanes) to give a mixture of compound 49 and 50 (3:1 ratio, 145 mg, 72% yield) as a white solid. Compound 49: m/z=482.3 (M+1). Compound 50: m/z=480.3 (M+1).

Compounds 51 and 52:

A solution of compound 49 and 50 (145 mg, 0.30 mmol) in $CH_2Cl_2$ (6 mL) was cooled to 0° C. DAST (59 μL, 0.45 mmol) was added. After the reaction was stirred at ambient temperature for 20 min, aq. $CaCl_2$ was added. The mixture was transferred to a separatory funnel, which was extracted with EtOAc. The organic extract was washed with water, dried with $MgSO_4$, and concentrated. The residue was purified by column chromatography (silica gel, eluting with 0% to 25% EtOAc in hexanes) to give a mixture of compound 51 and 52 (66 mg) as a white solid.

Compound 52:

The mixture of compound 51 and 52 was dissolved in acetone (3 mL), and was cooled to 0° C. Jones' reagent was added dropwise until the orange color persisted. After the reaction was stirred at 0° C. for 10 min, i-PrOH was added. After stirring for another 5 min at room temperature, the reaction was diluted with EtOAc. The mixture was transferred to a seperatory funnel, which was washed with water. The organic extract was dried with $MgSO_4$, and concentrated. The residue was purified by column chromatography (silica gel, eluting with 0% to 25% EtOAc in hexanes) to give compound 52 (57 mg, 39% yield from 49 and 50) as a white solid: m/z=482.2 (M+1).

Compound 53:

NaOMe (41 μL, 0.18 mmol) was added to a solution of compound 52 (57 mg, 0.12 mmol) in MeOH (1.2 mL) and THF (0.6 mL) at room temperature. After the reaction was heated at 55° C. for 1 h, MTBE was added. The mixture was transferred to a separatory funnel, which was washed with 1N aq. HCl and water. The organic extract was dried with $MgSO_4$, and concentrated to give compound 53 (57 mg) as a white solid: m/z=482.2 (M+1).

Compound TX63907:

A solution of DBDMH (17 mg, 0.059 mmol) in DMF (0.30 mL) was added to a solution of compound 53 (57 mg, 0.12 mmol) in DMF (0.29 mL) at 0° C. After Stirring at 0° C. for 1 h, pyridine (29 μL, 0.36 mmol) was added. The reaction was heated at 55° C. for 1.5 h. EtOAc was added. The mixture was transferred to a separatory funnel, which was washed with 1N aq. HCl, aq. $Na_2SO_3$ and water. The organic extract was separated, dried with $MgSO_4$, filtered, and concentrated. The residue was purified by column chromatography (silica gel, eluting with 0% to 45% EtOAc in hexanes) to give compound TX63907 (46 mg, 81% yield from 52) as a white solid: m/z=480.3 (M+1); $^1H$ NMR (500 MHz, $CDCl_3$) δ 8.11 (s, 1H), 5.84 (dd, 1H, J=2.6, 12.2 Hz), 5.09 (dd, 1H, J=2.6, 45.1 Hz), 2.56 (m, 1H), 2.46 (m, 1H), 2.19 (m, 1H), 1.44 (s, 3H), 1.30-1.85 (m, 14H), 1.25 (s, 3H), 1.25 (d, 3H, J=6.3 Hz), 0.99 (s, 3H), 0.94 (s, 3H), 0.94 (s, 3H).

Compound 54:

A solution of pyridinium tribromide (311 mg, 0.88 mmol) in MeCN (3 mL) was added to a solution of compound 34 (388 mg, 0.76 mmol) in MeCN (4.6 mL) at room temperature. After the reaction was stirred for 2 h, additional amount of pyridinium tribromide (62 mg, 0.17 mmol) in MeCN (1 mL) was added. The reaction was stirred for another 1 h. Aq. $Na_2SO_3$ was added. The mixture was transferred to a separatory funnel, which was extracted with EtOAc. The combined organic extracts were washed with 1 N aq. HCl and water, dried with $MgSO_4$, and concentrated. The residue was purified by column chromatography (silica gel, eluting with 0% to 30% EtOAc in hexanes) to give compound 54 (256 mg, 66% yield) as a white solid.

Compounds 55 and 56:

$LiAlH_4$ (2.0 M in THF, 0.25 mL, 0.50 mmol) was added to a solution of compound 54 (250 mg, 0.49 mmol) in THF (4.9 mL) at 0° C. After the reaction was stirred at 0° C. for 1 h, additional amount of $LiAlH_4$ (2.0 M in THF, 0.25 mL, 0.50 mmol) was added. The reaction was continued stirring for another 1 h. Water was added. The mixture was stirred at room temperature for 5 min. EtOAc and 1 N aq. HCl were added. The mixture was transferred to a separatory funnel. The organic extract was washed with water, dried with $MgSO_4$, filtered, and concentrated. The residue was purified by column chromatography (silica gel, eluting with 0% to 100% EtOAc in hexanes) to give compound 55 (106 mg, 46% yield). From the column, also get compound 56 (107 mg, 46% yield).

Compound 57:

Compound 55 (103 mg, 0.21 mmol) and 56 (60 mg, 0.12 mmol), NMO (82 mg, 0.70 mmol), 4 Å MS and $CH_2Cl_2$ (9 mL) were stirred at room temperature for 10 min. TPAP (16 mg, 0.045 mmol) was added. After stirring at room temperature for 1 h, the mixture was filtered through a silica gel plug, which was washed with $CH_2Cl_2$/EtOAc (2:1). The combined filtrate and washes were transferred to a separatory funnel, which was washed with 1 N HCl and water. The organic extract was dried with $MgSO_4$, and was concentrated. The residue was purified by column chromatography (silica gel, eluting with 0% to 30% EtOAc in hexanes) to give compound 57 (140 mg, 86% yield) as a white solid. $^1H$ NMR (500 MHz, $CDCl_3$) δ 9.40 (d, 1H, J=1.1 Hz), 8.08 (s, 1H), 5.93 (s, 1H), 2.84 (m, 1H), 2.75 (d, 1H, J=15.4 Hz), 2.71 (d, 1H, J=4.7 Hz), 2.55 (m, 1H), 2.41 (m, 1H), 1.94 (m, 1H), 1.88 (m, 1H), 1.75 (m, 1H), 1.39 (d, 3H, J=6.8 Hz), 1.28 (s, 3H), 1.07 (s, 3H), 1.15-1.70 (m, 12H), 1.02 (s, 3H), 1.00 (s, 3H), 0.92 (s, 3H).

Compound 58:

Compound 57 (133 mg, 0.29 mmol), $Na_2HPO_4$ (71 mg, 0.5 mmol), m-CPBA (94 mg, 0.42 mmol) in $CH_2Cl_2$ (5.5 mL) were stirred at room temperature for 6 h. Aq. $Na_2SO_3$ was added. The mixture was stirred for 5 min, and was transferred to a separatory funnel, which was extracted with $CH_2Cl_2$. The organic extract was washed with aq. $NaHCO_3$, dried with $MgSO_4$, filtered, and concentrated. The residue was purified by column chromatography (silica gel, eluting with 0% to 35% EtOAc in hexanes) to give compound 58 (117 mg, 85% yield): m/z=480.3 (M+1), 434.3.

Compound 59:

NaOMe (140 μL, 0.61 mmol) was added to a solution of compound 58 (117 mg, 0.24 mmol) in MeOH (2.4 mL) at room temperature. After the reaction was heated at 55° C. for 1 h, MTBE was added. The mixture was transferred to a separatory funnel, which was washed with 1N aq. HCl and water. The organic extract was dried with $MgSO_4$, and concentrated. The residue was purified by column chromatography (silica gel, eluting with 0% to 35% acetone in hexanes) to give compound 59 (96 mg, 90% yield) as a white solid: m/z=452.3 (M+1), 434.3.

Compound TX63925:

A solution of DBDMH (30 mg, 0.10 mmol) in DMF (0.5 mL) was added to a solution of compound 59 (96 mg, 0.21 mmol) in DMF (0.5 mL) at 0° C. After Stirring at 0° C. for 1 h, pyridine (51 μL, 0.63 mmol) was added. The reaction was heated at 55° C. for 2 h. EtOAc was added. The mixture was transferred to a separatory funnel, which was washed with 1N aq. HCl, aq. $Na_2SO_3$ and water. The organic extract was separated, dried with $MgSO_4$, filtered, and concentrated. The residue was purified by column chromatography (silica gel, eluting with 0% to 50% EtOAc in hexanes) to give compound TX63925 (90 mg, 94% yield) as a white solid: m/z=450.2 (M+1), 432.2; $^1$H NMR (500 MHz, $CDCl_3$) δ 8.04 (s, 1H), 6.03 (s, 1H), 3.48 (d, 1H, J=4.7 Hz), 2.50 (m, 1H), 2.39 (m, 1H), 2.11 (m, 1H), 1.99 (m, 1H), 1.90 (m, 1H), 1.49 (s, 3H), 1.47 (s, 3H), 1.27 (d, 3H, J=6.7 Hz), 1.18-1.81 (m, 11H), 1.10 (m, 1H), 1.03 (s, 3H), 1.00 (s, 3H), 0.94 (s, 1H), 0.90 (s, 3H).

Compound TX63928:

$Ac_2O$ (30 μL, 0.32 mmol) and $BF_3$—$OEt_2$ (15 μL, 0.12 mmol) were added sequentially to a solution of compound TX63925 (30 mg, 0.067 mmol) in $CH_2Cl_2$ (0.3 mL) at 0° C. After the reaction was stirred for 10 min at 0° C., aq. $NaHCO_3$ was added. The mixture was transferred to a separatory funnel, which was extracted with EtOAc. The organic extract was washed with aq. $NaHCO_3$ and water, dried with $MgSO_4$, and concentrated. The residue was purified by column chromatography (silica gel, eluting with 0% to 35% EtOAc in hexanes) to give compound TX63928 (11 mg, 34% yield) as a white solid: m/z=432.2 (M-OAc); $^1$H NMR (500 MHz, $CDCl_3$) δ 8.04 (s, 1H), 6.05 (s, 1H), 3.33 (d, 1H, J=4.7 Hz), 2.72 (m, 1H), 2.49 (m, 1H), 2.42 (m, 1H), 2.37 (m, 1H), 2.02 (s, 3H), 1.47 (s, 3H), 1.46 (s, 3H), 1.27 (d, 3H, J=6.7 Hz), 1.20-1.95 (m, 12H), 1.16 (m, 1H), 1.05 (s, 3H), 1.03 (s, 3H), 0.90 (s, 3H).

Compound TX63929:

Trichloroacetyl isocyanate (11 μL, 0.092 mmol) was added to a solution of compound TX63925 (30 mg, 0.066 mmol) in $CH_2Cl_2$ (1 mL) at room temperature. After the reaction was stirred for 2 h, the solvent was removed by evaporation to give compound 60. Compound 60 was dissolved in MeOH (1 mL), and $K_2CO_3$ (27 mg, 0.20 mmol) was added. After the reaction was stirred at room temperature for 1 h, EtOAc was added. The mixture was transferred to a separatory funnel, which was washed with water. The organic extract was dried with $MgSO_4$, and concentrated. The residue was purified by column chromatography (silica gel, eluting with 0% to 50% EtOAc in hexanes) to give compound TX63929 (20 mg, 61% yield from TX63925) as a white solid: m/z=432.2 (M-$OCONH_2$); $^1$H NMR (500 MHz, $CDCl_3$) δ 8.05 (s, 1H), 6.06 (s, 1H), 4.47 (bs, 2H), 3.33 (d, 1H, J=4.7 Hz), 2.69 (m, 1H), 2.51 (m, 1H), 2.44 (m, 2H), 1.55-2.00 (m, 9H), 1.49 (s, 3H), 1.48 (s, 3H), 1.28 (d, 3H, J=6.6 Hz), 1.37 (m, 1H), 1.24-1.33 (m, 2H), 1.19 (m, 1H), 1.07 (s, 3H), 1.05 (s, 3H), 0.92 (s, 3H).

Compound 61:

NaOMe (31 μL, 0.14 mmol) was added to a solution of compound 55 (43 mg, 0.089 mmol) in MeOH (0.89 mL) at room temperature. After the reaction was heated at 55° C. for 1 h, MTBE was added. The mixture was transferred to a separatory funnel, which was washed with 1N aq. HCl and water. The organic extract was dried with $MgSO_4$, and concentrated. The residue was purified by column chromatography (silica gel, eluting with 0% to 100% EtOAc in hexanes) to give compound 61 (35 mg, 81% yield) as a white solid.

Compound TX63923:

A solution of DBDMH (10.7 mg, 0.037 mmol) in DMF (0.37 mL) was added to a solution of compound 61 (35 mg, 0.074 mmol) in DMF (0.37 mL) at 0° C. After Stirring at 0° C. for 1 h, pyridine (18 μL, 0.22 mmol) was added. The reaction was heated at 55° C. for 3 h. EtOAc was added. The mixture was transferred to a reparatory funnel, which was washed with 1N aq. HCl, aq. $Na_2SO_3$ and water. The organic extract was separated, dried with $MgSO_4$, filtered, and concentrated. The residue was purified by column chromatography (silica gel, eluting with 0% to 65% EtOAc in hexanes) to give compound TX63923 (28 mg, 80% yield) as a white solid: m/z=448.3 (M−17), 430.3 (M−35); $^1$H NMR (500 MHz, $CDCl_3$) δ 8.14 (s, 1H), 5.72 (d, 1H, J=3.1 Hz), 4.30 (m, 1H), 3.62 (m, 2H), 2.42 (m, 1H), 2.19 (m, 1H), 2.02 (m, 1H), 1.44 (s, 3H), 1.38 (s, 3H), 1.22-1.84 (m, 13H), 1.22 (d, 3H, J=6.7 Hz), 1.14 (m, 1H), 1.04 (m, 1H), 0.98 (s, 3H), 0.95 (s, 3H), 0.89 (s, 3H).

Compound TX63820:

Compound TX63520 (95.5 mg, 0.2 mmol), alkyl iodide (0.2 mmol), DBU (33.5 mg, 0.22 mmol) were dissolved in toluene (2 mL). The reaction mixture was stirred at RT for 21 hr. The reaction mixture was directly loaded on a silica gel column, and purified by column chromatography (silica gel, 0-20% EtOAc in Hexanes) to give TX63820 (18.6 mg, 18.4%, only the pure fractions were collected, purification was not optimized). $^1$H NMR (500 MHz, $CDCl_3$) δ 8.02 (s, 1H), 6.02 (s, 1H), 4.12-4.22 (m, 2H), 3.01-3.09 (m, 1H), 2.97 (d, 1H, J=4.5 Hz), 2.43-2.51 (m, 1H), 1.80-1.94 (m, 3H), 1.60-1.79 (m, 5H), 1.46-1.59 (m, 4H), 1.44 (s, 3H), 1.33 (s, 3H), 1.16-1.36 (m, 9H), 1.01 (s, 3H), 1.00 (s, 3H), 0.90 (s, 3H); m/z 506 (M+1).

Compound TX63821:

Compound TX63520 (95.5 mg, 0.2 mmol), alkyl iodide (0.2 mmol), DBU (33.5 mg, 0.22 mmol) were dissolved in toluene (2 mL). The reaction mixture was stirred at RT for 18 h, then 80° C. for 2 h. The reaction mixture was directly loaded on a silica gel column, and purified by column chromatography (silica gel, 0-20% EtOAc in Hexanes) to give TX73821 (84.1 mg, 75%). $^1$H NMR (500 MHz, $CDCl_3$) δ 8.02 (s, 1H), 6.02 (s, 1H), 4.09 (t, 2H, J=6.6 Hz), 2.93-3.10 (m, 1H), 2.96 (d, 1H, J=4.6 Hz), 2.43-2.51 (m, 1H), 1.80-1.94 (m, 3H), 1.40-1.95 (m, 15H), 1.44 (s, 3H), 1.34 (s, 3H), 1.16-1.40 (m, 10H), 1.25 (d, 1H, J=6.7 Hz), 1.01 (s, 3H), 1.00 (s, 3H), 0.90 (s, 3H), 0.88 (t, 3H, J=6.8 Hz); m/z 562 (M+1).

TABLE 2

| Product Name | Substituted Amine (mmol) | | Temperature/ Time | Yield (%) |
|---|---|---|---|---|
| TX63878 | $HNMe_2$ 2.0 M in THF | (1.0) | 80° C./3.5 h | 63.5 |
| TX63824 | $H_2NMe$•HCl | (1.0) | r.t./19 h | 10 |
| TX63877 | $H_2N$-n-$C_4H_9$ | (1.0) | 80° C./3 h | 45.6 |
| TX63823 | 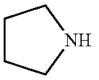 | (1.0) | r.t./1.5 h | 60 |
| TX63880 | 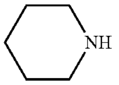 | 1.0) | r.t./3 h | 58 |
| TX63881 | 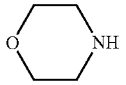 | (1.0) | r.t./3.5 h | 55 |

TABLE 2-continued

| Product Name | Substituted Amine (mmol) | | Temperature/ Time | Yield (%) |
|---|---|---|---|---|
| TX63822 | 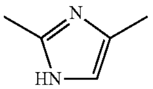 | (0.6) | See the experiment for details | 22 |
| TX64005 | 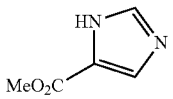 | (1.5) | r.t./16 h | 30 |
| TX63882 | $H_2NOMe$•HCl | (1.0) | r.t./3.5 h | 8.2 |
| TX64006 | $H_2NOH$•HCl | (0.9) | r.t./20 h | 30 |
| TX63825 | 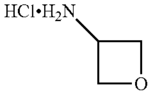 | (0.6) | r.t./19 h | 27 |
| TX64007 | 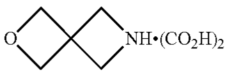 | (0.66) | r.t./5h | 34 |

Compound TX63822:

Compound 11 (0.2 mmol) and 2,4-Dimethyl-1H-imidazole (19.2 mg, 0.2 mmol) were taken up in toluene (1 mL), and the mixture was stirred at room temperature for 65 h, no reaction happened. Additional 2,4-Dimethyl-1H-imidazole (76.8 mg, 0.8 mmol) and toluene (2 mL) was added, and the mixture was stirred at room temperature for 3 h. The reaction mixture was quenched with $H_2O$ (10 mL) and extracted with $CH_2Cl_2$ (2×5 mL). The combined organic phase was filtered through a $Na_2SO_4$ plug, then directly loaded on a silica gel column and purified by column chromatography (silica gel, twice, 0-65% EtOAc in Hexanes then 0-60% EtOAc in Hexanes) to give the compound TX63822 as a white solid (22.2 mg, 22%). $^1$H NMR (500 MHz, $CDCl_3$) δ 8.02 (s, 1H), 7.22 (s, 1H), 6.03 (s, 1H), 3.25-3.30 (m, 1H), 3.06 (d, 1H, J=4.5 Hz), 2.56 (s, 3H), 2.42-2.51 (m, 1H), 2.19 (s, 3H), 1.95-2.16 (m, 3H), 1.83-1.93 (m, 2H), 1.58-1.77 (m, 4H), 1.15-1.45 (m, 6H), 1.44 (s, 3H), 1.30 (s, 3H), 1.24 (d, 3H, J=6.5 Hz), 1.06 (s, 3H), 1.04 (s, 3H), 0.95 (s, 3H); m/z 556 (M+1).

Compound TX64005:

Compound 11 (0.3 mmol) and methyl 4-imidazolecarboxylate (185 mg, 1.5 mmol) were taken up in $CH_2Cl_2$ (5 mL), and the mixture was stirred at room temperature for 16 h. The reaction mixture was quenched with $H_2O$ (10 mL) and extracted with $CH_2Cl_2$ (10 mL). The combined organic phase was washed by NaCl (Sat.), dried over $Na_2SO_4$, then directly loaded on a silica gel column and purified by column chromatography (silica gel, 0-70% EtOAc in Hexanes) to give the compound TX64005 as a white solid (52.6 mg, 30%) (only the pure fractions were collected, purification was not optimized). $^1$H NMR (500 MHz, $CDCl_3$) δ 8.32 (s, 1H), 8.26 (s, 1H), 8.02 (s, 1H), 6.05 (s, 1H), 3.94 (s, 3H), 3.23 (d, 1H, J=4.5 Hz), 3.15-3.22 (m, 1H), 2.43-2.52 (m, 1H), 2.23-2.32 (m, 1H), 1.83-2.05 (m, 4H), 1.56-1.79 (m, 4H), 1.15-1.52 (m, 6H), 1.45 (s, 3H), 1.28 (s, 3H), 1.24 (d, 3H, J=6.5 Hz), 1.06 (s, 3H), 1.05 (s, 3H), 0.97 (s, 3H); m/z 586 (M+1).

Compound TX64006:

Compound 11 (0.3 mmol) and hydroxylamine hydrochloride (62.6 mg, 0.9 mmol) were taken up in THF (4.5 mL). $Et_3N$ (0.5 mL) and $H_2O$ (0.3 mL) were added and the mixture was stirred at room temperature for 20 h. The reaction mixture was quenched with HCl (15 mL) and extracted with EtOAc (2×15 mL). The combined organic phase was washed by NaCl (Sat.), dried over $Na_2SO_4$ and concentrated under reduced pressure to afforded a solid residue, which was purified by column chromatography (silica gel, 0-50% EtOAc in Hexanes) to give the compound TX64006 as a white solid (44.4 mg, 30%) (only the pure fractions were collected, purification was not optimized). $^1$H NMR (500 MHz, $CDCl_3$) δ 9.21 (s, br, 1H), 8.04 (s, 1H), 7.85 (s, br, 1H), 6.12 (s, 1H), 3.01 (d, 1H, J=4.5 Hz), 2.86-2.97 (m, 1H), 2.42-2.52 (m, 1H), 1.95-2.06 (m, 1H), 1.80-1.92 (m, 2H), 1.15-1.79 (m, 12H), 1.43 (s, 3H), 1.33 (s, 3H), 1.25 (d, 3H, J=6.5 Hz), 1.02 (s, 3H), 1.01 (s, 3H), 0.92 (s, 3H); m/z 493 (M+1).

Compound TX64007:

Compound 11 (0.3 mmol) and 2-oxa-6-azaspiro[3,3]heptanes oxalate (124.7 mg, 0.66 mmol) were taken up in $CH_2Cl_2$ (5 mL). $Et_3N$ (418 μL, 3 mmol) was added and the mixture was stirred at room temperature for 5 h. The reaction mixture was quenched with HCl (5 mL) and extracted with $CH_2Cl_2$ (2×10 mL). The combined organic phase was washed by NaCl (Sat.), dried over $Na_2SO_4$, then directly loaded on a silica gel column and purified by column chromatography (silica gel, 0-75% EtOAc in Hexanes) to give the compound TX64007 as a white foam (56.8 mg, 34%) (only the pure fractions were collected, purification was not optimized). $^1$H NMR (500 MHz, $CDCl_3$) δ 8.01 (s, 1H), 6.01 (s, 1H), 4.79 (s, 4H), 4.33 (s, br, 4H), 2.90-3.01 (m, 2H), 2.41-2.51 (m, 1H), 1.83-1.96 (m, 2H), 1.13-1.82 (m, 13H), 1.44 (s, 3H), 1.32 (s, 3H), 1.25 (d, 3H, J=6.4 Hz), 1.01 (s, 3H), 1.01 (s, 3H), 0.91 (s, 3H); m/z 559 (M+1).

General Method A:

Compound 11 (~0.2 mmol) and substituted amine (See Table 2 for the amount) were taken up in toluene (2 mL), and the mixture was stirred at room temperature for 1 min. NaOH (10%, 1 mL) was added and the mixture was stirred at room temperature (See Table 2 for the reaction time). The reaction mixture was quenched with HCl (5 mL) and extracted with $CH_2Cl_2$ (10 mL). The combined organic phase was washed with NaCl (Sat.), dried over $Na_2SO_4$, then directly loaded on a silica gel column and purified by column chromatography (silica gel, 0-30% EtOAc in Hexanes) to give the corresponding derivatives:

Compound TX63823:

white solid (59.1 mg, 60%). $^1$H NMR (500 MHz, $CDCl_3$) δ 8.04 (s, 1H), 6.00 (s, 1H), 3.57 (s, br, 4H), 3.19-3.22 (m, 1H), 3.15 (d, 1H, J=3.5 Hz), 2.44-2.51 (m, 1H), 1.52-2.03 (m, 14H), 1.14-1.52 (m, 5H), 1.44 (s, 3H), 1.32 (s, 3H), 1.25 (d, 3H, J=7.0 Hz), 1.03 (s, 3H), 1.01 (s, 3H), 0.91 (s, 3H); m/z 531 (M+1).

Compound TX63880:

white foam (63.3 mg, 58%). $^1$H NMR (500 MHz, $CDCl_3$) δ 8.03 (s, 1H), 5.99 (s, 1H), 3.62 (s, br, 4H), 3.29-3.45 (m, 1H), 3.09-3.13 (m, 1H), 2.41-2.51 (m, 1H), 1.95-2.05 (m, 1H), 1.14-1.92 (m, 20H), 1.44 (s, 3H), 1.33 (s, 3H), 1.25 (d, 3H, J=6.5 Hz), 1.03 (s, 3H), 1.01 (s, 3H), 0.91 (s, 3H); m/z 545 (M+1).

Compound TX63881:

white foam (60.4 mg, 55%). $^1$H NMR (500 MHz, $CDCl_3$) δ 8.03 (s, 1H), 6.00 (s, 1H), 3.59-3.79 (m, 8H), 3.38 (s, br, 1H), 3.05-3.15 (m, 1H), 2.42-2.51 (m, 1H), 1.97-2.07 (m, 1H), 1.82-1.91 (m, 2H), 1.15-1.52 (m, 12H), 1.44 (s, 3H), 1.32 (s, 3H), 1.25 (d, 3H, J=6.5 Hz), 1.03 (s, 3H), 1.01 (s, 3H), 0.91 (s, 3H); m/z 547 (M+1).

General Method B:

Compound 11 (~0.2 mmol) and substituted amine (See Table 2 for the amount) were taken up in $CH_2Cl_2$ (2 mL). $Et_3N$ (0.5 mL) was added and the mixture was stirred at room temperature (See Table 2 for the reaction time). The reaction mixture was quenched with HCl (5 mL) and extracted with $CH_2Cl_2$ (10 mL). The organic phase was washed by NaCl (Sat.), dried over $Na_2SO_4$, then directly loaded on a silica gel column and purified by column chromatography (silica gel, EtOAc in Hexanes) to give the corresponding derivatives:

Compound TX63824:

white solid (9.9 mg, 10%); (silica gel, 0-30% EtOAc in Hexanes; only the pure fractions were collected, purification was not optimized). $^1H$ NMR (500 MHz, $CDCl_3$) δ 8.04 (s, 1H), 6.03 (s, 1H), 5.75-5.81 (m, 1H), 3.06 (d, 1H, J=4.5 Hz), 2.75-2.89 (m, 4H), 2.45-2.52 (m, 1H), 1.53-2.01 (m, 8H), 1.40-1.52 (m, 2H), 1.44 (s, 3H), 1.13-1.40 (m, 5H), 1.33 (s, 3H), 1.25 (d, 3H, J=7.0 Hz), 1.02 (s, 3H), 1.00 (s, 3H), 0.91 (s, 3H); m/z 491 (M+1).

Compound TX63882:

white foam (8.3 mg, 8.2%); (silica gel, twice, 0-15% EtOAc in Hexanes, then 0-35% EtOAc in Hexanes; only the pure fractions were collected, purification was not optimized). $^1H$ NMR (500 MHz, $CDCl_3$) δ 8.47 (s, 1H), 8.02 (s, 1H), 6.04 (s, 1H), 3.76 (s, 3H), 3.11 (d, 1H, J=4.0 Hz), 2.80-2.87 (m, 1H), 2.43-2.51 (m, 1H), 1.95-2.04 (m, 1H), 1.15-1.92 (m, 14H), 1.45 (s, 3H), 1.37 (s, 3H), 1.26 (d, 3H, J=7.0 Hz), 1.02 (s, 3H), 1.00 (s, 3H), 0.91 (s, 3H); m/z 507 (M+1).

Compound TX63825:

white solid (29.0 mg, 27%) (silica gel, 0-20% EtOAc in Hexanes; only the pure fractions were collected, purification was not optimized). $^1H$ NMR (500 MHz, $CDCl_3$) δ 8.02 (s, 1H), 6.16 (s, br, 1H), 6.03 (s, 1H), 4.90-5.00 (m, 3H), 4.40-4.52 (m, 2H), 3.06 (d, 1H, J=4.5 Hz), 2.87-2.93 (m, 1H), 2.44-2.52 (m, 1H), 1.98-2.07 (m, 1H), 1.15-1.93 (m, 14H), 1.45 (s, 3H), 1.33 (s, 3H), 1.25 (d, 3H, J=6.5 Hz), 1.03 (s, 3H), 1.01 (s, 3H), 0.92 (s, 3H); m/z 533 (M+1).

General Method C:

Compound 11 (~0.2 mmol) and substituted amine (See Table 2 for the amount) were taken up in toluene (2 mL) and the mixture was stirred at 80° C. (See Table 2 for the reaction time). The reaction mixture was quenched with HCl (5 mL) and extracted with $CH_2Cl_2$ (10 mL). The combined organic phase was washed NaCl (Sat.), dried over $Na_2SO_4$, then directly loaded on a silica gel column and purified by column chromatography (silica gel, EtOAc in Hexanes) to give the corresponding derivatives:

Compound TX63878:

white foam (64.1 mg, 63.5%); (silica gel, 0-15% EtOAc in Hexanes). $^1H$ NMR (500 MHz, $CDCl_3$) δ 8.03 (s, 1H), 5.99 (s, 1H), 3.18-3.30 (m, 2H), 3.08 (s, 6H), 2.43-2.50 (m, 1H), 1.96-2.05 (m, 1H), 1.15-1.91 (m, 14H), 1.44 (s, 3H), 1.32 (s, 3H), 1.25 (d, 3H, J=6.5 Hz), 1.02 (s, 6H), 0.91 (s, 3H); m/z 505 (M+1).

Compound TX63877:

very light yellow solid (48.6 mg, 45.6%); (silica gel, 0-15% EtOAc in Hexanes). $^1H$ NMR (500 MHz, $CDCl_3$) δ 8.02 (s, 1H), 6.02 (s, 1H), 5.76 (t, 1H, J=5.0 Hz), 3.20-3.33 (m, 2H), 3.07 (d, 1H, J=4.5 Hz), 2.83-2.90 (m, 1H), 2.43-2.52 (m, 1H), 1.85-2.01 (m, 2H), 1.15-1.84 (m, 17H), 1.47 (s, 3H), 1.33 (s, 3H), 1.25 (d, 3H, J=7.0 Hz), 1.02 (s, 3H), 1.00 (s, 3H), 0.92 (t, 3H, J=7.5 Hz), 0.91 (s, 3H); m/z 533 (M+1).

Compound 11:

DMF (5 drops) was added to a 0° C. solution of TX63520 (771 mg, 1.61 mmol) and $(COCl)_2$ (0.41 mL, 4.8 mmol) in $CH_2Cl_2$ (16 mL) and stirred at 0° C. for 15 min, then warmed to room temperature for 4 h. The resultant solution was concentrated to a yellow foam, azeotroped with $CH_2Cl_2$ (15 mL), and dried under vacuum to give 11 as a yellow foam. The yellow foam was dissolved in $CH_2Cl_2$ (16 mL) to give a stock solution (~0.1 M) that was used in subsequent reactions.

Compound TX63784:

Methoxyacetic acid hydrazide (67.2 mg, 0.645 mmol) and TEA (0.21 mL, 1.5 mmol) were added to stock 11 (0.1 M in $CH_2Cl_2$, 3.7 mL, 0.37 mmol), and the mixture stirred at room temperature for 23 h. The resultant solution was diluted with EtOAc (70 mL), washed with 1 M HCl (25 mL) and brine (25 mL), dried with $Na_2SO_4$, and concentrated. The crude residue was purified by column chromatography (silica gel, 0→100% EtOAc in Hexanes) to give TX63784 (151 mg, 72%) as a white solid: $^1H$ NMR (500 MHz, $CDCl_3$) δ 8.44 (d, 1H, J=3.5 Hz), 8.02 (s, 1H), 7.90 (d, 1H, J=4.0 Hz), 6.02 (s, 1H), 4.04 (s, 2H), 3.46 (s, 3H), 3.18 (d, 1H, J=4.4 Hz), 3.03 (m, 1H), 2.47 (qd, 1H, J=6.7, 12.8 Hz), 1.99 (m, 4H), 1.63 (m, 7H), 1.44 (s, 3H), 1.39 (s, 3H), 1.33 (m, 4H), 1.25 (d, J=6.5 Hz, 3H), 1.03 (s, 3H), 1.01 (s, 3H), 0.91 (s, 3H); m/z 564.3 (M+1).

Compound TX63790:

A mixture of TX63784 (136 mg, 0.241 mmol), TsOH.$H_2O$ (43.4 mg, 0.228 mmol) and PhMe (12 mL) was heated to vigorous reflux with Dean-Stark removal of water for 1 h. The resultant mixture was cooled to room temperature, diluted with EtOAc (30 mL), washed with sat. $NaHCO_3$ (15 mL) and brine (15 mL), dried with $Na_2SO_4$, and concentrated. The crude residue was purified by column chromatography (silica gel, 0→70% EtOAc in Hexanes) to give TX63790 (67.0 mg, 51%) as a white solid: $^1H$ NMR (500 MHz, $CDCl_3$) δ 8.00 (s, 1H), 6.01 (s, 1H), 4.63 (s, 2H), 3.43 (s, 3H), 3.19 (m, 1H), 3.03 (d, 1H, J=4.6 Hz), 2.46 (qd, 1H, J=6.6, 12.8 Hz), 2.21 (dt, 1H, J=4.0, 13.2 Hz), 1.91 (m, 4H), 1.65 (m, 5H), 1.41 (s, 3H), 1.35 (m, 5H), 1.24 (d, 3H, J=6.6 Hz), 1.16 (s, 3H), 1.06 (s, 6H), 0.95 (s, 3H); m/z 546.3 (M+1).

Compound TX63785:

Formic acid hydrazide (55.9 mg, 0.931 mmol) and TEA (0.26 mL, 1.9 mmol) were added to stock 11 (0.1 M in $CH_2Cl_2$, 4.6 mL, 0.46 mmol), and the mixture stirred at room temperature for 23 h. The resultant solution was diluted with EtOAc (70 mL), washed with 1 M HCl (25 mL) and brine (25 mL), dried with $Na_2SO_4$, and concentrated. The crude residue was purified by column chromatography (silica gel, 0→100% EtOAc in Hexanes) to give TX63785 (112 mg, 47%) as a white solid: $^1H$ NMR (500 MHz, $CDCl_3$) δ 8.17 (s, 1H), 8.10 (d, 1H, J=4.0 Hz), 8.02 (s, 1H), 7.90 (d, 1H, J=4.0 Hz), 6.03 (s, 1H), 3.17 (d, 1H, J=4.0 Hz), 3.02 (m, 1H), 2.47 (qd, 1H, J=6.8, 12.6 Hz), 2.09 (m, 1H), 1.89 (m, 3H), 1.64 (m, 8H), 1.44 (s, 3H), 1.37 (s, 3H), 1.32 (m, 3H), 1.25 (d, 3H, J=6.7 Hz), 1.03 (s, 3H), 0.99 (s, 3H), 0.91 (s, 3H); m/z 520.3 (M+1).

Compound TX63789:

A mixture of TX63785 (94 mg, 0.181 mmol), TsOH.$H_2O$ (34.4 mg, 0.181 mmol) and PhMe (12 mL) was heated to vigorous reflux with Dean-Stark removal of water for 45 min. The resultant mixture was cooled to room temperature, diluted with EtOAc (50 mL), washed with sat. $NaHCO_3$ (25 mL) and brine (25 mL), dried with $Na_2SO_4$, and concentrated. The crude residue was purified by column chromatography (silica gel, 0→75% EtOAc in Hexanes) to give TX63789 (31.0 mg, 34%) as a white solid: $^1H$ NMR (500 MHz, $CDCl_3$) δ 8.36 (s, 1H), 8.00 (s, 1H), 6.01 (s, 1H), 3.20 (m, 1H), 2.93 (d, 1H, J=3.2 Hz), 2.46 (qd, 1H, J=6.2, 12.4 Hz), 2.22 (dt, 1H, J=3.9, 14.1 Hz), 1.91 (m, 4H), 1.64 (m, 5H), 1.41 (s, 3H), 1.32 (m, 5H), 1.24 (d, 3H, J=6.5 Hz), 1.15 (s, 3H), 1.06 (s, 6H), 0.95 (s, 3H); m/z 502.3 (M+1).

Compound TX63786:

Acetamide oxime (34.4 mg, 0.464 mmol) and TEA (0.14 mL, 1.00 mmol) were added to stock 11 (0.1 M in $CH_2Cl_2$, 2.5 mL, 0.25 mmol), and the mixture stirred at room temperature for 23 h. The resultant solution was concentrated and the crude residue was purified by column chromatography (silica gel, 0→100% EtOAc in Hexanes) to give TX63786 (82 mg, 61%) as a white solid: $^1H$ NMR (500 MHz, $CDCl_3$) δ 8.03 (s, 1H), 6.02 (s, 1H), 4.68 (br s, 2H), 3.10 (m, 1H), 3.06 (d, 1H, J=4.5 Hz), 2.47 (qd, 1H, J=6.7, 12.6 Hz), 1.98 (s, 3H), 1.81 (m, 7H), 1.51 (m, 2H), 1.44 (s, 3H), 1.34 (s, 3H), 1.29 (m, 6H), 1.24 (d, 3H, J=6.9 Hz), 1.02 (s, 3H), 1.01 (s, 3H), 0.90 (s, 3H); m/z 534.3 (M+1).

Compound TX63787:

A solution of TX63786 (74 mg, 1 mmol) in EtOAc (0.15 mL) and PhMe (1.35 mL) were sealed in a microwave vial and heated to 200° C. for 20 min. The solution was concentrated and the crude residue was purified by column chromatography (silica gel, 0→55% EtOAc in Hexanes) to give TX63787 (17.2 mg, 24%) as an off-white solid: $^1$H NMR (500 MHz, $CDCl_3$) δ 8.01 (s, 1H), 6.02 (s, 1H), 3.25 (m, 1H), 3.05 (d, 1H, J=4.6 Hz), 2.46 (qd, 1H, J=6.5, 12.8 Hz), 2.38 (s, 3H), 2.20 (dt, 1H, J=4.0, 14.0 Hz), 1.90 (m, 3H), 1.65 (m, 7H), 1.41 (s, 3H), 1.33 (m, 4H), 1.23 (d, 3H, J=8.0 Hz), 1.12 (s, 3H), 1.05 (s, 3H), 1.05 (s, 3H), 0.94 (s, 3H); m/z 516.3 (M+1).

Compound 62:

A mixture of methyl magnesium carbonate (2.0 M in DMF, 2.25 mL, 4.50 mmol) and 7 (238 mg, 0.508 mmol) was heated to 110° C. with a constant $N_2$ sparge for 1.5 h. The resultant solution was cooled to room temperature, diluted with EtOAc (75 mL), washed with 1M HCl (50 mL) and brine (25 mL), dried with $Na_2SO_4$ and concentrated to give 62 (257 mg, 99%) as an off-white solid: m/z 513.3 (M+1).

Compound 63:

$TMSCHN_2$ (2.0 M in THF, 0.51 mL, 1.02 mmol) was added to a 0° C. solution of 62 (257 mg, 0.501 mmol) in THF (8.0 mL) and MeOH (2.0 mL). The resultant solution was stirred for 1.5 h at 0° C., diluted with EtOAc (150 mL), washed with sat. $NaHCO_3$ (50 mL) and brine (25 mL), dried with $Na_2SO_4$ and concentrated. The crude residue was purified by column chromatography (silica gel, 0→45% EtOAc in Hexanes) to give 63 as a glassy solid that was used as-is in next reaction: m/z 527.4 (M+1).

Compound TX63788:

Pyridine (77 uL, 0.95 mmol) was added to a 0° C. solution of PhSeCl (168 mg, 0.876 mmol) in $CH_2Cl_2$ (3 mL). After 15 min a solution of 63 (228 mg, 0.433 mmol) in $CH_2Cl_2$ (8.7 mL) was added and the reaction stirred at 0° C. for 1.5 h. The resultant solution was diluted with $CH_2Cl_2$ (10 mL), washed with 1M HCl (2×5 mL), cooled to 0° C., and $H_2O_2$ (30%, 0.42 mL) added. The biphasic mixture was vigorously stirred for 1 h, then diluted with $CH_2Cl_2$ (50 mL), washed with 10% $Na_2SO_3$ (25 mL) and brine (25 mL), dried with $Na_2SO_4$ and concentrated. The crude residue was purified by column chromatography (silica gel, 0→50% EtOAc in Hexanes) to give TX63788 (175 mg, 67% from 63) as a white solid: $^1$H NMR (500 MHz, $CDCl_3$) δ 8.00 (s, 1H), 6.12 (s, 1H), 3.80 (s, 3H), 3.70 (s, 3H), 3.05 (m, 1H), 2.94 (d, 1H, J=4.0 Hz), 2.42 (qd, 1H, J=6.5, 11.8 Hz), 1.87 (m, 3H), 1.59 (m, 8H), 1.39 (s, 3H), 1.32 (s, 3H), 1.25 (m, 4H), 1.22 (d, 3H, J=6.4 Hz), 1.01 (s, 3H), 1.00 (s, 3H), 0.89 (s, 3H); m/z 525.3 (M+1).

Compound TX63830:

A suspension of TX63788 (353 mg, 0.673 mmol), KOH (1.89 g, 33.7 mmol), $H_2O$ (7 mL), and MeOH (21 mL) was heated to reflux for 10 min. The resultant solution was cooled to room temperature, diluted with EtOAc (75 mL), washed with 1 M HCl (50 mL) and brine (25 mL), dried with $Na_2SO_4$, and concentrated. The crude residue was purified by column chromatography (silica gel, 0→60% EtOAc in Hexanes each containing 0.5% HOAc) to give TX63830 (210 mg, 61%) as a white solid: $^1$H NMR (500 MHz, $CDCl_3$) δ 12.50 (br s, 1H), 8.77 (s, 1H), 6.22 (s, 1H), 3.69 (s, 3H), 3.05 (m, 1H), 2.93 (d, 1H, J=4.7 Hz), 2.60 (qd, 1H, J=6.7, 12.7 Hz), 1.79 (m, 7H), 1.53 (m, 4H), 1.44 (s, 3H), 1.34 (s, 3H), 1.26 (d, 3H, J=6.6 Hz), 1.25 (m, 4H), 1.00 (s, 6H), 0.89 (s, 3H); m/z 511.4 (M+1).

Compound TX63831:

A mixture of TX63788 (100.6 mg, 0.192 mmol) and $NH_3$ (2.0 M in MeOH, 9.5 mL, 19 mmol) was stirred at room temperature for 12 d. The resultant solution was concentrated and purified by column chromatography (silica gel, 0→100% EtOAc in Hexanes) to give TX63831 (39 mg, 40%) as a white solid: $^1$H NMR (500 MHz, $CDCl_3$) δ 8.66 (s, 1H), 8.44 (br s, 1H), 6.27 (s, 1H), 5.62 (br s, 1H), 3.69 (s, 3H), 3.05 (m, 1H), 2.91 (d, 1H, J=4.6 Hz), 2.49 (qd, 1H, J=6.7, 12.2 Hz), 1.87 (m, 3H), 1.69 (m, 5H), 1.50 (m, 3H), 1.40 (s, 3H), 1.32 (s, 3H), 1.26 (m, 4H), 1.23 (d, 3H, J=6.7 Hz), 1.00 (s, 6H), 0.89 (s, 3H); m/z 510.3 (M+1).

Compound TX63716:

EDCI (192 mg, 1.00 mmol) was added to a room temperature solution of TX63545 (286 mg, 0.617 mmol), N-Boc-Gly-OH (165 mg, 0.942 mmol), DMAP (20.7 mg, 0.169 mmol), and $CH_2Cl_2$ (12.4 mL) and the mixture stirred at room temperature for 19 h. The resultant solution was diluted with EtOAc (100 mL), washed with 1 M HCl (25 mL) and brine (25 mL), dried with $Na_2SO_4$, and concentrated. The crude residue was purified by column chromatography (silica gel, 0→75% EtOAc in Hexanes) to give TX63716 (326 mg, 85%) as a white solid: $^1$H NMR (500 MHz, $CDCl_3$) δ 8.02 (s, 1H), 6.03 (s, 1H), 5.00 (br s, 1H), 4.14 (m, 2H), 3.95 (m, 2H), 2.98 (d, 1H, J=3.5 Hz), 2.48 (qd, 1H, J=6.0, 12.6 Hz), 2.35 (br d, 1H, J=12.5 Hz), 1.89 (m, 2H), 1.73 (m, 4H), 1.49 (m, 2H), 1.45 (s, 9H), 1.48 (s, 3H), 1.46 (s, 3H), 1.27 (m, 5H), 1.26 (d, 3H, J=6.8 Hz), 1.12 (m, 2H), 1.02 (s, 3H), 0.94 (s, 3H), 0.88 (s, 3H); m/z 565.3 (M−55) ($M-C_4H_8+H$).

Compound TX63717:

HCl (4.0 M in 1,4-dioxane, 0.94 mL, 3.76 mmol) was added to a room temperature solution of TX63716 (293 mg, 0.472 mmol) in $CH_2Cl_2$ (10 mL). After 6 h the solution was diluted with EtOAc (100 mL), washed with sat. $NaHCO_3$ (30 mL) and brine (30 mL), dried with $Na_2SO_4$, and concentrated. The crude residue was purified by column chromatography (silica gel, 50→100% EtOAc in Hexanes, each with 0.5% TEA) to give TX63717 (209 mg, 85%) as a pale-yellow solid: $^1$H NMR (500 MHz, $CDCl_3$) δ 8.03 (s, 1H), 6.04 (s, 1H), 4.18 (d, 1H, J=11.0 Hz), 4.09 (d, 1H, J=11.3 Hz), 3.48 (s, 2H), 3.01 (d, 1H, J=4.6 Hz), 2.49 (qd, 1H, J=6.6, 12.7 Hz), 2.37 (m, 1H), 1.92 (m, 2H), 1.63 (m, 7H), 1.50 (s, 3H), 1.47 (s, 3H), 1.27 (d, 3H, J=6.6 Hz), 1.26 (m, 5H), 1.09 (m, 3H), 1.03 (s, 3H), 0.94 (s, 3H), 0.89 (s, 3H); m/z 521.3 (M+1).

Compound TX63832:

PhSeCl (334 mg, 1.74 mmol) was added to a room temperature suspension of 7 (469 mg, 1.00 mmol) in EtOAc (20 mL). After 6 h the resultant solution was washed with water (2×25 mL), and the mixture stored at −20° C. overnight. The solution was warmed to room temperature and THF (8 mL) and $H_2O_2$ (30%, 1.0 mL) were added. The mixture was stirred at room temperature for 1 h, diluted with EtOAc (50 mL), washed with 10% $Na_2SO_3$ (25 mL) and brine (25 mL), dried with $Na_2SO_4$, and concentrated. The crude residue was purified by column chromatography (silica gel, 0→30% EtOAc in Hexanes) to give TX63832 (255 mg, 55%) as a white solid: $^1$H NMR (500 MHz, $CDCl_3$) δ 7.31 (d, 1H, J=10.4 Hz), 6.05 (s, 1H), 5.89 (d, 1H, J=10.3 Hz), 3.69 (s, 3H), 3.05 (m, 1H), 2.92 (d, 1H, J=4.6 Hz), 2.38 (qd, 1H, J=5.8, 12.5 Hz), 1.87 (m, 3H), 1.57 (m, 8H), 1.36 (s, 3H), 1.31 (s, 3H), 1.27 (m, 4H), 1.19 (d, 3H, J=6.7 Hz), 1.01 (s, 3H), 1.00 (s, 3H), 0.89 (s, 3H); m/z 467.4 (M+1).

Compound TX63833:

A solution of TX63832 (231 mg, 0.495 mmol), $I_2$ (251 mg, 0.989 mmol), pyridine (0.12 mL, 1.48 mmol), and THF (10 mL) was heated to reflux for 17 h. The resultant mixture was cooled to room temperature; diluted with EtOAc (100 mL); washed with sat. $Na_2S_2O_3$ (40 mL), 1 M HCl (50 mL), and sat. $NaHCO_3$ (25 mL); dried with $Na_2SO_4$ and concentrated. The crude residue was purified by column chromatography (silica gel, 0→30% EtOAc in Hexanes) to give TX63833 (175 mg, 60%) as a white solid: $^1$H NMR (500 MHz, $CDCl_3$) δ 8.10 (s, 1H), 6.04 (s, 1H), 3.69 (s, 3H), 3.05 (m, 1H), 2.93 (d, 1H, J=4.5 Hz), 2.55 (qd, 1H, J=6.1, 12.6 Hz), 1.69 (m, 11H), 1.38 (s, 3H), 1.30 (s, 3H), 1.27 (m, 4H), 1.26 (d, 3H, J=6.7 Hz), 1.02 (s, 3H), 1.00 (s, 3H), 0.89 (s, 3H); m/z 593.2 (M+1).

Compound 64:

LAH (2.0 M in THF, 32 mL, 64 mmol) was added to a 0° C. solution of 7 (6.06 g, 12.9 mmol) in THF (225 mL). The mixture was stirred at 0° C. for 1 h; warmed to room temperature for 26 h; cooled to 0° C.; quenched by the successive addition of water (2.4 mL), 4 M NaOH (2.4 mL, and water (2.4 mL); warmed to room temperature; diluted with MTBE (100 mL); stirred for 1 h; filtered through celite; eluted with $CH_2Cl_2$ (100 mL) and concentrated to give 64 (5.79 g, quantitative) as a white foam that was used without further purification: m/z 427.3 (M−17), (M-$H_2O$+H).

Compound 65:

A biphasic solution of 64 (all above obtained, ~12.9 mmol), $PhI(OAc)_2$ (9.35 g, 29.0 mmol), TEMPO (2.01 g, 12.9 mmol), water (13 mL), and $CH_2Cl_2$ (1.3 L) was stirred vigorously at room temperature for 21 h. The resultant mixture was dried with $Na_2SO_4$ and concentrated. The crude residue was purified by column chromatography (silica gel, 0→100% EtOAc in Hexanes) to give 65 (1.56 g, 27%) as a white solid: m/z 425.3 (M−17), (M-$H_2O$+H).

Compound 66:

Triethyl phosphonoacetate (3.52 mL, 17.7 mmol) was added to a 0° C. suspension of NaH (60%, 712 mg, 17.8 mmol) in THF (53 mL) and warmed to room temperature over 15 min. The resultant solution was cooled to 0° C. and a solution of 65 (1.56 g, 3.52 mmol) in THF (17.5 mL) was added and the transfer completed with THF (5 mL). The mixture was warmed to room temperature and stirred for 17.5 h, quenched by the addition of water (50 mL) and 1 M HCl (25 mL), and extracted with $CH_2Cl_2$ (300 mL, then 100 mL). The combined organic fractions were washed with sat. $NaHCO_3$ (100 mL) and brine (50 mL), dried with $Na_2SO_4$, and concentrated. The crude residue was purified by column chromatography (silica gel, 0→100% EtOAc in Hexanes) to give 66 (1.212 g, 67%) as a white solid: m/z 495.3 (M−17), (M-$H_2O$+H).

Compound 67:

TPAP (82 mg, 0.233 mmol) was added to a room temperature solution of 66 (1.212 g, 2.364 mmol), NMO (831 mg, 7.09 mmol) and 4 Å molecular sieves (3.04 g) in $CH_2Cl_2$ (50 mL). The resultant mixture was stirred at room temperature for 1.5 h, concentrated to ~3 mL, and purified by column chromatography (silica gel, 0→65% EtOAc in Hexanes) to give 67 (1.057 g, 88%) as a white solid: m/z 509.3 (M+1).

Compound 68:

A flask containing a room temperature suspension of 67 (1.057 g, 2.078 mmol) and Pd/C (10%, 260 mg) in THF (42 mL) was purged with $N_2$ then $H_2$. The suspension was stirred under $H_2$ (balloon) for 17 h, sparged with $N_2$, filtered through celite, eluted with THF (50 mL), and concentrated to give 68 (1.094 g, quantitative) as a white solid that was used without further purification: m/z 511.3 (M+1).

Compound 69:

A solution of 68 (all above obtained, ~2.078 mmol), NaOMe (25% in MeOH, 5.25 mL) and EtOCHO (15.75 mL) was stirred at room temperature for 3.5 h, diluted with 1 M HCl (50 mL), and extracted with EtOAc (2×100 mL). The combined organic fractions were washed with brine (25 mL), dried with $Na_2SO_4$, and concentrated to give 69 (mixture of Me- and Et-esters ~1:2.4) as an off-white foam solid that was used without further purification: Me-ester m/z 525.3 (M+1), Et-ester m/z 539.3 (M+1).

Compound 70:

A mixture of 69 (all above obtained, ~2.078 mmol), $NH_2OH.HCl$ (192 mg, 2.76 mmol), EtOH (18 mL) and water (3 mL) was heated to 55° C. for 17 h. The resultant solution was cooled to room temperature, diluted with 1 M HCl (50 mL) and extracted with EtOAc (100 mL, then 75 mL). The combined organic fractions were dried with $Na_2SO_4$ and concentrated. The resultant residue was dissolved in MeOH (100 mL), treated with 12 M HCl (0.25 mL), and stirred at room temperature for 3 h. The mixture was diluted with 1 M HCl (50 mL) and extracted with EtOAc (2×100 mL). The combined organic fractions were washed with brine (50 mL), dried with $Na_2SO_4$, and concentrated. The crude residue was purified by column chromatography (silica gel, 0→60% EtOAc in Hexanes) to give 70 (876 mg, Me-:Et-ester=41:57, 80% from 68) as a white solid: Me-ester m/z 522.3 (M+1), Et-ester m/z 536.3 (M+1).

Compound 71:

A solution of 70 (876 mg, Me-:Et-ester=41:57, 1.65 mmol), NaOMe (1.0 mL, 25% in MeOH), and MeOH (21 mL) was heated to 55° C. for 2 h. The resultant mixture was diluted 1 M HCl (50 mL) and extracted with EtOAc (100 mL, then 2×50 mL). The combined organic fractions were washed with brine (25 mL), dried with $Na_2SO_4$, and concentrated to give 71 (900 mg, quantitative) as a white foam solid that was used without further purification: m/z 522.3 (M+1).

Compound TX63867:

DBDMH (236.5 mg, 0.827 mmol) was added to a 0° C. solution of 71 (all above obtained, ~1.65 mmol) in DMF (20 mL). The mixture was stirred at 0° C. for 2.5 h, pyridine (0.53 mL, 6.6 mmol) added, and the reaction heated to 55° C. for 16 h. The reaction was cooled to room temperature; diluted with EtOAc (200 mL); washed with 1 M HCl (25 mL), 10% $Na_2SO_3$ (25 mL) and brine (25 mL); dried with $Na_2SO_4$ and concentrated. The crude residue was purified by column chromatography (silica gel, 0→75% EtOAc in Hexanes) to give TX63867 (708 mg, 82%) as a white solid: $^1$H NMR (400 MHz, $CDCl_3$) δ 8.02 (s, 1H), 6.03 (s, 1H), 3.67 (s, 3H), 3.07 (d, 1H, J=4.6 Hz), 2.48 (qd, 1H, J=6.7, 12.3 Hz), 2.30 (m, 3H), 1.68 (m, 11H), 1.51 (s, 3H), 1.46 (s, 3H), 1.26 (d, 3H, J=6.7 Hz), 1.25 (m, 4H), 1.04 (m, 2H), 1.02 (s, 3H), 0.93 (s, 3H), 0.88 (s, 3H); m/z 520.3 (M+1).

Compound TX63891:

A suspension of TX63867 (643 mg, 1.24 mmol) in MeCN (37.5 mL) and 1 M HCl (12.5 mL) was heated to 65° C. overnight. The resultant solution was cooled to room temperature, diluted with 1 M HCl (50 mL) and extracted with EtOAc (150 mL, then 100 mL). The combined organic fractions were washed with brine (50 mL), dried with $Na_2SO_4$, and concentrated. The crude residue was purified by column chromatography (silica gel, 0→100% EtOAc in Hexanes both containing 0.5% HOAc), like fractions were combined, concentrated, azeotroped with PhMe (100 mL) then EtOH (50 mL), and dried to give TX63891 (583 mg, 93%) as a white solid: $^1$H NMR (500 MHz, $CDCl_3$) δ 9.88 (br s, 1H), 8.03 (s, 1H), 6.04 (s, 1H), 3.08 (d, 1H, J=4.5 Hz), 2.48 (qd, 1H, J=6.7, 12.6 Hz), 2.32 (m, 3H), 1.69 (m, 11H), 1.49 (s, 3H), 1.46 (s, 3H), 1.27 (m, 4H), 1.26 (d, 3H, J=6.8 Hz), 1.04 (m, 2H), 1.01 (s, 3H), 0.92 (s, 3H), 0.87 (s, 3H); m/z 506.3 (M+1).

Compound TX63886:

EDCI (39.3 mg, 0.205 mmol) was added to a solution of TX63891 (50.5 mg, 0.0999 mmol), $MeNH_2$.HCl (16.3 mg, 0.241 mmol), TEA (28 uL, 0.20 mmol) and DMAP (25.8 mg, 0.211 mmol) in $CH_2Cl_2$ (2 mL) and stirred at room temperature for 18 h. The resultant solution was diluted with EtOAc (25 mL), washed with 1 M HCl (15 mL) and brine (10 mL), dried with $Na_2SO_4$ and concentrated. The crude residue was purified by column chromatography (silica gel, 0→100% EtOAc in Hexanes), like fractions were combined, concentrated, azeotroped with EtOH, and dried to give TX63886 (39.3 mg, 76%) as a white solid: $^1$H NMR (500 MHz, $CDCl_3$) δ 8.03 (s, 1H), 6.02 (s, 1H), 5.44 (br s, 1H), 3.10 (d, 1H, J=3.9 Hz), 2.80 (d, 3H, J=4.5 Hz), 2.48 (qd, 1H, J=6.5, 12.4 Hz), 2.23 (m, 1H), 2.13 (m, 2H), 1.88 (m, 4H), 1.59 (m, 7H), 1.53 (s, 3H), 1.46 (s, 3H), 1.26 (d, 3H, J=6.9 Hz), 1.25 (m, 4H), 1.02 (m, 2H), 1.00 (s, 3H), 0.92 (s, 3H), 0.87 (s, 3H); m/z 519.3 (M+1).

Compound TX63892:

EDCI (39.0 mg, 0.203 mmol) was added to a solution of TX63891 (50.3 mg, 0.0995 mmol), $EtNH_2$.HCl (18.5 mg, 0.227 mmol), TEA (28 uL, 0.20 mmol) and DMAP (24.8 mg, 0.203 mmol) in $CH_2Cl_2$ (2 mL) and stirred at room temperature for 17 h. The resultant solution was diluted with EtOAc (25 mL), washed with 1 M HCl (15 mL) and brine (10 mL), dried with $Na_2SO_4$ and concentrated. The crude residue was purified by column chromatography (silica gel, 0→100% EtOAc in Hexanes), like fractions were combined, concentrated, azeotroped with EtOH, and dried to give TX63892 (44.9 mg, 85%) as a white solid: $^1$H NMR (500 MHz, $CDCl_3$) δ 8.03 (s, 1H), 6.02 (s, 1H), 5.41 (br s, 1H), 3.28 (dq, 2H, J=6.6, 7.0 Hz), 3.11 (d, 1H, J=4.2 Hz), 2.48 (qd, 1H, J=6.5, 12.5 Hz), 2.23 (m, 1H), 2.12 (t, 2H, J=8.0 Hz), 1.89 (m, 4H), 1.60 (m, 7H), 1.53 (s, 3H), 1.46 (s, 3H), 1.26 (d, 3H, J=6.8 Hz), 1.23 (m, 4H), 1.13 (t, 3H, J=7.3 Hz), 1.02 (m, 2H), 1.00 (s, 3H), 0.92 (s, 3H), 0.87 (s, 3H); m/z 533.4 (M+1).

Compound TX63887:

EDCI (39.0 mg, 0.203 mmol) was added to a solution of TX63891 (50.6 mg, 0.100 mmol), 2,2,2-trifluoroethylamine hydrochloride (27.7 mg, 0.204 mmol), TEA (28 uL, 0.20 mmol) and DMAP (25.0 mg, 0.205 mmol) in $CH_2Cl_2$ (2 mL) and stirred at room temperature for 18 h. The resultant solution was diluted with EtOAc (25 mL), washed with 1 M HCl (25 mL) and brine (10 mL), dried with $Na_2SO_4$ and concentrated. The crude residue was purified by column chromatography (silica gel, 0→100% EtOAc in Hexanes), like fractions were combined, concentrated, azeotroped with EtOH, and dried to give TX63887 (45.0 mg, 77%) as a white solid: $^1$H NMR (500 MHz, $CDCl_3$) δ 8.03 (s, 1H), 6.03 (s, 1H), 5.70 (br s, 1H), 3.98 (m, 1H), 3.86 (m, 1H), 3.08 (d, 1H, J=4.1 Hz), 2.48 (qd, 1H, J=6.5, 11.9 Hz), 2.22 (m, 3H), 1.78 (m, 8H), 1.51 (s, 3H), 1.48 (m, 3H), 1.46 (s, 3H), 1.26 (d, 3H, J=6.6 Hz), 1.25 (m, 4H), 1.02 (m, 2H), 1.01 (s, 3H), 0.92 (s, 3H), 0.88 (s, 3H); m/z 587.3 (M+1).

Compound TX63888:

EDCI (38.5 mg, 0.201 mmol) was added to a solution of TX63891 (49.8 mg, 0.0985 mmol), morpholine (18 uL, 0.207 mmol), TEA (28 uL, 0.20 mmol) and DMAP (24.5 mg, 0.201 mmol) in $CH_2Cl_2$ (2 mL) and stirred at room temperature for 18 h. The resultant solution was diluted with EtOAc (25 mL), washed with 1 M HCl (25 mL) and brine (10 mL), dried with $Na_2SO_4$ and concentrated. The crude residue was purified by column chromatography (silica gel, 0→100% EtOAc in Hexanes), like fractions were combined, concentrated, azeotroped with EtOH, and dried to give TX63888 (38.9 mg, 69%) as a white solid: $^1$H NMR (500×MHz, $CDCl_3$) δ 8.02 (s, 1H), 6.02 (s, 1H), 3.64 (m, 6H), 3.48 (m, 2H), 3.10 (d, 1H, J=3.8 Hz), 2.48 (qd, 1H, J=6.2, 12.9 Hz), 2.33 (m, 1H), 2.23 (m, 2H), 1.77 (m, 8H), 1.50 (s, 3H), 1.50 (m, 3H), 1.45 (s, 3H), 1.26 (d, 3H, J=6.2 Hz), 1.25 (m, 4H), 1.04 (m, 2H), 1.01 (s, 3H), 0.93 (s, 3H), 0.88 (s, 3H); m/z 575.4 (M+1).

Compound TX63889:

EDCI (39.0 mg, 0.203 mmol) was added to a solution of TX63891 (50.2 mg, 0.0993 mmol), azetidine hydrochloride (19.0 mg, 0.203 mmol), TEA (28 uL, 0.20 mmol) and DMAP (25.0 mg, 0.205 mmol) in $CH_2Cl_2$ (2 mL) and stirred at room temperature for 18 h. The resultant solution was diluted with EtOAc (25 mL), washed with 1 M HCl (15 mL) and brine (10 mL), dried with $Na_2SO_4$ and concentrated. The crude residue was purified by column chromatography (silica gel, 0→100% EtOAc in Hexanes), like fractions were combined, concentrated, azeotroped with EtOH, and dried to give TX63889 (45.6 mg, 84%) as a white solid: $^1$H NMR (500 MHz, $CDCl_3$) δ 8.02 (s, 1H), 6.01 (s, 1H), 4.16 (m, 2H), 4.00 (t, 2H, J=7.6 Hz), 3.12 (d, 1H, J=7.6 Hz), 2.48 (d, 1H, J=6.6, 12.5 Hz), 2.25 (m, 3H), 1.75 (m, 13H), 1.52 (s, 3H), 1.46 (s, 3H), 1.25 (d, 3H, J=6.7 Hz), 1.24 (m, 4H), 1.00 (s, 3H), 0.97 (m, 2H), 0.93 (s, 3H), 0.87 (s, 3H); m/z 545.3 (M+1).

Compound TX63893:

EDCI (39.3 mg, 0.205 mmol) was added to a solution of TX63891 (51.3 mg, 0.101 mmol), pyrrolidine (17 uL, 0.206 mmol), TEA (28 uL, 0.20 mmol) and DMAP (25.3 mg, 0.207 mmol) in $CH_2Cl_2$ (2 mL) and stirred at room temperature for 17 h. The resultant solution was diluted with EtOAc (25 mL), washed with 1 M HCl (15 mL) and brine (10 mL), dried with $Na_2SO_4$ and concentrated. The crude residue was purified by column chromatography (silica gel, 0→100% EtOAc in Hexanes), like fractions were combined, concentrated, azeotroped with EtOH, and dried to give TX63893 (41.5 mg, 74%) as a white solid: $^1$H NMR (500 MHz, $CDCl_3$) δ 8.02 (s, 1H), 6.01 (s, 1H), 3.44 (t, 4H, J=6.7 Hz), 3.14 (d, 1H, J=4.3 Hz), 2.48 (qd, 1H, J=6.5, 12.4 Hz), 2.22 (m, 3H), 1.91 (m, 7H), 1.60 (m, 7H), 1.53 (s, 3H), 1.45 (s, 3H), 1.25 (d, 3H, J=6.6 Hz), 1.24 (m, 5H), 1.02 (m, 2H), 1.01 (s, 3H), 0.93 (s, 3H), 0.87 (s, 3H); m/z 559.4 (M+1).

Compound TX63890:

EDCI (39.7 mg, 0.207 mmol) was added to a solution of TX63891 (49.9 mg, 0.0987 mmol), 3,3-difluoropyrrolidine hydrochloride (28.6 mg, 0.199 mmol), TEA (28 uL, 0.20 mmol) and DMAP (23.8 mg, 0.195 mmol) in $CH_2Cl_2$ (2 mL) and stirred at room temperature for 18 h. The resultant solution was diluted with EtOAc (25 mL), washed with 1 M HCl (25 mL) and brine (10 mL), dried with $Na_2SO_4$ and concentrated. The crude residue was purified by column chromatography (silica gel, 0→100% EtOAc in Hexanes), like fractions were combined, concentrated, azeotroped with EtOH, and dried to give TX63890 (46.3 mg, 79%) as a white solid: $^1$H NMR (500 MHz, $CDCl_3$) δ 8.02 (s, 1H), 6.02 (s, 1H), 3.75 (m, 4H), 3.11 (d, 1H, J=4.0 Hz), 2.31 (m, 6H), 1.89 (m, 4H), 1.70 (m, 4H), 1.52 (s, 3H), 1.50 (m, 3H), 1.46 (s, 3H), 1.26 (d, 3H, J=6.6 Hz), 1.25 (m, 4H), 1.03 (m, 2H), 1.01 (s, 3H), 0.93 (s, 3H), 0.88 (s, 3H); m/z 595.4 (M+1).

Compound TX63914:

EDCI (38.8 mg, 0.202 mmol) was added to a solution of TX63891 (49.9 mg, 0.0987 mmol), oxetan-3-amine hydrochloride (22.7 mg, 0.207 mmol), TEA (40 uL, 0.29 mmol) and DMAP (25.9 mg, 0.212 mmol) in $CH_2Cl_2$ (2 mL) and stirred at room temperature for 17 h. The resultant solution was diluted with EtOAc (50 mL), washed with 1 M HCl (20 mL) and brine (15 mL), dried with $Na_2SO_4$ and concentrated. The crude residue was purified by column chromatography (silica gel, 0→100% EtOAc in Hexanes), like fractions were combined, concentrated, azeotroped with EtOH, and dried to give TX63914 (41.4 mg, 75%) as a white solid: $^1$H NMR (400 MHz, $CDCl_3$) δ 8.00 (s, 1H), 6.00 (s, 1H), 5.93 (d, 1H, J=6.7 Hz), 5.01 (m, 1H), 4.90 (dt, 2H, J=2.6, 6.9 Hz), 4.46 (dt, 2H, J=3.1, 6.5 Hz), 3.06 (d, 1H, J=4.5 Hz), 2.46 (qd, 1H, J=6.7, 12.3 Hz), 2.22 (m, 1H), 2.16 (t, 2H, J=8.3 Hz), 1.67 (m, 10H), 1.49 (s, 3H), 1.44 (s, 3H), 1.24 (d, 3H, J=6.8 Hz), 1.23 (m, 5H), 1.01 (m, 2H), 0.99 (s, 3H), 0.91 (s, 3H), 0.86 (s, 3H); m/z 561.3 (M+1).

Compound TX63915:

EDCI (59.0 mg, 0.308 mmol) was added to a solution of TX63891 (76.5 mg, 0.151 mmol), acetic acid hydrazide (22.0 mg, 0.297 mmol), TEA (0.050 mL, 0.36 mmol) and DMAP (37.3 mg, 0.305 mmol) in $CH_2Cl_2$ (3 mL) and stirred at room temperature for 17 h. The resultant solution was diluted with EtOAc (50 mL), washed with 1 M HCl (20 mL) and brine (15 mL), dried with $Na_2SO_4$ and concentrated. The crude residue was purified by column chromatography (silica gel, 0→75% EtOAc in Hexanes) to give TX63915 (63 mg, 74%) as a white solid: $^1$H NMR (400 MHz, $CDCl_3$) δ 8.02 (s, 1H), 7.91 (m, 2H), 6.03 (s, 1H), 3.09 (d, 1H, J=4.5 Hz), 2.48 (qd, 1H, J=6.9, 12.7 Hz), 2.06 (s, 3H), 1.64 (m, 14H), 1.52 (s, 3H), 1.46 (s, 3H), 1.26 (d, 3H, J=6.7 Hz), 1.24 (m, 4H), 1.03 (m, 2H), 1.02 (s, 3H), 0.93 (s, 3H), 0.88 (s, 3H); m/z 562.3 (M+1).

Compound TX63916:

A mixture of TX63915 (49 mg, 0.087 mmol), TsOH.$H_2O$ (10 mg, 0.053 mmol) and PhMe (10 mL) was heated to vigorous reflux with Dean-Stark removal of water for 2 h. The resultant mixture was concentrated, and the crude residue was purified by column chromatography (silica gel, 0→100% EtOAc in Hexanes) to give TX63916 (34.4 mg, 73%) as a white solid: $^1$H NMR (400 MHz, $CDCl_3$) δ 8.01 (s, 1H), 6.03 (s, 1H), 3.05 (d, 1H, J=4.6 Hz), 2.79 (t, 2H, J=8.4 Hz), 2.49 (s, 3H), 2.48 (qd, 1H, J=6.7, 12.2 Hz), 2.28 (m, 1H), 1.97 (m, 3H), 1.63 (m, 7H), 1.48 (s, 3H), 1.46 (s, 3H), 1.27 (m, 5H), 1.26 (d, 3H, J=6.7 Hz), 1.07 (m, 2H), 1.03 (s, 3H), 0.95 (s, 3H), 0.90 (s, 3H); m/z 544.3 (M+1).

Compound 72:

DIBAL-H (1.0 M in PhMe, 5.0 mL, 5.0 mmol) was added to a 0° C. solution of 8 (R=Me:Et ~30:68, 502 mg, 0.94 mmol) in THF (10 mL). The mixture was stirred at 0° C. for 15 min then warmed to room temperature for 2.5 h. The homogeneous solution was cooled to 0° C., carefully quenched with sat. NaK tartrate (10 mL), diluted with MTBE (25 mL), and stirred at room temperature. The mixture was diluted with water (20 mL) and sat NaK tartrate (20 mL), the organic fraction separated and the aqueous layer extracted with MTBE (25 mL×2). The combined organic fractions were washed with brine (25 mL), dried with $Na_2SO_4$ and concentrated to give crude 72 (509 mg, quantitative) as a white foam that was used without further purification: m/z 496.3 (M+1).

Compound 73:

NBS (250 mg, 1.40 mmol) was added in one portion to a solution of 72 (above obtained, ~0.94 mmol) in DME/$H_2O$ (9:1, 10 mL) at room temperature, and the flask wrapped in foil. After 2 h 2% $Na_2SO_3$ (30 mL) was added and the mixture stirred at room temperature for 30 min. The resultant mixture was extracted with EtOAc (60 mL), the organic fraction washed with brine (25 mL), dried with $Na_2SO_4$ and concentrated. The crude residue was purified by column chromatography (silica gel, 0→100% EtOAc in Hexanes) to give 73 (378 mg, 81% from 8) as a white solid: m/z 494.3 (M+1).

Compound 74:

A solution of 73 (378 mg, 0.766 mmol), NaOMe (1.05 mL, 25% in MeOH), and MeOH (25 mL) was heated to 55° C. for 1.5 h. The resultant mixture was diluted with EtOAc (175 mL), washed with 1 M HCl (50 mL) and brine (25 mL), dried with $Na_2SO_4$ and concentrated. The crude residue was purified by column chromatography (silica gel, 0→100% EtOAc in Hexanes) to give 74 (254 mg, 67%) as a white solid: m/z 494.3 (M+1).

Compound TX63918:

DBDMH (74.7 mg, 0.261 mmol) was added to a 0° C. solution of 74 (254 mg, 0.514 mmol) in DMF (10 mL). The mixture was stirred at 0° C. for 2.5 h, pyridine (0.17 mL, 2.1 mmol) added, and the reaction heated to 55° C. The reaction was cooled to room temperature after 4 h and stirred n additional 16 h. The resultant solution was diluted with EtOAc (150 mL), washed with 1 M HCl (50 mL) and brine (25 mL), dried with $Na_2SO_4$ and concentrated. The crude residue was purified by column chromatography (silica gel, 0→100% EtOAc in Hexanes), like fractions were combined, concentrated, azeotroped with EtOH, and dried to give TX63918 (210 mg, 83%) as a white solid: $^1$H NMR (500 MHz, $CDCl_3$) δ 8.03 (s, 1H), 6.03 (s, 1H), 3.68 (m, 3H), 3.07 (d, 1H, J=4.3 Hz), 2.48 (dq, 1H, J=6.6, 12.6 Hz), 2.25 (br d, 1H, J=13.0 Hz), 1.73 (m, 6H), 1.50 (m, 4H), 1.47 (s, 3H), 1.46 (s, 3H), 1.25 (m, 10H), 1.03 (m, 2H), 1.01 (s, 3H), 0.93 (s, 3H), 0.87 (s, 3H); m/z 491.9 (M+1).

Compound TX63920:

A solution of TX63918 (50 mg, 0.10 mmol), $Ac_2O$ (53 uL, 0.56 mmol), pyridine (90 uL, 1.1 mmol) and DMAP (4.0 mg, 0.33 mmol) in $CH_2Cl_2$ (2 mL) was stirred at room temperature for 18 h. The resultant solution was diluted with EtOAc (70 mL), washed with 1 M HCl (25 mL) and brine (15 mL), dried with $Na_2SO_4$, and concentrated. The crude residue was purified by column chromatography (silica gel, 0→100% EtOAc in Hexanes), like fractions were combined, concentrated, azeotroped with EtOH, and dried to give TX63920 (50.6 mg, 95%) as a white solid: $^1$H NMR (500 MHz, $CDCl_3$) δ 8.03 (s, 1H), 6.03 (s, 1H), 4.05 (m, 2H), 3.04 (d, 1H, J=3.8 Hz), 2.48 (qd, 1H, J=6.7, 12.6 Hz), 2.24 (br d, 1H, J=13.6 Hz), 2.04 (s, 3H), 1.89 (m, 2H), 1.60 (m, 10H), 1.47 (s, 3H), 1.46 (s, 3H), 1.26 (d, 3H, J=6.5 Hz), 1.24 (m, 5H), 1.05 (m, 2H), 1.01 (s, 3H), 0.93 (s, 3H), 0.87 (s, 3H); m/z 533.9 (M+1).

Compound TX63919:

A solution of TX63918 (49.2 mg, 0.100 mmol), MeOTf (65 uL, 0.57 mmol) and 2,6-$^t$Bu-4-Me-pyridine in $CH_2Cl_2$ (2 mL) was stirred at room temperature for 18.5 h. The resultant solution was diluted with EtOAc (70 mL), washed with 1 M HCl (20 mL) and brine (10 mL), dried with $Na_2SO_4$, and concentrated. The crude residue was purified by column chromatography (silica gel, 0→100% EtOAc in Hexanes), like fractions were combined, concentrated, azeotroped with EtOH, and dried to give TX63919 (36.8 mg, 73%) as a white solid: $^1$H NMR (500 MHz, $CDCl_3$) δ 8.03 (s, 1H), 6.02 (s, 1H), 3.36 (m, 2H), 3.32 (s, 3H), 3.08 (d, 1H, J=4.2 Hz), 2.48 (qd, 1H, J=6.6, 12.5 Hz), 2.24 (br d, 1H, J=13.0 Hz), 1.78 (m, 6H), 1.51 (m, 6H), 1.47 (s, 3H), 1.46 (s, 3H), 1.26 (t, 3H, J=6.5 Hz), 1.24 (m, 5H), 1.03 (m, 2H), 1.00 (s, 3H), 0.92 (s, 3H), 0.87 (s, 3H); m/z 505.9 (M+1).

Compound TX63982:

A solution of TX63918 (39.5 mg, 0.0803 mmol) and EtNCO (64 uL, 0.81 mmol) in PhMe (0.5 mL) was stirred at room temperature for 1 h, heated to 70° C. for ~5 h, and stirred at room temperature an additional 19 h. The resultant solution was purified by column chromatography (silica gel, 0→100% EtOAc in Hexanes), like fractions were combined, concentrated, azeotroped with EtOH, and dried to give TX63982 (33.2 mg, 73%) as a white solid: $^1$H NMR (400 MHz, $CDCl_3$) δ 8.02 (s, 1H), 6.03 (s, 1H), 4.55 (br s, 1H), 4.05 (m, 2H), 3.21 (m, 2H), 3.04 (d, 1H, J=4.6 Hz), 2.48 (qd, 1H, J=7.0, 12.3 Hz), 2.26 (td, 1H, J=4.3, 17.3 Hz), 1.66 (m, 12H), 1.46 (s, 6H), 1.26 (d, 3H, J=6.7 Hz), 1.25 (m, 5H), 1.13 (t, 3H, J=7.2 Hz), 1.05 (m, 2H), 1.01 (s, 3H), 0.93 (s, 3H), 0.87 (s, 3H); m/z 563.4 (M+1).

Compound TX63448:

Compound TX63435 (20 mg, 0.041 mmol) and $SeO_2$ (13.5 mg, 0.12 mmol) were mixed with 1,4-dioxane (1 mL). After heated at 100° C. for 16 h, the reaction mixture was cooled to room temperature, and was filtered through a pad of silica gel, which was eluted with EtOAc. The combined filtrate and washes were concentrated to give the crude product, which contains 12% of TX63448. The crude product was repeatedly purified by column chromatography (silica gel, eluting with 0% to 30% EtOAc in hexanes or 0-10% EtOAc in $CH_2Cl_2$) to compound TX63448 (1.1 mg) as a white solid: m/z=490.3 (M+1); $^1$H NMR (500 MHz, $CDCl_3$) δ 7.87 (s, 1H), 5.96 (s, 1H), 3.73 (s, 3H), 3.06 (m, 1H), 2.99 (d, 1H, J=4.5 Hz), 2.94 (m, 1H), 2.62 (m, 1H), 2.02 (s, 3H), 1.67 (s, 3H), 1.50 (s, 3H), 1.10-1.95 (m, 12H), 1.01 (s, 3H), 0.90 (s, 3H), 0.87 (s, 3H).

Compound TX63936:

A solution of compound TX63520 (370 mg, 0.77 mmol) in $CH_2Cl_2$ (8 mL) was added to $XeF_2$ (157 mg, 0.93 mmol) at room temperature in a PTFE tube. After stirred at room temperature for 16 h, EtOAc was added. The mixture was transferred to a reparatory funnel, which was washed with aq. $NaHCO_3$ solution, and water. The organic extract was dried with $MgSO_4$, filtered, and concentrated. The residue was purified by column chromatography (silica gel, eluting with 0-25% EtOAc in hexanes) to give product TX63936 (80 mg), which was contaminated with some impurities. The product was purified again by column chromatography (silica gel, eluting with 0-2% acetone in $CH_2Cl_2$) to give purified TX63936 (32 mg, 9% yield) as a white solid: m/z=452.2 (M+1); $^1$H NMR (500 MHz, $CDCl_3$) δ 8.04 (s, 1H), 6.05 (s, 1H), 3.30 (d, 1H, J=4.9 Hz), 2.70 (m, 1H), 2.50 (m, 1H), 1.48 (s, 6H), 1.27 (d, 3H, J=6.7 Hz), 1.12-2.08 (m, 15H), 1.07 (s, 3H), 1.02 (s, 3H), 0.91 (s, 3H).

Compound 75:

A mixture of compound 7 (1.16 g, 2.47 mmol), $NH_2OH$—HCl (398 mg, 5.72 mmol), NaOAc (466 mg, 5.68 mmol), $CH_2Cl_2$ (12 mL) and MeOH (12 mL) were heated at 60° C. (oil bath temperature) for 1.5 h. EtOAc was added. The mixture was washed with water. Organic extract was dried with $MgSO_4$, and concentrated to give compound 77 (1.20 g) as a white foam solid: m/z 484.3 (M+1). Compound 75 was used in the next step without further purification.

Compound 76:

Compound 75 (1.20 g, 2.47 mmol) was dissolved in AcOH (2.9 mL) and $Ac_2O$ (0.35 mL, 3.70 mmol). After the reaction was stirred at room temperature for 1 h, $PhI(OAc)_2$ (1.195 g, 3.71 mmol), $Pd(OAc)_2$ (28 mg, 0.13 mmol, 0.05 eq.) and $ClCH_2CH_2Cl$ (5.8 mL) were added. After the reaction was heated at 60° C. for 15 h, and 80° C. for 3 h, additional amount of $Pd(OAc)_2$ (28 mg, 0.13 mmol, 0.05 eq.) was added. After another 3 h at 80° C., the reaction was cooled to room temperature. Solvent was removed by evaporation. Aq. $NaHCO_3$ was added. The mixture was extracted with EtOAc. The combined organic extracts were dried with $MgSO_4$, and concentrated. The residue was purified by column chromatography (silica gel, eluting with 0% to 50% EtOAc in hexanes) to give product 76 (629 mg, 44% yield from 7) as a light orange foam solid. Compound 76 is 3:1 mixture 2 isomers: m/z 584.3 (M+1).

Compound 77:

$K_2CO_3$ (742 mg, 5.37 mmol) was added to a solution of compound 76 (627 mg, 1.07 mmol) in MeOH (22 mL) at 0° C. After the reaction was stirred at room temperature for 1.5 h, $CH_2Cl_2$ and 12 N HCl (0.90 mL, 10.8 mmol) were added. After stirring for 5 min, the mixture was transferred to a separatory funnel. Water was added. The product was extracted $CH_2Cl_2$. The combined organic extracts were dried with $MgSO_4$, and concentrated to give compound 77 as a light yellow foam. Compound 77 was a 4.5:1 mixture of 2 isomers: m/z 500.2 (M+1).

Compound 78:

A mixture of compound 77 obtained above, $NaHSO_3$ (58.5% $SO_2$, 410 mg, 3.73 mmol), EtOH (7.5 mL) and water (2.5 mL) were heated at 80° C. for 1 h. Additional amount of $NaHSO_3$ (58.5% $SO_2$, 100 mg, 0.91 mmol) was added. After the reaction was heated at 80° C. for another 3 h, EtOAc was added. The mixture was transferred to a separatory funnel, which was washed with water. The organic extract was dried with $MgSO_4$, and concentrated. The residue was purified by column chromatography (silica gel, eluting with 0-100% EtOAc in hexanes) to give compound 78 (380 mg, 73% yield from 76) as a white solid: m/z 485.2 (M+1).

Compound 80:

Jones' reagent was added dropwise to a solution of compound 78 (51.6 mg, 0.11 mmol) in acetone (1 mL) at 0° C. until the orange color persisted. The reaction was stirred until compound 78 was completely consumed. EtOAc was added. The mixture was transferred to a separatory funnel, which was washed with water. The organic extract was dried with $MgSO_4$, and concentrated. The crude product, a mixture of compound 79 (m/z=499.2 (M+1)) and 80 ((m/z=455.2 (M+1)), was heated at 80° C. for 2 h, and 120° C. for 30 min under vacuum. After cooled to room temperature, the residue was purified by column chromatography (silica gel, eluting with 0-40% EtOAc in hexanes) to give compound 80 (39 mg, 81% yield from 78) as a white solid: m/z 455.2 (M+1).

Compound 81:

NaOMe (279 μL, 1.22 mmol) was added to a mixture of compound 80 (37 mg, 0.08 mmol) and $HCO_2Et$ (196 μL, 2.44 mmol) at 0° C. After the mixture was stirred at ambient temperature for 10 min, THF (0.3 mL) was added. The reaction was continued at room temperature for 5 h, and cooled to 0° C. MTBE and 6 N HCl (0.22 mL, 1.32 mmol) were added. The mixture was transferred to a separatory funnel, which was extracted with EtOAc. The organic extract was washed with water, dried with $MgSO_4$, and concentrated. The crude product was mixed with $NH_2OH$—HCl (9 mg, 0.13 mmol), EtOH (4 mL) and water (0.2 mL). After the reaction was heated at 55° C. for 18 h, EtOAc was added. The mixture was transferred to a separatory funnel, which was washed with water. The organic extract was dried with $MgSO_4$, and concentrated. The residue was purified by column chromatography (silica gel, eluting with 0% to 10% EtOAc in $CH_2Cl_2$) to give compound 81 (18 mg, 45% yield) as a white solid: m/z 480.2 (M+1). Compound 81 was contaminated with some impurities.

Compound 82:

NaOMe (12 μL, 0.052 mmol) was added to a suspension of compound 81 (17 mg, 0.035 mmol) in MeOH (0.70 mL) and THF (0.35 mL) at room temperature. After the reaction was heated at 55° C. for 2.5 h, additional amount of NaOMe (12 μL, 0.052 mmol) and MeOH (0.70 mL) were added. The mixture was heated at 55° C. for another 1 h, and was cooled to room temperature. MTBE was added. The mixture was transferred to a separatory funnel, which was washed with 1 N aq. HCl, and water. The organic extract was dried with $MgSO_4$, and concentrated. The residue was purified by column chromatography (silica gel, eluting with 0-70% EtOAc in hexanes) to give compound 82 (8.7 mg, 51% yield) as a white solid: m/z 480.2 (M+1).

Compound TX63614:

A solution of 1,3-dibromo-5,5-dimethylhydantoin (2.6 mg, 0.009 mmol) in DMF (21 μL) was added to a solution of compound 82 (8.7 mg, 0.018 mmol) in DMF (100 μL) at 0° C. After the reaction was stirred at 0° C. for 1 hr, pyridine (5 μL, 0.062 mmol) was added. The reaction was heated at 55° C. for 3 h, and was cooled to room temperature. The mixture was diluted with EtOAc, and was transferred to a reparatory funnel, which was washed with 1 N aq. HCl, aq. $Na_2SO_3$ solution, and water. The organic extract was dried with $MgSO_4$ and concentrated. The residue was purified by column chromatography (silica gel, eluting with 0% to 50% EtOAc in hexanes) to give TX63614 (7 mg, 81% yield) as a white solid: $^1$H NMR (500 MHz, $CDCl_3$) δ 8.06 (s, 1H), 6.03 (s, 1H), 3.70 (s, 3H), 3.05 (m, 1H), 2.96 (d, 1H, J=4.5 Hz), 2.48-2.56 (m, 2H), 2.12 (m, 1H), 1.42 (s, 3H), 1.33 (s, 3H), 1.15-1.95 (m, 14H), 1.03 (s, 3H), 1.01 (s, 3H), 0.90 (s, 3H); m/z 478.2 (M+1).

Compound TX63693:

A solution of compound TX63618 (200 mg, 0.421 mmol) in methanol (20 mL) and benzene (1 ml) was heated at 85° C. for 20 hours. The solvent was removed, and the residue was purified by column chromatography (silica gel, 0 to 80% EtOAc in Hexanes) to give compound TX63693 (149 mg, 69%) as white foam solid: $^1$H NMR (500 MHz, $CDCl_3$) δ 8.02 (s, 1H), 6.03 (s, 1H), 4.37 (s, 1H), 3.62 (s, 3H), 3.12 (d, 1H, J=4.6 Hz), 2.71 (m, 1H), 2.49 (m, 1H), 1.46 (s, 3H), 1.45 (s, 3H), 1.26 (d, 3H, J=6.7 Hz), 1.10-2.10 (m, 15H), 1.04 (s, 3H), 1.02 (s, 3H), 0.90 (s, 3H); m/z 432.2 (M-$NHCO_2CH_3$).

Compound TX63800:

A solution of compound TX63618 (200 mg, 0.421 mmol) in ethanol (20 mL) and benzene (1 ml) was heated at 85° C. for 20 hours. The solvent was removed, and the residue was purified by column chromatography (silica gel, 0 to 75% EtOAc in Hexanes) to give compound TX63800 (156 mg, 71%) as white foam solid: $^1$H NMR (500 MHz, $CDCl_3$) δ 8.02 (s, 1H), 6.03 (s, 1H), 4.35 (s, 1H), 4.06 (m, 2H), 3.13 (d, 1H, J=4.5 Hz), 2.70 (m, 1H), 2.48 (m, 1H), 1.45 (s, 6H), 1.26 (d, 3H, J=6.7 Hz), 1.10-2.06 (m, 18H), 1.03 (s, 3H), 1.02 (s, 3H), 0.89 (s, 3H)); m/z 432.2 (M-$NHCO_2CH_2CH_3$).

Compound TX63819:

A solution of compound TX63618 (150 mg, 0.316 mmol) in 2-propanol (20 mL) and benzene (1 ml) was heated at 85° C. for 20 hours. The solvent was removed, and the residue was purified by column chromatography (silica gel, 0 to 60% EtOAc in Hexanes) to give compound TX63819 (100 mg, 59%) as white foam solid: $^1$H NMR (500 MHz, $CDCl_3$) δ 8.02 (s, 1H), 6.03 (s, 1H), 4.87 (m, 1H), 4.31 (s, 1H), 3.13 (d, 1H, J=4.5 Hz), 2.69 (m, 1H), 2.48 (m, 1H), 1.46 (s, 3H), 1.45 (s, 3H), 1.26 (d, 3H, J=6.7 Hz), 1.21 (d, 6H, J=5.6 Hz), 1.10-2.06 (m, 15H), 1.04 (s, 3H), 1.02 (s, 3H), 0.90 (s, 3H); m/z 432.2 (M-$NHCO_2CH(CH_3)_2$).

Compound TX63862:

$NH_3$ in Methanol (2M solution, 0.83 ml, 1.67 mmol) was added to a solution of compound TX63618 (158.6 mg, 0.334 mmol) in THF (2.5 ml) at 0° C. The mixture was stirred at room temperature for 4 hours. The solvent was removed, and the residue was purified by trituration in Ethanol to give compound TX63862 (125 mg, 76%) as white foam solid: $^1$H NMR (500 MHz, $CDCl_3$) δ 8.02 (s, 1H), 6.02 (s, 1H), 3.15 (d, 1H, J=4.6 Hz), 1.42 (s, 3H), 1.41 (s, 3H), 1.24 (d, 3H, J=6.7 Hz), 1.08-2.50 (m, 17H), 0.99 (s, 3H), 0.98 (s, 3H), 0.87 (s, 3H); m/z 492.2 (M+1)

Compound TX63826:

Ethylamine in THF (2M solution, 0.193 ml, 0.386 mmol) was added to a solution of compound TX63618 (152.8 mg, 0.322 mmol) in THF (2.5 ml). The mixture was stirred at room temperature for 2 hours. The solvent was removed, and the residue was purified by column chromatography (silica gel, 0 to 90% EtOAc in Hexanes) to give compound TX63826 (85 mg, 50%) as white foam solid: $^1$H NMR (500 MHz, $CDCl_3$) δ 8.01 (s, 1H), 6.02 (s, 1H), 4.32 (t, 1H, J=5.2 Hz), 3.98 (s, 1H), 3.13-3.24 (m, 3H), 2.47 (m, 2H), 2.28 (m, 1H), 2.13 (m, 1H), 1.44 (s, 3H), 1.43 (m, 3H), 1.27 (d, 3H, J=6.7 Hz), 1.23-1.96 (m, 13H), 1.13 (t, 3H, J=7.2 Hz), 1.03 (s, 3H), 1.02 (s, 3H), 0.89 (s, 3H); m/z 520.3 (M+1).

Compound TX63875:

Dimethyl amine in THF (2M solution, 0.195 ml, 0.391 mmol) was added to a solution of compound TX63618 (154.6 mg, 0.325 mmol) in THF (2.5 ml). The mixture was stirred at room temperature for 20 hours. The solvent was removed, and the residue was purified by column chromatography (silica gel, 0 to 80% EtOAc in Hexanes) to give compound TX63875 (108 mg, 63%) as white foam solid: $^1$H NMR (500 MHz, $CDCl_3$) δ 8.05 (s, 1H), 6.07 (s, 1H), 3.86 (s, 1H), 3.25 (d, 1H, J=4.5 Hz), 2.91 (s, 6H), 2.59 (m, 1H), 2.51 (m, 1H), 2.30 (m, 1H), 2.15 (m, 1H), 1.48 (s, 6H), 1.29 (d, 3H, J=6.7 Hz), 1.10-1.97 (m, 13H), 1.06 (s, 3H), 1.05 (s, 3H), 0.92 (s, 3H); m/z 520.3 (M+1).

Compound TX63876:

Methyl amine in THF (2M solution, 0.187 ml, 0.375 mmol) was added to a solution of compound TX63618 (148.3 mg, 0.312 mmol) in THF (2.5 ml). The mixture was stirred at room temperature for 20 hours. The solvent was removed, and the residue was purified by column chromatography (silica gel, 0 to 80% EtOAc in Hexanes) to give compound TX63876 (100 mg, 63%) as white foam solid: $^1$H NMR (500 MHz, $CDCl_3$) δ 8.04 (s, 1H), 6.04 (s, 1H), 4.45 (m, 1H), 4.13 (s, 1H), 3.18 (d, 1H, J=4.6 Hz), 2.79 (d, 3H, J=4.8 Hz), 2.49 (m, 2H), 2.32 (m, 1H), 2.16 (m, 1H), 1.46 (s, 3H), 1.44 (s, 3H), 1.29 (d, 3H, J=6.7 Hz), 1.10-1.97 (m, 13H), 1.05 (s, 6H), 0.92 (s, 3H); m/z 506.3 (M+1).

Compound TX63798:

$Et_3N$ (400 μL, 2.88 mmol) and Benzoyl chloride (50 μL, 0.431 mmol) were added sequentially to a solution of compound TX63620 (129 mg, 0.288 mmol) in $CH_2Cl_2$ (2 mL) at 0° C. After the reaction was stirred at 0° C. for 1 hr, aq. $NaHCO_3$ was added. The mixture was transferred to a separatory funnel, which was extracted with EtOAc. The organic extract was washed with water, dried with $MgSO_4$, and concentrated. The residue was purified by column chromatography (silica gel, 0 to 60% EtOAc in hexanes) to give compound TX63798 (50.4 mg, 31%) as white foam solid: $^1$H NMR (500 MHz, $CDCl_3$) δ 8.02 (s, 1H), 7.71 (d, 2H, J=7.6 Hz), 7.49 (t, 1H, J=7.6 Hz), 7.42 (t, 2H, J=7.6 Hz), 6.06 (s, 1H), 5.68 (s, 1H), 3.23 (d, 1H, J=4.5 Hz), 2.77 (m, 1H), 2.46 (m, 2H), 2.19 (m, 1H), 2.01 (m, 2H), 1.44 (s, 3H), 1.42 (s, 3H), 1.25 (d, 3H, J=6.6 Hz), 1.19-1.93 (m, 11H), 1.07 (s, 6H), 0.92 (s, 3H);), m/z 553. (M+1).

Compound TX63818:

$Et_3N$ (57 μL, 0.408 mmol) and 2,2,2-Trifluoroethyl sulfonyl chloride (39 μL, 0.353 mmol) were added sequentially to a solution of compound TX63620 (122 mg, 0.272 mmol) in $CH_2Cl_2$ (2 mL) at 0° C. After the reaction was stirred at 0° C. for 1 hr, aq. $NaHCO_3$ was added. The mixture was transferred to a separatory funnel, which was extracted with EtOAc. The organic extract was washed with water, dried with $MgSO_4$, and concentrated. The residue was purified by column chromatography (silica gel, 0 to 60% EtOAc in hexanes) to give compound TX63818 (77 mg, 47%) as white foam solid: $^1$H NMR (500 MHz, $CDCl_3$) δ 8.05 (s, 1H), 6.20 (s, 1H), 5.14 (s, 1H), 3.92 (m, 2H), 3.05 (d, 1H, J=4.4 Hz), 2.64 (m, 1H), 2.48

(m, 1H), 1.46 (s, 3H), 1.43 (s, 3H), 1.26 (d, 3H, J=6.7 Hz), 1.12-2.18 (m, 15H), 1.05 (s, 3H), 1.02 (s, 3H), 0.93 (s, 3H); m/z 595.3 (M+1).

Compound TX63863:

Cyclobutanecarbonyl chloride (0.152 ml, 1.34 mmol) was added at room temperature to a solution of TX63620 (300 mg, 0.669 mmol), triethylamine (0.466 ml, 3.34 mmol) and DCM (4 ml). The mixture was stirred at room temperature for 2 hours. The organic was washed with 1M HCl, saturated NaHCO3, brine and water, dried with $MgSO_4$, and concentrated. The residue was purified by column chromatography (silica gel, 0 to 70% EtOAc in hexanes) to give compound TX63863 (200 mg, 56%) as white foam solid: $^1$H NMR (500 MHz, $CDCl_3$) δ 8.02 (s, 1H), 6.04 (s, 1H), 4.85 (s, 1H), 3.06 (d, 1H, J=4.5 Hz), 2.95 (m, 1H), 2.63 (m, 1H), 2.48 (m, 1H), 1.45 (s, 3H), 1.41 (s, 3H), 1.26 (d, 3H, J=6.7 Hz), 1.10-2.30 (m, 21H), 1.03 (s, 3H), 1.02 (s, 3H), 0.89 (s, 3H); m/z 531.3 (M+1).

Compound TX63864:

Propionyl chloride (0.048 ml, 0.274 mmol) was added at room temperature to a solution of TX63620 (123 mg, 0.274 mmol), triethylamine (0.191 ml, 1.37 mmol) and DCM (4 ml). The mixture was stirred at room temperature for 2 hours. The organic was washed with 1M HCl, saturated NaHCO3, brine and water, dried with $MgSO_4$, and concentrated. The residue was purified by column chromatography (silica gel, 0 to 70% EtOAc in hexanes) to give compound TX63864 (80 mg, 57%) as white foam solid: $^1$H NMR (500 MHz, $CDCl_3$) δ 8.02 (s, 1H), 6.04 (s, 1H), 5.01 (s, 1H), 3.07 (d, 1H, J=4.6 Hz), 2.61 (m, 1H), 2.48 (m, 1H), 2.27 (m, 1H), 2.17 (q, 2H, J=7.5 Hz), 2.06 (m, 1H), 1.45 (s, 3H), 1.42 (s, 3H), 1.26 (d, 3H, J=6.7 Hz), 1.14 (t, 3H, J=7.5 Hz), 1.10-1.95 (m, 13H), 1.03 (s, 6H), 0.89 (s, 3H); m/z 505.3 (M+1).

Compound TX63865:

Heptanoyl chloride (0.083 ml, 0.539 mmol) was added at room temperature to a solution of TX63620 (0.121 mg, 0.270 mmol), triethylamine (0.190 ml, 1.36 mmol) and DCM (4 ml). The mixture was stirred at room temperature for 2 hours. The organic was washed with 1M HCl, saturated NaHCO3, brine and water, dried with $MgSO_4$, and concentrated. The residue was purified by column chromatography (silica gel, 0 to 70% EtOAc in hexanes) to give compound TX63865 (110 mg, 72%) as white foam solid: $^1$H NMR (400 MHz, $CDCl_3$) δ 8.00 (s, 1H), 6.03 (s, 1H), 4.95 (s, 1H), 3.04 (d, 1H, J=4.5 Hz), 2.62 (m, 1H), 2.47 (m, 1H), 2.24 (m, 1H), 1.44 (s, 3H), 1.41 (s, 3H), 1.10-2.19 (m, 27H), 1.02 (s, 6H), 0.90 (s, 3H), 0.87 (3H, m); m/z 561.4 (M+1).

Compound TX63681:

$Et_3N$ (124 μL, 0.89 mmol) and acetic formic anhydride (7.4 M solution prepared in situ, 48 μL, 0.356 mmol) were added sequentially to a solution of compound TX63620 (80 mg, 0.178 mmol) in $CH_2Cl_2$ (2 mL) at 0° C. After the reaction was stirred at 0° C. for 1 hr, aq. $NaHCO_3$ was added. The mixture was transferred to a separatory funnel, which was extracted with EtOAc. The organic extract was washed with water, dried with $MgSO_4$, and concentrated. The residue was purified by column chromatography (silica gel, 0 to 100% EtOAc in hexanes) to give compound TX63681 (58 mg, 68%) as white foam solid: $^1$H NMR (500 MHz, $CDCl_3$) δ 8.38 (d, 0.45H, J=12.3 Hz), 8.19 (s, 0.55H), 8.03 (s, 0.55H), 8.02 (s, 0.45H), 6.06 (s, 1H), 5.49 (d, 0.45H, J=12.3 Hz), 5.02 (s, 0.55H), 3.14 (d, 0.45H, J=4.5 Hz), 3.09 (d, 0.55H, J=4.5 Hz), 1.48 (s, 3H), 1.46 (s, 3H), 1.27 (d, 3H, J=6.6 Hz), 1.17-2.70 (m, 17H), 1.06 (s, 1.35H), 1.05 (s, 3H), 1.03 (s, 1.65H), 0.94 (s, 1.35H), 0.91 (s, 1.65H); m/z 477.3 (M+1).

Compound TX63799:

3,3,3-Trifluoropropionic acid (47 μL, 0.534 mmol) and $Et_3N$ (186 μL, 1.33 mmol) were added sequentially to a solution of compound TX63620 (200 mg, 0.445 mmol) in $CH_2Cl_2$ (2 mL) at RT. The solution was cooled at RT, and T3P (50% in EtOAc, 283 mg, 0.891 mmol) was added. After the reaction was stirred at RT for 2 hr, aq. $NaHCO_3$ was added. The mixture was stirred at RT for 1 hr, then transferred to a separatory funnel, which was extracted with EtOAc. The organic extract was washed with aq. $NaHCO_3$ and water, dried with $MgSO_4$, and concentrated. The residue was purified by column chromatography (silica gel, 0 to 50% EtOAc in hexanes) to give compound TX63799 (50 mg, 20%) as white foam solid: $^1$H NMR (500 MHz, $CDCl_3$) δ 8.00 (s, 1H), 6.04 (s, 1H), 5.42 (s, 1H), 3.05 (m, 2H), 3.01 (d, 1H, J=4.5 Hz), 2.66 (m, 1H), 2.48 (m, 1H), 2.25 (m, 1H), 2.09 (m, 1H), 1.45 (s, 3H), 1.40 (s, 3H), 1.26 (d, 3H, J=6.7 Hz), 1.16-1.96 (m, 13H), 1.03 (s, 6H), 0.90 (s, 3H): m/z 559.3 (M+1).

Compound TX63866:

Cyclopropane carboxylic acid (25 μL, 0.326 mmol) and $Et_3N$ (111 μL, 0.816 mmol) were added sequentially to a solution of compound TX63620 (122 mg, 0.272 mmol) in $CH_2Cl_2$ (2 mL) at RT. The solution was cooled at RT, and T3P (50% in EtOAc, 330 μL, 0.543 mmol) was added. After the reaction was stirred at RT for 2 hr, aq. $NaHCO_3$ was added. The mixture was stirred at RT for 1 hr, then transferred to a separatory funnel, which was extracted with EtOAc. The organic extract was washed with aq. $NaHCO_3$ and water, dried with $MgSO_4$, and concentrated. The residue was purified by trituration in EtOH to give compound TX63866 (60 mg, 42%) as white foam solid: $^1$H NMR (500 MHz, $CDCl_3$) δ 8.02 (s, 1H), 6.05 (s, 1H), 5.21 (s, 1H), 3.16 (d, 1H, J=4.5 Hz), 2.64 (m, 1H), 2.49 (m, 1H), 2.25 (m, 1H), 2.02 (m, 1H), 1.46 (s, 6H), 1.26 (d, 3H, J=6.7 Hz), 1.04 (s, 3H), 1.03 (s, 3H), 0.89 (s, 3H), 0.89-1.96 (m, 16H), 0.69 (m, 2H). m/z 517.3 (M+1).

All of the compounds, compositions and methods disclosed and claimed herein can be made and executed without undue experimentation in light of the present disclosure. While the disclosure may have only focused on a several invention have been described in terms of preferred embodiments, it will be apparent to those of skill in the art that variations may be applied to the compounds, compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

Abraham and Kappas, *Free Radical Biol. Med.,* 39:1-25, 2005.

Ahmad et al., *Cancer Res.,* 68:2920-2926, 2008.

Ahmad et al., *J. Biol. Chem.,* 281:35764-9, 2006.

Araujo et al., *J. Immunol.,* 171(3):1572-1580, 2003.

Bach, *Hum. Immunol.,* 67(6):430-432, 2006.

Chauhan and Chauhan, *Pathophysiology,* 13(3):171-181 2006.

Dickerson et al., *Prog Neuropsychopharmacol Biol. Psychiatry*, Mar. 6, 2007.
Dinkova-Kostova et al., *Proc. Natl. Acad. Sci. USA,* 102(12): 4584-4589, 2005.
Dudhgaonkar et al., *Eur. J. Pain,* 10(7):573-9, 2006.
Forstermann, *Biol. Chem.,* 387:1521, 2006.
*Handbook of Pharmaceutical Salts: Properties, and Use*, Stahl and Wermuth Eds.), Verlag Helvetica Chimica Acta, 2002.
Hanson et al., *BMC Medical Genetics,* 6(7), 2005.
Honda et al. *Bioorg. Med. Chem. Lett.,* 12:1027-1030, 2002.
Honda et al., *J. Med. Chem.,* 43:4233-4246, 2000a.
Honda, et al., *J. Med. Chem.,* 43:1866-1877, 2000b.
Honda et al., *Bioorg. Med. Chem. Lett.,* 7:1623-1628, 1997.
Salvemini et al., *J. Clin. Invest.,* 93(5):1940-1947, 1994.
Sarchielli et al., *Cephalalgia,* 26(9):1071-1079, 2006.
Satoh et al., *Proc. Natl. Acad. Sci. USA,* 103(3):768-773, 2006.
Schulz et al., *Antioxid. Redox. Sig.,* 10:115, 2008.
Strejan et al., *J. Neuroimmunol.,* 7:27, 1984.
Suh et al., *Cancer Res.,* 58:717-723, 1998.
Suh et al., *Cancer Res.,* 59(2):336-341, 1999.
Szabo et al., *Nature Rev. Drug Disc.,* 6:662-680, 2007.
Takahashi et al., *Cancer Res.,* 57:1233-1237, 1997.
Tamir and Tannebaum, *Biochim. Biophys. Acta,* 1288:F31-F36, 1996.
Xie et al., *J. Biol. Chem.,* 270(12):6894-6900, 1995.
Zhou et al., *Am. J. Pathol.,* 166(1):27-37, 2005.

SEQUENCE LISTING

```
<160> NUMBER OF SEQ ID NOS: 1

<210> SEQ ID NO 1
<211> LENGTH: 26
<212> TYPE: DNA
<213> ORGANISM: Artificial Sequence
<220> FEATURE:
<223> OTHER INFORMATION: Synthetic primer

<400> SEQUENCE: 1

cagtcacagt gactcagcag aatctg                                          26
```

Honda et al., *Bioorg. Med. Chem. Lett.,* 9(24):3429-3434, 1999.
Honda et al., *Bioorg. Med. Chem. Lett.,* 8(19):2711-2714, 1998.
Honda et al., *Bioorg. Med. Chem. Lett.,* 16(24):6306-6309, 2006.
Ishikawa et al., *Circulation,* 104(15):1831-1836, 2001.
Kawakami et al., *Brain Dev.,* 28(4):243-246, 2006.
Kendall-Tackett, *Trauma Violence Abuse,* 8(2):117-126, 2007.
Kruger et al., *J. Pharmacol. Exp. Ther.,* 319(3):1144-1152, 2006.
Lee et al., *Glia.,* 55(7):712-22, 2007.
Lencz et al., *Mol. Psychiatry,* 12(6):572-80, 2007.
Liby et al., *Cancer Res.,* 65(11):4789-4798, 2005.
Liby et al., *Nat. Rev. Cancer,* 7(5):357-356, 2007a.
Liby et al., *Mol. Cancer. Ther.,* 6(7):2113-9, 2007b.
Liby et al., 2007b
Liu et al., *FASEB J.,* 20(2):207-216, 2006.
Lu et al., *J. Clin. Invest.,* 121(10):4015-29, 2011.
*March's Advanced Organic Chemistry: Reactions*, Mechanisms, and Structure, 2007.
McIver et al., *Pain,* 120(1-2):161-9, 2005.
Morris et al., *J. Mol. Med.,* 80(2):96-104, 2002.
Morse and Choi, *Am. J. Respir. Crit. Care Med.,* 172(6):660-670, 2005.
Morse and Choi, *Am. J. Respir. Crit. Care Med.,* 27(1):8-16, 2002.
Pall, *Med. Hypoth.,* 69:821-825, 2007.
Place et al., *Clin. Cancer Res.,* 9(7):2798-806, 2003.
Rajakariar et al., *Proc. Natl. Acad. Sci. USA,* 104(52):20979-84, 2007.
Ross et al., *Am. J. Clin. Pathol.,* 120(Suppl):553-71, 2003.
Ross et al., *Expert Rev. Mol. Diagn.,* 3(5):573-585, 2003.
Ruster et al., *Scand. J. Rheumatol.,* 34(6):460-3, 2005.
Sacerdoti et al., *Curr Neurovasc Res.* 2(2):103-111, 2005.

What is claimed is:

1. A compound of the formula:

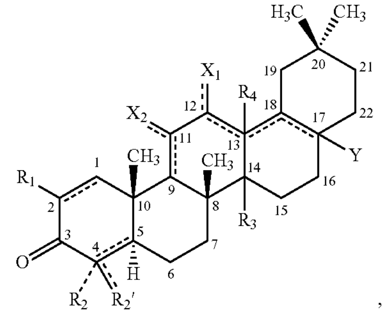

(I)

, wherein:

$X_1$ and $X_2$ are independently hydrogen, halo, hydroxy, amino or oxo, provided that $X_1$ is not oxo when carbon atoms 12 and 13 are connected to one another with a double bond, further provided that $X_2$ is not oxo when carbon atoms 9 and 11 are connected to one another with a double bond;

$R_1$ is —CN, iodo, —$CF_3$, or —$C(O)R_a$, wherein $R_a$ is —OH, alkoxy$_{(C1-4)}$, —$NH_2$, alkylamino$_{(C1-4)}$, or —NH—$S(O)_2$-alkyl$_{(C1-4)}$;

$R_2$ is hydrogen or $R_2$ is absent when the atom to which it is bound forms part of a double bond;

$R_2$' is hydrogen, =$CH_2$, alkyl$_{(C\leq 8)}$, or substituted alkyl$_{(C\leq 8)}$;

$R_3$ and $R_4$ are each independently hydrogen, hydroxy, methyl or as defined below when either of these groups is taken together with group $R_c$; and Y is:

—H, —OH, —SH, —CN, —F, —$CF_3$, —$NH_2$ or —NCO;

alkyl$_{(C\leq8)}$, alkenyl$_{(C\leq8)}$, alkynyl$_{(C\leq8)}$, aryl$_{(C\leq12)}$, aralkyl$_{(C\leq12)}$, heteroaryl$_{(C\leq8)}$, heterocycloalkyl$_{(C\leq12)}$, alkoxy$_{(C\leq8)}$, aryloxy$_{(C\leq12)}$, acyloxy$_{(C\leq8)}$, alkylamino$_{(C\leq8)}$, dialkylamino$_{(C\leq8)}$, alkenylamino$_{(C\leq8)}$, arylamino$_{(C\leq8)}$, aralkylamino$_{(C\leq8)}$, alkylthio$_{(C\leq8)}$, acylthio$_{(C\leq8)}$, alkylsulfonylamino$_{(C\leq8)}$, or substituted versions of any of these groups;

-alkanediyl$_{(C\leq8)}$-$R_b$, -alkenediyl$_{(C\leq8)}$-$R_b$, or a substituted version of any of these groups, wherein $R_b$ is:

hydrogen, hydroxy, halo, amino or thio; or heteroaryl$_{(C\leq8)}$, alkoxy$_{(C\leq8)}$, alkenyloxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, alkylamino$_{(C\leq8)}$, dialkylamino$_{(C\leq8)}$, alkenylamino$_{(C\leq8)}$, arylamino$_{(C\leq8)}$, aralkylamino$_{(C\leq8)}$, heteroarylamino$_{(C\leq8)}$, alkylsulfonylamino$_{(C\leq8)}$, amido$_{(C\leq8)}$, —OC(O)NH-alkyl$_{(C\leq8)}$, —OC(O)$CH_2$NHC(O)O-t-butyl, —$OCH_2$-alkylthio$_{(C\leq8)}$, or a substituted version of any of these groups;

—$(CH_2)_m$C(O)$R_c$, wherein m is 0-6 and $R_c$ is:

hydrogen, hydroxy, halo, amino, —NHOH,

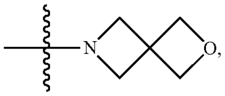

or thio; or alkyl$_{(C\leq8)}$, alkenyl$_{(C\leq8)}$, alkynyl$_{(C\leq8)}$, aryl$_{(C\leq8)}$, aralkyl$_{(C\leq8)}$, heteroaryl$_{(C\leq8)}$, heterocycloalkyl$_{(C\leq8)}$, alkoxy$_{(C\leq8)}$, alkenyloxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, alkylamino$_{(C\leq8)}$, dialkylamino$_{(C\leq8)}$, arylamino$_{(C\leq8)}$, alkylsulfonylamino$_{(C\leq8)}$, amido$_{(C\leq8)}$, —NH-alkoxy$_{(C\leq8)}$, —NH-heterocycloalkyl$_{(C\leq8)}$, —NHC(NOH)-alkyl$_{(C\leq8)}$, —NH-amido$_{(C\leq8)}$, or a substituted version of any of these groups;

$R_c$ and $R_3$, taken together, are —O— or —$NR_d$—, wherein $R_d$ is hydrogen or alkyl$_{(C\leq4)}$; or $R_c$ and $R_4$, taken together, are —O— or —$NR_d$—, wherein $R_d$ is hydrogen or alkyl$_{(C\leq4)}$; or —NHC(O)$R_e$, wherein $R_e$ is:

hydrogen, hydroxy, amino; or alkyl$_{(C\leq8)}$, alkenyl$_{(C\leq8)}$, alkynyl$_{(C\leq8)}$, aryl$_{(C\leq8)}$, aralkyl$_{(C\leq8)}$, heteroaryl$_{(C\leq8)}$, heterocycloalkyl$_{(C\leq8)}$, alkoxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, alkylamino$_{(C\leq8)}$, dialkylamino$_{(C\leq8)}$, arylamino$_{(C\leq8)}$, or a substituted version of any of these groups;

or a pharmaceutically acceptable salt or tautomer thereof.

2. The compound of claim 1, further defined by the formula:

(II)

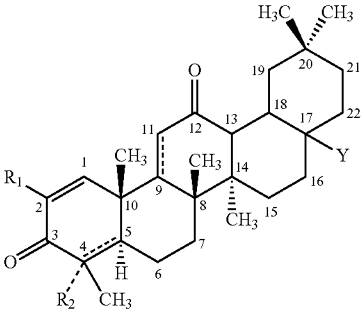

, wherein:

$R_1$ is —CN, iodo, —$CF_3$, or —C(O)$R_a$, wherein $R_a$ is —OH, alkoxy$_{(C1\text{-}4)}$, —$NH_2$, alkylamino$_{(C1\text{-}4)}$, or —NH—S(O)$_2$-alkyl$_{(C1\text{-}4)}$;

$R_2$ is hydrogen or $R_2$ is absent when the atom to which it is bound forms part of a double bond; and Y is:

—H, —OH, —SH, —CN, —F, —$CF_3$, —$NH_2$ or —NCO;

alkyl$_{(C\leq8)}$, alkenyl$_{(C\leq8)}$, alkynyl$_{(C\leq8)}$, aryl$_{(C\leq12)}$, aralkyl$_{(C\leq12)}$, heteroaryl$_{(C\leq8)}$, heterocycloalkyl$_{(C\leq12)}$, alkoxy$_{(C\leq8)}$, aryloxy$_{(C\leq12)}$, acyloxy$_{(C\leq8)}$, alkylamino$_{(C\leq8)}$, dialkylamino$_{(C\leq8)}$, alkenylamino$_{(C\leq8)}$, arylamino$_{(C\leq8)}$, aralkylamino$_{(C\leq8)}$, alkylthio$_{(C\leq8)}$, acylthio$_{(C\leq8)}$, alkylsulfonylamino$_{(C\leq8)}$, or substituted versions of any of these groups;

-alkanediyl$_{(C\leq8)}$-$R_b$, -alkenediyl$_{(C\leq8)}$-$R_b$, or a substituted version of any of these groups, wherein $R_b$ is:

hydrogen, hydroxy, halo, amino or thio; or heteroaryl$_{(C\leq8)}$, alkoxy$_{(C\leq8)}$, alkenyloxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, alkylamino$_{(C\leq8)}$, dialkylamino$_{(C\leq8)}$, alkenylamino$_{(C\leq8)}$, arylamino$_{(C\leq8)}$, aralkylamino$_{(C\leq8)}$, heteroarylamino$_{(C\leq8)}$, alkylsulfonylamino$_{(C\leq8)}$, amido$_{(C\leq8)}$, —OC(O)NH-alkyl$_{(C\leq8)}$, —OC(O)$CH_2$NHC(O)O-t-butyl, —$OCH_2$-alkylthio$_{(C\leq8)}$, or a substituted version of any of these groups;

—$(CH_2)_m$C(O)$R_c$, wherein m is 0-6 and $R_c$ is:

hydrogen, hydroxy, halo, amino, —NHOH,

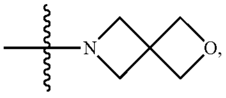

or thio; or alkyl$_{(C\leq8)}$, alkenyl$_{(C\leq8)}$, alkynyl$_{(C\leq8)}$, aryl$_{(C\leq8)}$, aralkyl$_{(C\leq8)}$, heteroaryl$_{(C\leq8)}$, heterocycloalkyl$_{(C\leq8)}$, alkoxy$_{(C\leq8)}$, alkenyloxy$_{(C\leq8)}$, aryloxy$_{(C\leq8)}$, aralkoxy$_{(C\leq8)}$, heteroaryloxy$_{(C\leq8)}$, acyloxy$_{(C\leq8)}$, alkylamino$_{(C\leq8)}$, dialkylamino$_{(C\leq8)}$, arylamino$_{(C\leq8)}$, alkyl-sulfonylamino$_{(C\leq8)}$, amido$_{(C\leq8)}$, —NH-alkoxy$_{(C\leq8)}$, —NH-heterocycloalkyl$_{(C\leq8)}$, —NHC(NOH)-alkyl$_{(C\leq8)}$, —NH-amido$_{(C\leq8)}$, or a substituted version of any of these groups; or —NHC(O)$R_e$, wherein $R_e$ is:

hydrogen, hydroxy, amino; or alkyl$_{(C\leq8)}$, alkenyl$_{(C\leq8)}$, alkynyl$_{(C\leq8)}$, aryl$_{(C\leq8)}$, aralkyl$_{(C\leq8)}$, heteroaryl$_{(C\leq8)}$, heterocycloalkyl$_{(C\le8)}$, alkoxy$_{(C\le8)}$, aryloxy$_{(C\le8)}$, aralkoxy$_{(C\le8)}$, heteroaryloxy$_{(C\le8)}$, acyloxy$_{(C\le8)}$, alkylamino$_{(C\le8)}$, dialkylamino$_{(C\le8)}$, arylamino$_{(C\le8)}$, or a substituted version of any of these groups;

or a pharmaceutically acceptable salt or tautomer thereof.

3. The compound of claim 2, further defined by the formula:

(III)

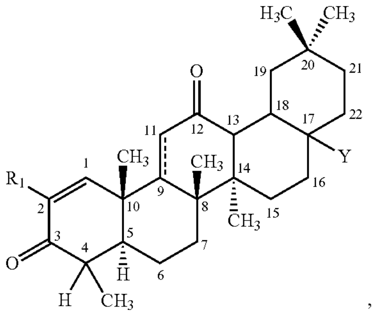

, wherein:

$R_1$ is —CN, iodo, —$CF_3$, or —C(O)$R_a$, wherein $R_a$ is —OH, alkoxy$_{(C1\text{-}4)}$, —$NH_2$, alkylamino$_{(C1\text{-}4)}$, or —NH—$S(O)_2$-alkyl$_{(C1\text{-}4)}$; and Y is:

—H, —OH, —SH, —CN, —F, —$CF_3$, —$NH_2$ or —NCO;

alkyl$_{(C\le8)}$, alkenyl$_{(C\le8)}$, alkynyl$_{(C\le8)}$, aryl$_{(C\le12)}$, aralkyl$_{(C\le12)}$, heteroaryl$_{(C\le8)}$, heterocycloalkyl$_{(C\le12)}$, alkoxy$_{(C\le8)}$, aryloxy$_{(C\le12)}$, acyloxy$_{(C\le8)}$, alkylamino$_{(C\le8)}$, dialkylamino$_{(C\le8)}$, alkenylamino$_{(C\le8)}$, aryl-amino$_{(C\le8)}$, aralkylamino$_{(C\le8)}$, alkylthio$_{(C\le8)}$, acylthio$_{(C\le8)}$, alkyl-sulfonylamino$_{(C\le8)}$, or substituted versions of any of these groups;

-alkanediyl$_{(C\le8)}$-$R_b$, -alkenediyl$_{(C\le8)}$-$R_b$, or a substituted version of any of these groups, wherein $R_b$ is:

hydrogen, hydroxy, halo, amino or thio; or heteroaryl$_{(C\le8)}$, alkoxy$_{(C\le8)}$, alkenyloxy$_{(C\le8)}$, aryloxy$_{(C\le8)}$, aralkoxy$_{(C\le8)}$, heteroaryloxy$_{(C\le8)}$, acyloxy$_{(C\le8)}$, alkylamino$_{(C\le8)}$, dialkylamino$_{(C\le8)}$, alkenylamino$_{(C\le8)}$, arylamino$_{(C\le8)}$, aralkylamino$_{(C\le8)}$, heteroarylamino$_{(C\le8)}$, alkylsulfonylamino$_{(C\le8)}$, amido$_{(C\le8)}$, —OC(O)NH-alkyl$_{(C\le8)}$, —OC(O)$CH_2$NHC(O)O-t-butyl, —$OCH_2$-alkylthio$_{(C\le8)}$, or a substituted version of any of these groups;

—$(CH_2)_m$C(O)$R_c$, wherein m is 0-6 and $R_c$ is:

hydrogen, hydroxy, halo, amino, —NHOH,

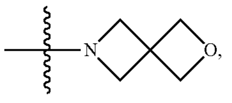

or thio; or alkyl$_{(C\le8)}$, alkenyl$_{(C\le8)}$, alkynyl$_{(C\le8)}$, aryl$_{(C\le8)}$, aralkyl$_{(C\le8)}$, heteroaryl$_{(C\le8)}$, heterocycloalkyl$_{(C\le8)}$, alkoxy$_{(C\le8)}$, alkenyl-oxy$_{(C\le8)}$, aryloxy$_{(C\le8)}$, aralkoxy$_{(C\le8)}$, heteroaryloxy$_{(C\le8)}$, acyloxy$_{(C\le8)}$, alkylamino$_{(C\le8)}$, dialkylamino$_{(C\le8)}$, arylamino$_{(C\le8)}$, alkylsulfonylamino$_{(C\le8)}$, amido$_{(C\le8)}$, —NH-alkoxy$_{(C\le8)}$, —NH-heterocycloalkyl$_{(C\le8)}$, —NHC(NOH)-alkyl$_{(C\le8)}$, —NH-amido$_{(C\le8)}$, or a substituted version of any of these groups; or —NHC(O)$R_e$, wherein $R_e$ is:

hydrogen, hydroxy, amino; or alkyl$_{(C\le8)}$, alkenyl$_{(C\le8)}$, alkynyl$_{(C\le8)}$, aryl$_{(C\le8)}$, aralkyl$_{(C\le8)}$, heteroaryl$_{(C\le8)}$, heterocycloalkyl$_{(C\le8)}$, alkoxy$_{(C\le8)}$, aryloxy$_{(C\le8)}$, aralkoxy$_{(C\le8)}$, heteroaryloxy$_{(C\le8)}$, acyloxy$_{(C\le8)}$, alkylamino$_{(C\le8)}$, dialkylamino$_{(C\le8)}$, arylamino$_{(C\le8)}$, or a substituted version of any of these groups;

or a pharmaceutically acceptable salt or tautomer thereof.

4. The compound of claim 3, further defined by the formula:

(IV)

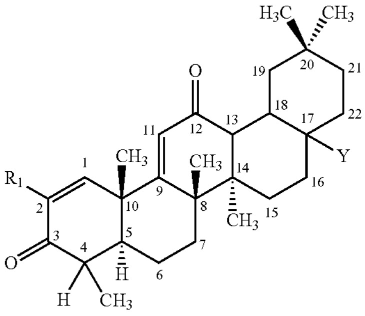

, wherein:

$R_1$ is —CN, iodo, —$CF_3$, or —C(O)$R_a$, wherein $R_a$ is —OH, alkoxy$_{(C1\text{-}4)}$, —$NH_2$, alkylamino$_{(C1\text{-}4)}$, or —NH—$S(O)_2$-alkyl$_{(C1\text{-}4)}$; and Y is:

—H, —OH, —SH, —CN, —F, —$CF_3$, —$NH_2$ or —NCO;

alkyl$_{(C\le8)}$, alkenyl$_{(C\le8)}$, alkynyl$_{(C\le8)}$, aryl$_{(C\le12)}$, aralkyl$_{(C\le12)}$, heteroaryl$_{(C\le8)}$, heterocycloalkyl$_{(C\le12)}$, alkoxy$_{(C\le8)}$, aryloxy$_{(C\le12)}$, acyloxy$_{(C\le8)}$, alkylamino$_{(C\le8)}$, dialkylamino$_{(C\le8)}$, alkenylamino$_{(C\le8)}$, arylamino$_{(C\le8)}$, aralkylamino$_{(C\le8)}$, amido$_{(C\le8)}$, alkylthio$_{(C\le8)}$, acylthio$_{(C\le8)}$, alkyl-sulfonylamino$_{(C\le8)}$, or substituted versions of any of these groups;

-alkanediyl$_{(C\le8)}$-$R_b$, -alkenediyl$_{(C\le8)}$-$R_b$, or a substituted version of any of these groups, wherein $R_b$ is:

hydrogen, hydroxy, halo, amino or thio; or heteroaryl$_{(C\le8)}$, alkoxy$_{(C\le8)}$, alkenyloxy$_{(C\le8)}$, aryloxy$_{(C\le8)}$, aralkoxy$_{(C\le8)}$, heteroaryloxy$_{(C\le8)}$, acyloxy$_{(C\le8)}$, alkylamino$_{(C\le8)}$, dialkylamino$_{(C\le8)}$, alkenylamino$_{(C\le8)}$, arylamino$_{(C\le8)}$, aralkylamino$_{(C\le8)}$, heteroarylamino$_{(C\le8)}$, alkylsulfonyl-OC(O)$CH_2$NHC(O)O-t-butyl, —$OCH_2$-alkylthio$_{(C\le8)}$, or a substituted version of any of these groups;

—$(CH_2)_m$C(O)$R_c$, wherein m is 0-6 and $R_c$ is:

hydrogen, hydroxy, halo, amino, —NHOH,

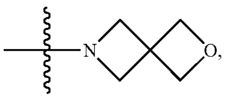 [SMILES: *N1CC2(COC2)C1]

or thio; or alkyl$_{(C\le8)}$, alkenyl$_{(C\le8)}$, alkynyl$_{(C\le8)}$, aryl$_{(C\le8)}$, aralkyl$_{(C\le8)}$, heteroaryl$_{(C\le8)}$, heterocycloalkyl$_{(C\le8)}$, alkoxy$_{(C\le8)}$, alkenyloxy$_{(C\le8)}$, aryloxy$_{(C\le8)}$, aralkoxy$_{(C\le8)}$, heteroaryloxy$_{(C\le8)}$, acyloxy$_{(C\le8)}$, alkylamino$_{(C\le8)}$, dialkylamino$_{(C\le8)}$, arylamino$_{(C\le8)}$, alkylsulfonylamino$_{(C\le8)}$, amido$_{(C\le8)}$, —NH-alkoxy$_{(C\le8)}$, —NH-heterocycloalkyl$_{(C\le8)}$, —NHC(NOH)-alkyl$_{(C\le8)}$, —NH-amido$_{(C\le8)}$, or a substituted version of any of these groups; or —NHC(O)$R_e$, wherein $R_e$ is:

hydrogen, hydroxy, amino; or alkyl$_{(C\le8)}$, alkenyl$_{(C\le8)}$, alkynyl$_{(C\le8)}$, aryl$_{(C\le8)}$, aralkyl$_{(C\le8)}$, heteroaryl$_{(C\le8)}$, heterocycloalkyl$_{(C\le8)}$, alkoxy$_{(C\le8)}$, aryloxy$_{(C\le8)}$, aralkoxy$_{(C\le8)}$, heteroaryloxy$_{(C\le8)}$, acyloxy$_{(C\le8)}$, alkylamino$_{(C\le8)}$, dialkylamino$_{(C\le8)}$, arylamino$_{(C\le8)}$, or a substituted version of any of these groups;

or a pharmaceutically acceptable salt or tautomer thereof.

5. The compound of claim 4, wherein $R_1$ is —CN.

6. The compound of claim 5, wherein Y is —$(CH_2)_m$C(O)$R_c$, wherein m is 0-6 and $R_c$ is hydrogen, hydroxy, amino, —NHOH,

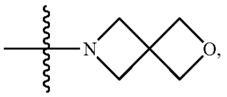 [SMILES: *N1CC2(COC2)C1]

alkyl$_{(C\le8)}$, alkenyl$_{(C\le8)}$, alkynyl$_{(C\le8)}$, aryl$_{(C\le8)}$, aralkyl$_{(C\le8)}$, heteroaryl$_{(C\le8)}$, heterocycloalkyl$_{(C\le8)}$, alkoxy$_{(C\le8)}$, alkenyloxy$_{(C\le8)}$, aryloxy$_{(C\le8)}$, aralkoxy$_{(C\le8)}$, acyloxy$_{(C\le8)}$, alkylamino$_{(C\le8)}$, dialkylamino$_{(C\le8)}$, arylamino$_{(C\le8)}$, alkylsulfonylamino$_{(C\le8)}$, amido$_{(C\le8)}$, —NH-alkoxy$_{(C\le8)}$, —NH—heterocycloalkyl$_{(C\le8)}$, —NHC(NOH)-alkyl$_{(C\le8)}$, —NH-amido$_{(C\le8)}$, or a substituted version of any of these groups other than hydrogen, hydroxy, amino, and —NHOH.

7. The compound of claim 6, wherein $R_c$ is alkoxy$_{(C\le8)}$.

8. The compound of claim 6, wherein $R_c$ is alkylamino$_{(C\le8)}$ or substituted alkylamino$_{(C\le8)}$.

9. The compound of claim 6, wherein $R_c$ is heteroaryl$_{(C\le8)}$.

10. The compound of claim 6, wherein $R_c$ is heterocycloalkyl$_{(C\le8)}$ or substituted heterocycloalkyl$_{(C\le8)}$.

11. The compound of claim 6, wherein $R_c$ is —NH-heterocycloalkyl$_{(C\le8)}$.

12. The of claim 6, wherein m is 0.

13. The compound of claim 5, wherein Y is -alkanediyl$_{(C\le8)}$-$R_b$.

14. The compound of claim 13, wherein Y is —$CH_2$—$R_b$.

15. The compound of claim 13, wherein $R_b$ is acyloxy$_{(C\le8)}$ or substituted acyloxy$_{(C\le8)}$.

16. The compound of claim 13, wherein $R_b$ is alkoxy$_{(C\le8)}$ or substituted alkoxy$_{(C\le8)}$.

17. The compound of claim 13, wherein $R_b$ is heteroaryl$_{(C\le8)}$.

18. The compound of claim 5, wherein Y is alkylsulfonylamino$_{(C\le8)}$ or substituted alkylsulfonylamino$_{(C\le8)}$.

19. The compound of claim 5, wherein Y is heteroaryl$_{(C\le8)}$.

20. The compound of claim 5, wherein Y is —NHC(O)$R_e$, wherein $R_e$ is hydrogen, hydroxy, amino, alkyl$_{(C\le8)}$, aryl$_{(C\le8)}$, alkoxy$_{(C\le8)}$, acyloxy$_{(C\le8)}$, alkylamino$_{(C\le8)}$, dialkylamino$_{(C\le8)}$, or substituted version of any of these groups other than hydrogen, hydroxy and amino.

21. The compound of claim 20, wherein $R_e$ is alkyl$_{(C\le8)}$ or substituted alkyl$_{(C\le8)}$.

22. The compound of claim 20, wherein $R_e$ is aryl$_{(C\le8)}$.

23. The compound of claim 20, wherein $R_e$ is alkoxy$_{(C\le8)}$.

24. The compound of claim 20, wherein $R_e$ is alkylamino$_{(C\le8)}$ or dialkylamino$_{(C\le8)}$.

25. The compound of claim 1, selected from the group consisting of:

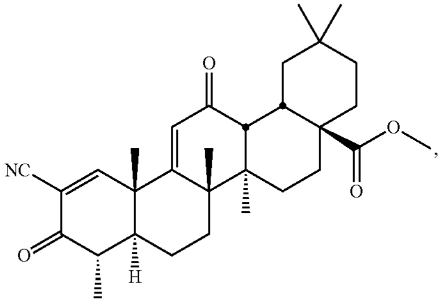

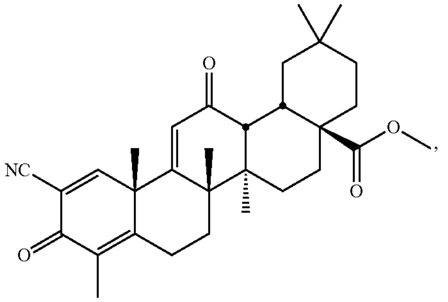

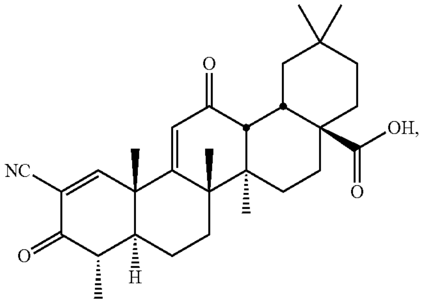

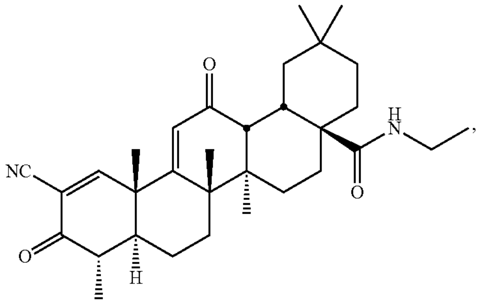

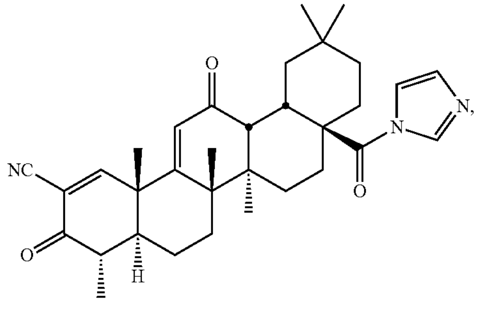

-continued
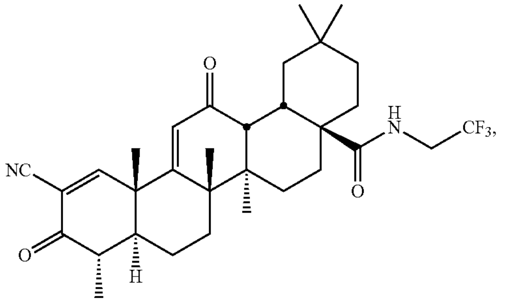
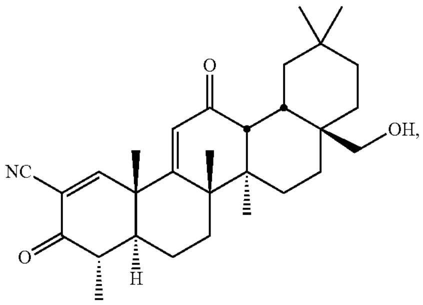
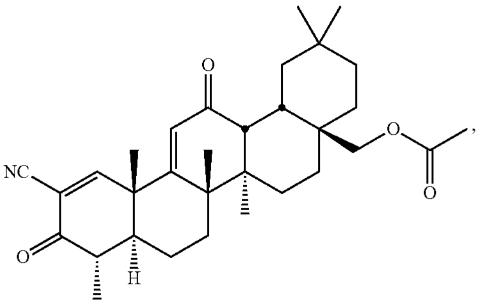
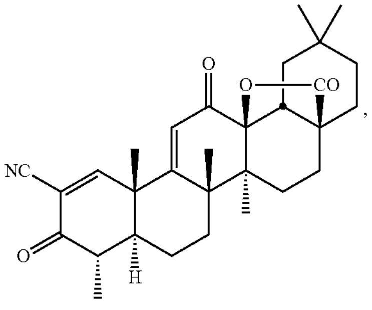
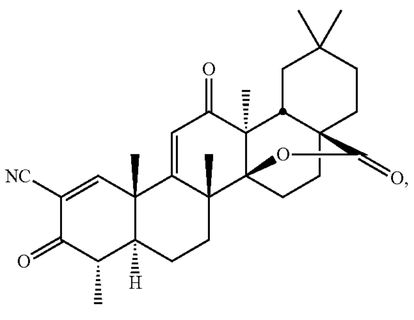
-continued
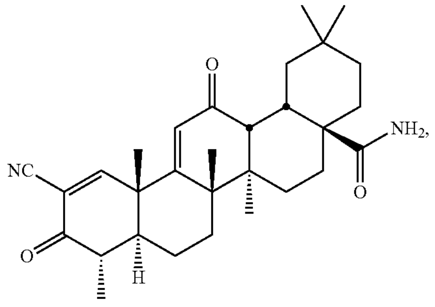
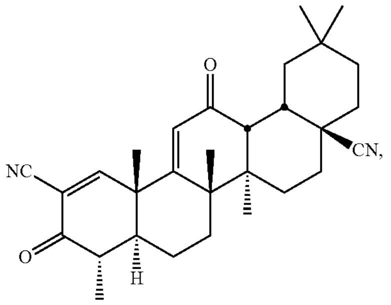
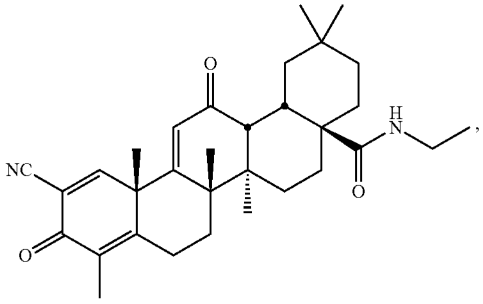
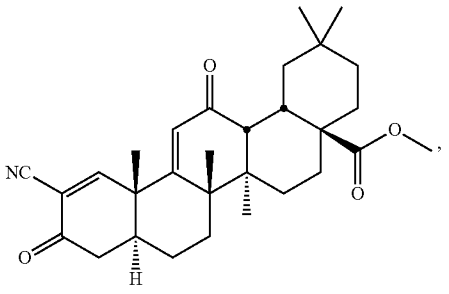
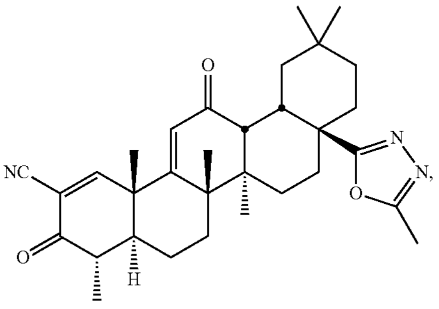

-continued
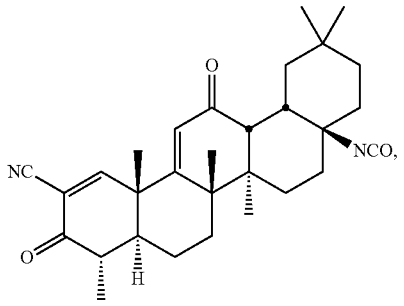
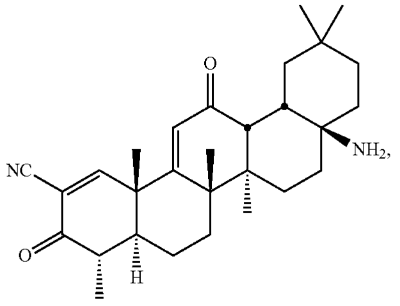
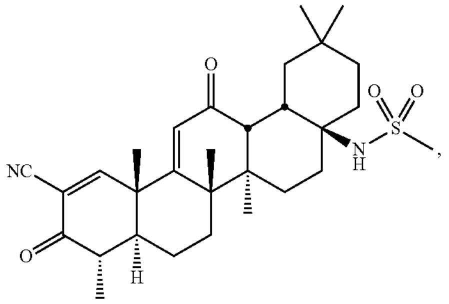
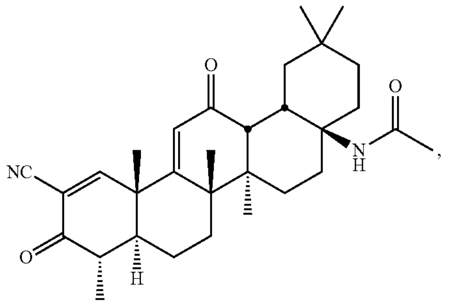
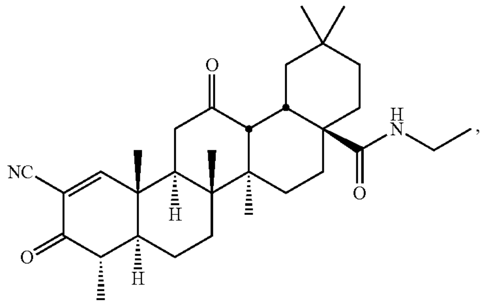
-continued
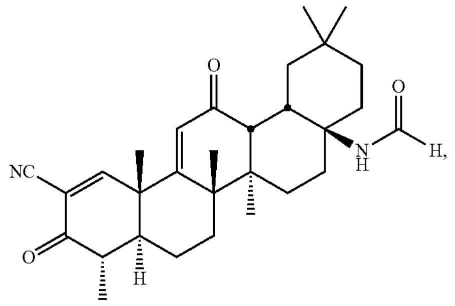
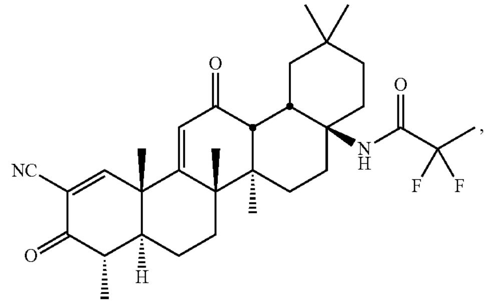
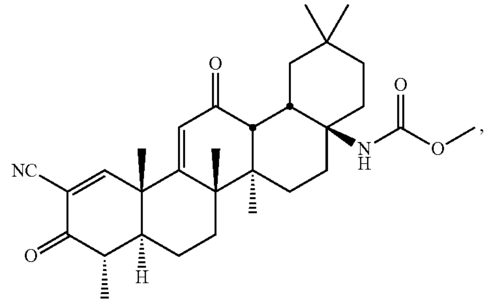
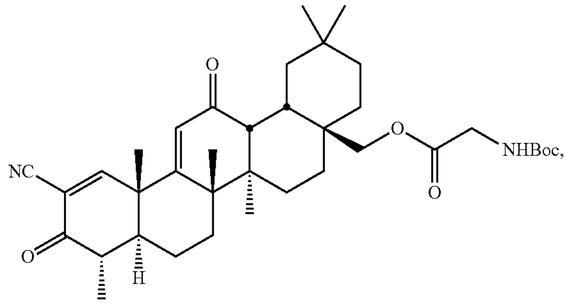
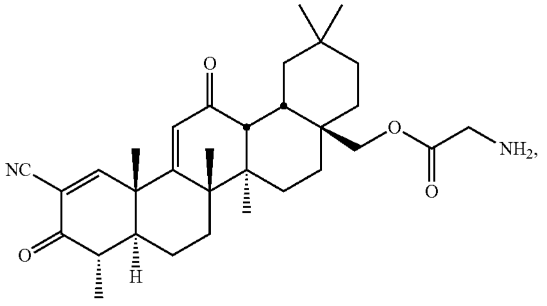

-continued
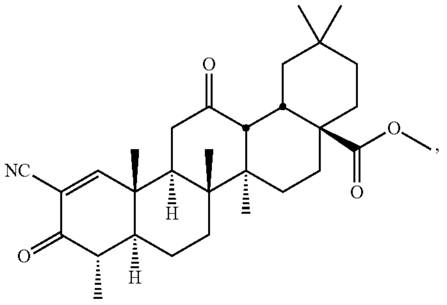
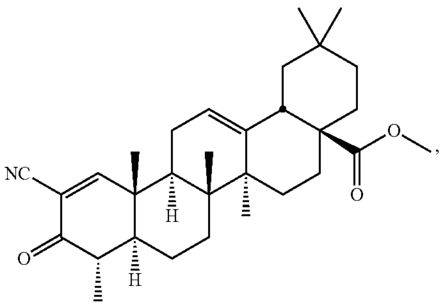
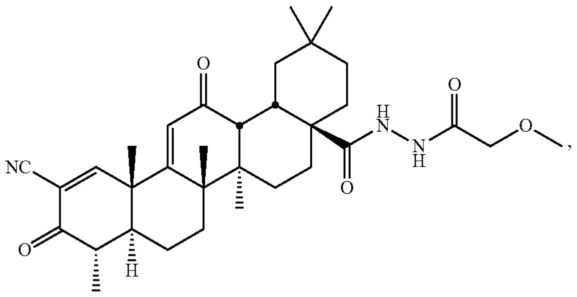
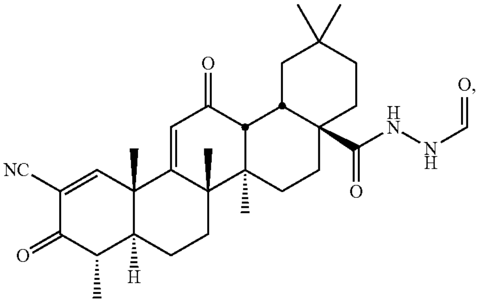
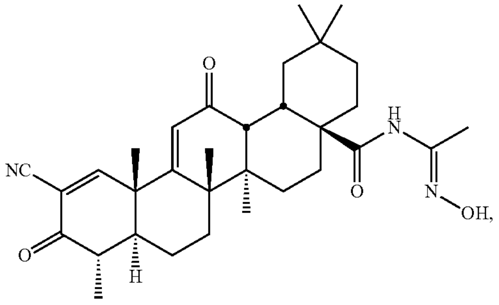
-continued
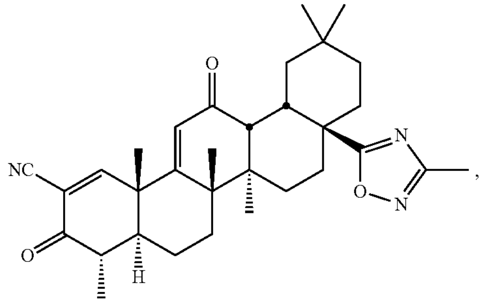
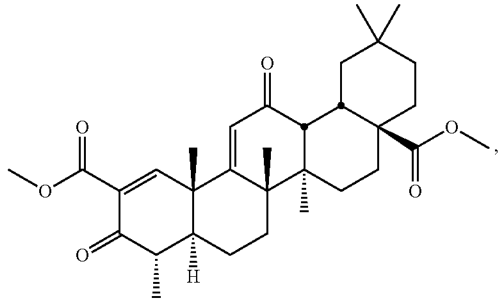
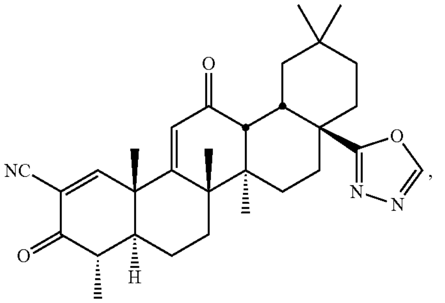
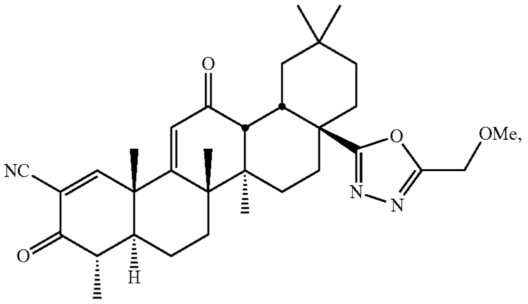
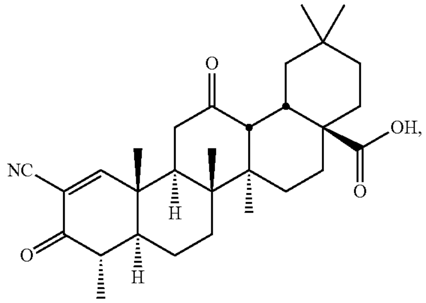

-continued
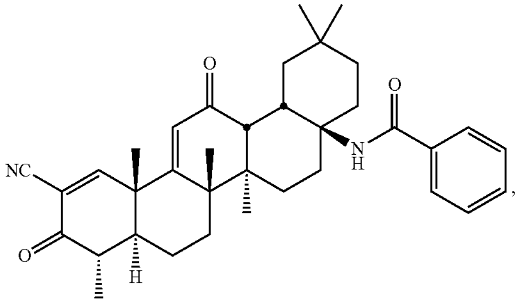
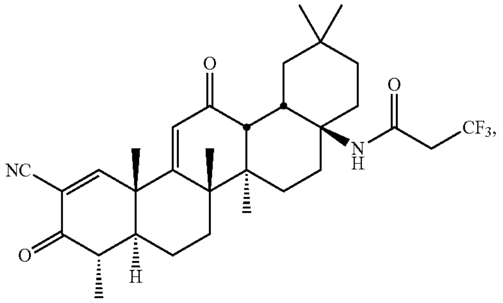
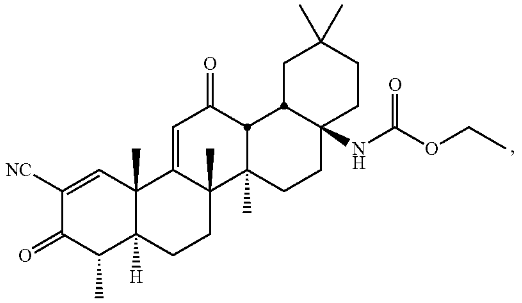
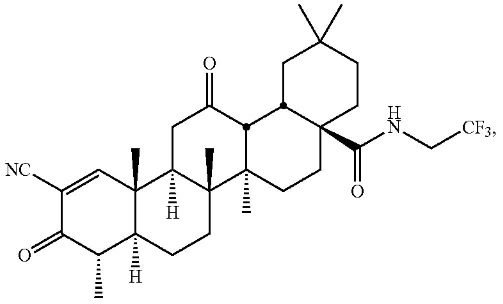
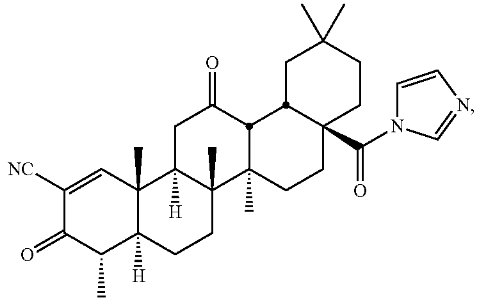
-continued
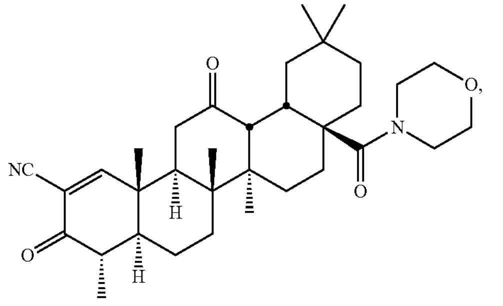
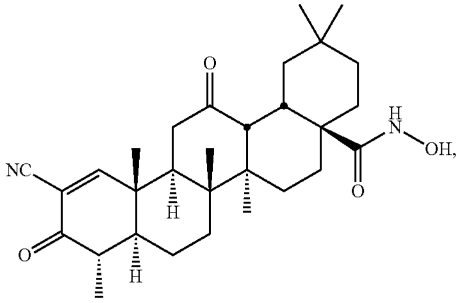
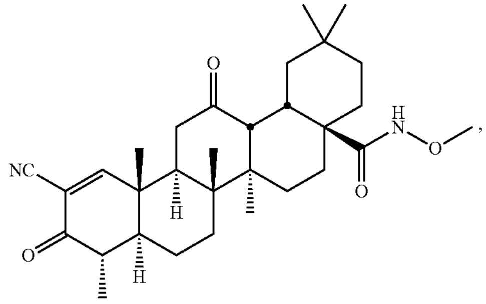
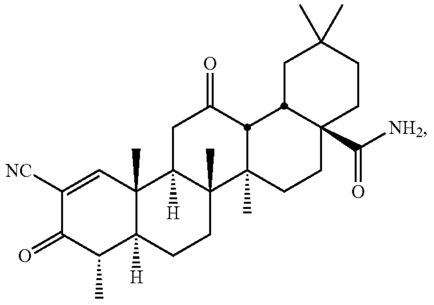
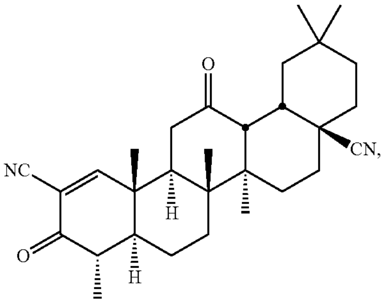

-continued
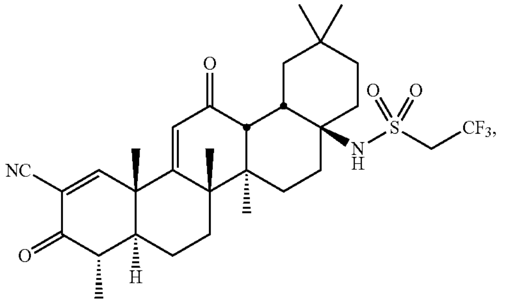
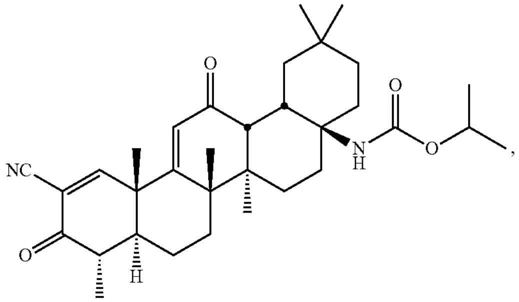
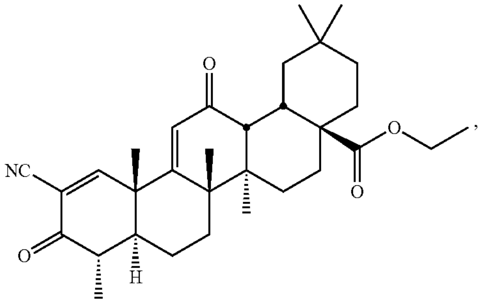
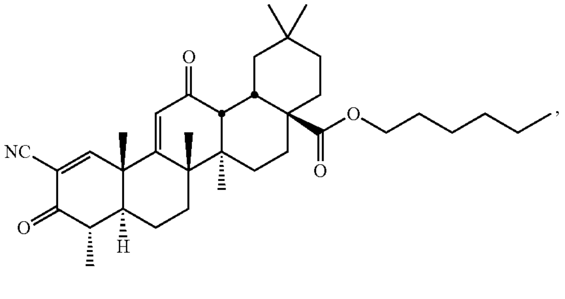
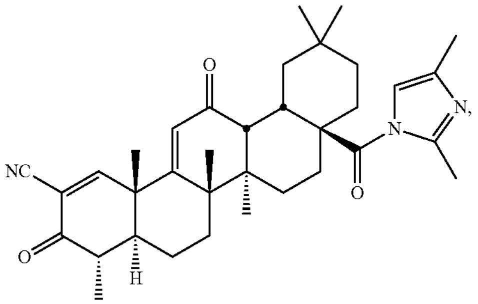
-continued
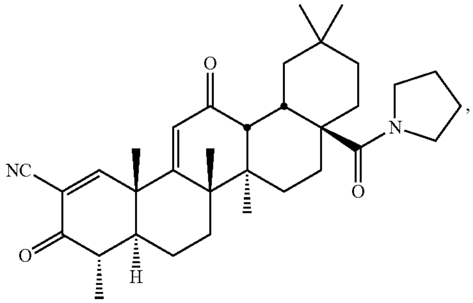
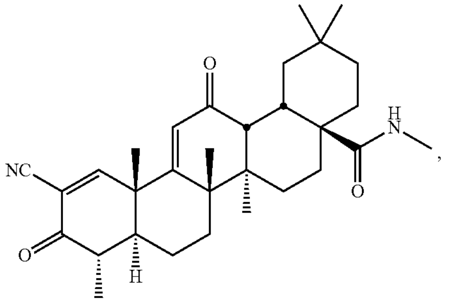
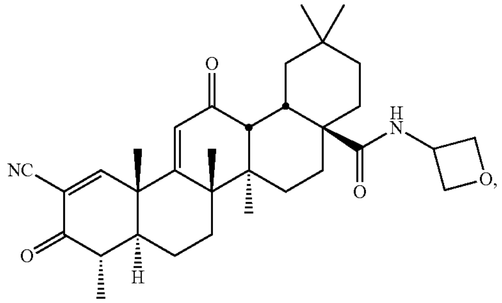
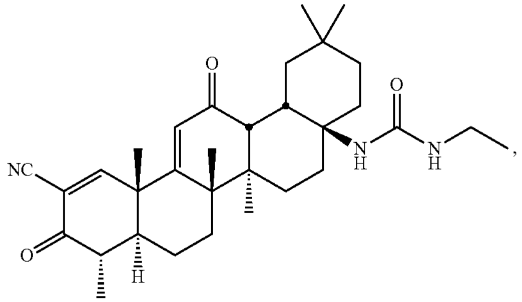
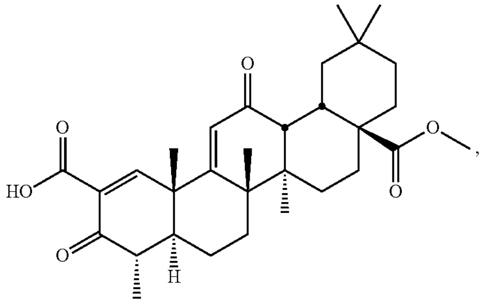

-continued
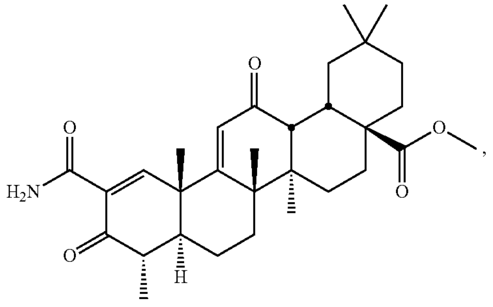,
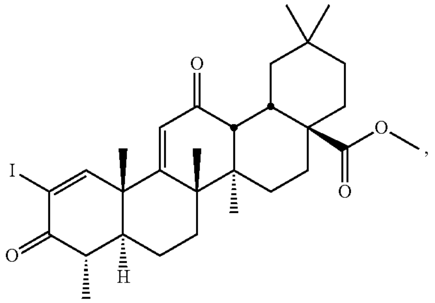,
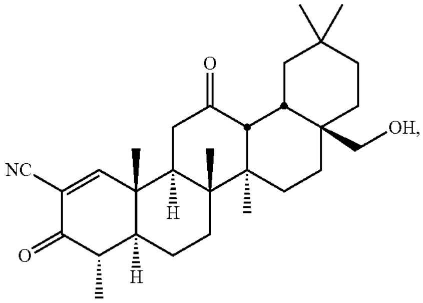,
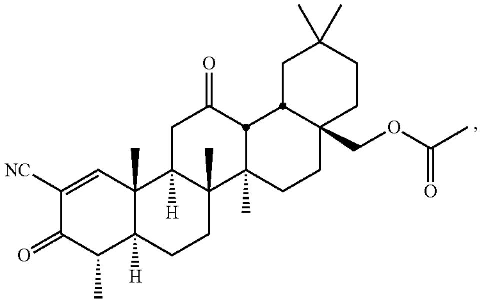,
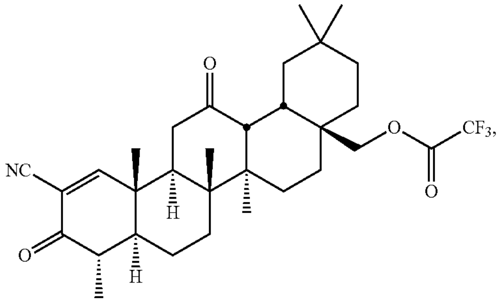,
-continued
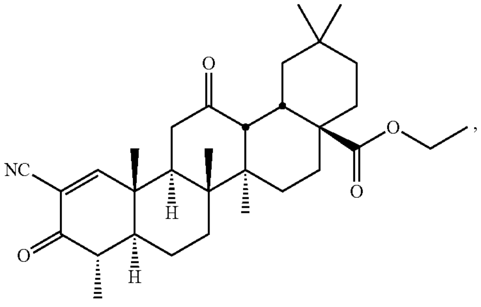,
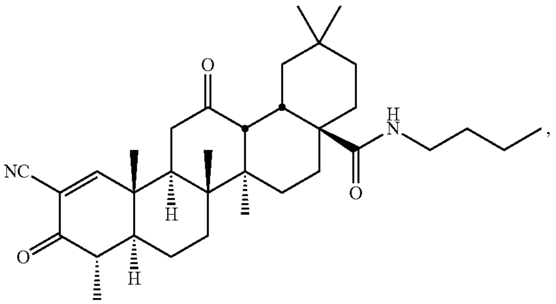,
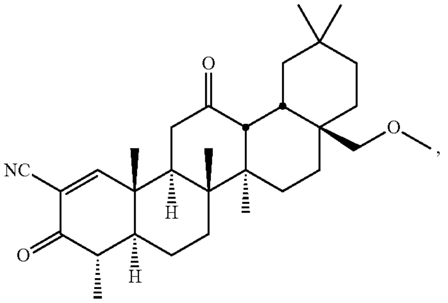,
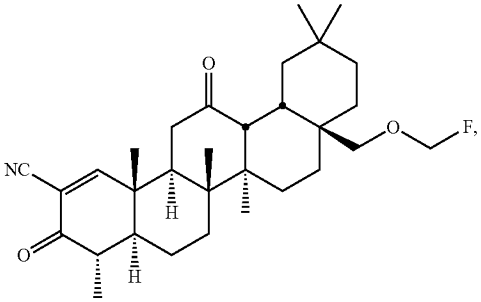,
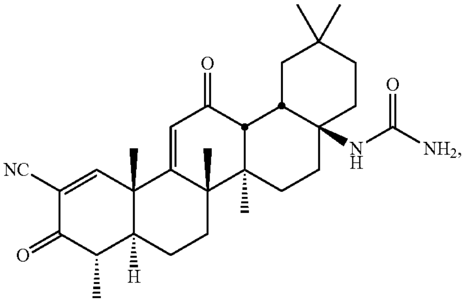, -continued
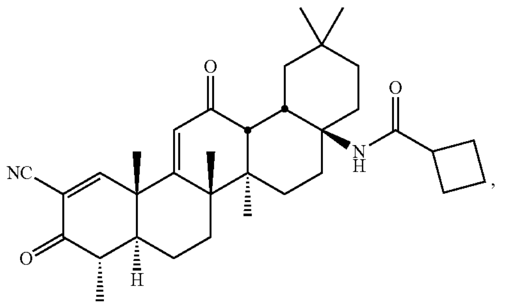
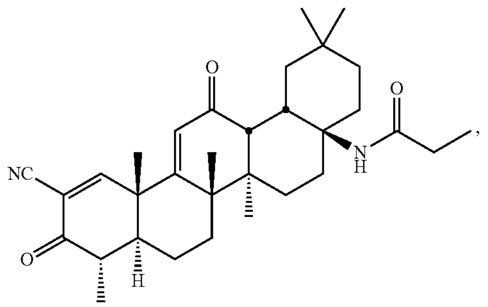
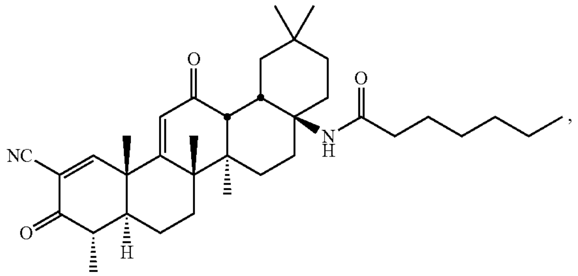
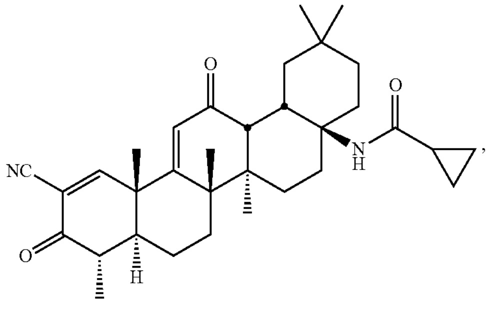
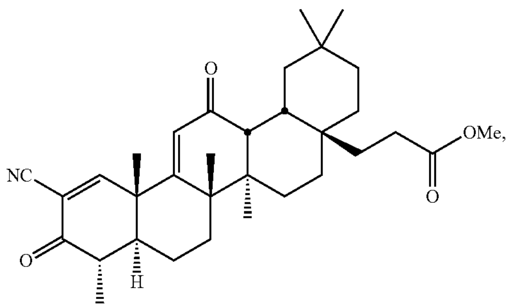
-continued
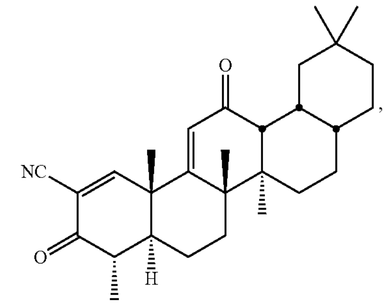
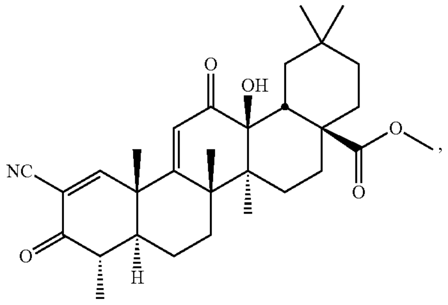
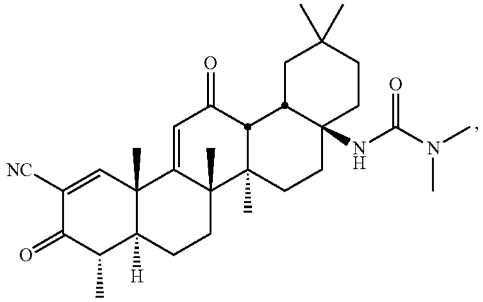
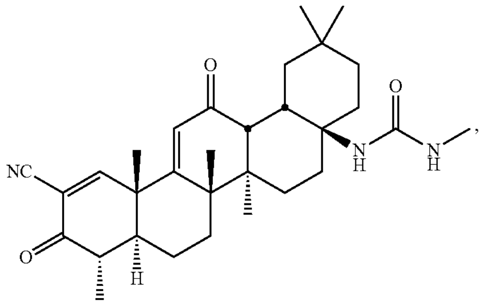
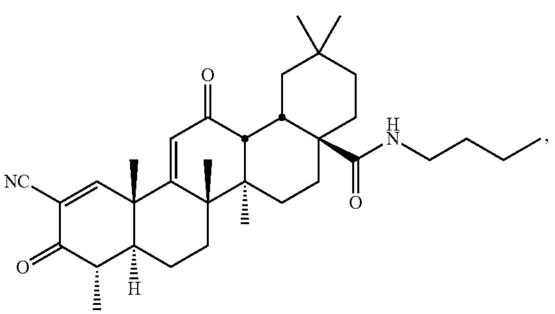

-continued
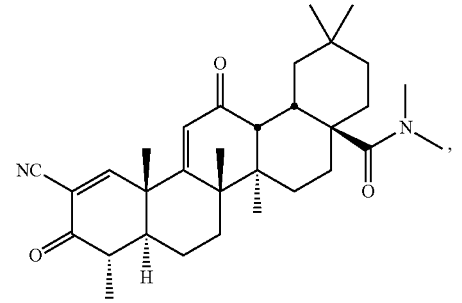
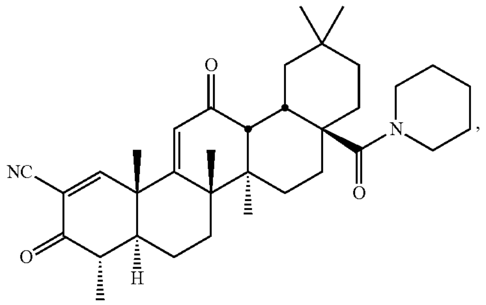
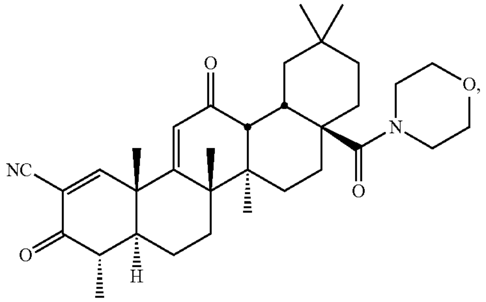
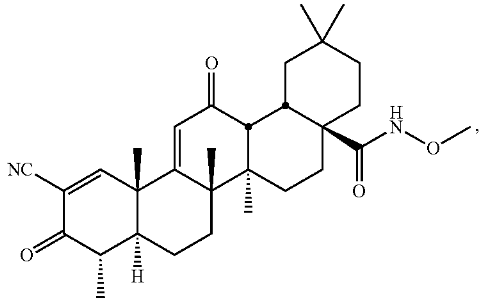
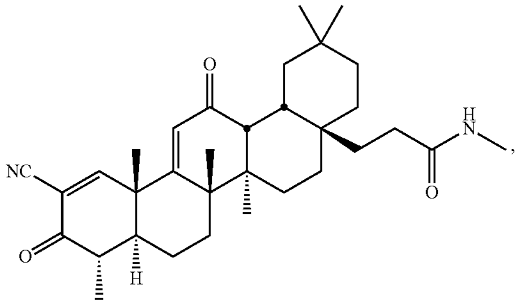
-continued
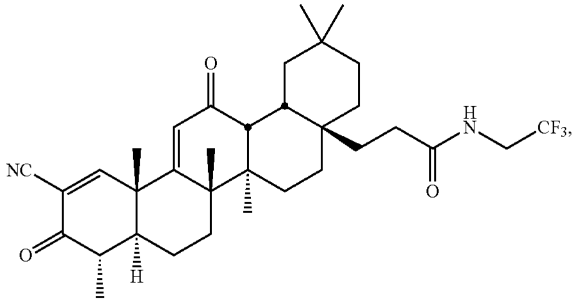
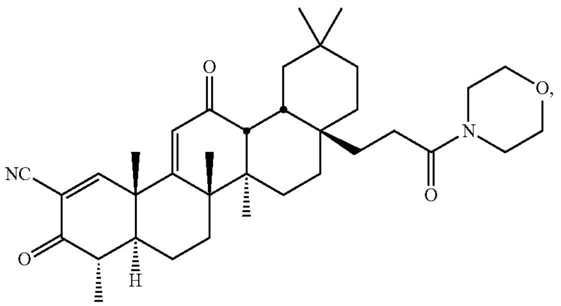
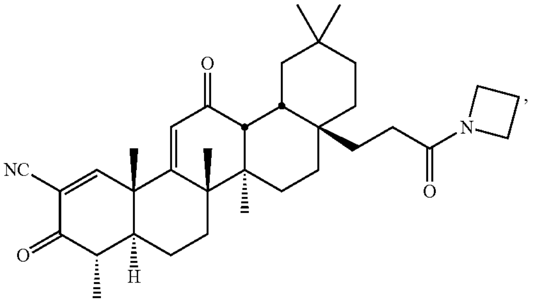
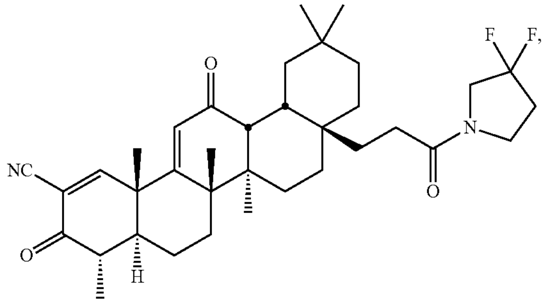
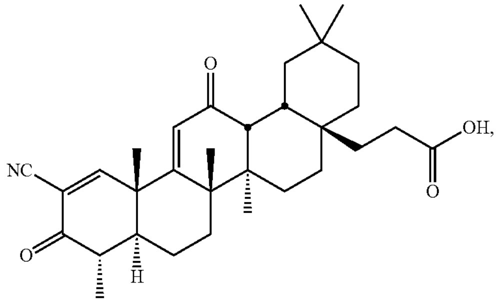

-continued
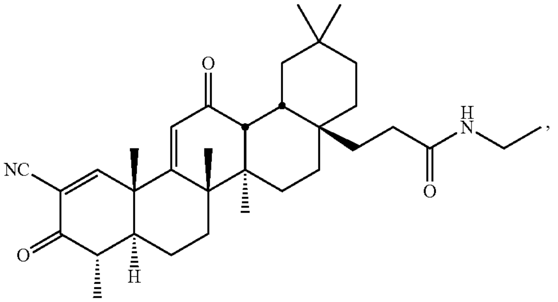
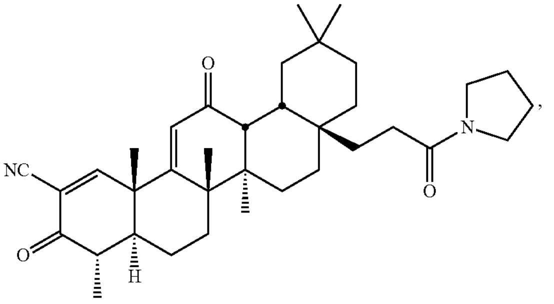
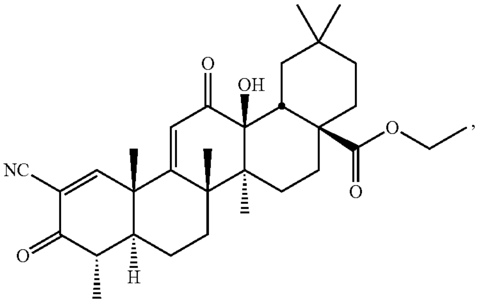
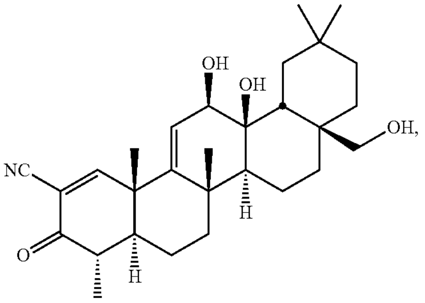
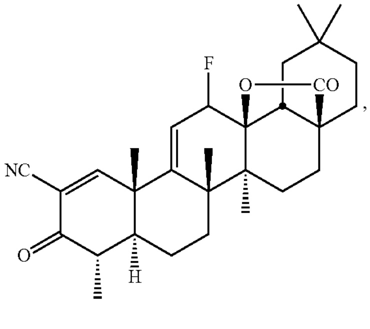
-continued
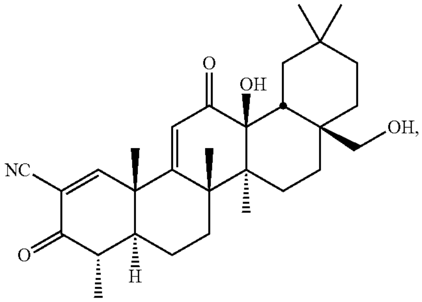
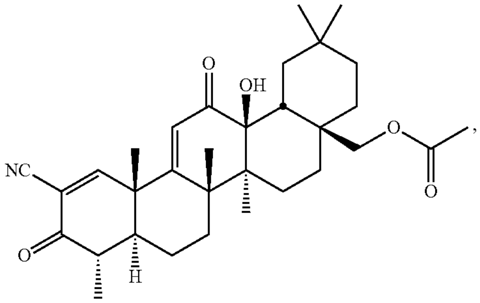
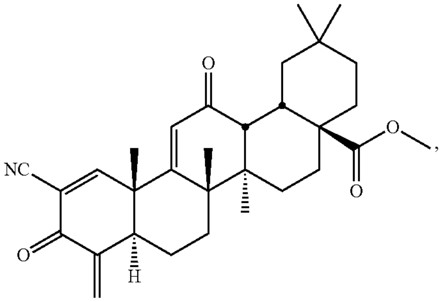
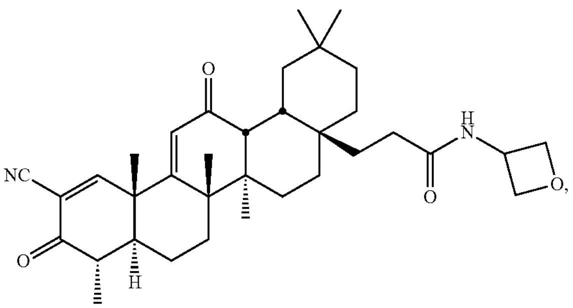
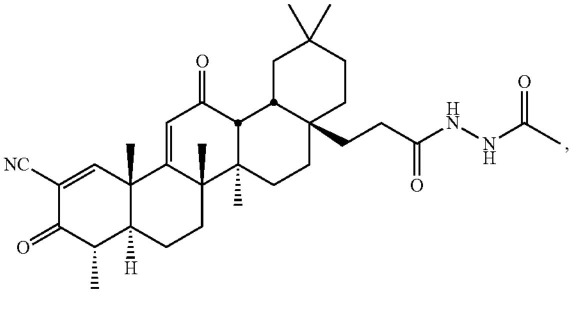

-continued
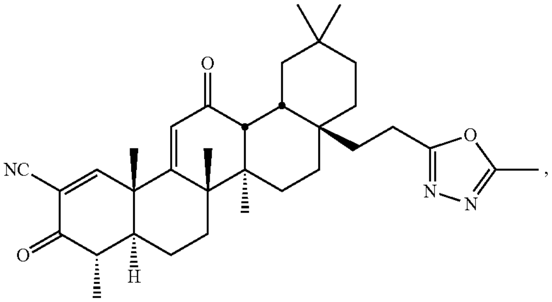
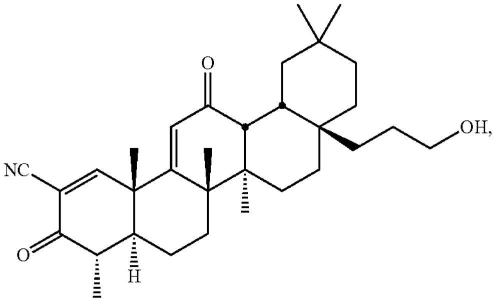
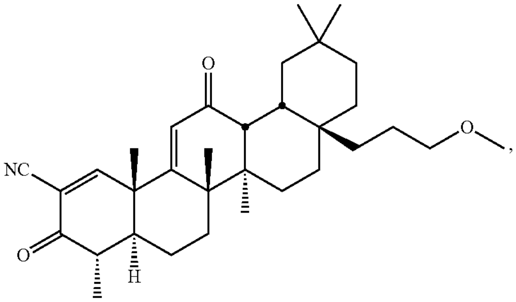
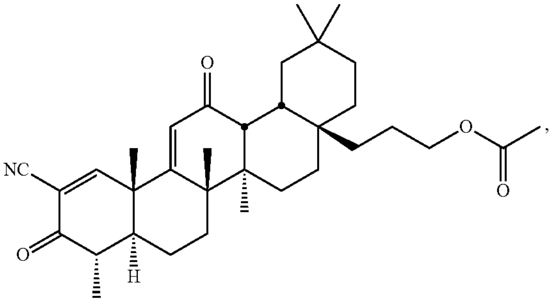
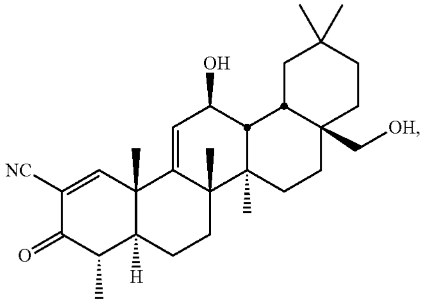
-continued
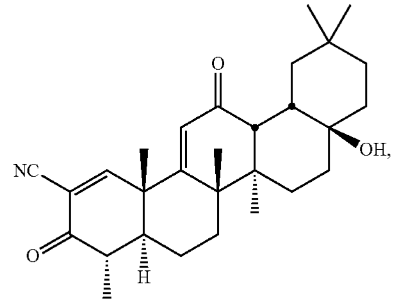
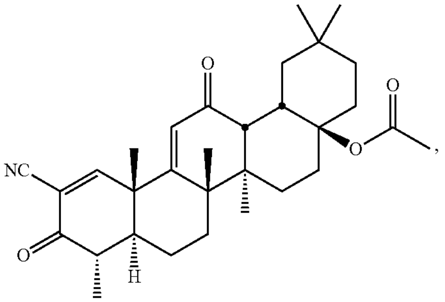
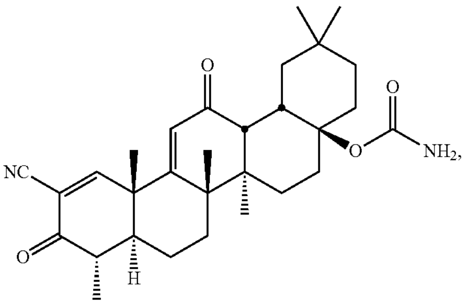
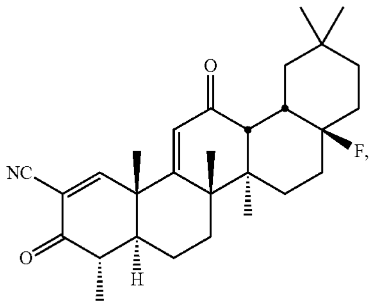
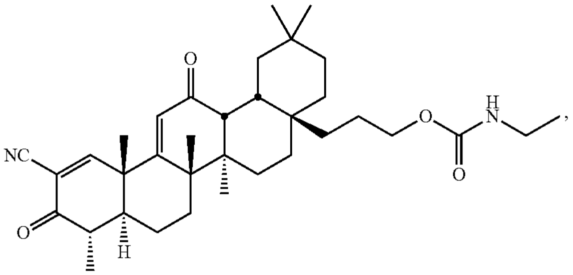

-continued
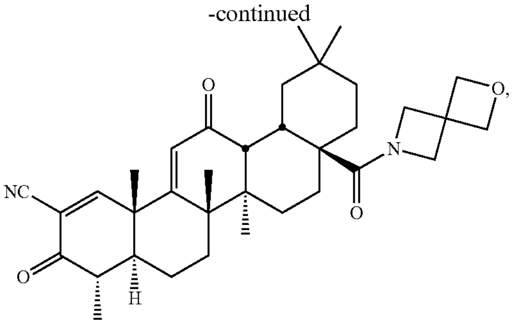
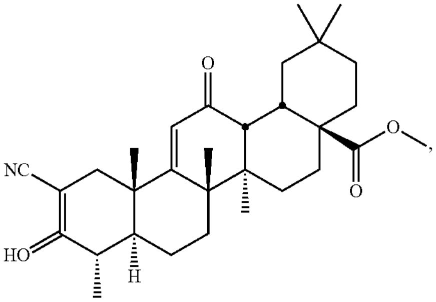
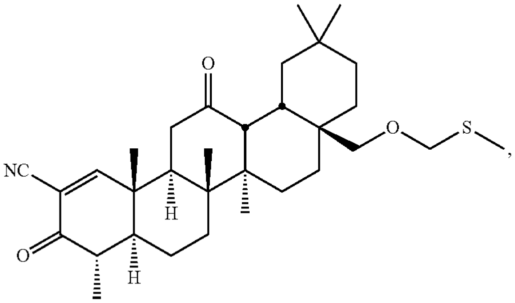
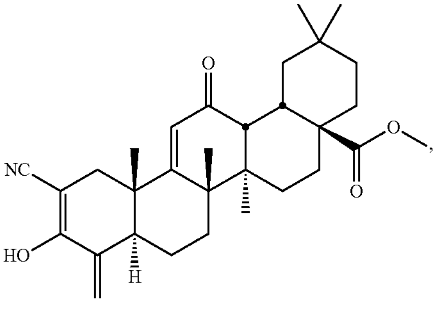
, and
-continued
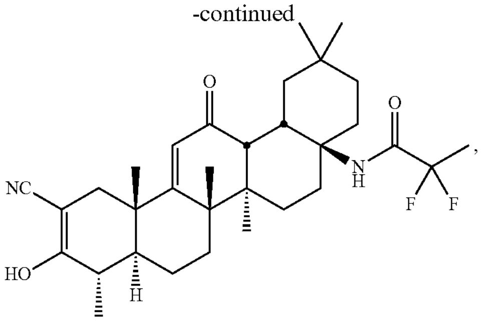
or a pharmaceutically acceptable salt or tautomer thereof.
26. A pharmaceutical composition comprising:
a) the compound of claim 1; and
b) an excipient.
27. A compound selected from the group consisting of:
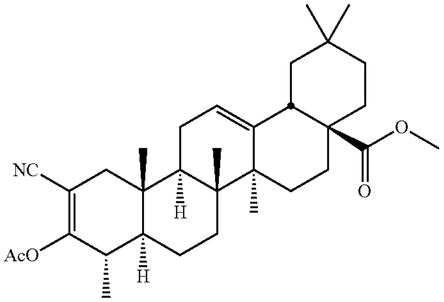
and
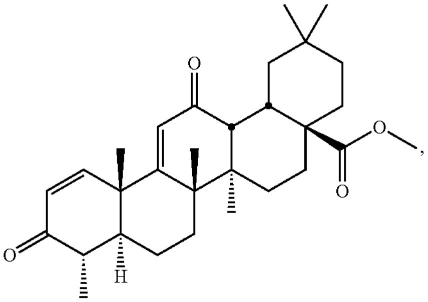
or a pharmaceutically acceptable salt thereof.
* * * * *

UNITED STATES PATENT AND TRADEMARK OFFICE

CERTIFICATE OF CORRECTION

PATENT NO. : 9,290,536 B2
APPLICATION NO. : 13/417519
DATED : March 22, 2016
INVENTOR(S) : Eric Anderson et al.

It is certified that error appears in the above-identified patent and that said Letters Patent is hereby corrected as shown below:

In the Claims

In claim 4, column 210, lines 51-52, delete "alkylsulfonyl-OC(O)$CH_2$NHC(O)O–t-butyl," and insert --alkylsulfonylamino$_{(C\leq 8)}$, amido$_{(C\leq 8)}$, –OC(O)NH–alkyl$_{(C\leq 8)}$, –OC(O)$CH_2$NHC(O)O-t-butyl,-- therefor.

Signed and Sealed this
Ninth Day of August, 2016

Michelle K. Lee
*Director of the United States Patent and Trademark Office*